US008440427B2

(12) United States Patent
Brehm et al.

(10) Patent No.: US 8,440,427 B2
(45) Date of Patent: *May 14, 2013

(54) PREPARATION OF PROTECTIVE ANTIGEN

(75) Inventors: John Brehm, Salisbury (GB); Ian McEntee, Salisbury (GB); Philip Vincent, Salisbury (GB); Nigel Allison, Salisbury (GB); Rossalyn Brehm, Salisbury (GB); George Jack, Salisbury (GB); Michael Herbert, Auckland (NZ); Barbara T. Solow, Monrovia, MD (US); Juan Arroyo, Frederick, MD (US); Randall K. Lapcevich, Dickerson, MD (US)

(73) Assignees: Health Protection Agency, Salisbury (GB); Dynport Vaccine Company LLC, Frederick, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/534,911

(22) Filed: Jun. 27, 2012

(65) Prior Publication Data

US 2013/0017573 A1 Jan. 17, 2013

Related U.S. Application Data

(60) Division of application No. 13/246,659, filed on Sep. 27, 2011, now Pat. No. 8,323,927, which is a division of application No. 12/042,150, filed on Mar. 4, 2008, now Pat. No. 8,101,735, which is a continuation-in-part of application No. 11/153,865, filed on Jun. 15, 2005, now Pat. No. 7,355, 027.

(60) Provisional application No. 60/579,687, filed on Jun. 16, 2004.

(30) Foreign Application Priority Data

Jun. 16, 2004 (GB) .................................. 0413475.5

(51) Int. Cl.
*C12N 15/31* (2006.01)
(52) U.S. Cl.
USPC ........................................................ 435/69.3
(58) Field of Classification Search .................. None
See application file for complete search history.

(56) References Cited

U.S. PATENT DOCUMENTS

| | | | |
|---|---|---|---|
| 5,670,333 | A | 9/1997 | Alldread et al. |
| 7,355,027 | B2 | 4/2008 | Brehm et al. |
| 8,101,735 | B2 | 1/2012 | Brehm et al. |
| 8,323,927 | B2 | 12/2012 | Brehra et al. |
| 2004/0028695 | A1 | 2/2004 | Park |

FOREIGN PATENT DOCUMENTS

| | | |
|---|---|---|
| EP | 0121352 | 10/1984 |
| WO | WO 98/08952 | 3/1998 |
| WO | WO 01/45639 | 6/2001 |
| WO | WO 02/04646 | 1/2002 |
| WO | WO 03/037370 | 5/2003 |
| WO | WO 03/040179 | 5/2003 |
| WO | WO 2004/003139 | 1/2004 |
| WO | WO 2004/024067 | 3/2004 |
| WO | WO 2005/123764 | 12/2005 |

OTHER PUBLICATIONS

Bowie et al (Science, 1990, 257:1306-1310).
Burgess et al (J. of Cell Bio. 111:2129-2138, 1990).
Lazar et al. (Molecular and Cellular Biology, 1988, 8:1247-1252).
Bork (Genome Research, 2000,10:398-400).
Colman, Res. Immunol., 145:33-36, 1994.
Lewin, Genes IV, Oxford Univ. Press, 1990, p. 68.
Sigmund, Arterioscler. Thromb. Vasc. Biol., 20:1425-1429, 2000.
Bampton et al., Brain Res., 841:123-134, 1999.
Invitrogen Product Catalog, 2001.
Novagen Catalog, 2002-2003.
By Manju Sharma et at, "Expression and Purification of Anthrax Toxin Protective Antigen from Escherichia colt", Protein Expression and Purification, vol. 7, Article No. 0005, 1996, pp. 33-38.
Minton et al., The Complete Nucleotide Sequence of the Pseudomonas Gene Coding for Carboxypeptidase G2, Gene, 31 (1984) 31-38, XP002038770.
Ascenzi et al., Anthrax Toxin: A Tripartite Lethal Combination, FEBS Letters 531 (2002) 384-388.
Abrahmsen, L. et al., "Secretion of heterologous gene products to the culture medium of *Escherichia coli*" Nucleic Acids Research, vol. 14, No. 18, pp. 7487-7500, (1986).
Ahuja, N. et al., "Hydrophobic residues Phe552, Phe554, Ile562, Leu566, and Ile574 are required for oligomerization of anthrax protective antigen" Biochemical and Biophysical Research Communications, vol. 287, pp. 542-549, (2001).
Alldread, R.M. et al., "Overexpression of the thermos aquaticus B malate dehydrogenase-encoding gene in *Escherichia coli*", Gene, vol. 114, pp. 139-143, (1992).
Altschul, S.F. et al., "Basic local alignment search tool", Journal of Molecular Biology, vol. 215, pp. 403-410, (1990).
Baillie, L. et al., "Characterization of the human immune response to the UK anthrax vaccine", FEMS Immunology and Medical Microbiology, vol. 42, pp. 267-270, (2004).
Baillie, L. "The development of new vaccines against bacillus anthracis" Journal of Applied Microbiology, vol. 91, pp. 609-613, (2001).
Batra, S. et al., "Trp 346 and Leu 352 residues in protective antigen are required for the expression of anthrax lethal toxin activity", Biochemical and Biophysical Research Communications, vol. 281, pp. 186-192, (2001).
Better, M. et al. "*Escherichia coli* secretion of an active chimeric antibody fragment", Science, vol. 240, pp. 1041-1043, (1988).

(Continued)

*Primary Examiner* — Brian J Gangle
(74) *Attorney, Agent, or Firm* — Evan Law Group LLC

(57) ABSTRACT

A polynucleotide sequence is provided comprising a nucleic acid sequence encoding recombinant Protective Antigen (rPA).
Also provided are expression vectors and host cells comprising the polynucleotide sequence of the invention, and methods for producing rPA.

35 Claims, 23 Drawing Sheets

OTHER PUBLICATIONS

Bhatnagar, R. et al., "Anthrax Toxin", Critical Reviews in Microbiology, vol. 27, No. 3, pp. 167-200, (2001).

Bolivar, F. et al., "Construction and characterization of new cloning vehicles, a multipurpose cloning system", Gene, vol. 2, pp. 95-113, (1977).

Brehm, J.K. et al., "Molecular cloning and nucleotide sequence determination of the bacillus stearothermophilus NCA 1503 superoxide dismutase gene and its overexpression in *Escherichia coli*", Applied Microbiology and Biotechnology, vol. 36, pp. 358-363, (1991).

Brosius, J. et al., "Gene organization and primary structure of a ribosomal RNA operon from *Escherichia coli*", Journal of Molecular Biology, vol. 148, pp. 107-127, (1981).

Chambers, S.P. et al., "The pMTL nic⁻ cloning vectors. I. Improved pUC polylinker regions to facilitate the use of sonicated DNA for nucleotide sequencing", Gene, vol. 68, issue 1, pp. 139-149, (1988).

Chambers, S.P. et al., "Physical characterisation and over-expression of the bacillus caldotenax superoxide dismutase gene", FEMS Microbiology Letters, vol. 91, pp. 277-284, (1992).

Chen, Z. et al., "Efficient neutralization of anthrax toxin by chimpanzee monoclonal antibodies against protective antigen", The Journal of Infectious Diseases, vol. 193, pp. 625-633, (2006).

Denefle, P. et al., "Heterologous protein export in *Escherichia coli*: influence of bacterial signal peptides on the export of human interleukin 1β" Gene, vol. 85, pp. 499-510, (1989).

Fujimoto, K. et al., "Expression and secretion of human epidermal growth factor by *Escherichia coli* using enterotoxin signal sequences", Journal of Biotechnology, vol. 8, pp. 77-86, (1988).

Ghrayeb J. et al., "Secretion cloning vectors in *Escherichia coli*", The EMBO Journal, vol. 3, No. 10, pp. 2437-2442, (1984).

Gray, G.L. et al., "Periplasmic production of correctly processed juman growth hormone in *Escherichia coli*: natural and bacterial signal sequences are interchangeable", Gene, vol. 39, pp. 247-254, (1985).

Hoffman, C.S. et al., "Fusions of secreted proteins to alkaline phosphatise: an approach for studying protein secretion", Proceedings of the National Academy of Science, vol. 82, pp. 5107-5111, (1985).

Johnson, D.L. et al., "Refolding, purification, and characterization of human erythropoietin binding protein produced in *Escherichia coli*", Protein Expression and Purification, vol. 7, pp. 104-113, (1996).

Kadonaga, J.T. et al., "The role of the β-Lactamase signal sequence in the secretion of proteins by *Escherichia coli*", The Journal of Biological Chemistry, vol. 259, No. 4, pp. 2149-2154, (1984).

Kanehisa, M., "Use of statistical criteria for screening potential homologies in nucleic acid sequences" Nucleic Acids Research, vol. 12, No. 1, pp. 203-213, (1984).

Laffly, E. et al., "Selection of a macaque fab with framework regions like those in humans, high affinity, and ability to neutralize the protective antigen (PA) of bacillus anthracis by binding to the segment of PA between residues 686 and 694", Antimicrobial Agents and Chemotherapy, vol. 49, No. 8, pp. 3414-3420, (2005).

Laughlin, E.M. et al., "Antigen-specific CD4⁺T cells recognize epitopes of protective antigen following vaccination with an anthrax vaccine", Infection and Immunity, vol. 75, No. 4, pp. 1852-1860, (2007).

Le Calvez, H. et al., "Increased efficiency of alkaline phosphatise production levels in *Escherichia coli* using a degenerate PelB signal sequence", Gene, vol. 170, pp. 51-55, (1996).

Lei, S-P. et al., "Characterization of the erwinia carotovora pelB gene and its product pectate lyase", Journal of Bacteriology, vol. 169, No. 9, pp. 4379-4383, (1987).

Little, S.F. et al., "Comparative efficacy of bacillus anthracis live spore vaccine and protective antigen vaccine against anthrax in the Guinea pig", Infection and Immunity, vol. 52, No. 2, pp. 509-512, (1986).

MacIntyre, S. et al., "The role of the mature part of secretory proteins in translocation across the plasma membrane and in regulation of their synthesis in *Escherichia coli*", Biochimie, vol. 72, pp. 157-167, (1990).

Makrides, S.C. "Strategies for achieving high-level expression of genes in *Escherichia coli*", Microbiological Reviews, vol. 60, No. 3, pp. 512-538, (1996).

Michael, N.P. et al., "Physical characterisation of the *Escherichia coli* B gene encoding nitroreductase and its over-expression in *Escherichia coli* K12", FEMS Microbiology Letters, vol. 124, pp. 195-202, (1994).

Miller, C.A. et al., "Nucleotide sequence of the partition locus of *Escherichia coli* plasmid pSC101" Gene, vol. 24, pp. 309-315, (1983).

Minton, N.P. et al., "Copy number and mobilization properties of pUC plasmids", Focus, vol. 10, No. 3, p. 56, (1988).

Morioka-Fujimoto, K. et al., "Modified enterotoxin signal sequences increase secretion level of the recombinant human epidermal growth factor in *Escherichia coli*", The Journal of Biological Chemistry, vol. 266, No. 3, pp. 1728-1732, (1991).

Needleman, S.B. et al., "A general method applicable to the search for similarities in the amino acid sequence of two proteins", Journal of Molecular Biology, vol. 48, pp. 443-453, (1970).

Oka, T. et al., "Synthesis and secretion of human epidermal growth factor by *Escherichia coli*", Proceedings of the National Academy of Science, vol. 82, pp. 7212-7216, (1985).

Pearson, W.R. et al., "Improved tools for biological sequence comparison" Proceedings of the National Academy of Science, vol. 85, pp. 2444-2448, (1988).

Price, B.M. et al., "Protection against anthrax lethal toxin challenge by genetic immunization with a plasmid encoding the lethal factor protein", Infection and Immunity, vol. 69, No. 7, pp. 4509-4515, (2001).

Proudfoot, A.E.I. et al., "Extension of recombinant human RANTES by the retention of the initiating methionine produces a potent antagonist", The Journal of Biological Chemistry, vol. 271, No. 5, pp. 2599-2603, (1996).

Schein, C.H. et al., "Secretion of mammalian ribonucleases from *Escherichia coli* using the signal sequence of murine spleen ribonuclease", The Biochemical Journal, vol. 283, pp. 137-144, (1992).

Smith, T.F. et al., "Comparison of Biosequences", Advances in Applied Mathematics, vol. 2, pp. 482-489, (1981).

Sterne, M. "The use of anthrax vaccines prepared from avirulent (uncapsulated) variants of bacillus anthracis", Onderstepoort Journal of Veterinary Science and Animal Industry, vol. 13, No. 2, pp. 307-312, (1939).

Villa-Komaroff, L. et al., "A bacterial clone synthesizing proinsulin", Proceedings of the National Academy of Science, vol. 75, No. 8, pp. 3727-3731, (1978).

Vodkin, M.H. et al., "Cloning of the protective antigen gene of bacillus anthracis", Cell, vol. 34, pp. 693-697, (1983).

Watson, M.E.E. "Compilation of published signal sequences", Nucleic Acids Research, vol. 12, No. 13, pp. 5145-5164, (1984).

Welkos, S.L., et al., "Sequence and analysis of the DNA encoding protective antigen of bacillus anthracis", Gene, vol. 69, No. 2, pp. 287-300, (1988).

Wetmur, J.G. et al., "Kinetics of renaturation of DNA", Journal of Molecular Biology, vol. 31, pp. 349-370, (1968).

Williamson, E.D. et al.,"Immunogenicity of recombinant protective antigen and efficacy against aerosol challenge with anthrax", Infection and Immunity, vol. 73, No. 9, pp. 5978-5987, (2005).

Federal Register, vol. 66, No. 4, Jan. 5, 2001.

U.S. Appl. No. 11/153,865, mailed Apr. 27, 2006, 6 pages.

U.S. Appl. No. 11/153,865, mailed Aug. 24, 2006, 20 pages.

U.S. Appl. No. 11/153,865, mailed Apr. 20, 2007, 17 pages.

U.S. Appl. No. 11/153,865, mailed Nov. 2, 2007, 8 pages.

AU 2005254774, mailed Feb. 25, 2010, 2 pages.

EP 05751997.7, mailed Nov. 9, 2007, 3 pages.

EP 05751997.7, mailed Dec. 8, 2008, 3 pages.

EP 05751997.7, mailed Nov. 4, 2010, 4 pages.

U.S. Appl. No. 12/042,150, mailed Jun. 6, 2011, 7 pages.

U.S. Appl. No. 12/042,150, mailed Mar. 11, 2011, 16 pages.

U.S. Appl. No. 12/042,150, mailed Oct. 14, 2010, 19 pages.

U.S. Appl. No. 12/042,150, mailed May 24, 2010, 5 pages.

U.S. Appl. No. 12/042,150, mailed Apr. 15, 2011, 3 pages.

U.S. Appl. No. 13/246,659, mailed Jun. 1, 2012, 2 pages.

U.S. Appl. No. 13/246,659, mailed Mar. 5, 2012, 11 pages.

U.S. Appl. No. 13/246,659, mailed Jun. 27, 2012, 9 pages.

KR 10-2007-7001092, mailed Nov. 20, 2012, 5 pages.

CA 2,570,508, mailed Feb. 28, 2012, 5 pages.

FIG 13(A1)

```
                           10         20         30         40         50         60         70
DVC.Synthetic.rP   ATGGAAGTTAAACAGGAGAAACCGTTTGTTGAATGATGAATCTAGTTCTCAGGGGTTGCTGGGCTACT  70
AP.PA.wt.Sequenc   ATGGAAGTTAAACAGGAGAAACCGTCTGCTGAACGAAAGCGAATCTAGCTCTCAGGGCCTGCTGGGCTACT  70

80         90        100        110        120        130        140
DVC.Synthetic.rP   ATTTTAGTGATTTGAATTTTCAGGCACCGATGGTTGTTACCTCTTGTACTACCGGGGATTTGTGTATTCC  140
AP.PA.wt.Sequenc   ATTTTGAGTTGATTTGAATTTTCAAGCACCATGGTTACCTGTTGTTGACCTCTAGCACGACCGGCGATCTGAGCATTCC  140

150        160        170        180        190        200        210
DVC.Synthetic.rP   TAGTTGTGTGAGTTGGAGAATATTCCGTGGGAGAACCAGTATTTTCAGTCTGCTATTTTGGTCGGCTTTATC  210
AP.PA.wt.Sequenc   TAGTTCTGTGAGTTAGAAAATATTCCATGGGAGAACCAGTACTTTCAGTCTGCTGATTTGGAGCGGCTTCATC  210
```

FIG 13(A2)

```
                     AAAGTTAAGAAGAGTGATGAGTATACCTTTGCTACTTCTGCTGATAATCATGTGACCATGTGGTGGATG
DVC.Synthetic.rP    AAAGTGAAGAAAAAGCGATGAGTATACCTTTGCGACGTCTGCGGATAACCATGTGACCATGTGGTGGACG 280
AP.PA.wt.Sequenc    AAAGTTAAGAAGAGTGATGAATATACATTTGCTACTTCCGCTGATAATCATGTAACAATGTGGTAGATG 280
                        220       230       240       250       260       270       280

ATCAGGAAGTTGATTAATAAAGCTTGTAATTGTAACAAGATTCGCTTGGAGAAGGGTGCTTGTATCAGAT
DVC.Synthetic.rP    ATCAGGAAGTGATCAACAAAGCGAGCAACAGCCAACAAGATTCGCCTGGAGAAGGTCGCCTGTATCAGAT 350
AP.PA.wt.Sequenc    ACCAAGAAGTGATTAATAAAGCTTCTAATTCTAACAAAATCAGATTAGAAAATCAAAATTATATCAAAT 350
                        290       300       310       320       330       340       350

CAAGATTCAGTATCAGCGCCGAGAATCCTACTGAGAAAAGGCTTGAGATTTCAAGTTGTACTGGACCGATTGT
DVC.Synthetic.rP    CAAGATTCAGTATCAGCGCCGAGAATCCGACCGGCGAGAAACCCTGGATTTCAAACTGTACTGGACCCGATAGC 420
AP.PA.wt.Sequenc    AAAAATTCAATATCAACGAGAAAAATCCTACTGAAAAAGGATTGGATTTCAAGTTGTACTGGACCGATTCT 420
                        360       370       380       390       400       410       420
```

FIG 13(B1)

```
                                     ATTCATGAGAAGAAAGGCTTGACCAAGTATAAATGTCTTCCTGAGAAGTGGAGCACGGCTTGTGATCCGT
                                         |         |         |         |         |         |         |
                                        640       650       660       670       680       690       700
DVC.Synthetic.rP. ATTCATGAGAAGAAAGGCCTGACCAAGTACAAAAGCAGCCCGGAGAAGTGGAGCACCGGAGCGATCCGT 700
AP.PA.wt.Sequenc  ATTCATGAAAAAGAAAGGATTAACCAAATATAAATCATCTCCTGAAAAAATGGAGCACGGCTTCTGATCCGT 700

ATAGTGATTTGAGAAGGTTACCGGCCGGATTGATAAGAATGTGTGCCCGGAGGGCGTCACCCCCTTGT
                                         |         |         |         |         |         |         |
                                        710       720       730       740       750       760       770
DVC.Synthetic.rP. ATAGCGACTTTGAGAAAGTGACCGGCCGCCATTGATGAAGAACGTGAGCCCGGAAGCGCGTCACCACTGGT 770
AP.PA.wt.Sequenc  ACAGTGATTTCGAAAAAGGTTACAGGACGGATTGATAAGAATGTATCACCAGAGGCAAGAGACACCCCTTGT 770

TGCAGCTTATCCGATTGTGCATGTTGCATGTTGACATGGAGAACATCATTCTGAGCAAGAACGAAGATCAGAGCACC
                                         |         |         |         |         |         |         |
                                        780       790       800       810       820       830       840
DVC.Synthetic.rP. TGCAGCCGTATCCGATTGTGCATGTTGCATGTTGACATGGAGAACATCATTCTGAGCAAGAACGAAGATCAGAGCACC 840
AP.PA.wt.Sequenc  GGCAGCTTATCCGATTGTACATGTAGATATGGAGAATATTATTCTCTCAAAAAATGAGGATCAATCCACA 840
```

FIG 13(B2)

```
                   CAGAATACTGATAGTCAGACGCGCACGATCAGTAAGAATACTTGTACGAGTCGTACCCATACTAGTGAAG
                      850       860       870       880       890       900       910
DVC.Synthetic.rP   CAGAACACGGATAGCCAGACCCGCACGATCAGCAAGAACACCAGCACGAGCCGTACCCATACCAGCGAAG  910
AP.PA.wt.Sequenc   CAGAATACTGATAGTCAAACGAGAACAATAAGTAAAAATACTTCTACAAGTAGGACACATACTAGTGAAG  910

TGCATGGCAATGCGAAGTCATGCGGTGGTTCTTTGATATTGGTGGGAGTGTGTGCGGGCTTTAGTAA
                      920       930       940       950       960       970       980
DVC.Synthetic.rP   TGCATGGCAATGCGGAAGTGCATGCGAGCTTCTTTGACATTGGTGCGAGCCGTGAGCGCGGGCTTCAGCAA  980
AP.PA.wt.Sequenc   TACATGGAAATGCAGAAGTGCATGCGTCGTTCGTTCTTTGATATTGGTGGGAGTGTATCTGCAGGATTTAGTAA  980

TTGGAATTGCAGTACGGTGGCGATTGATCATTGCCTGTGCTCGGCGGGGAACGTACTTGGGCTGAAACC
                      990      1000      1010      1020      1030      1040      1050
DVC.Synthetic.rP   CAGCAACAGCAGCACCGTGGCGATTGATCATAGCCTGGCGGCCGAACGTACCTGGGCCGGAAACC  1050
AP.PA.wt.Sequenc   TTCGAATTCAAGTACGGTCGCAATTGATCATTCACTACTTCTCTAGCAGGGAAAGAACTTGGGCTGAAACA  1050
```

FIG 13(B3)

```
DVC.Synthetic.rP ATGGGTTTGAATACGGCTGATACGGCACGTTTGAATGCCATTACTCGCTATGTGAATACTGGTACGGCTC
AP.PA.wt.Sequenc ATGGGCCCTGAACACGGCGGATACGGCACGTCTGAATGCGTATGTGAACACTGGTACGCGC 1120
                 1060      1070      1080      1090      1100      1110      1120

DVC.Synthetic.rP CAATCTATAACGTTTTGCCGACGACTTGGTTGTGTTGGG

FIG. 13(C1)

```
                      1270       1280       1290       1300       1310       1320       1330
DVC.Synthetic.rP GCACTGAATGCGCAGGATGACTTCAGCAGACACCCCGATCACCATGAACTACAATCAGTTTCTGGAGCTGG 1330
AP.PA.wt.Sequenc GCATTAAATGCACAGACGATTCAGTTCTACTCCAATTACAATGAATTACAATCAATTCTTGAGTTAG 1330

1340       1350       1360       1370       1380       1390       1400
DVC.Synthetic.rP AGAAGACGAAACAATTGCGCTTGGATACGGATCAGGTGTATGGAATATTGCGACCTACAACTTTGAGAA 1400
AP.PA.wt.Sequenc AAAAAACGAAACAATTAAGATTAGATACGGATCAAGTATATGGAATATAGCAACATACAATTTTGAAAA 1400

1410       1420       1430       1440       1450       1460       1470
DVC.Synthetic.rP TGGCCGCGTTCGGGTGATACCGGTTGAACTGGTGTTGCCGCAGATTCAGGAAACGACTGCG 1470
AP.PA.wt.Sequenc TGGAAGAGTGAGGGTGATACCGGTGAACTGAGTGAAGTGTTACCGCAAATTCAAGAAACAACTGCA 1470
```

FIG. 13(C2)

```
                  ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
                  CGTATCATTTTTAATGGCAAAGATTTGAATCTGGTGTGGAACGTCGGATCGCGGCGGTTAATCCTGTGATC
                      1480      1490      1500      1510      1520      1530      1540

DVC.Synthetic.rP  CGCATCATCTCTTCAACGGCAAAGATCTGAACCTGGTGTGGAACGTCGCGGCGCACTGAACCTGAACCTGATC  1540
AP.PA.wt.Sequenc  CGTATCATTTTTAATGGAAAAGATTTAAATCTGGTAGAAAAGGCGGATAGCGGCGGTTAATCCTAGTGATC  1540

▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
                  CATTGGAAACGACTAAACCGGATATGACCCTTGAAAGAAGCGCTTAAGATTGCATTTGGCTTTAACGAACC
                      1550      1560      1570      1580      1590      1600      1610

DVC.Synthetic.rP  CACTGGAAACGACCAAACCGGACATGACCCTGAAAGAAGCGCTGAAGATTGCATTTGGCTTCAACGAACC  1610
AP.PA.wt.Sequenc  CATTAGAAACGACTAAACCGGATATGACCCTTAAAATAGAAGCCCTTAAAATAGCATTTGATTAACGAACC  1610

▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
                  GAATGGCAACTTGCAGTATCAGGGCAAAGAGACATCACCGAGTTTGATTTTAATTTTGATCAACAGACCTCT
                      1620      1630      1640      1650      1660      1670      1680

DVC.Synthetic.rP  GAATGGCAACCTGCAGTATCAGGGCAAAGACATCACCGAGTTTGACTTCAACTTTGATCAACAGACCTCT  1680
AP.PA.wt.Sequenc  GAATGGAAACTTACAATATCAAGGGAAAGACATAACCGAATTTGATTTGATTTCGATCAACAAACATCT  1680
```

FIG. 13(C3)

```
DVC.Synthetic.rP  CAGAATATCAAGAATCAGTTGGGCGGAATTGAATGCGACTAACATCTATACTGTGTTGATAAGATCAAAC 1750
AP.PA.wt.Sequenc  CAGAACATCAAGAACCAGCTGCAGAACTGAATGCGACCAACATCTACACCGTGCTGACAAGATCAAAT 1750
                  1690      1700      1710      1720      1730      1740      1750

DVC.Synthetic.rP  TGAATGCAAAGATGAATATTTTGATTCGTGATAAACGTTTTCATTATGATCGTAATAACATTGCGGTTGG 1820
AP.PA.wt.Sequenc  TGAACGCAAAGATGAACATTCGATTCGTGACAAACGCTTCCACTATGATCGTAACAACATTGCGGTGGG 1820
                  1760      1770      1780      1790      1800      1810      1820

DVC.Synthetic.rP  TGCGGATGAGTGCGTTGTTAAGGAGGCTCATCGTGAAGTGATTAATTCTTGCACCGAGGGCTTGTTGTTG 1890
AP.PA.wt.Sequenc  GGCGGATGAGTCAGTAGTTAAGGAGGCTCATAGAGAAGTAATTAATTCGTCAACAGAGGGATTATTGTTA 1890
                  1830      1840      1850      1860      1870      1880      1890

                        SEQUENCE LISTING

<160> NUMBER OF SEQ ID NOS: 111

<210> SEQ ID NO 1
<211> LENGTH: 2208
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: modified rPA gene sequence

<400> SEQUENCE: 1
gaagtgaaac aggagaaccg tctgctgaac gaaagcgaat ctagctctca gggcctgctg      60
ggctactatt tcagcgatct gaactttcag gcaccgatgg ttgtgacctc tagcacgacc     120
ggcgatctga gcattccgag cagcgaactg gagaacattc cgagcgagaa ccagtacttt     180
cagtctgcga tttggagcgg cttcatcaaa gtgaagaaaa gcgatgagta tacctttgcg     240
acgtctgcgg ataaccatgt gaccatgtgg gtggacgatc aggaagtgat caacaaagcg     300
agcaacagca caaagattcg cctggagaag ggtcgcctgt atcagatcaa gattcagtat     360
cagcgcgaga tccgaccga gaaaggcctg gatttcaaac tgtactggac cgatagccag     420
aacaagaaag aagtgattag ctctgataac ctgcaactgc cggaactgaa acagaagagc     480
agcaacagcc gcaagaaacg cagcacctct gcaggcccga ccgttccaga tcgcgacaac     540
gatggcattc cggacagcct ggaagtggaa ggttataccg ttgatgtgaa gaacaaacgc     600 accttttctga gcccgtggat tagcaacatt catgagaaga aggcctgac caagtacaaa     660 agcagcccgg agaagtggag caccgcgagc gatccgtata gcgactttga gaaagtgacc     720
ggccgcattg ataagaacgt gagcccggaa gcgcgtcacc cactggttgc agcgtatccg     780
attgtgcatg ttgacatgga aacatcatt ctgagcaaga acgaagatca gagcacccag     840
aacacggata gccagacccg cacgatcagc aagaacacca gcacgagccg tacccatacc     900
agcgaagtgc atggcaatgc ggaagtgcat gcgagcttct ttgacattgg tggcagcgtg     960
agcgcgggct tcagcaacag caacagcagc accgtggcga ttgatcatag cctgagcctg    1020
gcgggcgaac gtacctgggc ggaaaccatg ggcctgaaca cggcggatac ggcacgtctg    1080
aatgcgaaca ttcgctatgt gaacaccggt accgcgccaa tctataacgt tctgccgacc    1140
acgagcctgg tgctgggcaa gaatcagacc ctggcgacca tcaaagcgaa agagaaccag    1200
ctgtctcaga ttctggcacc gaacaactac atccgagca gaaacctggc accgattgca    1260
ctgaatgcgc aggatgactt cagcagcacc ccgatcacca tgaactacaa tcagtttctg    1320
gagctggaga gaccaaaca actgcgcctg gataccgatc aggtgtatgg caacattgcg    1380
acctacaact tgagaacgg ccgcgttcgc gtggataccg gtagcaactg gtctgaagtg    1440
ctgccgcaga ttcaggaaac gaccgcgcgc atcatcttca acggcaaaga tctgaacctg    1500
gtggaacgtc gcatcgcggc agtgaaccca tctgatccac tggaaacgac caaaccggac    1560
atgaccctga aagaagcgct gaagattgca tttggcttca acgaaccgaa tggcaacctg    1620
cagtatcagg gcaaagacat caccgagttt gacttcaact ttgatcaaca gacctctcag    1680
aacatcaaga accagctggc agaactgaat gcgaccaaca tctacaccgt gctggacaag    1740
```

| | |
|---|---:|
| atcaaactga acgcaaagat gaacattctg attcgtgaca aacgcttcca ctatgatcgt | 1800 |
| aacaacattg cggtgggtgc agatgaaagc gttgtgaaag aagcgcatcg tgaagtgatc | 1860 |
| aactctagca ccgaaggcct gctgctgaac attgacaaag acatccgtaa gattctgagc | 1920 |
| ggctacattg tggagattga agataccgaa ggtctgaaag aagtgatcaa cgatcgctat | 1980 |
| gacatgctga acatctctag cctgcgccag gatggcaaga ccttcattga cttcaagaag | 2040 |
| tacaacgaca aactgccgct gtacatcagc aatccgaact acaaagtgaa cgtgtatgcg | 2100 |
| gtgaccaaag agaacaccat cattaaccca agcgagaatg gcgataccag caccaacggc | 2160 |
| atcaagaaga ttctgatctt cagcaagaaa ggctatgaga ttggctaa | 2208 |

<210> SEQ ID NO 2
<211> LENGTH: 2208
<212> TYPE: DNA
<213> ORGANISM: Bacillusanthracis

<400> SEQUENCE: 2

| | |
|---|---:|
| gaagttaaac aggagaaccg gttattaaat gaatcagaat caagttccca ggggttacta | 60 |
| ggatactatt ttagtgattt gaattttcaa gcacccatgg tggttacctc ttctactaca | 120 |
| ggggatttat ctattcctag ttctgagtta gaaaatattc catcggaaaa ccaatatttt | 180 |
| caatctgcta tttggtcagg atttatcaaa gttaagaaga gtgatgaata cattttgct | 240 |
| acttccgctg ataatcatgt aacaatgtgg gtagatgacc aagaagtgat taataaagct | 300 |
| tctaattcta acaaaatcag attagaaaaa ggaagattat atcaaataaa aattcaatat | 360 |
| caacgagaaa atcctactga aaaggattg gatttcaagt tgtactggac cgattctcaa | 420 |
| aataaaaaag aagtgatttc tagtgataac ttacaattgc cagaattaaa acaaaaatct | 480 |
| tcgaactcaa gaaaaaagcg aagtacaagt gctggaccta cggttccaga ccgtgacaat | 540 |
| gatggaatcc ctgattcatt agaggtagaa ggatatacgg ttgatgtcaa aaataaaaga | 600 |
| acttttcttt caccatggat ttctaatatt catgaaaaga aaggattaac caaatataaa | 660 |
| tcatctcctg aaaaatggag cacggcttct gatccgtaca gtgatttcga aaaggttaca | 720 |
| ggacggattg ataagaatgt atcaccagag gcaagacacc cccttgtggc agcttatccg | 780 |
| attgtacatg tagatatgga gaatattatt ctctcaaaaa atgaggatca atccacacag | 840 |
| aatactgata gtcaaacgag aacaataagt aaaaatactt ctacaagtag gacacatact | 900 |
| agtgaagtac atggaaatgc agaagtgcat gcgtcgttct ttgatattgg tgggagtgta | 960 |
| tctgcaggat ttagtaattc gaattcagt acggtcgcaa ttgatcattc actatctcta | 1020 |
| gcaggggaaa gaacttgggc tgaaacaatg ggtttaaata ccgctgatac agcaagatta | 1080 |
| aatgccaata ttagatatgt aaatactggg acggctccaa tctacaacgt gttaccaacg | 1140 |
| acttcgttag tgttaggaaa aaatcaaaca ctcgcgacaa ttaaagctaa ggaaaaccaa | 1200 |
| ttaagtcaaa tacttgcacc taataattat tatccttcta aaaacttggc gccaatcgca | 1260 |
| ttaaatgcac aagacgattt cagttctact ccaattacaa tgaattacaa tcaatttctt | 1320 |
| gagttagaaa aaacgaaaca attaagatta gatacggatc aagtatatgg gaatatagca | 1380 |
| acatacaatt ttgaaaatgg aagagtgagg gtggatacag gctcgaactg gagtgaagtg | 1440 |
| ttaccgcaaa ttcaagaaac aactgcacgt atcatttta atggaaaaga tttaaatctg | 1500 |
| gtagaaaggc ggatagcggc ggttaatcct agtgatccat tagaaacgac taaaccggat | 1560 |
| atgacattaa aagaagccct taaaatagca tttggattta acgaaccgaa tggaaactta | 1620 |
| caatatcaag ggaaagacat aaccgaattt gatttaatt tcgatcaaca acatctcaa | 1680 |

```
aatatcaaga atcagttagc ggaattaaac gcaactaaca tatatactgt attagataaa    1740
atcaaattaa atgcaaaaat gaatatttta ataagagata aacgttttca ttatgataga    1800 ataacatag cagttggggc ggatgagtca gtagttaagg aggctcatag agaagtaatt     1860
aattcgtcaa cagagggatt attgttaaat attgataagg atataagaaa aatattatca    1920
ggttatattg tagaaattga agatactgaa gggcttaaag aagttataaa tgacagatat    1980
gatatgttga atatttctag tttacggcaa gatggaaaaa catttataga ttttaaaaaa    2040
tataatgata aattaccgtt atatataagt aatcccaatt ataaggtaaa tgtatatgct    2100
gttactaaag aaaacactat tattaatcct agtgagaatg gggatactag taccaacggg    2160
atcaagaaaa ttttaatctt ttctaaaaaa ggctatgaga taggataa                 2208

<210> SEQ ID NO 3
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: polynucleotide encoding cpg secretion sequence

<400> SEQUENCE: 3
catatgcgcc catccatcca ccgcacagcc atcgccgccg tgctggctac cgccttcgtg    60
gcgggcaccg ccctggcc                                                  78

<210> SEQ ID NO 4
<211> LENGTH: 3527
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: plasmid pMTL1015

<400> SEQUENCE: 4
cagtaagacg ggtaagcctg ttgatgatac cgctgcctta ctgggtgcat tagccagtct    60
gaatgacctg tcacgggata tcccgaagtg gtcagactgg aaaatcagag ggcaggaact    120
gctgaacagc aaaaagtcag atagcaccac atagcagacc cgccataaaa cgccctgaga    180
agcccgtgac gggcttttct tgtattatgg gtagtttcct tgcatgaatc cataaaaggc    240
gcccaatacg caaccgcct ctccccgcgc gttggagctt gcatgcaaat tctgcttaaa     300
agtaaattaa ttgttatcaa attgatgttg ttttggctga acggtagggt atattgtcac    360
cacctgttgg aatgttgcgc taatgcataa gcgactgtta attacgtaag ttaggttcct    420
gattacggca attaaatgca taaacgctaa acttgcgtga ctacacattc ttgagatgtg    480
gtcattgtaa acggcaattt gtggattaa ggtcgcggca gcgagcaac atatcttagt      540 ttatcaatat aataaggagt tcatatgac catgattacg aattcgagct cggtacccgg     600
ggatcctcta gagtcgacgt cacgcgtcca tggagatctc gaggcctgca ggcatgcaag    660
cttggcactg gccgtcgttt tacaacgtcg tgactgggaa aaccctggcg ttacccaact    720
taatcgcctt gcagcacatc cccctttcgc gagctggcgt aatagcgaag aggcccgcac    780
cgatcgccct tcccaacagt tgcgcagcct gaatggcgaa tggcgccgat ggtagtgtgg    840
ggtctcccca tgcgagagta gggaactgcc aggcatcaaa taaaacgaaa ggctcagtcg    900
aaagactggg cctttcgttt tatctgttgt ttgtcggtga acgctctcct gagtaggaca    960
```

```
aatccgccgg gagcggattt gaacgttgcg aagcaacggc ccggagggtg gcgggcagga    1020
cgcccgccat aaactgccag gcatcaaatt aagcagaagg ccatcctgac ggatggcctt    1080
tttgcgtttc tacaaactct tttgtttatt tttctaaata cattcaaata tgtatccgct    1140
catgagacaa taaccctgat aaatgcttca ataatgatct gttaattcga gctcgcccaa    1200
ttctcatgtt tgacagctta tcatcgaata gctttaatgc ggtagtttat cacagttaaa    1260
ttgctaacgc agtcaggcac cgtgtatgaa atctaacaat gcgctcatcg tcatcctcgg    1320
caccgtcacc ctggatgctg taggcatagg cttggttatg ccggtactgc cgggcctctt    1380
gcgggacatc gtccattccg acagcatcgc cagtcactat ggcgtgctgc tagcgctata    1440
tgcgttgatg caatttctat gcgcacccgt tctcggagca ctgtccgacc gctttggccg    1500
ccgcccagtc ctgctcgctt cgctacttgg agccactatc gactacgcga tcatggcgac    1560
cacacccgtc ctgtggattc tctacgccgg acgcatcgtg gccggcatca ccggcgccac    1620
aggtgcggtt gctggcgcct atatcgccga catcaccgat ggggaagatc gggctcgcca    1680
cttcgggctc atgagcgctt gtttcggcgt gggtatggtg gcaggccccg tggccggggg    1740
actgttgggc gccatctcct tgcacgcacc attccttgcg gcggcggtgc tcaacggcct    1800
caacctacta ctgggctgct tcctaatgca ggagtcgcat aagggagagc gtcgtccgat    1860
gcccttgaga gccttcaacc cagtcagctc cttccggtgg gcgcggggca tgactatcgt    1920
cgccgcactt atgactgtct tctttatcat gcaactcgta ggacaggtgc cggcagcgct    1980
ctgggtcatt ttcggcgagg accgctttcg ctggagcgcg acgatgatcg gcctgtcgct    2040
tgcggtattc ggaatcttgc acgccctcgc tcaagccttc gtcactggtc ccgccaccaa    2100
acgtttcggc gagaagcagg ccattatcgc cggcatggcg gccgacgcgc tgggctacgt    2160
cttgctggcg ttcgcgacgc gaggctggat ggccttcccc attatgattc ttctcgcttc    2220
cggcggcatc gggatgcccg cgttgcaggc catgctgtcc aggcaggtag atgacgacca    2280
tcagggacag cttcaaggat cgctcgcggc tcttaccagc ctaacttcga tcattggacc    2340
gctgatcgtc acggcgattt atgccgcctc ggcgagcaca tggaacgggt tggcatggat    2400
tgtaggcgcc gccctatacc ttgtctgcct ccccgcgttg cgtcgcggtg catggagccg    2460
ggccacctcg acctgaatgg aagccggcgg cacctcgcta acggattcac cactccaaga    2520
attggagcca atcaattctt gcggagaact gtgaatgcgc aaaccaaccc ttggcagaac    2580
atatccatcg cgtccgccat tccagcagc cgcacgcggc gcatctcggg gggatcaact    2640
gatcaaaagg atctaggtga agatcctttt tgataatctc atgaccaaaa tcccttaacg    2700
tgagttttcg ttccactgag cgtcagaccc cgtagaaaag atcaaaggat cttcttgaga    2760
tccttttttt ctgcgcgtaa tctgctgctt gcaaacaaaa aaaccaccgc taccagcggt    2820
ggtttgtttg ccggatcaag agctaccaac tcttttccg aaggtaactg gcttcagcag    2880
agcgcagata ccaaatactg ttcttctagt gtagccgtag ttaggccacc acttcaagaa    2940
ctctgtagca ccgcctacat acctcgctct gctaatcctg ttaccagtgg ctgctgccag    3000
tggcgataag tcgtgtctta ccgggttgga ctcaagacga tagttaccgg ataaggcgca    3060
gcggtcgggc tgaacggggg gttcgtgcac acagcccagc ttggagcgaa cgacctacac    3120
cgaactgaga tacctacagc gtgagctatg agaaagcgcc acgcttcccg aagggagaaa    3180
ggcggacagg tatccggtaa gcggcagggt cggaacagga gagcgcacga gggagcttcc    3240
agggggaaac gcctggtatc tttatagtcc tgtcgggttt cgccacctct gacttgagcg    3300
tcgatttttg tgatgctcgt caggggggcg gagcctatgg aaaaacgcca gcaacgcggc    3360
```

```
cttttacgg ttcctggcct ttttgctggcc ttttgctcac atgttctttc ctgcgttatc    3420
ccctgattct gtggataacc gtattaccgc ctttgagtga gctgataccg ctcgccgcag    3480
ccgaacgacc gagcgcagcg agtcagtgag cgaggaagcg gaagagc                  3527
```

<210> SEQ ID NO 5
<211> LENGTH: 735
<212> TYPE: PRT
<213> ORGANISM: Bacillusanthracis

<400> SEQUENCE: 5

```
Glu Val Lys Gln Glu Asn Arg Leu Leu Asn Glu Ser Glu Ser Ser
 1               5                  10                  15

Gln Gly Leu Leu Gly Tyr Tyr Phe Ser Asp Leu Asn Phe Gln Ala Pro
             20                  25                  30

Met Val Thr Ser Ser Thr Thr Gly Asp Leu Ser Ile Pro Ser Ser
         35                  40                  45

Glu Leu Glu Asn Ile Pro Ser Glu Asn Gln Tyr Phe Gln Ser Ala Ile
 50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350
```

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 6
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide -continued <220> FEATURE:
<223> OTHER INFORMATION: rPA protein sequence with N-terminal methionine

<400> SEQUENCE: 6

Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
            20                  25                  30

Pro Met Val Val Thr Ser Ser Thr Gly Asp Leu Ser Ile Pro Ser
        35                  40                  45

Ser Glu Leu Glu Asn Ile Pro Ser Glu Asn Gln Tyr Phe Gln Ser Ala
    50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
        115                 120                 125

Lys Gly Leu Asp Phe Lys Leu Tyr Trp Thr Asp Ser Gln Asn Lys Lys
130                 135                 140

Glu Val Ile Ser Ser Asp Asn Leu Gln Leu Pro Glu Leu Lys Gln Lys
145                 150                 155                 160

Ser Ser Asn Ser Arg Lys Lys Arg Ser Thr Ser Ala Gly Pro Thr Val
                165                 170                 175

Pro Asp Arg Asp Asn Asp Gly Ile Pro Asp Ser Leu Glu Val Glu Gly
            180                 185                 190

Tyr Thr Val Asp Val Lys Asn Lys Arg Thr Phe Leu Ser Pro Trp Ile
        195                 200                 205

Ser Asn Ile His Glu Lys Lys Gly Leu Thr Lys Tyr Lys Ser Ser Pro
210                 215                 220

Glu Lys Trp Ser Thr Ala Ser Asp Pro Tyr Ser Asp Phe Glu Lys Val
225                 230                 235                 240

Thr Gly Arg Ile Asp Lys Asn Val Ser Pro Glu Ala Arg His Pro Leu
                245                 250                 255

Val Ala Ala Tyr Pro Ile Val His Val Asp Met Glu Asn Ile Ile Leu
            260                 265                 270

Ser Lys Asn Glu Asp Gln Ser Thr Gln Asn Thr Asp Ser Gln Thr Arg
        275                 280                 285

Thr Ile Ser Lys Asn Thr Ser Thr Ser Arg Thr His Thr Ser Glu Val
290                 295                 300

His Gly Asn Ala Glu Val His Ala Ser Phe Phe Asp Ile Gly Gly Ser
305                 310                 315                 320

Val Ser Ala Gly Phe Ser Asn Ser Asn Ser Ser Thr Val Ala Ile Asp
                325                 330                 335

His Ser Leu Ser Leu Ala Gly Glu Arg Thr Trp Ala Glu Thr Met Gly
            340                 345                 350

Leu Asn Thr Ala Asp Thr Ala Arg Leu Asn Ala Asn Ile Arg Tyr Val
        355                 360                 365

Asn Thr Gly Thr Ala Pro Ile Tyr Asn Val Leu Pro Thr Thr Ser Leu
370                 375                 380

Val Leu Gly Lys Asn Gln Thr Leu Ala Thr Ile Lys Ala Lys Glu Asn
385                 390                 395                 400

```
Gln Leu Ser Gln Ile Leu Ala Pro Asn Asn Tyr Tyr Pro Ser Lys Asn
                405                 410                 415
Leu Ala Pro Ile Ala Leu Asn Ala Gln Asp Asp Phe Ser Ser Thr Pro
            420                 425                 430
Ile Thr Met Asn Tyr Asn Gln Phe Leu Glu Leu Glu Lys Thr Lys Gln
        435                 440                 445
Leu Arg Leu Asp Thr Asp Gln Val Tyr Gly Asn Ile Ala Thr Tyr Asn
    450                 455                 460
Phe Glu Asn Gly Arg Val Arg Val Asp Thr Gly Ser Asn Trp Ser Glu
465                 470                 475                 480
Val Leu Pro Gln Ile Gln Glu Thr Thr Ala Arg Ile Ile Phe Asn Gly
                485                 490                 495
Lys Asp Leu Asn Leu Val Glu Arg Arg Ile Ala Ala Val Asn Pro Ser
            500                 505                 510
Asp Pro Leu Glu Thr Thr Lys Pro Asp Met Thr Leu Lys Glu Ala Leu
        515                 520                 525
Lys Ile Ala Phe Gly Phe Asn Glu Pro Asn Gly Asn Leu Gln Tyr Gln
    530                 535                 540
Gly Lys Asp Ile Thr Glu Phe Asp Phe Asn Phe Asp Gln Gln Thr Ser
545                 550                 555                 560
Gln Asn Ile Lys Asn Gln Leu Ala Glu Leu Asn Ala Thr Asn Ile Tyr
                565                 570                 575
Thr Val Leu Asp Lys Ile Lys Leu Asn Ala Lys Met Asn Ile Leu Ile
            580                 585                 590
Arg Asp Lys Arg Phe His Tyr Asp Arg Asn Asn Ile Ala Val Gly Ala
        595                 600                 605
Asp Glu Ser Val Val Lys Glu Ala His Arg Glu Val Ile Asn Ser Ser
    610                 615                 620
Thr Glu Gly Leu Leu Leu Asn Ile Asp Lys Asp Ile Arg Lys Ile Leu
625                 630                 635                 640
Ser Gly Tyr Ile Val Glu Ile Glu Asp Thr Glu Gly Leu Lys Glu Val
                645                 650                 655
Ile Asn Asp Arg Tyr Asp Met Leu Asn Ile Ser Ser Leu Arg Gln Asp
            660                 665                 670
Gly Lys Thr Phe Ile Asp Phe Lys Lys Tyr Asn Asp Lys Leu Pro Leu
        675                 680                 685
Tyr Ile Ser Asn Pro Asn Tyr Lys Val Asn Val Tyr Ala Val Thr Lys
    690                 695                 700
Glu Asn Thr Ile Ile Asn Pro Ser Glu Asn Gly Asp Thr Ser Thr Asn
705                 710                 715                 720
Gly Ile Lys Lys Ile Leu Ile Phe Ser Lys Lys Gly Tyr Glu Ile Gly
                725                 730                 735

<210> SEQ ID NO 7
<211> LENGTH: 2211
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: modified rPA gene sequence with 5'
      methionine-encoding codon

<400> SEQUENCE: 7
atggaagtga acaggagaa ccgtctgctg aacgaaagcg aatctagctc tcagggcctg      60
ctgggctact atttcagcga tctgaacttt caggcaccga tggttgtgac ctctagcacg     120
```

```
accggcgatc tgagcattcc gagcagcgaa ctggagaaca ttccgagcga gaaccagtac    180
tttcagtctg cgatttggag cggcttcatc aaagtgaaga aaagcgatga gtatacctttt   240 gcgacgtctg cggataacca tgtgaccatg tgggtggacg atcaggaagt gatcaacaaa    300
gcgagcaaca gcaacaagat tcgcctggag aagggtcgcc tgtatcagat caagattcag    360
tatcagcgcg agaatccgac cgagaaaggc ctggatttca aactgtactg gaccgatagc    420
cagaacaaga aagaagtgat tagctctgat aacctgcaac tgccggaact gaaacagaag    480
agcagcaaca gccgcaagaa acgcagcacc tctgcaggcc cgaccgttcc agatcgcgac    540
aacgatggca ttccggacag cctggaagtg aaggttata ccgttgatgt gaagaacaaa    600
cgcacctttc tgagcccgtg gattagcaac attcatgaga gaaaggcct gaccaagtac    660 aaaagcagcc cggagaagtg gagcaccgcg agcgatccgt atagcgactt tgagaaagtg    720
accggccgca ttgataagaa cgtgagcccg gaagcgcgtc acccactggt tgcagcgtat    780
ccgattgtgc atgttgacat ggagaacatc attctgagca gaacgaaga tcagagcacc    840 cagaacacgg atagccagac cgcacgatc agcaagaaca ccagcacgag ccgtacccat    900
accagcgaag tgcatggcaa tgcggaagtg catgcgagct ctttgacat tggtggcagc    960 gtgagcgcgg gcttcagcaa cagcaacagc agcaccgtgg cgattgatca tagcctgagc   1020
ctggcgggcg aacgtacctg gcggaaaccc atgggcctga cacggcgga tacggcacgt   1080 ctgaatgcga acattcgcta tgtgaacacc ggtaccgcgc caatctataa cgttctgccg   1140
accacgagcc tggtgctggg caagaatcag accctggcga ccatcaaagc gaaagagaac   1200
cagctgtctc agattctggc accgaacaac tactatccga gcaagaacct ggcaccgatt   1260
gcactgaatg cgcaggatga cttcagcagc accccgatca ccatgaacta caatcagttt   1320
ctggagctgg agaagaccaa acaactgcgc ctggataccg atcaggtgta tggcaacatt   1380
gcgacctaca actttgagaa cggccgcgtt cgcgtggata ccggtagcaa ctggtctgaa   1440
gtgctgccgc agattcagga aacgaccgcg cgcatcatct tcaacggcaa agatctgaac   1500
ctggtggaac gtcgcatcgc ggcagtgaac ccatctgatc cactggaaac gaccaaaccg   1560
gacatgaccc tgaaagaagc gctgaagatt gcatttggct tcaacgaacc gaatggcaac   1620
ctgcagtatc agggcaaaga catcaccgag tttgacttca actttgatca acagacctct   1680
cagaacatca agaaccagct ggcagaactg aatgcgacca catctacac cgtgctggac   1740 aagatcaaac tgaacgcaaa gatgaacatt ctgattcgtg acaaacgctt ccactatgat   1800
cgtaacaaca ttgcggtggg tgcagatgaa agcgttgtga agaagcgca tcgtgaagtg   1860 atcaactcta gcaccgaagg cctgctgctg aacattgaca agacatccg taagattctg   1920 agcggctaca ttgtggagat tgaagatacc gaaggtctga agaagtgat caacgatcgc   1980 tatgacatgc tgaacatctc tagcctgcgc caggatggca agaccttcat tgacttcaag   2040
aagtacaacg acaaactgcc gctgtacatc agcaatccga actacaaagt gaacgtgtat   2100
gcggtgacca agagaacac catcattaac ccaagcgaga atggcgatac cagcaccaac   2160
ggcatcaaga agattctgat cttcagcaag aaaggctatg agattggcta a           2211
```

<210> SEQ ID NO 8
<211> LENGTH: 2211
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: Wild-type PA gene sequence plus 5' methionine-encoding codon

<400> SEQUENCE: 8

```
atggaagtta aacaggagaa ccggttatta aatgaatcag aatcaagttc ccaggggtta     60
ctaggatact attttagtga tttgaatttt caagcaccca tggtggttac ctcttctact    120
acaggggatt tatctattcc tagttctgag ttagaaaata ttccatcgga aaaccaatat    180
tttcaatctg ctatttggtc aggatttatc aaagttaaga agagtgatga atatacattt    240
gctacttccg ctgataatca tgtaacaatg tgggtagatg accaagaagt gattaataaa    300
gcttctaatt ctaacaaaat cagattagaa aaaggaagat tatatcaaat aaaaattcaa    360
tatcaacgag aaaatcctac tgaaaaagga ttggatttca agttgtactg gaccgattct    420
caaaataaaa aagaagtgat ttctagtgat aacttacaat tgccagaatt aaaacaaaaa    480
tcttcgaact caagaaaaaa gcgaagtaca agtgctggac ctacggttcc agaccgtgac    540
aatgatggaa tccctgattc attagaggta gaaggatata cggttgatgt caaaaataaa    600
agaacttttc tttcaccatg gatttctaat attcatgaaa agaaaggatt aaccaaatat    660
aaatcatctc ctgaaaaatg gagcacggct tctgatccgt acagtgattt cgaaaaggtt    720
acaggacgga ttgataagaa tgtatcacca gaggcaagac acccccttgt ggcagcttat    780
ccgattgtac atgtagatat ggagaatatt attctctcaa aaaatgagga tcaatccaca    840
cagaatactg atagtcaaac gagaacaata agtaaaaata cttctacaag taggacacat    900
actagtgaag tacatggaaa tgcagaagtg catgcgtcgt tctttgatat tggtgggagt    960
gtatctgcag gatttagtaa ttcgaattca agtacggtcg caattgatca ttcactatct   1020
ctagcagggg aaagaacttg ggctgaaaca atgggtttaa ataccgctga tacagcaaga   1080
ttaaatgcca atattagata tgtaaatact gggacggctc caatctacaa cgtgttacca   1140
acgacttcgt tagtgttagg aaaaaatcaa acactcgcga caattaaagc taaggaaaac   1200
caattaagtc aaatacttgc acctaataat tattatcctt ctaaaaactt ggcgccaatc   1260
gcattaaatg cacaagacga tttcagttct actccaatta caatgaatta caatcaattt   1320
cttgagttag aaaaaacgaa acaattaaga ttagatacgg atcaagtata tgggaatata   1380
gcaacataca attttgaaaa tggaagagtg agggtggata caggctcgaa ctggagtgaa   1440
gtgttaccgc aaattcaaga aacaactgca cgtatcattt ttaatggaaa agatttaaat   1500
ctggtagaaa ggcggatagc ggcggttaat cctagtgatc cattagaaac gactaaaccg   1560
gatatgacat taaaagaagc ccttaaaata gcatttggat ttaacgaacc gaatggaaac   1620
ttacaatatc aagggaaaga cataaccgaa tttgatttta atttcgatca acaaacatct   1680
caaaatatca agaatcagtt agcggaatta aacgcaacta acatatatac tgtattagat   1740
aaaatcaaat taaatgcaaa aatgaatatt ttaataagag ataaacgttt tcattatgat   1800
agaaataaca tagcagttgg ggcggatgag tcagtagtta aggaggctca tagagaagta   1860
attaattcgt caacagaggg attattgtta aatattgata aggatataag aaaaatatta   1920
tcaggttata ttgtagaaat tgaagatact gaagggctta aagaagttat aaatgacaga   1980
tatgatatgt tgaatatttc tagtttacgg caagatggaa aaacatttat agattttaaa   2040
aaatataatg ataaattacc gttatatata agtaatccca attataaggt aaatgtatat   2100
gctgttacta aagaaaacac tattattaat cctagtgaga atggggatac tagtaccaac   2160
gggatcaaga aaattttaat cttttctaaa aaaggctatg agataggata a            2211

<210> SEQ ID NO 9
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99% identity) of SEQ ID No 1

<400> SEQUENCE: 9

```
gaagtgaaac aggagaaccg tctgctgaac gaaagcgaat ctagctctca gggcctgctg      60
ggctactatt ttagcgatct gaactttcag gcaccgatgg ttgtgacctc tagcacgacc     120
ggcgacctga gcattccgag cagcgaactg gagaacattc cgagcgagaa ccagtacttt     180
cagtctgcga tttggagcgg cttcatcaaa gtgaagaaaa gcgatgagta ccctttgcg      240
acgtctgcgg ataaccatgt gaccatgtgg gtggacgatc aggaagtgat caacaaagcg     300
agcaacagca acaagattcg cctggagaag ggtcgcctgt atcagatcaa gattcagtat     360
cagcgcgaga tccgaccga gaaaggcctg gatttcaaac tgtactggac cgatagccag      420
aacaaaaaag aagtgattag ctctgataac ctgcaactgc cggaactgaa acagaagagc     480
agcaacagcc gcaagaaacg cagcacctct gcaggcccga ccgttccaga tcgcgacaac     540
gatggcattc cggacagcct ggaagtgaa ggttataccg ttgatgtgaa gaacaaacgt      600
acctttctga gcccgtggat tagcaacatt catgagaaga aaggcctgac caagtacaaa     660
agcagcccgg agaagtggag caccgcgagc gatccgtata gcgacttcga aaagtgacc      720
ggccgcattg ataagaacgt gagcccggaa gcgcgccacc cactggttgc agcgtatccg     780
attgtgcatg ttgacatgga aacatcatt ctgagcaaga acgaagacca gagcacccag      840
aacacggata gccagacccg cacgatcagc aagaacacca gcacgagccg cacccatacc     900
agcgaagtgc atggcaatgc ggaagtgcat gcgagcttct ttgacattgg tggcagcgtg     960
agcgcgggct cagcaacag caacagcagc accgtgcga ttgatcatag cctgagcctg     1020
gcgggcgaac gtacctgggc ggaaaccatg gcctgaaca cggcggatac ggcacgtctg     1080
aatgcgaaca ttcgctatgt gaacaccggt accgcgccaa tctataacgt gctgccgacc     1140
acgagcctgg tgctgggcaa gaatcagacc ctggcgacca tcaaagcgaa agagaaccag     1200
ctgtctcaga ttctggcacc gaacaactac tatccgagca gaacctggc accgattgca     1260
ctgaatgcgc aggatgactt cagcagcacc ccgatcacca tgaactacaa tcagtttctg     1320
gagctggaga gaccaaaca actgcgcctg gataccgatc aggtttatgg caacattgcg     1380
acctacaact ttgagaacgg ccgcgttcgc gtggataccg gtagcaactg gtctgaagtg     1440
ctgccgcaga ttcaggaaac gaccgcgcgt atcattttca cggcaaaga tctgaacctg     1500
gtggaacgtc gtatcgcggc agtgaaccca tctgatccac tggaaacgac caaaccggac     1560
atgacccctga agaagcact gaagattgca tttggcttca cgaaccgaa tggcaacctg     1620
cagtatcagg gcaaagacat caccgagttt gacttcaact ttgatcaaca gacctctcag     1680
aacatcaaga accagctggc agaactgaat gcgaccaaca tctacaccgt gctggacaag     1740
atcaaactga acgcgaagat gaacattctg attcgcgaca aacgcttcca ctatgatcgt     1800
aacaacatcg cggtgggtgc agatgaaagc gttgtgaagg aagcgcatcg tgaagtgatc     1860
aactctagca ccgaaggcct gctgctgaac attgataaag acatccgtaa gattctgagc     1920
ggctacattg tggagattga agacaccgaa ggtctgaaag aagtgatcaa cgatcgctat     1980
gatatgctga acatctctag cctgcgccag gatggcaaga ccttcattga tttcaagaag    2040
```

```
tacaacgaca aactgccgct gtacatcagc aatccgaact acaaagtgaa cgtgtatgcg    2100
gtgaccaaag agaacaccat cattaaccca agcgagaatg gcgataccag caccaacggc    2160
atcaagaaga ttctgatctt cagcaagaaa ggctatgaga ttggc                    2205
```

<210> SEQ ID NO 10
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (99% identity) of SEQ ID No 1

<400> SEQUENCE: 10

```
gaagtgaagc aggagaaccg tctgctgaac gaaagcgagt ctagctctca gggcctgctg      60
ggctactatt tcagcgatct gaactttcag gcaccgatgg ttgtgacctc tagcacgacc     120
ggcgatctga gcattccgag cagcgaactg agaacattc cgagcgagaa ccagtacttt      180
cagtctgcga tttggagcgg cttcatcaaa gtgaagaaaa gcgatgagta cctttgcg      240 acgtctgcga taaccatgt gaccatgtgg gtggacgatc aggaagtgat caacaaagca      300
agcaacagca caagattcg cctggagaag ggtcgcctgt atcagatcaa gattcagtat      360
cagcgcgaga tccgaccga aaaggcctg gatttcaaac tgtactggac cgatagccag      420
aacaagaaag aggtgattag ctctgataac ctgcaactgc cggaactgaa acagaagagc      480
agcaacagcc gcaagaaacg cagcacctct gcaggtccga ccgttccaga tcgcgacaac      540
gatggcattc cggacagcct ggaagtggaa ggctataccg ttgatgtgaa gaacaaacgc      600 accttctctga gcccgtggat tagcaacatt catgagaaga aaggcctgac caagtacaaa      660
agcagcccgg agaaatggag caccgcgagc gatccgtata gcgactttga aaggtgacc      720 ggccgcattg ataagaacgt gagcccggaa gcgcgtcacc cactggttgc agcgtatccg      780
attgtgcatg ttgacatgga aacatcatt ctgagcaaga acgaagatca gagcacccag      840
aacacggata gccagacccg cacgattagc aagaacacca gcacgagccg taccccatacc      900 agcgaagtgc atggcaatgc ggaagtgcat gcgagcttct ttgacattgg tggcagcgtg      960
agcgcgggct tcagcaacag caacagcagc accgtggcga ttgatcatag cctgagcctg     1020
gcgggcgaac gtacctgggc ggaaaccatg gcctgaaca cggcggatac ggcacgtctg     1080
aatgcgaaca tccgctatgt gaacaccggt accgcgccaa tctataacgt tctgccgacc     1140
acgagcctgg tgctgggcaa gaatcagacc ctggcgacca tcaaagcgaa agagaaccag     1200
ctgtctcaga ttctggcacc gaacaactac tatccgagca gaacctggc gccgattgca     1260 ctgaatgcgc aggatgactt cagcagcacc ccgatcacca tgaactacaa tcagtttctg     1320
gagctggaaa agaccaaaca actgcgcctg gataccgatc aggtgtatgg caacattgcg     1380
acctacaact tcgagaacgg ccgcgttcgc gtggataccg cagcaactg gtctgaagtg     1440 ctgccgcaga ttcaggaaac gaccgcgcgc atcatcttca cggcaaagc tctgaacctg     1500 gtggaacgtc gcatcgcggc agtgaaccca tctgatccac tggaaacgac caaaccggac     1560
atgaccctga agaagcgct gaaaattgca tttggcttca cgagccgaa tggcaacctg     1620 cagtatcagg gcaaagacat caccgagttt gacttcaact tgatcaaca gacctctcag     1680 aacatcaaga accagctggc agaactgaat gcgaccaaca tctacaccgt gctggacaag     1740
atcaaactga acgcaaagat gaacattctg attcgtgaca aacgctttca ctatgatcgt     1800
aacaacattg cggtgggtgc agatgaaagc gttgtgaaag aagcgcatcg tgaagtgatc     1860
```

```
aactctagca ccgaaggcct gctgctgaac attgacaaag acatccgtaa gattctgagc    1920
ggctacattg tggaaattga agataccgaa ggtctgaaag aagtgatcaa cgatcgctat    1980
gacatgctga acatctctag cctgcgccag gatggcaaga ccttcatcga cttcaagaag    2040
tacaacgaca aactgccgct gtacatcagc aatccgaact acaaagtgaa cgtgtatgcg    2100
gtgaccaaag agaacaccat cattaaccca agcgagaatg gcgataccag caccaacggc    2160
attaagaaga ttctgatctt cagcaagaaa ggttatgaga ttggc                    2205
```

<210> SEQ ID NO 11
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (99% identity) of SEQ ID NO. 1

<400> SEQUENCE: 11

```
gaagtgaaac aggagaaccg tctgctgaac gaaagcgaat ctagctctca gggcctgctg     60
ggctattatt tcagcgatct gaacttccag gcaccaatgg ttgtgacctc ttctacgacc    120
ggcgatctga gcattccgag cagcgaactg gagaacattc cgagcgagaa ccagtacttt    180
cagagcgcga tttggagcgg cttcatcaaa gtgaagaaaa gcgatgagta ccctttgcg     240 acgtctgcgg ataaccatgt gaccatgtgg gtggacgatc aggaagtgat caacaaagcg    300
agcaacagca acaagattcg cctggagaag ggtcgcctgt atcagatcaa gattcagtac    360
cagcgcgaga tccgaccga gaaaggcctg gatttcaaac tgtactggac cgatagccag    420
aacaagaaag aagtgattag ctctgataac ctgcaactgc cggaactgaa acagaagagc    480
agcaacagcc gcaagaaacg cagcacctct gcaggcccga ccgttccaga tcgcgacaac    540
gatggcattc cggacagcct ggaagtggaa ggttataccg tggatgtgaa gaacaaacgc    600
acctttctga gcccgtggat tagcaacatt catgagaaga aaggcctgac caagtacaaa    660
agcagcccgg agagtggag caccgcgagc gatccgtata gcgactttga gaaagtgacc    720
ggccgcattg ataagaacgt gagcccggaa gcgcgtcacc cactggttgc agcgtatccg    780
attgtgcatg ttgacatgga gaacatcatt ctgagcaaga cgaagatca gagcacccag    840 aacacggata gccagacccg cacgatcagc aagaacacca gcacgagccg taccccatacc   900 agcgaagtgc atggcaatgc ggaagtgcat gcaagcttct ttgacattgg tggcagcgtg    960
agcgcgggct tcagcaacag caacagcagc accgtggcga ttgatcatag cctgagcctg   1020
gcgggcgaac gtacctgggc ggaaaccatg gccctgaaca cggcggatac ggcacgtctg   1080
aatgcgaaca ttcgttatgt gaacaccggt accgcgccaa tctataacgt tctgccgacc   1140
acgagcctgg tgctgggcaa gaatcagacc ctggcgacca tcaaagcgaa agagaaccag   1200
ctgtctcaga ttctggcacc gaacaactac tatccgagca agaacctggc gccgattgca   1260
ctgaacgcgc aggatgactt cagcagcacc ccgatcacca tgaactacaa tcagtttctg   1320
gagctggaga agaccaaaca actgcgcctg gataccgatc aggtgtatgg caacattgcg   1380
acctacaact tgagaacgg ccgcgttcgc gtggataccg gtagcaactg gtctgaagtg   1440
ctgccgcaga ttcaggaaac gaccgcgcgc atcatcttca cggcaaaga tctgaatctg   1500 gtggaacgcc gcatcgcggc agtgaaccca tctgatccgc tggaaacgac caaaccggat   1560 atgacccctga aagaagcgct gaagattgca tttggcttca cgaaccgaa tggcaaccctg   1620
```

| | |
|---|---|
| cagtatcagg gcaaagacat caccgagttt gacttcaact ttgatcaaca gacctctcag | 1680 |
| aacatcaaga accagctggc agaactgaat gcgaccaaca tctacaccgt gctggacaag | 1740 |
| atcaaactga acgcaaagat gaacattctg attcgtgaca aacgctttca ctatgatcgt | 1800 |
| aacaacattg cggtgggtgc agacgaaagc gttgtgaaag aagcgcatcg tgaagtgatc | 1860 |
| aactctagca ccgaaggcct gctgctgaac attgacaaag acatccgtaa gattctgagc | 1920 |
| ggctacattg tggagattga agataccgaa ggtctgaaag aagttatcaa cgatcgctat | 1980 |
| gacatgctga acatctctag cctgcgccag gatggcaaga ccttcattga cttcaagaag | 2040 |
| tacaacgaca aactgccgct gtacatcagc aatccgaact acaaagtgaa cgtgtatgcg | 2100 |
| gtgaccaaag agaacaccat cattaaccca agcgagaatg gcgataccag caccaacggc | 2160 |
| atcaagaaga ttctgatctt cagcaagaaa ggctatgaga ttggc | 2205 |

<210> SEQ ID NO 12
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (98% identity) of SEQ ID No 1

<400> SEQUENCE: 12

| | |
|---|---|
| gaagtgaaac aggagaaccg tctgctgaac gaaagcgaat ctagctctca gggcctgctg | 60 |
| ggctactatt ttagcgatct gaactttcag gcaccgatgg ttgtgacctc tagcacgacc | 120 |
| ggcgacctga gcattccgag cagcgaactg gagaacattc cgagcgagaa ccagtacttt | 180 |
| cagtctgcga tttggagcgg cttcatcaaa gtgaagaaaa gcgatgagta tacctttgcg | 240 |
| acgtctgcgg ataaccatgt gaccatgtgg gtggacgatc aggaggtgat caacaaagcg | 300 |
| agcaacagca acaagattcg cctggagaag gtcgcctgt atcagatcaa gattcagtat | 360 |
| cagcgcgaga tccgaccga gaaaggcctg gatttcaaac tgtactggac cgatagccag | 420 |
| aacaaaaaag aagtgattag ctctgataac ctgcaactgc cggaactgaa acagaagagc | 480 |
| agcaacagcc gcaagaaacg cagcaccagc gcaggcccga ccgttccaga tcgcgacaac | 540 |
| gatggcattc cggacagcct ggaagtggaa ggttataccg ttgatgtgaa gaacaaacgt | 600 |
| accttttctga gcccgtggat tagcaacatt catgagaaga agggcctgac caagtacaaa | 660 |
| agcagcccgg agaagtggag caccgcgtct gatccgtata gcgacttcga aaagtgacc | 720 |
| ggccgcattg ataagaacgt gagcccggaa gcgcgccacc cactggttgc agcgtatccg | 780 |
| atcgtgcatg ttgacatgga aacatcatt ctgagcaaga acgaagacca gagcaccccag | 840 |
| aacacggata gccagacccg cacgatcagc aagaacacca gcacgagccg tacccatacc | 900 |
| agcgaagtgc atggcaatgc ggaagtgcat gcgagcttct tcgacattgg tggcagcgtg | 960 |
| agcgcgggct tcagcaacag caacagcagc accgtggcga ttgatcatag cctgagcctg | 1020 |
| gcgggcgaac gtacctgggc ggaaaccatg gccctgaaca cggcggatac ggcacgtctg | 1080 |
| aatgcgaaca ttcgctatgt gaacaccggt accgcgccaa tctataacgt gctgccgacc | 1140 |
| acgagcctgg tgctgggcaa gaatcagacc ctggcgacca tcaaagcgaa agagaaccag | 1200 |
| ctgtctcaga ttctggcacc gaacaactac tatccgtcta aaaacctggc accgattgca | 1260 |
| ctgaatgcgc aggatgactt cagcagcacc ccgatcacca tgaactacaa tcagtttctg | 1320 |
| gagctggaga agaccaaaca actgcgcctg gataccgatc aggtttatgg caacattgcg | 1380 |
| acctacaact tgagaacgg ccgcgttcgc gtggataccg gtagcaactg gtctgaagtg | 1440 |

```
ctgccgcaga ttcaggaaac gaccgcgcgt atcatttta acggcaaaga tctgaacctg    1500
gtggaacgtc gtatcgcggc agtgaaccca agcgacccac tggaaacgac caagccggac    1560
atgaccctga agaagcact gaagattgca tttggcttca acgaaccgaa tggcaacctg     1620
cagtatcagg gcaaagacat caccgagttt gacttcaact ttgatcaaca gacctctcag    1680
aacatcaaga accagctggc agaactgaat gcgaccaaca tctacaccgt gctggacaaa    1740
atcaaactga acgcgaagat gaacattctg attcgcgaca aacgcttcca ctatgatcgt    1800
aacaacatcg cggtgggtgc agatgaaagc gttgtgaagg aagcgcatcg tgaagtgatc    1860
aactctagca ccgaaggcct gctgctgaac attgataaag acattcgcaa gattctgagc    1920
ggctacattg tggagattga agataccgaa ggtctgaaag aagtgatcaa cgatcgctat    1980
gatatgctga acatctctag cctgcgccag gatggcaaga ccttcattga tttcaagaag    2040
tacaacgaca aactgccgct gtacatcagc aatccgaact acaaagtgaa cgtgtatgcg    2100
gtgaccaaag aaaacaccat cattaaccca agcgagaatg gcgataccag caccaacggc    2160
atcaagaaga ttctgatctt cagcaagaaa ggctatgaga ttggc                    2205

<210> SEQ ID NO 13
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98% identity) of SEQ ID No. 1

<400> SEQUENCE: 13
gaagtgaagc aggagaaccg tctgctgaac gagagcgagt ctagctctca gggcctgctg     60
ggctactatt tcagcgatct gaactttcag gcaccgatgg ttgtgacctc tagcacgacc    120
ggcgatctga gcattccgag cagcgaactg agaacattc cgagcgagaa ccagtacttt     180
cagtctgcga tttggagcgg cttcatcaaa gtgaagaaaa gcgatgagta cctttgcg     240 acgtctgcgg ataaccatgt gaccatgtgg gtggacgatc aggaagtgat caacaaagca    300
agcaacagca caagattcg cctggagaag ggtcgcctgt atcagatcaa gattcagtat    360
cagcgcgaga atccgaccga aaaaggcctg gatttcaaac tgtactggac cgatagccag    420
aacaagaaag aggtgattag ctctgataac ctgcagctgc cggaactgaa acagaagagc    480
agcaacagcc gcaagaaacg cagcacctct gcgggtccga ccgttccaga tcgcgacaac    540
gatggcattc cggacagcct ggaagtggaa ggctataccg ttgatgtgaa aacaaacgc     600 accttcctga gcccgtggat tagcaacatt catgagaaga aaggcctgac caagtacaaa    660
agcagcccgg agaaatggag caccgcgagc gatccgtata gcgattttga aaggtgacc    720 ggccgcattg ataagaacgt gagcccggaa gcgcgtcacc cactggttgc agcgtatccg    780
attgtgcatg ttgatatgga aacatcatt ctgagcaaga acgaagatca gagcacccag    840
aacacggata gccagacccg cacgattagc aagaacacca gcacgagccg tacccatacc    900
agcgaagtgc atggcaatgc ggaagtgcat gcgagcttct ttgacattgg tggcagcgtg    960
agcgcgggct tcagcaacag caacagcagc accgtggcga ttgatcatag cctgagcctg    1020
gcgggcgaac gtacctgggc ggaaaccatg gcctgaaca cggcggatac ggcacgtctg    1080
aatgcgaaca tccgctatgt gaacaccggt accgcgccaa tctataacgt tctgccgacc    1140
acgagcctgg tgctgggcaa gaatcagacc ctggcgacca tcaaagcgaa agaaaaccag    1200
```

```
ctgtctcaga ttctggcacc gaacaactac tatccgagca agaacctggc gccgattgca    1260
ctgaatgcac aggatgactt cagcagcacc ccgatcacca tgaactacaa tcagtttctg    1320
gagctggaaa agaccaaaca actgcgcctg acaccgatc aggtgtatgg caacattgcg    1380
acctacaact ttgagaacgg ccgcgttcgc gtggataccg gcagcaactg gtctgaagtg    1440
ctgccgcaga ttcaggaaac gaccgcgcgc atcatcttta acggcaaaga tctgaacctg    1500
gtggaacgtc gcatcgcggc agtgaaccca agcgatccac tggaaacgac caaaccggac    1560
atgaccctga agaagcgct gaaaattgca tttggcttca acgagccgaa tggcaacctg    1620
cagtatcagg gcaaagacat caccgagttt gacttcaact tcgatcaaca gacctctcag    1680
aacatcaaga accagctggc agaactgaat gcgaccaaca tctacaccgt gctggacaag    1740
atcaaactga acgcaaagat gaacattctg attcgtgaca aacgctttca ctatgatcgt    1800
aacaacattg cggtgggtgc agacgaaagc gttgtgaaag aagcgcatcg tgaagtgatc    1860
aactctagca ccgaaggcct gctgctgaac attgacaaaa atatccgtaa gattctgagc    1920
ggctacattg tggaaattga agataccgaa ggtctgaaag aagtgatcaa cgatcgctat    1980
gacatgctga acatctctag cctgcgccaa gatggcaaga ccttcatcga cttcaagaag    2040
tacaacgaca aactgccgct gtacatcagc aatccgaact acaaagtgaa cgtgtatgcg    2100
gtgaccaaag agaacaccat cattaaccca agcgagaatg gcgacacctc taccaacggc    2160
attaagaaga ttctgatctt cagcaagaaa ggttatgaga ttggc                   2205

<210> SEQ ID NO 14
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98% identity) of SEQ ID No. 1

<400> SEQUENCE: 14
gaagtgaaac aggagaaccg tctgctgaac gaaagcgaat ctagctctca gggcctgctg      60
ggctattatt tcagcgatct gaacttccag gcaccaatgg ttgtgacctc ttctacgacc     120
ggcgatctga gcattccgag cagcgagctg gagaacattc cgagcgagaa ccagtacttt     180
cagagcgcga tttggagcgg cttcatcaaa gtgaagaaaa gcgatgagta tacctttgcg     240
acgtctgcgg ataaccatgt gaccatgtgg gtggacgatc aggaagtgat caacaaagca     300
agcaacagca acaagattcg cctggagaag ggtcgcctgt atcagattaa gattcagtac     360
cagcgcgaga tccgaccga aaaggcctg gatttcaaac tgtactggac cgatagccag     420
aacaagaaag aagtgattag ctctgataac ctgcaactgc cggaactgaa acagaagagc     480
agcaacagcc gcaagaaacg cagcacctct gcaggcccga ccgttccgga tcgcgacaac     540
gatggcattc cggacagcct ggaagtggaa ggttataccg tggatgtgaa gaacaaacgc     600
accttcctga gcccgtggat tagcaacatt catgagaaga aaggcctgac caagtacaaa     660
agcagcccgg agagtggag caccgcgagc gatccgtata gcgactttga gaaagtgacc     720
ggccgcattg ataagaacgt gagcccggaa gcgcgtcacc cactggttgc agcgtatccg     780
attgtgcatg ttgacatgga gaacatcatt ctgagcaaga acgaagatca gagcacccag     840
aacacggata gccagacccg cacgatcagc aagaacacct ctacgagccg tacccatacc     900
agcgaagtgc atggcaatgc ggaagtgcat gcaagcttct ttgacattgg tggcagcgtg     960
agcgcgggct tcagcaacag caacagcagc accgtggcga ttgatcatag cctgagcctg    1020
```

```
gcgggcgaac gtacctgggc ggaaaccatg ggcctgaaca cggcggatac ggcacgtctg    1080
aatgcgaaca ttcgttatgt gaacaccggc accgcgccaa tctataacgt tctgccgacc    1140
acgagcctgg tgctgggcaa gaatcagacc ctggcgacca tcaaagcgaa agagaaccag    1200
ctgtctcaga ttctggcacc gaacaactac tatccaagca agaacctggc gccgattgca    1260
ctgaacgcgc aggatgactt tagcagcacc ccgatcacca tgaactacaa tcagtttctg    1320
gaactggaga agaccaaaca actgcgcctg gataccgatc aggtgtatgg caacattgcg    1380
acctacaact tgagaacgg ccgcgttcgc gtggataccg gtagcaactg gagcgaagtg    1440
ctgccgcaga tccaggaaac caccgcgcgc atcatcttca acggcaaaga tctgaatctg    1500
gtggaacgcc gcatcgcggc ggtgaaccca tctgatccgc tggaaacgac caaaccggat    1560
atgaccctga agaagcgct gaagattgca tttggcttca cgaaccgaa tggcaacctg    1620 cagtatcagg gcaaagacat caccgagttt gacttcaact tgaccaaca gacctctcag    1680 aacatcaaga ccagctggc agaactgaat gcgaccaaca tctacaccgt gctggacaag    1740
atcaaactga acgcaaagat gaacattctg attcgtgaca aacgctttca ctatgatcgt    1800
aacaacattg cggtgggtgc agacgaaagc gttgtgaaag aagcgcatcg tgaagtgatc    1860
aactctagca ccgaaggtct gctgctgaac attgacaaag acatccgtaa gattctgagc    1920
ggctacattg tggagattga agataccgaa ggtctgaaag aagttatcaa cgatcgctat    1980
gatatgctga acatctctag cctgcgccag gatggcaaga cgttcattga cttcaagaag    2040
tacaacgaca aactgccgct gtacatcagc aatccgaact acaaagtgaa cgtgtatgcg    2100
gtgaccaaag agaacaccat cattaaccca agcgagaatg gcgataccag caccaacggc    2160
atcaagaaga ttctgatctt cagcaagaaa ggctatgaga ttggc                    2205
```

<210> SEQ ID NO 15
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97% identity) of SEQ ID No. 1

<400> SEQUENCE: 15

```
gaagtgaaac aggagaaccg tctgctgaac gaatctgaat ctagctctca gggcctgctg      60
ggctactatt tttctgatct gaactttcag gcaccgatgg ttgtgaccag cagcacgacc     120
ggcgacctga gcattccgag cagcgaactg gagaacattc cgagcgagaa ccagtacttt     180
cagagcgcga tttggagcgg cttcatcaaa gtgaagaaaa gcgatgagta tacctttgcg     240
acgtctgcgg ataaccatgt gaccatgtgg gtggacgatc aggaggtgat caacaaagcg     300
agcaacagca caagattcg cctggagaag ggtcgcctgt atcagatcaa gattcagtat     360
cagcgcgaga atccgaccga aaaggcctg gatttcaaac tgtactggac cgacagccag     420
aacaaaaaag aagtgattag ctctgataac ctgcaactgc cggaactgaa acagaagagc     480
agcaacagcc gcaagaaacg cagcacctct gcaggcccga ccgttccaga tcgcgacaac     540
gatggcattc cggatagcct ggaagtggaa ggttataccg ttgatgtgaa gaacaaacgt     600
acctttctga gcccgtggat tagcaacatt catgagaaga agggcctgac caagtacaaa     660
agcagcccgg agaagtggag caccgcgtct gatccgtata gcgacttcga gaaagtgacc     720
ggccgcattg ataagaacgt gagcccggaa gcgcgccacc cactggttgc agcgtatccg     780
```

```
atcgtgcatg ttgacatgga gaacatcatt ctgagcaaga acgaagacca gagcacccag    840
aacacggata gccagacccg cacgatcagc aagaacacca gcacgagccg tacccatacc    900
agcgaagtgc atggcaatgc ggaagtgcat gcgagcttct tcgacattgg tggcagcgtg    960
agcgcgggct tcagcaacag caacagcagc accgtggcga ttgatcatag cctgagcctg   1020
gcgggcgaac gtacctgggc agaaaccatg ggcctgaaca cggcggatac ggcacgtctg   1080
aatgcgaaca ttcgctatgt gaacaccggt accgcgccga tctataacgt gctgccgacc   1140
acgagcctgg tgctgggcaa gaatcagacc ctggcgacca tcaaagcgaa agagaaccag   1200
ctgagccaga ttctggcacc aaacaactac tatccgtcta aaaacctggc gccgattgca   1260
ctgaatgcgc aggatgactt cagcagcacc ccgatcacca tgaactacaa tcagtttctg   1320
gagctggaga agaccaaaca actgcgcctg gataccgatc aggtttacgg caacattgcg   1380
acctataact ttgagaacgg ccgcgttcgc gtggataccg gtagcaactg gtctgaagtg   1440
ctgccgcaga ttcaggaaac gaccgcgcgt atcattttta acggcaaaga tctgaacctg   1500
gtggaacgtc gtatcgcagc agtgaaccca agcgaccac tggaaacgac caagccggac   1560
atgacccctga aagaagcgct gaagattgca tttggcttca tgaaccgaa tggcaacctg   1620
cagtatcagg gcaaagacat caccgagttt gacttcaact ttgatcaaca gacctctcag   1680
aacatcaaga accagctggc agaactgaac gcgaccaaca tctacaccgt gctggacaaa   1740
atcaaactga acgcgaagat gaacattctg attcgcgaca aacgcttcca ctatgatcgt   1800
aacaacatcg cggtgggtgc agatgaaagc gttgtgaagg aagcgcatcg tgaagtgatc   1860
aactctagca ccgaaggcct gctgctgaac attgataaag acattcgcaa gattctgagc   1920
ggctacattg tggagattga agataccgaa ggtctgaaag aagtgatcaa cgatcgctat   1980
gatatgctga acatctctag cctgcgccag gatggcaaga ccttcattga tttcaagaag   2040
tacaacgaca aactgccgct gtacatcagc aatccgaact acaaagtgaa cgtgtatgcg   2100
gtgaccaaag aaaacaccat cattaaccca agcgagaatg cgataccag caccaacggc   2160
atcaagaaga ttctgatctt cagcaagaaa ggctatgaga ttggc              2205
```

<210> SEQ ID NO 16
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (97% identity) of SEQ ID NO. 1

<400> SEQUENCE: 16

```
gaagtgaaac aggagaaccg tctgctgaac gagagcgagt ctagctctca gggcctgctg     60
ggctactatt tcagcgatct gaactttcag gcaccgatgg ttgttacctc tagcacgacc    120
ggcgatctga gcattccgag cagcgaactg agaacattc cgagcgagaa ccagtacttt    180
cagtctgcga tttggagcgg cttcatcaaa gtgaagaaga gcgatgaata tacctttgcg    240
acgtctgcgg ataaccatgt gaccatgtgg gtggacgacc aggaggtgat caacaaagca    300
agcaacagca acaagattcg cctggagaag ggtcgcctgt atcagatcaa gatccagtat    360
cagcgcgaga atccgaccga aaaggcctg gatttcaaac tgtactggac cgatagccag    420
aacaagaaag aggtgattag ctctgataac ctgcagctgc cggaactgaa acagaagagc    480
agcaacagcc gcaagaaacg cagcacctct gcgggtccga ccgttccaga tcgcgacaac    540
gatggcattc cggacagcct ggaagtggaa ggctataccg ttgatgtgaa gaataaacgc    600
```

```
acgttcctga gcccgtggat cagcaacatt catgaaaaga aaggcctgac caagtacaaa      660
agcagcccgg agaaatggag caccgcgagc gatccgtata gcgattttga aaggtgacc       720 ggccgcattg ataagaacgt gagcccggaa gcgcgtcacc cactggttgc agcgtatccg      780
attgtgcatg tggatatgga gaacattatt ctgagcaaga acgaagatca gagcacccag      840
aacacggata gccagacccg taccattagc aagaacacca gcacgagccg tacccatacc      900
agcgaagtgc atggcaatgc ggaagtgcat gcgagcttct ttgacattgg tggcagcgtg      960
agcgcgggct tcagcaacag caacagcagc accgtggcaa ttgatcatag cctgagcctg     1020
gcgggcgaac gcacctgggc ggaaaccatg ggcctgaaca cggcggatac ggcacgtctg     1080
aatgcgaaca tccgctatgt gaacaccggt accgcgccaa tctataacgt tctgccgacc     1140
acgagcctgg tgctgggcaa gaatcagacc ctggcgacca tcaaagcgaa agaaaaccag     1200
ctgtctcaga ttctggcacc gaacaactac tatccgagca gaacctggc gccgattgcg      1260 ctgaatgcac aggatgactt tagcagcacc ccgatcacca tgaactacaa tcagtttctg     1320
gagctggaaa agaccaagca actgcgcctg gacaccgatc aggtgtatgg caacattgcg     1380
acctacaact ttgagaacgg ccgcgttcgc gtggataccg cagcaactg gtctgaggtg      1440 ctgccgcaga ttcaggaaac gaccgcgcgc atcattttca cggcaaaga tctgaacctg      1500 gtggaacgtc gcatcgcggc agtgaaccca agcgatccac tggaaacgac caaaccggac     1560
atgaccctga agaagcgct gaaaattgca tttggcttca acgagccgaa tggcaacctg      1620
cagtatcagg gcaaagacat caccgagttt gacttcaact tcgatcaaca gacctctcag     1680
aacatcaaga accagctggc agaactgaat gcgaccaaca tctacaccgt gctggacaag     1740
attaaactga acgcaaagat gaacattctg attcgtgata aacgctttca ctatgatcgt     1800
aacaacattg cggtgggtgc agacgaaagc gttgtgaaag aagcgcatcg tgaagtgatc     1860
aactctagca ccgaaggcct gctgctgaac attgacaaag atatccgtaa aattctgagc     1920
ggctacatcg tggaaattga agataccgaa ggtctgaaag aagtgatcaa cgatcgctat     1980
gacatgctga acatctctag cctgcgccaa gatggcaaga ccttcatcga cttcaagaag     2040
tacaacgaca aactgccgct gtacatcagc aacccgaact acaaagtgaa cgtgtatgcg     2100
gtgaccaaag agaacaccat cattaaccca agcgagaatg cgacacctc taccaacggc      2160 attaagaaga ttctgatctt cagcaagaaa ggttatgaga ttggc                     2205

<210> SEQ ID NO 17
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97% identity) of  SEQ ID NO 1

<400> SEQUENCE: 17
gaagtgaagc aggagaaccg tctgctgaac gaaagcgaat ctagctctca gggcctgctg       60
ggctattatt tcagcgatct gaacttccag gcaccaatgg ttgtgacctc ttctacgacc      120
ggcgatctga gcatcccgag cagcgagctg gagaacattc gagcgagaa ccagtacttt       180 cagagcgcga tttggagcgg cttcatcaaa gtgaagaaaa gcgatgagta tacctttgcg      240
acgtctgcag ataaccatgt gaccatgtgg tggatgatc aggaagtgat caacaaagcg       300
agcaacagca acaagatccg cctggagaag ggtcgcctgt atcagattaa gattcagtac      360
```

```
cagcgcgaga atccgaccga gaaaggcctg gatttcaaac tgtactggac ggatagccag    420
aacaagaaag aagtgattag ctctgataac ctgcaactgc cggaactgaa acagaagagc    480
agcaacagcc gcaagaaacg cagcacctct gcaggcccga ccgttccgga ccgcgacaac    540
gatggcatcc cggacagcct ggaagtggaa ggttataccg tggatgtgaa gaacaaacgc    600
accttcctga gcccgtggat tagcaacatt catgagaaga aaggcctgac caaatacaaa    660
agcagcccgg agaagtggag caccgcgagc gatccgtata gcgactttga gaaagtgacc    720
ggccgcattg ataagaacgt gagcccggaa gcgcgtcatc cactggttgc agcgtatccg    780
attgtgcatg ttgacatgga gaacattatt ctgagcaaga acgaagatca gagcacccag    840
aacacggata gccagacccg cacgatcagc aagaacacct ctacgagccg tacccatacc    900
agcgaagtgc atggcaatgc ggaagtgcat gcaagcttct ttgacattgg tggcagcgtg    960
agcgcgggct tcagcaacag caacagcagc acggtggcga ttgatcatag cctgagcctg   1020
gcgggcgaac gtacctgggc ggaaaccatg ggcctgaaca ccgcggatac ggcacgtctg   1080
aatgcgaaca ttcgttatgt gaacaccggc accgcgccaa tctataacgt tctgccgacc   1140
acgagcctgg tgctgggcaa gaatcagacc ctggcgacca tcaaagcgaa agagaaccag   1200
ctgtctcaga ttctggcacc gaacaactac tatccaagca agaacctggc gccgattgca   1260
ctgaacgcgc aggatgactt tagcagcacc ccgatcacca tgaactacaa tcagtttctg   1320
gaactggaga agaccaaaca actgcgcctg gataccgatc aggtgtatgg caacattgcg   1380
acctacaact tgagaacgg ccgcgttcgc gtggataccg gtagcaactg gagcgaagtg   1440
ctgccgcaga tccaggaaac caccgcgcgc atcattttca acggcaaaga tctgaatctg   1500
gtggaacgcc gcatcgcggc ggtgaaccca tctgacccgc tggaaacgac caaaccggat   1560
atgaccctga agaagcgct gaagattgca tttggcttca tgaaccgaa tggcaacctg   1620 cagtatcagg gtaaagacat caccgagttt gacttcaact tgaccaaca gacctctcag   1680 aacattaaga accagctggc agaactgaat gcgaccaaca tctacaccgt gctggacaag   1740
atcaaactga acgcaaagat gaacattctg attcgtgaca aacgctttca ctatgatcgc   1800
aacaacattg cggtgggtgc agacgaaagc gttgtgaaag aagcgcaccg tgaagtgatc   1860
aactctagca ccgaaggcct gctgctgaac attgacaaag acatccgtaa gattctgagc   1920
ggctacattg tggagatcga agataccgaa ggtctgaaag aagttattaa cgatcgctat   1980
gatatgctga acatctctag cctgcgtcag gatggcaaga ccttcattga cttcaagaag   2040
tacaacgata aactgccgct gtacatcagc aacccgaact acaaagtgaa cgtgtatgcg   2100
gtgaccaaag agaacaccat cattaaccca agcgagaatg gcgataccag caccaacggc   2160
atcaagaaga ttctgatctt cagcaagaaa ggctatgaga ttggc                   2205
```

<210> SEQ ID NO 18
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (96% identity) of SEQ ID NO 1

<400> SEQUENCE: 18

```
gaagtgaaac aggagaaccg tctgctgaac gaatctgaat ctagctctca gggcctgctg     60
ggctactatt tttctgatct gaactttcag gcaccgatgg ttgtgaccag ctctacgacc    120
ggcgacctga gcattccgag cagcgaactg gagaacattc gagcgagaa ccagtacttt    180
```

```
cagagcgcga tttggagcgg cttcatcaaa gtgaagaaaa gcgatgagta tacctttgcg    240
acgtctgcgg ataaccatgt gaccatgtgg gtggacgatc aggaggtgat caacaaagcg    300
agcaacagca acaagattcg cctggagaag ggtcgcctgt atcagatcaa gattcagtat    360
cagcgcgaga atccgaccga gaaaggcctg gatttcaaac tgtactggac cgatagccag    420
aacaaaaaag aagtgattag cagcgataac ctgcaactgc cggaactgaa gcagaagagc    480
agcaacagcc gcaagaaacg cagcacctct gcaggcccga ccgttccaga tcgcgacaac    540
gatggcattc cggatagcct ggaagtggaa ggttataccg ttgatgtgaa aaacaaacgt    600
acctttctga gcccgtggat tagcaacatt catgagaaga agggcctgac caagtacaaa    660
agcagcccgg agaagtggag caccgcgtct gatccgtata gcgacttcga gaaagtgacc    720
ggccgcattg ataaaaacgt gagcccggaa gcgcgccacc cactggttgc agcgtatccg    780
atcgtgcatg ttgacatgga gaacatcatt ctgagcaaga acgaagacca gagcacccag    840
aacacggaca gccagacccg cacgatcagc aagaacacca gcacgagccg tacccatacc    900
agcgaagtgc atggcaatgc ggaagtgcat gcgagcttct tcgacattgg tggcagcgtg    960
agcgcgggct tcagcaacag caacagcagc accgtggcga ttgatcatag cctgagcctg   1020
gcgggcgaac gtacctgggc agaaaccatg ggcctgaaca cggcggatac ggcacgtctg   1080
aatgcgaaca ttcgctatgt gaacaccggt accgcgccga tctataacgt gctgccgacc   1140
acgagcctgg tgctgggcaa gaatcagacc ctggcgacca tcaaagcgaa agagaaccag   1200
ctgagccaga ttctggcacc aaacaactac tatccgtcta aaaacctggc gccgattgca   1260
ctgaatgcgc aggatgactt cagcagcacc ccgatcacca tgaactacaa tcagttttctg   1320 gagctggaga agaccaaaca actgcgcctg ataccgatc aggtttacgg caacattgcg    1380
acctataact ttgagaacgg ccgcgttcgc gtggataccg gtagcaactg gtctgaagtg   1440
ctgccgcaga tccaggaaac gaccgcgcgt atcattttta acggcaagga cctgaacctg   1500
gtggaacgtc gtatcgcagc agtgaaccca agcgacccac tggaaacgac caagccggat   1560
atgaccctga agaagcgct gaagattgca tttggcttca atgagccgaa tgcaacctg    1620 cagtatcagg gcaaagatat caccgagttt gacttcaact ttgaccaaca gacctctcag   1680
aacatcaaga accagctggc agaactgaac gcgaccaaca tttacaccgt gctggacaaa   1740
atcaaactga acgcgaagat gaacattctg attcgcgaca aacgcttcca ctatgatcgt   1800
aacaacatcg cggtgggtgc agatgaaagc gttgtgaagg aagcgcatcg tgaagtgatc   1860
aactctagca ccgaaggcct gctgctgaac atcgataaag acattcgcaa gattctgagc   1920
ggctacattg tggagattga agataccgaa ggtctgaaag aagtgattaa cgatcgctat   1980
gatatgctga acatttctag cctgcgccag gatggcaaga ccttcatcga tttcaagaag   2040
tacaacgaca aactgccgct gtacatcagc aatccgaact acaaagtgaa cgtgtatgcg   2100
gtgaccaaag aaaacaccat cattaaccca agcgagaatg gcgataccag caccaacggc   2160
atcaagaaga ttctgatctt cagcaagaaa ggctatgaaa ttggc                   2205
```

<210> SEQ ID NO 19
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96% identity) of SEQ ID NO 1

<400> SEQUENCE: 19

```
gaagtgaaac aggagaaccg tctgctgaac gagagcgaga gcagctctca gggcctgctg      60
ggctactatt tcagcgatct gaactttcag gcaccgatgg tggttacctc tagcacgacc     120
ggcgatctga gcattccgag cagcgaactg gagaacattc cgagcgagaa ccagtacttt     180
cagtctgcga tttggagcgg cttcatcaaa gtgaagaaga gcgatgaata cctttgcg      240
acgagcgcgg ataaccatgt gacgatgtgg gtggacgacc aggaggtgat caacaaagca     300
agcaacagca acaagattcg cctggagaag ggtcgcctgt atcagatcaa gatccagtat     360
cagcgcgaaa atccgaccga aaaggcctg gatttcaaac tgtactggac cgatagccag     420
aacaagaaag aggtgattag ctctgataac ctgcagctgc cggaactgaa acagaagagc     480
agcaacagcc gcaagaaacg cagcacctct gcgggtccga ccgttccaga tcgcgacaac     540
gatggcattc cggatagcct ggaagtggaa ggctataccg ttgatgtgaa aataaacgc      600
accttcctga gcccgtggat cagcaacatt catgaaaaga aaggcctgac caagtacaaa     660
agcagcccgg agaagtggag caccgcgagc gatccgtata gcgattttga aaggtgacc      720
ggccgcattg ataagaacgt gagcccgaaa gcgcgtcacc cactggttgc agcgtatccg     780
attgtgcatg tggatatgga aacattatt ctgagcaaga acgaagatca gagcacccag      840
aacacggata gccagacccg taccattagc aagaacacca gcacgagccg tacccatacc     900
agcgaagttc atggcaatgc ggaagtgcat gcgagcttct ttgacattgg tggcagcgtg     960
agcgcgggct tcagcaacag caacagctct accgtggcaa ttgaccatag cctgtctctg    1020
gcgggcgaac gcacctgggc ggaaaccatg ggcctgaaca cggcggatac ggcacgtctg    1080
aatgcgaaca tccgctatgt gaacaccggt accgcgccaa tctataacgt tctgccgacc    1140
acgagcctgg tgctgggcaa gaatcagacc ctggcgacca tcaaagcgaa agaaaccag    1200
ctgtctcaga ttctggcacc gaacaactac tatccgagca gaacctggc gccgattgcg     1260
ctgaatgcac aggatgactt tagcagcacc ccgatcacca tgaactacaa tcaatttctg    1320
gagctggaaa agaccaagca gctgcgcctg gacaccgatc aggtgtatgg caacattgcg    1380
acctacaact ttgagaacgg ccgcgttcgc gtggataccg gcagcaactg gtctgaggtg    1440
ctgccacaga ttcaggaaac gaccgcgcgc atcattttca cggcaaaga tctgaacctg     1500
gtggaacgtc gcatcgcggc agtgaaccca agcgatccac tggaaacgac caaaccggac    1560
atgaccctga agaggcgct gaaaattgca tttggcttca acgagccgaa tggcaacctg     1620
cagtatcagg gcaagacat caccgagttt gacttcaact tcgatcaaca gacctctcag    1680
aacatcaaga accagctggc agaactgaat gcgaccaaca tctacaccgt gctggacaag    1740
attaaactga acgcaaagat gaacattctg attcgtgata aacgctttca ctatgatcgt    1800
aacaacattg cggtgggtgc agacgaaagc gttgtgaaag aagcgcatcg tgaagtgatc    1860
aactctagca ccgaaggcct gctgctgaac attgacaaag atatccgtaa aattctgagc    1920
ggctacatcg tggaaattga agataccgaa ggtctgaaag aagtgatcaa cgatcgctat    1980
gacatgctga acatctctag cctgcgccaa gatggcaaga ccttcatcga cttcaagaag    2040
tacaacgaca aactgccgct gtacatcagc aacccgaact acaaagtgaa cgtgtatgcg    2100
gtgaccaaag agaacaccat cattaacccg agcgagaatg cgacacctc taccaacggc    2160
attaaaaaga ttctgatctt cagcaagaaa ggttatgaga ttggc                    2205
```

<210> SEQ ID NO 20
<211> LENGTH: 2205
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (96% identity) of SEQ ID NO 1

<400> SEQUENCE: 20

```
gaagtgaagc aggagaaccg tctgctgaac gaaagcgaat ctagctctca gggcctgctg      60
ggctattatt tcagcgatct gaacttccag gcgccaatgg ttgtgaccag ctctacgacc     120
ggcgatctga gcatcccgag cagcgagctg gagaacattc cgagcgagaa ccagtacttt     180
cagagcgcga tttggagcgg cttcatcaaa gtgaagaaaa gcgatgagta cctttgcg      240
acgtctgcag ataaccatgt gaccatgtgg gtggatgatc aggaagtgat caacaaagcg     300
agcaacagca acaagatccg cctggagaag ggtcgcctgt atcagattaa gattcagtac     360
cagcgcgaga tccgaccga gaaaggcctg gacttcaaac tgtactggac ggatagccag      420
aacaagaaag aagtgattag ctctgataac ctgcaactgc cggaactgaa acagaagagc     480
agcaacagcc gcaagaaacg cagcacctct gcaggcccga ccgttccgga ccgcgacaac     540
gatggcatcc cggacagcct ggaagtggaa ggttataccg tggatgtgaa gaacaaacgc     600
accttcctga gcccgtggat tagcaacatt catgagaaga aaggcctgac caaatacaaa     660
agcagcccgg agagtggag caccgcgagc gatccgtata gcgactttga gaaagtgacc      720
ggccgcattg ataagaacgt gagcccggaa gcgcgtcatc cactggttgc agcgtatccg     780
attgtgcatg ttgacatgga gaacattatt ctgagcaaaa acgaagatca gagcacccag     840
aacacggaca gccagacccg cacgatcagc aagaacacct ctacgagccg tacccatacc     900
agcgaagtgc atggcaatgc ggaagtgcat gcaagcttct ttgacattgg tggcagcgtg     960
agcgcgggct tcagcaacag caacagcagc acggtggcaa ttgatcatag cctgagcctg    1020
gcgggcgaac gtacctgggc ggaaaccatg ggcctgaaca ccgcggatac ggcacgtctg    1080
aatgcgaaca ttcgttatgt gaacaccggc accgcgccaa tctataacgt tctgccgacc    1140
acgagcctgg tgctgggcaa gaaccagacc ctggcgacca tcaaagcaaa agagaaccag    1200
ctgtctcaga ttctggcacc gaacaactac tatccaagca gaacctggc gccgattgca     1260
ctgaacgcgc aggatgattt tagcagcacc ccgatcacca tgaactacaa tcagtttctg    1320
gaactggaga agaccaaaca actgcgcctg gataccgatc aggtgtatgg caacatcgcg    1380
acctacaact ttgagaacgg ccgcgttcgc gtggataccg gttctaactg gagcgaagtg    1440
ctgccgcaga tccaggaaac caccgcgcgc atcattttca acggcaaaga tctgaatctg    1500
gtggaacgcc gcatcgcggc ggtgaaccca tctgacccgc tggaaacgac caagccggat    1560
atgaccctga agaagcgct gaagattgcg tttggcttca atgaaccgaa tggcaacctg     1620
cagtatcagg gtaaagacat caccgagttt gacttcaact tgaccaaca gacctctcag     1680
aacattaaga accagctggc agaactgaat gcgaccaaca tctacaccgt gctggacaag    1740
atcaaactga acgcaaagat gaacattctg attcgtgata acgctttca ctatgatcgc     1800
aacaacattg cggtgggtgc agacgaaagc gttgtgaaag aagcgcaccg tgaagtgatc    1860
aactctagca ccgaaggcct gctgctgaac attgacaaag atattcgtaa gattctgagc    1920
ggctacattg tggagatcga agataccgaa ggtctgaaag aagttattaa cgatcgctat    1980
gatatgctga acatctctag cctgcgtcag gatggcaaga ccttcattga cttcaagaag    2040
tacaacgaca aactgccgct gtatatcagc aacccgaatt acaaagtgaa cgtgtacgcg    2100
gtgaccaaag agaacaccat cattaaccca agcgagaatg gcgataccag caccaacggc    2160
```
atcaagaaga ttctgatctt cagcaagaaa ggctatgaga ttggc            2205

<210> SEQ ID NO 21
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95% identity) of SEQ ID NO 1

<400> SEQUENCE: 21

| | |
|---|---|
| gaagtgaaac aggagaaccg tctgctgaac gaatctgaat ctagctctca gggcctgctg | 60 |
| ggctactatt tttctgatct gaacttccag gcaccgatgg ttgtgaccag ctctaccacc | 120 |
| ggcgacctga gcattccgag cagcgaactg gagaacattc cgagcgagaa ccagtacttt | 180 |
| cagagcgcga tttggagcgg cttcatcaaa gtgaagaaaa gcgatgagta ccctttgcg | 240 |
| acgtctgcgg ataaccatgt gaccatgtgg gtggacgatc aggaggtgat caacaaagca | 300 |
| agcaacagca acaagattcg cctggagaag ggtcgcctgt atcagatcaa gattcagtat | 360 |
| cagcgcgaga tccgaccga gaaggcctg gatttcaaac tgtactggac cgatagccag | 420 |
| aacaaaaaag aagtgattag cagcgataac ctgcaactgc cggaactgaa gcagaagagc | 480 |
| agcaacagcc gcaagaaacg cagcacgtct gcaggcccga ccgttccaga tcgcgacaac | 540 |
| gatggcattc cggatagcct ggaagtggaa ggttataccg ttgatgtgaa aaacaaacgt | 600 |
| acctttctga gcccgtggat tagcaacatt catgagaaga agggcctgac caagtacaaa | 660 |
| agcagcccgg agaagtggag caccgcgtct gatccgtata gcgactttga aaagtgacc | 720 |
| ggccgcattg ataaaaacgt gagcccggag gcgcgccacc cactggttgc ggcgtatccg | 780 |
| attgtgcatg ttgacatgga aacatcatc ctgagcaaga acgaagacca gagcacccag | 840 |
| aacacggaca gccagacccg cacgatcagc aagaacacca gcacgagccg tacgcatacc | 900 |
| agcgaagtgc atggcaatgc ggaagtgcat gcgagcttct tcgacattgg tggcagcgtg | 960 |
| agcgcgggct tcagcaacag caacagcagc accgtggcga ttgatcatag cctgagcctg | 1020 |
| gcgggcgaac gtacctgggc agaaaccatg ggcctgaaca cggcggatac ggcacgtctg | 1080 |
| aatgcgaaca ttcgctatgt gaacaccggt accgcaccga tttataacgt gctgccgacc | 1140 |
| acgagcctgg tgctgggtaa gaatcagacc ctggcgacca tcaaagcgaa agagaaccag | 1200 |
| ctgagccaga ttctggcacc aaacaactac tatccgtcta aaaacctggc gccgattgca | 1260 |
| ctgaatgcgc aggatgattt cagcagcacc ccgatcacca tgaactacaa tcagtttctg | 1320 |
| gagctggaga gaccaaaaca actgcgcctg gacaccgacc aggtttacgg caacattgcg | 1380 |
| acctataact ttgagaacgg ccgcgttcgc gtggacaccg tagcaactg tctgaagtg | 1440 |
| ctgccgcaga tccaggaaac gaccgcgcgt atcatttta acggcaagga tctgaacctg | 1500 |
| gtggaacgtc gtatcgcagc agtgaaccca agcgacccac tggaaaccac caagccggat | 1560 |
| atgaccctga agaagcgct gaagattgca tttggcttca atgagccgaa tggcaacctg | 1620 |
| cagtatcagg gcaaagatat caccgaattt gacttcaact tgaccaaca gacctctcag | 1680 |
| aacatcaaga accagctggc ggaactgaac gcgaccaaca tttacaccgt gctggacaaa | 1740 |
| atcaaactga acgcgaagat gaacattctg attcgcgaca aacgcttcca ctacgatcgt | 1800 |
| aacaacatcg cggtgggcgc agatgaaagc gttgtgaagg aagcgcatcg tgaagtgatc | 1860 |
| aactctagca ccgaaggcct gctgctgaac atcgataaag acattcgcaa gattctgagc | 1920 |

-continued

| | |
|---|---|
| ggctacattg tggagattga ggataccgaa ggtctgaaag aagtgattaa cgatcgctat | 1980 |
| gatatgctga acatctctag cctgcgccag gatggcaaga ccttcatcga tttcaagaaa | 2040 |
| tataacgata aactgccgct gtacatcagc aatccgaact acaaagtgaa cgtgtatgcg | 2100 |
| gtgaccaaag aaaacaccat cattaaccca agcgagaatg gcgataccag caccaacggc | 2160 |
| atcaagaaga ttctgatctt cagcaagaag ggctatgaaa ttggc | 2205 |

<210> SEQ ID NO 22
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95% identity) of SEQ ID NO 1

<400> SEQUENCE: 22

| | |
|---|---|
| gaagtgaaac aggagaaccg tctgctgaac gagagcgaga gctcttctca gggcctgctg | 60 |
| ggctactatt tcagcgatct gaactttcag gcaccgatgg ttgttacctc tagcaccacc | 120 |
| ggcgatctga gcattccgag cagcgaactg gaaaacattc cgagcgagaa ccagtacttt | 180 |
| cagtctgcga tttggagcgg cttcatcaaa gtgaagaaga gcgatgaata cctttgcg | 240 |
| acgagcgcgg ataaccatgt gacgatgtgg gtggacgacc aggaggtgat caacaaagca | 300 |
| agcaacagca caagattcg cctggagaag ggtcgcctgt atcagatcaa gatccagtat | 360 |
| cagcgcgaaa atccgaccga aaaggcctg gatttcaaac tgtactggac cgatagccag | 420 |
| aacaagaaag aggttattag ctctgataac ctgcagctgc cggaactgaa acagaagagc | 480 |
| agcaacagcc gcaagaaacg cagcacctct gcgggtccga ccgttccaga tcgcgacaac | 540 |
| gatggcattc cggatagcct ggaagtggaa ggctataccg tggatgtgaa gaataagcgc | 600 |
| accttcctga gcccgtggat cagcaatatt catgaaaaga aaggcctgac gaagtacaaa | 660 |
| agcagcccgg agaaatggag caccgcgagc gatccgtata gcgattttga aggtgacc | 720 |
| ggccgcattg ataagaacgt gagcccggaa gcgcgtcacc cactggttgc agcgtatccg | 780 |
| attgtgcatg tggatatgga gaacattatt ctgagcaaga acgaagatca gagcacccag | 840 |
| aacacggata gccagacccg taccattagc aagaacacca gcacgagccg tacccatacc | 900 |
| agcgaagttc atggcaatgc ggaagtgcat gcgagcttct ttgacattgg tggcagcgtg | 960 |
| agcgcgggct tcagcaacag caacagctct accgtggcga ttgaccatag cctgtctctg | 1020 |
| gcgggcgagc gcacctgggc ggaaaccatg ggcctgaaca cggcggatac ggcacgtctg | 1080 |
| aatgcaaaca tccgctatgt gaacaccggt accgcgccaa tctataacgt gctgccgacc | 1140 |
| accagcctgg tgctgggcaa gaaccagacc ctggcgacca tcaaagcgaa agaaaaccag | 1200 |
| ctgagccaga ttctggcgcc gaacaactat tatccgagca gaacctggc accgattgcg | 1260 |
| ctgaatgcac aggatgactt tagcagcacg ccgatcacca tgaactacaa tcaatttctg | 1320 |
| gagctggaaa agaccaagca gctgcgcctg gacaccgatc aggtgtacgg caacattgcg | 1380 |
| acctacaact ttgagaacgg ccgcgtgcgc gtggataccg gcagcaactg gtctgaggtg | 1440 |
| ctgccacaga ttcaggaaac gaccgcgcgc atcatcttca acggcaaaga tctgaacctg | 1500 |
| gtggaacgtc gcatcgcggc agtgaaccca agcgatccac tggaaacgac caaaccggac | 1560 |
| atgaccctga agaggcgct gaaaattgca tttggcttca acgagccgaa tggcaacctg | 1620 |
| cagtatcagg gcaagacat caccgagttt gacttcaact tcgatcaaca gacctctcag | 1680 |
| aacatcaaga accagctggc agaactgaat gcgaccaaca tctacaccgt gctggacaag | 1740 |

```
attaaactga acgcaaagat gaacattctg attcgtgata aacgctttca ctatgatcgt    1800
aacaacattg cggtgggtgc agacgaaagc gttgtgaaag aagcgcatcg tgaagtgatc    1860
aactctagca ccgaaggcct gctgctgaac attgacaaag atatccgtaa aattctgagc    1920
ggctacatcg tggaaattga agataccgaa ggtctgaaag aagtgatcaa cgatcgctat    1980
gacatgctga acatttctag cctgcgccaa gatggcaaga ccttcatcga cttcaagaag    2040
tacaacgaca aactgccgct gtacatcagc aacccgaact acaaagtgaa cgtttatgcg    2100
gtgaccaaag agaacaccat cattaacccg agcgagaatg gcgacacctc taccaacggc    2160
attaaaaaga ttctgatctt cagcaagaaa ggttatgaga ttggc                    2205
```

<210> SEQ ID NO 23
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95% identity) of SEQ ID NO 1

<400> SEQUENCE: 23

```
gaagtgaagc aggagaaccg tctgctgaac gaaagcgaat ctagctctca gggcctgctg      60
ggctattatt tcagcgatct gaacttccag gcgccaatgg ttgtgaccag ctctacgacc     120
ggcgatctga gcatcccgag cagcgagctg gagaacattc cgagcgagaa ccagtatttt     180
cagagcgcga tttggagcgg ctttattaaa gtgaagaaaa gcgatgagta acctttgcg     240 acgagcgcag ataaccatgt gaccatgtgg gtggatgatc aggaagtgat caacaaagcg     300
agcaacagca acaagatccg cctggagaag ggtcgcctgt atcagattaa gatccagtac     360
cagcgcgaga tccgaccga gaaaggcctg gacttcaaac tgtactggac ggatagccag     420
aacaagaaag aagtgattag ctctgataac ctgcaactgc cggaactgaa acagaagagc     480
agcaacagcc gtaagaaacg cagcacctct gcaggcccga ccgttccgga ccgcgacaac     540
gatggcattc cggacagcct ggaagtggaa ggttataccg tggatgtgaa gaacaaacgc     600
accttcctga gcccgtggat tagcaacatt catgagaaga aaggcctgac caaatacaaa     660
agcagcccgg agaagtggag caccgcgagc gatccgtata gcgatttttga aaagtgacc     720 ggccgcattg ataagaacgt gagcccggaa gcgcgccatc cactggttgc agcgtatccg     780
attgtgcatg ttgacatgga gaacattatt ctgagcaaaa acgaagatca gagcacccag     840
aacacggaca gccagacccg cacgatcagc aagaacacct ctacgagccg tacccatacc     900
agcgaagttc atggcaatgc ggaagtgcat gcaagcttct ttgacattgg tggcagcgtg     960
agcgcgggct tcagcaacag caacagcagc acggtggcaa ttgatcatag cctgagcctg    1020
gcgggcgaac gtacctgggc ggaaaccatg gccctgaaca ccgcggatac cgcacgtctg    1080
aatgcgaaca ttcgttatgt gaacaccggc accgcgccaa tctataacgt gctgccgacc    1140
acgagcctgg tgctgggcaa gaccagacc ctggcgacca tcaaagcaaa agagaaccag    1200
ctgtctcaga ttctggcacc gaacaactac tatccgagca agaacctggc gccaattgca    1260
ctgaacgcgc aggatgattt ttctagcacg ccgatcacca tgaactacaa tcagttctg    1320 gaactggaga aaaccaaaca actgcgcctg gataccgatc aggtgtatgg caacatcgcg    1380
acctacaact ttgagaacgg ccgcgttcgc gtggataccg ttctaactg gagcgaagtg    1440 ctgccgcaga tccaggaaac caccgcgcgc attatcttca acggcaaaga tctgaatctg    1500
```

| | |
|---|---|
| gtggaacgcc gcatcgcggc ggtgaaccca tctgacccgc tggaaacgac caagccggat | 1560 |
| atgaccctga agaagcgct gaagattgcg tttggcttca atgaaccgaa tggcaacctg | 1620 |
| cagtaccagg gtaaagacat caccgagttt gacttcaact tcgaccaaca gacctctcag | 1680 |
| aacattaaga accagctggc agaactgaat gcgaccaaca tctacaccgt gctggacaag | 1740 |
| atcaaactga acgcaaagat gaacattctg attcgtgata agcgctttca ctatgaccgc | 1800 |
| aacaacattg cggtgggtgc agacgaaagc gttgtgaaag aagcgcaccg tgaagtgatc | 1860 |
| aactctagca ccgaaggcct gctgctgaac attgacaaag atattcgtaa gattctgagc | 1920 |
| ggctacattg tggagatcga agataccgaa ggtctgaaag aagttattaa cgatcgctat | 1980 |
| gatatgctga acatctctag cctgcgtcag gatggcaaga ccttcatcga cttcaagaag | 2040 |
| tacaacgaca aactgccgct gtatatcagc aacccgaatt acaaagtgaa cgtgtacgcg | 2100 |
| gtgaccaaag agaacaccat cattaaccca agcgagaatg gcgataccag caccaacggc | 2160 |
| atcaagaaga ttctgatctt cagcaagaaa ggctatgaga ttggc | 2205 |

<210> SEQ ID NO 24
<211> LENGTH: 2205
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Sequence variant (94% identity) of SEQ ID No 1

<400> SEQUENCE: 24

| | |
|---|---|
| gaagtgaaac aggagaaccg tctgctgaac gaatctgaaa gcagctctca gggcctgctg | 60 |
| ggctactatt tttctgatct gaacttccag gcaccgatgg ttgtgaccag ctctaccacc | 120 |
| ggcgacctgt ctattccgag cagcgaactg agaacattc cgagcgaaaa ccagtacttt | 180 |
| cagagcgcga tttggagcgg ctttatcaaa gtgaagaaaa gcgatgagta cacctttgcg | 240 |
| acgtctgcgg ataaccatgt gaccatgtgg gtggacgatc aggaggtgat caacaaagca | 300 |
| agcaacagca acaagattcg cctggagaag ggtcgcctgt atcagatcaa gattcagtat | 360 |
| cagcgcgaga atccgaccga aaaggcctg gatttcaaac tgtattggac cgatagccag | 420 |
| aacaaaaaag aggtgattag cagcgataac ctgcaactgc cggaactgaa gcagaagagc | 480 |
| agcaacagcc gcaagaaacg cagcacgtct gcaggcccga ccgttccaga tcgcgacaac | 540 |
| gatggcattc cggatagcct ggaagtggaa ggttataccg ttgatgtgaa aaacaaacgt | 600 |
| acctttctga gcccgtggat tagcaacatt catgagaaga aaggcctgac caagtacaaa | 660 |
| agcagcccgg agaagtggag caccgcgtct gatccgtata gcgactttga gaaagtgacc | 720 |
| ggccgcattg ataaaaacgt gagcccggag gcgcgccacc cactggttgc ggcgtatccg | 780 |
| attgtgcatg ttgacatgga aaacatcatc ctgagcaaga acgaagacca gagcacccag | 840 |
| aacacggaca gccagacccg cacgatcagc aagaacacca gcacgagccg tacgcatacc | 900 |
| agcgaagtgc atggcaatgc ggaagtgcat gcgagcttct tcgacattgg tggcagcgtg | 960 |
| agcgcgggct tcagcaacag caacagcagc accgtgcgca ttgatcatag cctgagcctg | 1020 |
| gcgggcgaac gtacctgggc agaaaccatg gccctgaaca cggcggatac cgcacgtctg | 1080 |
| aatgcgaaca ttcgctatgt gaacaccggt accgcaccga tttataacgt gctgccgacc | 1140 |
| acgagcctgg tgcgggtaa gaatcagacc ctggcgacca tcaaagcgaa agagaaccag | 1200 |
| ctgagccaga ttctggcacc aaacaactac tacccgtcta aaaacctggc gccgattgca | 1260 |
| ctgaatgcgc aggatgattt cagcagcacc ccgatcacca tgaactataa tcagttcctg | 1320 |

```
gagctggaga agaccaaaca actgcgcctg gacaccgacc aggtttacgg caacatcgcg    1380
acctataact ttgagaacgg ccgcgttcgc gtggacaccg gtagcaactg gtctgaagtg    1440
ctgccgcaga tccaggaaac gaccgcgcgt attattttta acggcaagga tctgaacctg    1500
gtggaacgtc gtattgcagc agtgaaccca agcgacccac tggaaaccac caagccggat    1560
atgaccctga agaagcgct gaagattgca tttggcttca atgagccgaa tggcaacctg    1620
cagtatcagg gcaaggatat caccgaattt gacttcaact tgaccaaca gacctctcag    1680 aacatcaaga accagctggc ggaactgaac gcgaccaaca tctacaccgt gctggacaaa    1740
atcaaactga acgcgaagat gaacattctg attcgcgaca aacgcttcca ctacgatcgt    1800
aacaacatcg cggtgggcgc agatgaaagc gttgtgaagg aagcgcatcg tgaagtgatc    1860
aactctagca cggaaggcct gctgctgaac atcgataaag acattcgcaa gattctgagc    1920
ggctacattg tggagattga ggataccgaa ggtctgaaag aagtgattaa cgatcgctat    1980
gatatgctga acatctctag cctgcgccag gatggcaaga ccttcatcga tttcaagaaa    2040
tataacgata agctgccgct gtacatcagc aatccgaact ataaagtgaa cgtgtatgcg    2100
gtgaccaaag aaaacaccat cattaaccca agcgagaatg gcgataccag caccaacggc    2160
atcaaaaaga ttctgatctt cagcaagaag ggctacgaaa ttggc                    2205
```

<210> SEQ ID NO 25
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94% identity) of SEQ ID No 1

<400> SEQUENCE: 25

```
gaagttaaac aggagaaccg tctgctgaac gagagcgaat ctagcagcca gggcctgctg      60
ggttactatt tcagcgatct gaactttcag gcaccgatgg tggtgaccag cagcaccacc     120
ggcgatctga gcattccgag ctctgaactg gaaaacattc cgagcgagaa ccagtatttt     180
cagtctgcga tttggagcgg cttcattaag gtgaaaaaaa gcgatgagta cctttgca       240 acgtctgcga taaccatgt gaccatgtgg gtggatgatc aggaagtgat caacaaagcg     300
agcaacagca caagattcg cctggaaaaa ggtcgtctgt atcagatcaa gatccagtac     360
cagcgcgaaa acccgaccga aaaggtctg gacttcaaac tgtattggac cgatagccag     420
aacaaaaaag aggtgattag cagcgataac ctgcaactgc cggaactgaa acagaagagc     480
agcaacagcc gcaagaaacg cagcacctct gcaggcccga ccgttccaga tcgcgacaac     540
gatggcattc cggacagcct ggaagtggaa ggttataccg tggatgtgaa gaacaaacgc     600
accttcctga gcccgtggat tagcaacatt catgagaaga aaggcctgac caagtacaaa     660
agcagcccgg agaagtggag caccgcaagc gatccatata gcgattttga agaggttacc     720
ggccgtatcg ataagaacgt gtctccggaa gcgcgtcacc cactggttgc agcgtatccg     780
attgttcatg tggacatgga gaacatcatt ctgagcaaga acgaagatca gagcacccag     840 aacacgata gccagacccg cacgatcagc aagaacacca gcacgagccg tacccacacc     900
agcgaggtgc atggcaatgc ggaagtgcat gcagcttttt ttgacattgg cggcagcgtg     960
agcgcgggct ttagcaacag caacagcagc accgtggcga ttgatcatag cctgagcctg    1020
gcgggcgagc gtacctgggc ggaaaccatg ggcctgaaca cggcggatac ggcgcgcctg    1080
```

```
aatgcgaaca ttcgctatgt gaacaccggc accgcgccga tttataacgt gctgccgacc    1140
accagcctgg tgctgggcaa gaaccagacc ctggcgacca tcaaagcgaa ggagaaccag    1200
ctgtctcaaa ttctggcacc aaacaactac tatccgagca agaacctggc accgatcgcg    1260
ctgaatgcgc aggatgattt tagcagcacc ccgatcacca tgaactacaa tcagtttctg    1320
gagctggaga agaccaaaca gctgcgcctg gataccgatc aggtgtacgg caacatcgcg    1380
acctacaact ttgagaacgg ccgcgttcgc gtggataccg gctctaactg gagcgaagtg    1440
ctgccgcaga ttcaggaaac caccgcacgc attattttca acggcaaaga tctgaacctg    1500
gtggaacgcc gcattgcggc agtgaaccca tctgacccac tggaaacgac caagccggat    1560
atgaccctga agaagcgct gaagatcgca tttggcttca cgaaccgaa tggcaacctg     1620 cagtaccagg gcaaggacat caccgagttc gacttcaact tcgaccaaca gacctctcag    1680
aacatcaaaa accagctggc ggaactgaat gcgacgaaca tttacaccgt gctggacaag    1740
atcaaactga acgcaaagat gaacattctg attcgtgaca aacgcttcca ttatgatcgt    1800
aacaacattg cggttggtgc agacgaaagc gttgtgaagg aagcgcatcg tgaagtgatc    1860
aacagcagca ccgaaggcct gctgctgaac attgacaaag acattcgtaa aattctgagc    1920
ggctatattg tggagattga agataccgaa ggcctgaaag aagtgatcaa cgatcgctat    1980
gacatgctga acatctctag cctgcgccag gatggtaaga cgttcatcga cttcaaaaag    2040
tacaatgaca aactgccgct gtacatttct aatccgaact acaaagtgaa cgtgtatgcg    2100
gtgaccaagg aaaacacgat cattaatccg agcgagaatg gtgataccctc taccaacggc    2160 atcaagaaaa tcctgatctt cagcaagaaa ggctatgaga tcggc                   2205
```

<210> SEQ ID NO 26
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94% identity) of SEQ ID NO 1

<400> SEQUENCE: 26

```
gaagtgaagc aggagaaccg tctgctgaac gaaagcgaat ctagctctca gggtctgctg     60
ggctattatt tcagcgatct gaacttccag gcgccaatgg ttgtgaccag ctctacgacc    120
ggcgatctga gcatcccgag ctctgagctg gagaacattc cgagcgagaa ccagtatttt    180
cagagcgcga tttggagcgg cttttattaa gtgaagaaaa gcgatgagta acctttgcg    240 acgagcgcag ataaccatgt gaccatgtgg gtggatgatc aggaagtgat caacaaagcg    300
agcaacagca acaagatccg cctggagaag ggccgcctgt atcagattaa gatccagtac    360
cagcgcgaga atccgaccga gaaaggcctg gacttcaaac tgtactggac ggatagccag    420
aacaagaaag aagtgattag cagcgataac ctgcaactgc cggaactgaa acagaagagc    480
agcaacagcc gtaagaaacg cagcacctct gcaggcccga ccgttccgga ccgcgacaac    540
gacggcattc cggacagcct ggaagtggaa ggttataccg tggatgtgaa gaacaaacgc    600
accttcctga gcccgtggat tagcaacatt catgagaaga aaggcctgac caaatacaaa    660
tctagcccgg agaagtggag caccgcgagc gatccgtata gcgattttga gaaagtgacc    720
ggccgcattg ataagaacgt gagcccggaa gcgcgccatc cactggttgc agcgtatccg    780
attgtgcatt ttgacatgga gaacattatt ctgagcaaaa acgaagatca gagcacccag    840
aacacggaca gccagacccg cacgatcagc aagaacacct ctacgagccg tacccatacc    900
```

```
agcgaagttc atggcaatgc ggaagtgcat gcaagcttct ttgacattgg tggcagcgtg    960
agcgcgggct tcagcaacag caacagcagc acggtggcaa ttgatcatag cctgagcctg   1020
gcgggcgaac gtacctgggc ggaaaccatg ggcctgaaca ccgcggatac cgcacgtctg   1080
aatgcgaaca ttcgttatgt gaacaccggc accgcgccaa tctataacgt gctgccgacc   1140
acgagcctgg tgctgggcaa gaaccagacc ctggcgacca tcaaagcgaa agagaaccag   1200
ctgtctcaga ttctggcacc gaacaactac tatccgagca agaacctggc gccaattgca   1260
ctgaacgcgc aggatgattt ttctagcacg ccgatcacca tgaactacaa tcagtttctg   1320
gaactggaga aaaccaaaca actgcgcctg gataccgatc aggtgtatgg caacatcgca   1380
acctacaact tgagaacgg ccgcgttcgc gtggataccg gttctaactg gagcgaagtg   1440
ctgccgcaaa tccaggaaac caccgcgcgc attatcttca cggcaaaga tctgaatctg   1500 gtggaacgcc gcatcgcggc ggtgaaccca tctgacccgc tggaaaccac caagccggat   1560
atgaccctga agaagcgct gaagattgcg tttggcttca tgaaccgaa tggcaacctg   1620 cagtaccagg gtaaagacat caccgaattt gacttcaact tcgaccagca gacctctcag   1680
aacattaaga accagctggc agaactgaat gcgaccaaca tctacaccgt gctggataag   1740
atcaaactga acgcaaagat gaacattctg attcgtgata gcgctttca ctatgaccgc   1800 aacaacattg cggtgggtgc agacgaaagc gttgtgaaag aagcgcaccg tgaggtgatc   1860
aacagcagca ccgaaggcct gctgctgaac attgacaaag atattcgtaa gattctgagc   1920
ggctacattg tggagatcga agatacgaaa ggtctgaaag aagttattaa cgatcgctat   1980
gatatgctga acatctctag cctgcgtcag gatggcaaga ccttcatcga cttcaagaag   2040
tacaacgaca aactgccgct gtatatcagc aacccgaatt acaaagtgaa cgtgtacgcg   2100
gtgaccaaag agaacaccat cattaaccca agcgagaatg gcgataccag caccaacggc   2160
atcaagaaga ttctgatctt cagcaagaaa ggctatgaga ttggc                   2205
```

<210> SEQ ID NO 27  
<211> LENGTH: 2205  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<223> OTHER INFORMATION: Sequence variant (93% identity) of SEQ ID No 1

<400> SEQUENCE: 27

```
gaagtgaaac aggaaaatcg tctgctgaac gaatctgaaa gcagctctca gggcctgctg     60
ggctactatt tttctgatct gaacttccag gcaccgatgg ttgtgaccag ctctaccacc    120
ggcgacctgt ctattccgag cagcgaactg gagaacattc cgagcgaaaa ccagtacttt    180
cagagcgcga tttggagcgg ctttatcaaa gtgaagaaaa gcgatgagta cacctttgcg    240
acgtctgcgg ataaccatgt gaccatgtgg gtggacgacc aggaggtgat caacaaagcg    300
agcaacagca caagattcg cctggaaaag ggtcgcctgt atcagatcaa gattcagtat    360
cagcgcgaga acccgaccga agggcctg gatttcaaac tgtattggac cgatagccag    420
aacaaaaaag aggtgattag cagcgataac ctgcaactgc cggagctgaa gcagaagagc    480
agcaacagcc gcaaaaaacg cagcacgtct gcaggcccga ccgttccaga tcgcgacaac    540
gatggcattc cggatagcct ggaagtggaa ggttataccg ttgatgtgaa aaacaaacgt    600
acctttctga gcccgtggat tagcaacatt catgagaaga aaggcctgac caagtacaaa    660
```

```
agcagcccgg agaagtggag caccgcatct gatccgtata gcgactttga gaaagtgacc    720
ggccgcattg ataaaaacgt gagcccggag gcgcgccatc cactggttgc agcgtatccg    780
attgtgcatg ttgatatgga aacatcatc ctgagcaaga acgaagacca gagcacccag    840
aacaccgaca gccagacccg cacgatcagc aagaacacca gcacgagccg tacgcatacc    900
agcgaagtgc acggcaatgc agaagtgcat gcgagcttct tcgacattgg tggcagcgtg    960
agcgcgggct tcagcaactc taacagcagc accgtggcga ttgatcatag cctgagcctg   1020
gcgggcgagc gtacctgggc ggaaaccatg ggcctgaaca cggcggatac cgcgcgtctg   1080
aatgcgaaca ttcgctatgt gaacaccggt accgcaccga tttataacgt gctgccgacc   1140
acgagcctgg tgctgggtaa gaatcagacc ctggcaacca tcaaagcgaa agagaaccag   1200
ctgagccaga ttctggcacc aaacaactac tacccgagca aaaacctggc gccgattgcg   1260
ctgaatgcgc aggatgattt cagcagcacc ccgatcacca tgaactataa tcagttcctg   1320
gagctggaga gaccaaaaca actgcgcctg gacacggacc aggtttacgg caacatcgcg   1380
acctataact ttgagaacgg ccgcgttcgc gtggacaccg tagcaactg gtctgaggtg   1440 ctgccgcaga tccaggaaac gaccgcgcgt attattttta acggcaagga tctgaacctg   1500
gtggaacgtc gtattgcagc ggtgaaccca agcgacccac tggaaaccac caagccggat   1560
atgaccctga agaagcgct gaagattgca tttggcttca atgagccgaa tggcaacctg   1620
cagtatcagg gcaaggatat caccgaattt gacttcaact ttgaccaaca gacctctcag   1680
aacatcaaga accagctggc ggaactgaac gcaaccaaca tctacaccgt gctggataaa   1740
atcaaactga acgcgaagat gaacattctg attcgcgaca aacgcttcca ctacgaccgt   1800
aacaacatcg cggtgggcgc agatgaaagc gttgtgaagg aagcgcatcg tgaagtgatc   1860
aactctagca cggaaggcct gctgctgaac atcgataaag atattcgcaa gattctgagc   1920
ggctacattg tggagattga ggataccgaa ggtctgaaag aagtgattaa cgatcgctat   1980
gatatgctga acatctctag cctgcgccag gatggcaaga ccttcatcga cttcaagaaa   2040
tataacgata gctgccgct gtacatcagc aatccgaact ataaagtgaa cgtgtatgcg   2100
gtgaccaaag aaaacaccat cattaaccca agcgaaaatg gcgataccag caccaacggc   2160
atcaaaaaga ttctgatctt cagcaagaag ggctacgaaa ttggc                   2205
```

<210> SEQ ID NO 28
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93% identity) of SEQ ID NO 1

<400> SEQUENCE: 28

```
gaagttaaac aggagaaccg tctgctgaac gagagcgaat ctagcagcca gggcctgctg     60
ggttattatt tcagcgatct gaactttcag gcaccgatgg tggtgaccag cagcaccacc    120
ggcgatctga gcattccgag cagcgaactg gaaaacattc cgagcgagaa ccagtatttt    180
cagtctgcga tttggagcgg cttcattaag gtgaaaaaaa gcgatgaata cccttgca     240 acgtctgcga taaccatgt gaccatgtgg gttgatgatc aggaagtgat caacaaagcg    300
agcaacagca acaagattcg cctggaaaaa ggtcgtctgt atcagattaa gatccagtac    360
cagcgcgaaa acccgaccga gaaggtctg gacttcaaac tgtattggac cgatagccag    420
aacaaaaaag aggtgattag cagcgataac ctgcaactgc cggaactgaa acagaagagc    480
```

```
agcaacagcc gcaagaaacg cagcacctct gcaggcccaa ccgttccgga ccgcgacaac      540
gatggcattc cggacagcct ggaagtggaa ggttataccg tggatgtgaa aaacaaacgc      600
acgttcctga gcccgtggat tagcaacatc catgagaaga aaggcctgac caagtacaag      660
agcagcccgg aaaagtggag caccgcaagc gatccatata gcgattttga aaggttacc       720 ggccgtattg ataagaacgt gtctccggaa gcgcgtcacc cactggtggc agcgtatccg      780
attgttcatg tggacatgga aaacatcatt ctgagcaaga acgaagatca gagcacccag      840
aacacggata gccagacccg cacgatcagc aagaacacca gcacgagccg tacccacacc      900
agcgaggtgc atggcaatgc ggaagtgcat gcgagctttt ttgacattgg cggcagcgtg      960
agcgcgggct ttagcaacag caacagcagc accgtggcga ttgatcatag cctgagcctg     1020
gcgggcgagc gtacctgggc ggagaccatg ggcctgaaca cggcggatac cgcgcgcctg     1080
aacgcgaaca ttcgctatgt gaacaccggc accgcgccga tttataacgt gctgccgacc     1140
accagcctgg tgctgggcaa gaaccagacc ctggcgacca tcaaagcgaa ggagaaccag     1200
ctgtctcaaa ttctggcacc aaacaactac tatccgagca agaacctggc accgatcgcg     1260
ctgaatgcgc aggatgattt tagctctacc ccgatcacca tgaactacaa tcagtttctg     1320
gagctggaga agaccaaaca gctgcgcctg gataccgatc aggtgtacgg caacatcgcg     1380
acctacaact ttgagaacgg ccgcgttcgc gtggataccg gctctaactg gagcgaagtg     1440
ctgccgcaga ttcaggaaac caccgcacgc attattttca acggcaaaga tctgaacctg     1500
gtggaacgtc gcattgcggc agtgaaccca tctgacccac tggaaacgac caagccggat     1560
atgaccctga agaagcgct gaagatcgca tttggcttca acgaaccgaa tggcaacctg     1620
cagtaccagg gcaaggacat caccgagttc gacttcaact tcgaccaaca gacctctcag     1680
aacatcaaaa atcagctggc ggaactgaat gcgacgaaca tttacaccgt gctggacaag     1740
atcaaactga acgcaaagat gaacattctg attcgtgaca aacgcttcca ttacgatcgt     1800
aacaacattg cggttggtgc agacgagagc gttgtgaagg aagcgcatcg cgaggtgatc     1860
aacagcagca ccgaaggcct gctgctgaac attgacaaag acattcgtaa aattctgagc     1920
ggctatattg tggagatcga agataccgaa ggcctgaaag aagtgatcaa cgatcgctat     1980
gatatgctga acatctctag cctgcgccag gatggtaaga cgttcatcga cttcaaaaag     2040
tacaatgaca aactgccgct gtacatttct aatccgaact acaaagtgaa cgtgtatgcg     2100
gtgaccaagg aaaacacgat cattaatccg agcgagaatg gtgataccta ccaacggc       2160 atcaagaaaa tcctgatctt cagcaagaaa ggctatgaga tcggc                      2205
```

<210> SEQ ID NO 29
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93% identity) of SEQ ID No 1

<400> SEQUENCE: 29

```
gaagtgaagc aggagaaccg tctgctgaac gaaagcgaaa gcagcagcca gggtctgctg       60
ggctattatt tcagcgatct gaacttccag gcgccgatgg ttgtgaccag ctctacgacc      120
ggcgatctga gcatcccgag ctctgagctg gagaacattc gagcgagaa ccagtatttt       180 cagagcgcga tttggagcgg ctttattaaa gtgaagaaat ctgatgagta tacctttgcg      240
```

```
acgagcgcag ataaccatgt gaccatgtgg gtggatgatc aggaagtgat caacaaagcg      300
agcaacagca acaagatccg cctggaaaag ggccgcctgt atcagattaa gatccagtac      360
cagcgcgaga atccgaccga gaaaggcctg gacttcaaac tgtactggac ggatagccag      420
aacaagaaag aagtgattag cagcgataac ctgcaactgc cggaactgaa acagaagagc      480
agcaacagcc gtaagaaacg cagcacctct gcaggcccga ccgttccgga ccgcgacaac      540
gacggcattc cggacagcct ggaagtggag ggttataccg tggatgtgaa gaacaaacgc      600
accttcctga gcccgtggat tagcaacatt catgagaaga aaggcctgac caaatacaaa      660
tctagcccgg agaagtggag caccgcgagc gatccgtata gcgattttga gaaagtgacc      720
ggccgcattg ataagaacgt gagcccagaa gcgcgccatc cactggttgc agcgtatccg      780
attgtgcatg ttgacatgga gaacattatt ctgagcaaaa acgaagatca gagcacccag      840
aacacggaca gccagacccg cacgatcagc aagaacacct ctacgagccg tacccatacc      900
agcgaagtgc atggcaatgc ggaagtgcac gcaagcttct ttgacattgg tggcagcgtg      960
agcgcgggct tcagcaacag caacagcagc acggtggcaa ttgatcatag cctgagcctg     1020
gcgggcgaac gtacctgggc agaaaccatg ggcctgaaca ccgcagatac cgcacgtctg     1080
aatgcgaaca ttcgttatgt taacaccggc accgcgccaa tctataacgt gctgccgacc     1140
acgagcctgg tgctgggcaa gaaccagacc ctggcgacca tcaaagcgaa agagaaccag     1200
ctgtctcaga ttctggcacc gaacaactac tatccgtcta agaacctggc gccaattgca     1260
ctgaacgcgc aggatgattt ttctagcacg ccgatcacca tgaactacaa tcagtttctg     1320
gaactggaga aaaccaaaca actgcgcctg gataccgatc aggtgtatgg caacatcgca     1380
acctacaact ttgagaacgg ccgcgttcgc gtggataccg gttctaactg gagcgaagtg     1440
ctgccgcaga tccaagaaac caccgcgcgc attatcttca acggcaaaga tctgaatctg     1500
gtggaacgcc gtatcgcggc ggtgaaccca tctgacccgc tggaaaccac caagccggat     1560
atgaccctga agaagcgct gaagattgcg tttggcttca atgaaccgaa tggcaacctg     1620
cagtaccagg gtaaagacat caccgaattt gacttcaact tcgaccagca gacctctcag     1680
aacattaaga accagctggc ggaactgaat gcgaccaaca tctacaccgt gctggataaa     1740
atcaaactga acgcgaagat gaacattctg attcgtgata gcgctttca ttatgaccgc     1800
aacaacattg cggtgggtgc agacgaaagc gttgtgaaag aagcgcaccg tgaggtgatc     1860
aacagcagca ccgaaggcct gctgctgaac attgacaaag atattcgtaa gattctgagc     1920
ggctacattg tggagatcga agatacgaa ggtctgaaag aagttattaa cgatcgctat     1980
gatatgctga acatctctag cctgcgccag gatggcaaga ccttcatcga cttcaagaag     2040
tacaacgaca agctgccgct gtatatcagc aacccgaatt acaaagtgaa cgtgtacgcg     2100
gtgaccaaag agaacaccat cattaaccca agcgagaatg gcgataccag caccaacggc     2160
atcaagaaga ttctgatctt cagcaagaaa ggctatgaga ttggc                     2205
```

<210> SEQ ID NO 30
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92% identity) of SEQ ID NO 1

<400> SEQUENCE: 30

```
gaagtgaaac aggaaaatcg tctgctgaac gaaagcgaaa gcagcagcca gggcctgctg       60
```

```
ggctactatt tttctgatct gaacttccag gcaccaatgg ttgtgaccag ctctaccacc    120
ggcgacctga gcattccgag ctctgaactg gagaacattc cgagcgaaaa ccagtacttt    180
cagagcgcga tttggagcgg ctttatcaaa gtgaagaaat ctgatgagta ccctttgcg     240
acgtctgcgg ataaccatgt gaccatgtgg gttgacgacc aggaggtgat caacaaagcg    300
agcaacagca acaagattcg cctggaaaag ggtcgcctgt atcagatcaa gatccagtat    360
cagcgcgaga acccgaccga aagggcctg gatttcaaac tgtattggac cgatagccag     420
aacaaaaaag aggtgattag cagcgataac ctgcaactgc cggagctgaa gcagaagagc    480
agcaacagcc gcaaaaaacg cagcacgtct gcaggcccga ccgtgccgga tcgcgacaac    540
gatggcattc cggatagcct ggaagtggaa ggttataccg ttgatgtgaa aaacaagcgt    600
acctttctga gcccgtggat tagcaacatt catgagaaga aaggcctgac caagtacaaa    660
agcagcccgg agaagtggag caccgcatct gatccgtata gcgacttcga gaaagtgacc    720
ggccgtattg ataaaaacgt gagcccggag gcgcgccatc cgctggttgc agcgtatccg    780
attgtgcatg ttgatatgga aaacatcatc ctgagcaaga acgaagacca gtctacccag    840
aacaccgaca gccagacccg cacgatcagc aagaacacca gcaccagccg tacgcatacc    900
agcgaagtgc acggcaatgc agaagtgcat gcgagcttct tcgacattgg tggcagcgtg    960
agcgcgggct tcagcaactc taacagcagc accgtggcga ttgatcattc tctgagcctg   1020
gcgggcgagc gtacctgggc ggaaaccatg gcctgaaca cggcggatac ggcgcgtctg     1080
aatgcgaaca ttcgctatgt gaacaccggt accgcaccga tttataacgt gctgccgacc   1140
acgagcctgg tgctgggtaa gaatcagacc ctggcgacca tcaaagcgaa agagaaccag   1200
ctgagccaga ttctggcacc aaacaactac tacccaagca aaaacctggc gccgattgca   1260
ctgaatgcgc aggatgattt cagcagcacc ccgatcacca tgaactataa tcagttcctg   1320
gagctggaga agaccaaaca actgcgcctg gacacggacc aggtttacgg caacatcgcg   1380
acctataact ttgagaacgg ccgcgttcgc gtggacaccg gtagcaactg gtctgaagtg   1440
ctgccgcaga tccaggaaac gaccgcgcgt attatttta acggcaagga tctgaacctg    1500
gtggaacgtc gcattgcagc ggtgaaccca agcgaccac tggaaaccac caagccggat    1560
atgaccctga agaagcgct gaagattgca tttggcttca atgagccgaa tgcaacctg     1620
cagtatcagg gcaaggatat caccgaattt gactttaact tcgaccaaca gacctctcag   1680
aacatcaaga accagctggc ggaactgaac gcaaccaaca tctacaccgt gctggataaa   1740
atcaaactga cgcgaagat gaacattctg attcgcgaca gcgctttca ctacgaccgt     1800
aacaacatcg cggtgggcgc agatgaaagc gttgtgaagg aagcgcatcg tgaggtgatc   1860
aactctagca cggaaggcct gctgctgaac attgataaag atattcgcaa aattctgagc   1920
ggctacattg tggagattga ggataccgaa ggtctgaaag aagtgattaa cgatcgctat   1980
gatatgctga acatcagcag cctgcgccag gatggcaaga ccttcatcga cttcaagaag   2040
tataacgata agctgccgct gtacatcagc aatccgaact ataaagtgaa cgtgtatgcg   2100
gtgaccaaag aaaacaccat cattaaccca agcgaaaatg gcgataccag caccaacggc   2160
atcaaaaaaa ttctgatctt cagcaagaaa ggctacgaaa ttggc                   2205
```

<210> SEQ ID NO 31
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92% identity) of SEQ ID NO 1

<400> SEQUENCE: 31

```
gaagtgaaac aggaaaaccg tctgctgaac gagagcgaat ctagcagcca gggcctgctg      60
ggctattatt tcagcgatct gaactttcag gcaccgatgg tggtgacctc tagcaccacc     120
ggcgatctga gcattccgtc tagcgaactg gaaaatatcc aagcgagaa ccagtatttt      180
cagtctgcga tttggagcgg cttcattaag gttaaaaaaa gcgatgaata cctttgca       240
accagcgcgg ataaccatgt gaccatgtgg gttgatgatc aggaagtgat caacaaagcg     300
agcaacagca caagattcg cctggaaaaa ggtcgcctgt atcagattaa aatccagtac      360
cagcgtgaaa acccgaccga aaaggtctg gacttcaagc tgtattggac cgatagccag      420
aacaaaaaag aggtgattag cagcgataac ctgcaactgc cggaactgaa acagaagagc     480
agcaacagcc gcaagaaacg cagcacctct gcaggcccaa ccgttccgga ccgcgacaac     540
gatggcattc cggacagcct ggaagtggaa ggttataccg tggatgttaa aaacaaacgc     600
acgttcctga gcccgtggat tagcaacatc catgagaaga aaggcctgac caagtacaag     660
agcagcccgg aaaagtggag caccgcaagc gatccgtata gcgattttga aaggttacc     720
ggccgtattg ataagaacgt gtctccggaa gcgcgccacc cactggtggc agcgtacccg     780
attgttcatg tggatatgga gaacatcatt ctgagcaaga acgaagatca gagcacgcag     840
aacacggata gccagacccg caccatcagc aagaacacca gcaccagccg tacccacacc     900
agcgaggtgc atggcaatgc ggaagtgcat gcgagctttt ttgacattgg cggcagcgtg     960
agcgcgggct tttctaatag caacagcagc accgtggcga tcgatcatag cctgagcctg    1020
gcgggcgagc gtacctgggc ggagaccatg ggcctgaaca cggcggatac ggcgcgtctg    1080
aacgcgaaca ttcgctatgt gaacaccggc accgcgccga tttataacgt gctgccgacc    1140
accagcctgg tgctgggcaa gaaccagacc ctggcgacca tcaaagcgaa ggaaaaccag    1200
ctgtctcaaa ttctggcgcc aaacaactac tatccgagca agaacctggc accgatcgcg    1260
ctgaatgcgc aggatgattt tagctctacc ccgattacca tgaactacaa tcagtttctg    1320
gagctggaga agaccaaaca gctgcgtctg gatacggatc aggtgtacgg caacatcgcg    1380
acgtacaact tcgagaacgg ccgcgttcgc gtggataccg gcagcaactg gagcgaagtg    1440
ctgccgcaga ttcaggaaac cacggcacgc attattttca cggcaaaaga tctgaacctg    1500
gtggaacgtc gcattgcggc agtgaaccca tctgacccac tggagacgac caagccggat    1560
atgaccctga aggaggcgct gaagattgca tttggcttca cgaaccgaa cggcaacctg     1620
cagtaccagg gtaaggacat caccgaattt gacttcaact tcgaccaaca gacctctcag    1680
aacatcaaaa atcagctggc ggaactgaat gcaacgaaca tctacaccgt gctggacaag    1740
atcaaactga acgcaaaaat gaacattctg attcgtgaca aacgcttcca ttatgatcgt    1800
aacaacattg cggtgggtgc agacgaaagc gttgtgaagg aagcgcatcg cgaggtgatc    1860
aacagcagca ccgagggcct gctgctgaac attgacaaag acattcgcaa aattctgagc    1920
ggctatattg tggagatcga agataccgaa ggcctgaagg aagtgatcaa cgatcgctat    1980
gacatgctga acatttctag cctgcgccag gatggtaaga ccttcatcga cttcaagaaa    2040
tacaatgaca aactgccgct gtacattagc aatccgaact acaaagtgaa cgtgtatgcg    2100
gtgaccaagg agaacaccat cattaacccg agcgagaatg gtgataccag caccaacggc    2160
atcaaaaaaa tcctgatctt ctctaagaaa ggctatgaaa tcggc                    2205
```

<210> SEQ ID NO 32
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92% identity) of SEQ ID NO 1

<400> SEQUENCE: 32

```
gaagtgaagc aggagaaccg tctgctgaac gaaagcgaaa gcagcagcca gggtctgctg      60
ggctattatt tcagcgatct gaacttccag gcgccgatgg ttgtgaccag ctctaccacc     120
ggcgatctga gcatcccgag ctctgagctg agaacatcc cgagcgagaa ccagtatttt     180
cagagcgcga tttggagcgg ctttattaaa gtgaaaaaat ctgatgaata cctttgcg      240 acgagcgcag ataaccatgt gaccatgtgg gtggatgatc aggaagttat taacaaagcg     300
agcaacagca caagatccg cctggaaaag ggccgcctgt atcagattaa gatccagtac     360
cagcgcgaga tccgaccga aagggcctg gactttaaac tgtactggac ggatagccag     420
aacaagaaag aagtgattag cagcgacaac ctgcaactgc cggaactgaa acagaagagc     480
agcaacagcc gcaagaaacg cagcacctct gcaggcccga ccgttccgga ccgcgacaac     540
gacggcattc cggacagcct ggaagtggag ggttataccg tggatgtgaa gaacaaacgc     600
accttcctga gcccgtggat tagcaacatt catgagaaga aaggcctgac caaatacaaa     660
tctagcccgg agaagtggag caccgcgagc gatccgtata gcgattttga gaaagtgacc     720
ggccgcattg ataagaacgt gagcccagag gcgcgccatc cactggttgc ggcgtatccg     780
atcgtgcatg tggacatgga gaacattatc ctgagcaaaa acgaagacca gagcaccccag    840 aacacggaca gccagacccg cacgatcagc aagaacacct ctacgtctcg tacccacacc     900
agcgaagtgc atggcaatgc ggaagtgcat gcaagcttct ttgacattgg tggcagcgtg     960
agcgcgggct tcagcaacag caacagcagc acggtggcaa ttgatcatag cctgagcctg    1020
gcgggcgaac gtacctgggc agaaaccatg ggcctgaaca ccgcagatac cgcacgtctg    1080
aatgcgaaca ttcgttatgt taacaccggc accgcgccaa tctataacgt gctgccgacc    1140
acgagcctgg tgctgggcaa gaaccagacc ctggcgacca tcaaagcgaa agagaaccag    1200
ctgagccaga ttctggcacc aaacaactac tatccgtcta gaacctggc gccgattgca    1260 ctgaacgcgc aggatgattt ttctagcacg ccgatcacca tgaactacaa tcagtttctg    1320
gagctggaga aaaccaaaca actgcgcctg gataccgatc aggtgtatgg caacattgca    1380
acctacaact tgagaacgg ccgtgttcgc gtggataccg gttctaactg gagcgaagtg    1440
ctgccgcaga tccaagaaac gaccgcgcgc attatcttca acggcaaaga tctgaatctg    1500
gtggaacgcc gtatcgcggc ggtgaaccca tctgatccgc tggaaaccac caagccggat    1560
atgaccctga agaagcgct gaagattgcg tttggcttca tgaaccgaa tggcaacctg    1620 cagtaccagg gtaaagacat caccgaattc gacttcaact tcgatcagca gacctctcag    1680
aacattaaga accagctggc agaactgaat gcgaccaaca tctacaccgt gctggataaa    1740
atcaaactga acgcgaagat gaacattctg attcgtgata gcgctttca ttatgaccgc    1800 aacaacattg cggtgggcgc agacgaaagc gttgtgaaaa agcgcaccg tgaggtgatc    1860 aacagcagca ccgaaggcct gctgctgaac attgacaaag atattcgtaa gattctgagc    1920
ggttacattg tggagatcga agatacggaa ggtctgaaaa agttattaa cgaccgctat    1980 gatatgctga acatctctag cctgcgccag gatggcaaga ccttcatcga tttcaagaag    2040
```

| | |
|---|---|
| tacaacgaca agctgccgct gtatatcagc aacccgaatt acaaagtgaa cgtgtacgcg | 2100 |
| gtgaccaaag aaaacaccat tattaaccca agcgagaatg gcgataccag caccaacggc | 2160 |
| atcaagaaga ttctgatctt cagcaagaaa ggctatgaga ttggc | 2205 |

<210> SEQ ID NO 33
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (91% identity) of SEQ ID NO. 1

<400> SEQUENCE: 33

| | |
|---|---|
| gaagtgaaac aggaaaatcg tctgctgaac gaaagcgaaa gcagcagcca gggtctgctg | 60 |
| ggctactatt tttctgatct gaattttcag gcaccaatgg ttgtgaccag ctctaccacc | 120 |
| ggcgacctga gcattccgag ctctgaactg gagaacattc cgagcgaaaa ccagtacttt | 180 |
| cagagcgcga tttggagcgg ctttatcaaa gtgaagaaat ctgacgagta cacgtttgcg | 240 |
| acctctgcgg ataaccatgt gaccatgtgg gttgacgacc aggaggtgat caacaaagcg | 300 |
| agcaacagca ataagattcg cctggaaaag ggtcgcctgt atcagatcaa gatccagtat | 360 |
| cagcgcgaga acccgaccga aagggcctg gatttcaaac tgtattggac cgacagccag | 420 |
| aacaaaaaag aggtgattag cagcgataac ctgcaactgc cggaactgaa gcagaagagc | 480 |
| agcaacagcc gcaaaaaacg cagcacgtct gcaggcccga ccgtgccgga tcgcgataac | 540 |
| gatggcattc cggatagcct ggaagtgaaa ggctataccg ttgatgtgaa aaacaagcgt | 600 |
| acctttctga gcccgtggat tagcaacatt catgagaaga aaggcctgac caagtacaaa | 660 |
| agcagcccgg agaagtggag caccgcatct gatccgtata gcgacttcga aaggtgacc | 720 |
| ggccgtattg ataaaaacgt gagcccggag gcgcgccatc cgctggttgc agcgtatccg | 780 |
| attgtgcatg ttgatatgga aacatcatc ctgagcaaga acgaagacca gtctacgcag | 840 |
| aacaccgaca gccagacccg cacgatcagc aagaacacca gcaccagccg cacgcatacc | 900 |
| agcgaagtgc acggcaatgc agaagtgcat gcgagcttct tcgacatcgg tggcagcgtg | 960 |
| agcgcgggct tcagcaactc taacagcagc accgttgcga ttgatcattc tctgagcctg | 1020 |
| gcgggcgagc gtacctgggc ggaaaccatg ggcctgaaca cggcggatac ggcgcgtctg | 1080 |
| aatgcgaaca ttcgctatgt gaacaccggt accgcaccga tttataacgt gctgccaacc | 1140 |
| accagcctgg tgctgggtaa aaaccagacc ctggcgacca ttaaagcgaa agagaaccag | 1200 |
| ctgagccaga ttctggcacc aaacaactac tacccaagca aaaacctggc gccgattgca | 1260 |
| ctgaatgcgc aggatgattt cagcagcacc ccgatcacca tgaactataa tcagttcctg | 1320 |
| gagctggaga agaccaaaca actgcgcctg gacacggacc aggtttacgg caacattgcg | 1380 |
| acctataact ttgagaacgg ccgcgttcgc gtggacaccg gtagcaactg gtctgaagtg | 1440 |
| ctgccgcaga tccaggaaac gaccgcgcgt attatttta acggcaagga tctgaacctg | 1500 |
| gtggaacgtc gcattgcagc ggtgaaccca agcgacccac tggaaaccac caaaccggat | 1560 |
| atgacgctga agaagcgct gaagattgca tttggcttca atgagccgaa tgcaacctg | 1620 |
| cagtatcagg gcaaggatat caccgaattt gactttaact tcgatcaaca gacctctcag | 1680 |
| aacattaaga accagctggc ggaactgaac gcaaccaaca tctacaccgt gctggataaa | 1740 |
| atcaaactga acgcgaagat gaacatcctg attcgcgaca agcgtttcca ctacgaccgt | 1800 |

| | |
|---|---|
| aacaacatcg cggtgggcgc agatgaaagc gtggtgaagg aagcgcatcg tgaggtgatc | 1860 |
| aactctagca ccgaaggcct gctgctgaac attgataaag atattcgcaa aatcctgagc | 1920 |
| ggctacattg tggagattga ggataccgaa ggtctgaaag aagtgattaa cgatcgctat | 1980 |
| gatatgctga atatcagcag cctgcgccag gatggcaaga ccttcatcga cttcaagaag | 2040 |
| tataacgata agctgccgct gtacatcagc aacccgaact ataaagtgaa cgtgtatgcg | 2100 |
| gtgaccaaag agaacaccat cattaacccg agcgagaacg gcgataccag caccaacggc | 2160 |
| atcaaaaaga ttctgatttt cagcaagaaa ggctacgaaa tcggc | 2205 |

<210> SEQ ID NO 34
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91% identity) of SEQ ID NO. 1

<400> SEQUENCE: 34

| | |
|---|---|
| gaagtgaagc aggagaaccg cctgctgaac gaatctgaga gcagctctca gggcctgctg | 60 |
| ggctattact ttagcgatct gaactttcag gcaccgatgg tggtgacctc ttctaccacg | 120 |
| ggcgacctgt ctattccgag cagcgaactg gaaaacatcc cgagcgagaa ccagtacttc | 180 |
| cagtctgcaa tttggagcgg cttcattaag gtgaaaaaga gcgatgaata ccttcgcg | 240 |
| acctctgcgg ataaccatgt gaccatgtgg gtggatgacc aggaagtgat taacaaagcg | 300 |
| agcaacagca acaagattcg tctggagaag ggtcgcctgt accagattaa aattcagtac | 360 |
| cagcgcgaga acccgaccga aagggtctg gatttcaaac tgtattggac cgatagccag | 420 |
| aacaaaaagg aggtgattag ctctgataac ctgcagctgc cggaactgaa acagaagagc | 480 |
| agcaacagcc gcaaaaaacg cagcacctct gcaggcccaa cggtgccaga ccgcgacaac | 540 |
| gatggcattc cggacagcct ggaagttgaa ggctataccg tggatgtgaa aacaaacgc | 600 |
| acctttctga gcccgtggat tagcaacatc catgaaaaga aaggcctgac caaatataaa | 660 |
| agcagcccgg aaaagtggag caccgcgagc gatccgtaca gcgatttcga gaaagtgacc | 720 |
| ggccgcattg ataagaatgt gagcccggag gcgcgccacc cgctggtggc ggcgtatccg | 780 |
| attgtgcatg ttgatatgga gaacatcatc ctgagcaaga atgaagatca gagcacccag | 840 |
| aacacggaca gccagacccg cacgatcagc aagaacacca gcacgagccg tacccatacg | 900 |
| agcgaagttc atggcaacgc ggaagtgcat gcaagctttt tcgatattgg cggcagcgtg | 960 |
| agcgcaggct ttagcaacag caacagcagc accgtggcga ttgatcatag cctgagcctg | 1020 |
| gcgggcgaac gtacctgggc ggaaaccatg gcctgaaca ccgcggatac cgcgcgtctg | 1080 |
| aatgcgaaca tccgttatgt gaacaccggt accgcgccga tctataatgt tctgccgacc | 1140 |
| accagcctgg tgctgggcaa gaatcaaacc ctggcgacga tcaaagcgaa ggagaaccag | 1200 |
| ctgagccaga tcctggcgcc gaacaactac tacccaagca aaaacctggc gccgattgca | 1260 |
| ctgaacgcgc aggacgattt cagcagcacc ccgattacca tgaactataa tcagttcctg | 1320 |
| gaactggaaa agaccaaaca actgcgcctg gacaccgatc aggtgtacgg caacatcgcg | 1380 |
| acctataact tcgagaacgg tcgcgtgcgt gtggacaccg gtagcaactg gagcgaagtt | 1440 |
| ctgccgcaga ttcaggagac caccgcgcgc attattttca cggcaaaga tctgaacctg | 1500 |
| gtggaacgcc gcatcgcggc ggtgaaccca tctgatccgc tggaaaccac caaaccggac | 1560 |
| atgacccctga aagaagcact gaagattgca tttggcttta acgagccgaa cggtaacctg | 1620 |

| | |
|---|---|
| cagtaccagg gcaaagacat caccgagttt gattttaact ttgatcagca gacctctcag | 1680 |
| aatattaaaa accagctggc agaactgaat gcaaccaaca tctacaccgt tctggataag | 1740 |
| atcaaactga acgcaaaaat gaacattctg attcgtgaca agcgcttcca ctatgatcgt | 1800 |
| aacaacattg cagtgggcgc ggacgaaagc gttgtgaagg aagcgcatcg tgaagtgatc | 1860 |
| aactctagca cggaaggcct gctgctgaac attgacaagg atatccgtaa gattctgagc | 1920 |
| ggctatatcg ttgaaattga ggataccgag ggtctgaagg aggtgatcaa cgaccgctat | 1980 |
| gatatgctga acattagctc tctgcgccaa gatggcaaaa ccttcatcga cttcaagaag | 2040 |
| tataatgata aactgccgct gtatatcagc aacccaaact acaaagtgaa cgtgtacgcg | 2100 |
| gtgacgaagg aaaacacgat catcaaccca agcgagaatg cgacaccag caccaacggc | 2160 |
| attaagaaaa ttctgatttt tagcaaaaaa ggctatgaga tcggc | 2205 |

<210> SEQ ID NO 35
<211> LENGTH: 2205
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Sequence variant (91% identity) of SEQ ID NO. 1

<400> SEQUENCE: 35

| | |
|---|---|
| gaagtgaagc aggagaaccg tctgctgaac gaaagcgaaa gcagcagcca aggcctgctg | 60 |
| ggctattatt tcagcgatct gaacttccag gcgccgatgg ttgtgacctc ttctaccacc | 120 |
| ggcgatctga gcatcccgag ctctgagctg gaaaacatcc cgagcgagaa ccagtatttt | 180 |
| cagagcgcga tttggagcgg ctttattaaa gttaaaaaat ctgatgaata cacctttgcg | 240 |
| acgagcgcag ataaccacgt gaccatgtgg gtggatgatc aggaagttat taacaaagcg | 300 |
| agcaacagca acaagattcg tctggaaaag ggccgcctgt atcagattaa gatccagtac | 360 |
| cagcgcgaaa atccgaccga aagggtctg gactttaaac tgtactggac ggatagccag | 420 |
| aacaagaaag aagtgattag cagcgacaac ctgcaactgc cggaactgaa acagaagagc | 480 |
| agcaacagcc gcaagaaacg cagcacctct gcgggtccga ccgttccgga ccgcgacaac | 540 |
| gacggcattc cggacagcct ggaagtggag ggctataccg ttgatgttaa gaacaagcgc | 600 |
| accttcctga gcccgtggat tagcaacatt catgagaaga aaggcctgac caaatacaaa | 660 |
| tctagcccgg agaaatggag caccgcaagc gatccgtata gcgattttga gaaagtgacc | 720 |
| ggccgcattg ataagaacgt gagcccagag gcgcgccatc cactggtggc ggcgtatccg | 780 |
| atcgtgcatg tggacatgga gaatattatc ctgagcaaaa acgaagatca gagcacccag | 840 |
| aacacggaca gccagacccg cacgatcagc aagaacacct ctacgtctcg tacccatacc | 900 |
| agcgaagtgc atggtaacgc ggaagtgcat gcaagcttct ttgacattgg tggcagcgtg | 960 |
| agcgcgggct tcagcaacag caacagcagc acggtggcaa tcgatcatag cctgagcctg | 1020 |
| gcgggcgaac gcacctggc agaaaccatg gccctgaaca ccgcagatac cgcacgcctg | 1080 |
| aatgcgaaca ttcgttatgt gaacaccggc accgcgccga tctataacgt gctgccgacc | 1140 |
| acgagcctgg tgctgggcaa gaaccagacc ctggcgacca tcaaagcgaa agagaaccag | 1200 |
| ctgagccaga ttctggcacc aaacaactac tatccgtcta gaacctggc gccgattgca | 1260 |
| ctgaacgcgc aggatgactt ttctagcacg ccgatcacca tgaactacaa ccagtttctg | 1320 |
| gagctggaga aaccaaaca gctgcgtctg gataccgatc aggtgtatgg caacattgca | 1380 |

-continued

```
acctacaact tcgagaacgg ccgtgttcgt gtggataccg gtagcaactg gagcgaagtg    1440
ctgccacaga tccaggaaac gaccgcgcgc attatcttca atggcaaaga tctgaatctg    1500
gtggaacgcc gcatcgcggc ggtgaaccca tctgatccgc tggagaccac caagccggat    1560
atgaccctga agaagcgct gaagattgcg tttggcttca tgaaccgaa tggcaacctg      1620 cagtaccagg gcaaagacat caccgaattc gacttcaact ttgatcagca gacctctcaa    1680
aacattaaga accagctggc agaactgaat gcgaccaaca tctacaccgt gctggataaa    1740
atcaaactga acgcgaagat gaacattctg attcgtgata gcgctttca ttatgaccgc     1800 aacaacatcg cggtgggcgc agacgaaagc gtggtgaaag aagcgcaccg tgaggtgatc    1860
aacagcagca ccgagggcct gctgctgaac attgataaag acattcgtaa gattctgagc    1920
ggttacattg tggagatcga agatacgaa ggcctgaaa aagttattaa cgaccgctat       1980
gatatgctga acatttctag cctgcgccag gatggcaaga ccttcatcga tttcaagaag    2040
tataacgaca agctgccgct gtatatcagc aacccgaatt acaaagtgaa cgtgtacgcg    2100
gtgaccaaag aaaacaccat tattaaccca agcgagaatg gtgataccag caccaacggc    2160
atcaagaaga ttctgatctt cagcaagaaa ggctatgaga ttggc                    2205
```

<210> SEQ ID NO 36
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Truncated version of SEQ ID No: 1
      (bp 301 to 2055)

<400> SEQUENCE: 36

```
agcaacagca acaagattcg cctggagaag ggtcgcctgt atcagatcaa gattcagtat     60
cagcgcgaga atccgaccga gaaaggcctg gatttcaaac tgtactggac cgatagccag    120
aacaagaaag aagtgattag ctctgataac ctgcaactgc cggaactgaa acagaagagc    180
agcaacagcc gcaagaaacg cagcacctct gcaggcccga ccgttccaga tcgcgacaac    240
gatggcattc cggacagcct ggaagtggaa ggttataccg ttgatgtgaa gaacaaacgc    300
acctttctga gcccgtggat tagcaacatt catgagaaga aaggcctgac caagtacaaa    360
agcagcccgg agaagtggag caccgcgagc gatccgtata gcgactttga aaagtgacc    420 ggccgcattg ataagaacgt gagcccgaa gcgcgtcacc cactggttgc agcgtatccg     480
attgtgcatg ttgacatgga aacatcatt ctgagcaaga acgaagatca gagcacccag     540
aacacggata gccagacccg cacgatcagc aagaacacca gcacgagccg tacccatacc    600
agcgaagtgc atggcaatgc ggaagtgcat gcgagcttct ttgacattgg tggcagcgtg    660
agcgcgggct tcagcaacag caacagcagc accgtggcga ttgatcatag cctgagcctg    720
gcgggcgaac gtacctgggc ggaaaccatg gcctgaaca cggcggatac ggcacgtctg     780
aatgcgaaca ttcgctatgt gaacaccggt accgcgccaa tctataacgt tctgccgacc    840
acgagcctgg tgctgggcaa gaatcagacc ctggcgacca tcaaagcgaa agagaaccag    900
ctgtctcaga ttctggcacc gaacaactac tatccgagca gaacctggc accgattgca     960 ctgaatgcgc aggatgactt cagcagcacc ccgatcacca tgaactacaa tcagtttctg    1020
gagctggaga agaccaaaca actgcgcctg gataccgatc aggtgtatgg caacattgcg    1080
acctacaact ttgagaacgg ccgcgttcgc gtggataccg gtagcaactg gtctgaagtg    1140
```

```
ctgccgcaga ttcaggaaac gaccgcgcgc atcatcttca acggcaaaga tctgaacctg    1200
gtggaacgtc gcatcgcggc agtgaaccca tctgatccac tggaaacgac caaaccggac    1260
atgaccctga agaagcgct gaagattgca tttggcttca acgaaccgaa tggcaacctg    1320
cagtatcagg gcaaagacat caccgagttt gacttcaact ttgatcaaca gacctctcag    1380
aacatcaaga accagctggc agaactgaat gcgaccaaca tctacaccgt gctggacaag    1440
atcaaactga acgcaaagat gaacattctg attcgtgaca aacgcttcca ctatgatcgt    1500
aacaacattg cggtgggtgc agatgaaagc gttgtgaaag aagcgcatcg tgaagtgatc    1560
aactctagca ccgaaggcct gctgctgaac attgacaaaa catccgtaa gattctgagc    1620 ggctacattg tggagattga agataccgaa ggtctgaaag aagtgatcaa cgatcgctat    1680
gacatgctga acatctctag cctgcgccag gatggcaaga ccttcattga cttcaagaag    1740
tacaacgaca aactg                                                     1755

<210> SEQ ID NO 37
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (99%) of SEQ ID No. 36

<400> SEQUENCE: 37
agcaacagca acaagattcg cctggagaag ggtcgcctgt atcagatcaa gattcagtat      60
cagcgcgaga atccgaccga gaaaggcctg gatttcaaac tgtactggac cgatagccag    120
aacaagaaag aagtgattag ctctgataac ctgcaactgc cggaactgaa acagaagagc    180
agcaacagcc gcaagaaacg cagcacctct gcaggcccga ccgttccaga tcgcgacaac    240
gatggcattc cggacagcct ggaagtggaa ggttataccg ttgatgtgaa gaacaaacgc    300
acctttctga gcccgtggat tagcaacatt catgagaaga aaggcctgac caagtacaaa    360
agcagcccgg agaagtggtc taccgcgagc gatccgtata gcgactttga gaaagtgacc    420
ggccgcattg ataagaacgt gagcccggaa gcgcgtcacc cactggttgc agcgtatccg    480
attgtgcatg ttgacatgga gaacatcatt ctgagcaaga acgaagatca gagcacccag    540
aacacggata gccagacccg cacgatcagc aagaacacca gcaccagccg tacccatacc    600
agcgaagtgc atggcaatgc ggaagtgcat gcgagcttct ttgacattgg tggcagcgtg    660
agcgcgggct tcagcaacag caacagcagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggt accgcgccaa tctataacgt tctgccgacc    840
acgagcctgg tgctgggcaa gaatcagacc ctggcgacca tcaaagcgaa agagaaccag    900
ctgagccaga tcctggcacc gaacaactac tatccgagca agaacctggc accgattgca    960
ctgaatgcgc aggatgactt cagcagcacc ccgatcacca tgaactacaa tcagtttctg    1020
gagctggaga agaccaaaca actgcgcctg gataccgatc aggtgtatgg caacattgcg    1080
acctacaact ttgagaacgg ccgcgttcgc gtggataccg gtagcaactg gtctgaagtg    1140
ctgccgcaga ttcaggaaac gaccgcgcgc atcatcttca acggcaaaga tctgaacctg    1200
gtggaacgtc gcatcgcggc agtgaaccca tctgacccac tggaaacgac caaaccggac    1260
atgaccctga agaagcgct gaagattgca tttggcttca acgaaccgaa tggcaacctg    1320
cagtatcagg gcaaagacat caccgagttt gatttcaact ttgatcagca aacctctcag    1380
```

```
aacatcaaga accagctggc agaactgaat gcgaccaaca tctacaccgt gctggacaag    1440
atcaaactga acgcaaagat gaacattctg attcgtgaca aacgcttcca ctatgatcgt    1500
aacaacattg cggtgggtgc agatgagagc gttgtgaaag aagcgcatcg tgaagtgatc    1560
aactctagca cggaaggcct gctgctgaac attgacaaag acatccgcaa gattctgagc    1620
ggctacattg tggaaattga agataccgaa ggtctgaaag aagtgattaa cgatcgttat    1680
gacatgctga acatctctag cctgcgccag gatggcaaga ccttcattga cttcaagaag    1740
tacaacgaca aactg                                                    1755
```

<210> SEQ ID NO 38
<211> LENGTH: 1755
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Sequence variant (98%) of SEQ ID No. 36

<400> SEQUENCE: 38

```
agcaacagca acaagattcg tctggagaag ggtcgcctgt atcagatcaa gattcagtat     60
cagcgcgaga atccgaccga gaaaggcctg gatttcaaac tgtactggac cgatagccag    120
aacaagaaag aagtgatcag ctctgataac ctgcaactgc cggaactgaa acagaagagc    180
agcaacagcc gcaagaaacg cagcacctct gcaggcccga ccgttccaga tcgtgacaac    240
gatggcattc cggacagcct ggaagtggaa ggttataccg ttgatgtgaa gaacaaacgc    300
acctttctga gcccgtggat tagcaacatt catgaaaaga aaggcctgac caagtacaaa    360
agcagcccgg agaagtggtc taccgcgagc gatccgtata cgactttga gaaagtgacc    420 ggccgcatcg ataagaacgt gagcccggaa gcgcgtcacc cactggttgc agcgtatccg    480
attgtgcatg ttgacatgga gaacatcatt ctgagcaaga acgaagatca gagcacccag    540
aacacggata gccagacccg cacgatcagc aagaacacca gcaccagccg caccccatacc    600 agcgaagtgc atggcaatgc ggaagtgcat gcgagcttct ttgacattgg tggcagcgtg    660
agcgcgggct tcagcaacag caacagcagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggc accgcgccaa tctataacgt tctgccgacc    840
acgagcctgt gctgggcaa gaatcagacc ctggcgacca tcaaagcgaa agagaaccag    900
ctgagccaga tcctggcacc gaacaactac tatccgagca agaacctggc accgattgca    960
ctgaatgcgc aggatgattt cagcagcacc ccgatcacca tgaactacaa tcagtttctg   1020
gagctggaga agaccaaaca actgcgcctg gataccgatc aggtgtatgg caacattgcg   1080
acctacaact ttgagaacgg tcgcgttcgc gtggataccg gtagcaactg gtctgaagtg   1140
ctgccgcaga ttcaggaaac gaccgcgcgc atcatcttca acggtaaaga tctgaacctg   1200
gtggaacgcc gcatcgcggc agtgaaccca tctgacccac tggaaacgac caaaccggac   1260
atgaccctga agaagcgct gaagattgca tttggcttca cgaaccgaa tggcaacctg    1320 cagtatcagg gcaaagacat caccgagttc gacttcaact tgatcagca aacctctcag   1380 aacatcaaga accagctggc agaactgaat gcgaccaaca tttacaccgt gctggacaag   1440
attaaactga acgcaaagat gaacattctg attcgtgaca aacgcttcca ctatgatcgt   1500
aacaacattg cggtgggcgc agatgagagc gttgtgaaag aagcgcatcg tgaagtgatc   1560
```

| aactctagca cggagggcct gctgctgaac attgacaaag acatccgcaa gattctgagc | 1620 |
| ggctacattg tggaaattga agataccgaa ggtctgaaag aagtgattaa cgatcgttat | 1680 |
| gacatgctga acatctctag cctgcgccag gatggcaaga ccttcattga ctttaagaag | 1740 |
| tacaacgaca aactg | 1755 |

```
<210> SEQ ID NO 39
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97%) of SEQ ID No. 36

<400> SEQUENCE: 39
```

| agcaacagca acaagattcg tctggagaag ggtcgcctgt atcagatcaa gattcagtat | 60 |
| cagcgcgaaa atccgaccga gaaaggcctg gattttaagc tgtactggac cgatagccag | 120 |
| aacaagaaag aagtgatcag ctctgataac ctgcaactgc cggaactgaa gcagaagagc | 180 |
| agcaacagcc gcaagaaacg cagcacctct gcaggcccga ccgttccaga tcgtgacaac | 240 |
| gatggcattc cggacagcct ggaggtggaa ggttataccg ttgatgtgaa gaacaaacgc | 300 |
| acctttctga gcccgtggat tagcaacatt catgaaagaa aaggcctgac caaatacaaa | 360 |
| agcagcccgg agaagtggtc taccgcgagc gatccatata gcgacttcga aaaagtgacc | 420 |
| ggccgcatcg ataagaacgt gagcccgaaa gcgcgtcacc cactggttgc agcgtatccg | 480 |
| attgtgcatg ttgacatgga gaacatcatt ctgagcaaaa acgaagatca gagcacccag | 540 |
| aacacggata gccagacccg cacgatcagc aagaacacca gcaccagccg cacccatacc | 600 |
| agcgaagtgc atggcaatgc ggaagtgcat gcgagcttct ttgacattgg tggcagcgtg | 660 |
| agcgcgggct tcagcaacag caacagcagc accgtggcga ttgatcatag cctgagcctg | 720 |
| gcgggcgaac gtacctgggc ggaaaccatg ggcctgaaca cggcggatac cgcacgcctg | 780 |
| aatgcgaaca ttcgctatgt gaacaccggc accgcgccaa tctataacgt tctgccgacg | 840 |
| acgagcctgg tgctgggcaa gaatcagacc ctggcgacca tcaaagcgaa agagaaccag | 900 |
| ctgagccaga tcctggcacc gaacaactac tatccgagca agaacctggc accgattgca | 960 |
| ctgaatgcgc aggatgattt cagcagcacc ccgatcacca tgaactacaa tcagtttctg | 1020 |
| gagctggaga agaccaaaca actgcgcctg gataccgatc aggtgtatgg caacattgcg | 1080 |
| acctacaact ttgagaacgg tcgcgttcgc gtggataccg gcagcaactg gtctgaagtg | 1140 |
| ctgccgcaga ttcaggaaac gaccgcgcgt atcatcttca cggtaaagga tctgaacctg | 1200 |
| gtggaacgcc gcatcgcggc agtgaacccg tctgacccac tggaaacgac caaaccggac | 1260 |
| atgaccctga agaagcgct gaagattgca tttggtttca cgaaccgaa tggcaacctg | 1320 |
| cagtatcagg gcaaagacat caccgagttc gacttcaact ttgatcagca aacctctcag | 1380 |
| aacatcaaga accagctggc agaactgaat gcgaccaaca tttacaccgt gctggacaag | 1440 |
| attaaactga acgcaaagat gaacattctg attcgtgaca aacgcttcca ctatgatcgt | 1500 |
| aacaacattg cggtgggcgc agatgagagc gttgtgaaag aagcgcatcg tgaggtgatc | 1560 |
| aactctagca cggagggcct gctgctgaac attgacaaag acatccgcaa gattctgagc | 1620 |
| ggctacattg tggaaattga agataccgaa ggtctgaaag aagtgattaa cgatcgttat | 1680 |
| gacatgctga acatctctag cctgcgccag gatggcaaga ccttcattga ctttaagaag | 1740 |
| tacaacgaca aactg | 1755 |

<210> SEQ ID NO 40
<211> LENGTH: 1755
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 36

<400> SEQUENCE: 40

```
agcaacagca acaagattcg tctggagaag ggtcgcctgt atcagatcaa gattcagtat      60
cagcgcgaaa atccgaccga gaaaggcctg gattttaagc tgtactggac cgatagccag     120
aacaagaaag aagtgatcag ctctgataac ctgcagctgc cggaactgaa gcagaagagc     180
agcaacagcc gcaagaaacg cagcacctct gcaggcccga ccgttccaga tcgtgacaac     240
gatggcattc cggacagcct ggaggtggaa ggttataccg ttgatgtgaa gaacaaacgc     300
acctttctga gcccgtggat tagcaacatt catgaaaaga aaggcctgac caaatacaaa     360
agcagcccgg agaagtggtc taccgcgagc gatccatata gcgacttcga aaaagtgacc     420
ggccgcatcg ataagaatgt gagcccggaa gcgcgtcacc cactggttgc agcgtatccg     480
attgtgcatg tggacatgga aacatcatt ctgagcaaaa acgaagatca gagcacccag     540
aacacggata gccagacccg cacgatcagc aagaacacca gcaccagccg cacccatacc     600
agcgaagtgc atggcaatgc ggaagtgcat gcgagcttct ttgacattgg tggctctgtg     660
agcgcgggct tcagcaacag caacagcagc accgtggcga ttgatcatag cctgagcctg     720
gcgggcgaac gtacctgggc ggaaaccatg ggcctgaaca cggcggatac cgcacgcctg     780
aacgcgaaca ttcgctatgt gaacaccggc accgcgccaa tctataacgt tctgccgacg     840
acgagcctgg ttctgggcaa gaatcagacc ctggcgacca tcaaagcgaa agagaaccag     900
ctgagccaga tcctggcacc gaacaactac tatccgagca gaacctggc accgattgca     960
ctgaatgcgc aggatgattt cagcagcacc ccaattacca tgaactacaa tcagtttctg    1020
gagctggaga agaccaaaca actgcgcctg gataccgatc aagtgtatgg caacattgcg    1080
acctacaact ttgagaacgg tcgcgttcgc gtggataccg gcagcaactg gtctgaagtg    1140
ctgccgcaga ttcaggaaac gaccgcgcgt atcatcttca acggtaaaga tctgaacctg    1200
gtggaacgcc gcatcgcggc agtgaacccg tctgacccgc tggaaacgac caaaccggac    1260
atgaccctga agaagcgct gaagattgca tttggtttca cgaaccgaa tggcaacctg    1320
cagtatcagg gcaaagacat caccgagttc gacttcaact ttgatcagca aacctctcag    1380
aacatcaaga accagctggc agaactgaat gcgaccaaca tttacaccgt gctggacaag    1440
attaaactga acgcaaagat gaacattctg attcgtgaca aacgcttcca ctatgatcgt    1500
aacaacatcg cggtgggcgc agatgagagc gttgtgaaag aagcgcatcg tgaggtgatt    1560
aactctagca cggagggcct gctgctgaac attgacaaag atatccgcaa gattctgagc    1620
ggctacattg tggaaattga agataccgaa ggtctgaaag aagtgattaa cgatcgttat    1680
gacatgctga acatcagcag cctgcgccag gacggcaaga ccttcatcga ctttaagaag    1740
tacaacgaca aactg                                                    1755
```

<210> SEQ ID NO 41
<211> LENGTH: 1755
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: Sequence variant (95%) of SEQ ID No. 36

<400> SEQUENCE: 41

```
agcaacagca acaagattcg tctggagaag ggtcgcctgt atcagatcaa gatccagtat      60
cagcgcgaaa atccgaccga gaaaggcctg gattttaagc tgtactggac cgatagccag     120
aacaagaaag aagtgatcag ctctgataac ctgcagctgc cggaactgaa gcagaagagc     180
agcaacagcc gcaagaaacg cagcacctct gcaggcccga ccgttccgga tcgtgacaac     240
gatggcattc cggacagcct ggaggttgaa ggttataccg tggatgtgaa gaacaaacgc     300
accttcctga gcccgtggat tagcaacatt catgaaaaaa aaggcctgac caaatacaaa     360
agcagcccgg agaagtggtc taccgcgagc gacccatata gcgacttcga aaaagtgacg     420
ggccgcatcg ataagaatgt gagcccggaa gcgcgtcacc cactggttgc agcgtatccg     480
attgtgcatg tggacatgga aacatcatt ctgagcaaaa acgaagatca gagcacccag     540
aacacggata gccagacccg caccatcagc aagaacacca gcaccagccg caccatacc     600
agcgaagtgc atggcaatgc agaagtgcat gcgagcttct ttgacattgg tggctctgtg     660
agcgcgggct tcagcaacag caacagcagc accgtggcga ttgatcatag cctgagcctg     720
gcgggcgaac gtacctgggc ggaaaccatg ggcctgaaca cggcggatac cgcacgcctg     780
aacgcgaaca ttcgctatgt gaacaccggc accgcgccaa tctataacgt tctgccgacg     840
acgagcctgg ttctgggcaa gaatcagacc ctggcgacca tcaaagcgaa agagaaccag     900
ctgagccaaa tcctggcacc gaacaactac tatccgagca agaacctggc accgattgca     960
ctgaatgcgc aggatgattt cagcagcacc ccaattacca tgaactacaa tcagtttctg    1020
gagctggaga agaccaaaca gctgcgcctg gataccgatc aagtgtatgg caacattgcg    1080
acctacaact ttgagaacgg tcgcgttcgc gtggataccg gcagcaactg gtctgaagtg    1140
ctgccgcaga ttcaggaaac gaccgcgcgt atcatcttta acggtaaaga tctgaacctg    1200
gtggaacgcc gcatcgcggc agtgaacccg tctgaccccg ctggaaacgac caaaccggac    1260
atgaccctga agaagcgct gaagattgca tttggtttca cgaaccaaa tggcaacctg    1320
cagtatcagg gcaaagacat caccgagttc gacttcaact tgatcagca aacctctcag    1380
aacatcaaga accagctggc agaactgaat gcgaccaaca tttacaccgt gctggacaag    1440
attaaactga cgcaaagat gaacattctg attcgtgaca aacgcttcca ctatgatcgt    1500
aacaacattg cggtgggcgc ggatgagagc gttgtgaaag aagcgcatcg tgaggtgatt    1560
aactctagca cggagggcct gctgctgaac attgacaaag atatccgcaa gattctgagc    1620
ggctacattg tggaaattga agataccgaa ggtctgaagg aagtgattaa cgatcgttat    1680
gatatgctga acatcagcag cctgcgccag gacggcaaga ccttcatcga ctttaagaag    1740
tacaacgaca aactg                                                     1755
```

<210> SEQ ID NO 42
<211> LENGTH: 1755
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (94%) of SEQ ID No. 36

<400> SEQUENCE: 42

```
agcaacagca acaagattcg tctggagaag ggtcgcctgt atcagatcaa gatccagtat    60
cagcgcgaaa atccgaccga gaaaggcctg gattttaagc tgtactggac cgatagccag   120
aacaagaaag aagtgatcag ctctgataac ctgcaactgc cggaactgaa gcagaagagc   180
agcaacagcc gcaagaaacg cagcaccagc gcaggcccga ccgttccgga tcgtgacaac   240
gatggcattc cggacagcct ggaggttgaa ggttataccg tggatgtgaa gaacaaacgc   300
accttcctga gcccgtggat tagcaacatt catgaaaaaa aaggcctgac caaatacaaa   360
agcagcccgg agaagtggtc taccgcgagc gacccatata gcgacttcga aaaagtgacg   420
ggccgcatcg ataagaatgt gagcccggaa gcacgtcacc cactggttgc agcgtatccg   480
attgtgcatg tggacatgga gaacatcatt ctgagcaaaa acgaagatca gagcacgcag   540
aacacggata gccagacccg caccatcagc aagaacacca gcaccagccg cacccatacc   600
agcgaagtgc atggcaatgc agaagtgcat gcgagcttct ttgacattgg tggcagcgtg   660
agcgcgggct tcagcaacag caactctagc accgtggcga ttgatcatag cctgagcctg   720
gcgggcgaac gtacctgggc ggaaacgatg ggcctgaaca ccgcggatac cgcacgcctg   780
aacgcgaaca ttcgctacgt gaacaccggc accgcgccaa tctataacgt tctgccgacg   840
acgagcctgg ttctgggcaa gaatcagacc ctggcgacca tcaaagcgaa agagaaccag   900
ctgagccaaa tcctggcacc gaacaactac tatccgagca gaacctggc accgattgcg   960 ctgaatgcgc aggatgattt tagcagcacc ccaattacca tgaactataa ccagttcctg  1020
gagctggaga gaccaaaaca gctgcgcctg gataccgatc aggtgtatgg caacattgcg  1080
acctacaact ttgagaacgg tcgcgttcgc gtggataccg gcagcaactg gtctgaagtg  1140
ctgccgcaga ttcaggaaac gaccgcgcgt atcatcttta cggtaaaga tctgaacctg  1200 gtggaacgcc gcatcgcggc agtgaacccg tctgaccccgc tggaaaccac caaaccggac  1260
atgaccctga agaagcgct gaagattgca tttggtttca cgaaccaaa tggcaacctg  1320 cagtatcagg gcaaagacat caccgagttc gatttcaact ttgatcagca gacctctcag  1380
aacatcaaga accaactggc agaactgaat gcgaccaaca tttacaccgt gctggacaag  1440
attaaactga acgcaaagat gaacattctg attcgtgaca aacgcttcca ctatgatcgt  1500
aacaacatcg cggtgggcgc ggatgagagc gttgtgaaag aagcgcatcg tgaggtgatt  1560
aactctagca cggagggcct gctgctgaac attgacaaag acattcgcaa gattctgtct  1620
ggctacattg tggaaattga agataccgaa ggtctgaagg aagtgattaa cgatcgttat  1680
gatatgctga atatcagcag cctgcgccag gacggcaaga ccttcatcga ctttaagaag  1740
tacaacgaca aactg                                                   1755
```

<210> SEQ ID NO 43
<211> LENGTH: 1755
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93%) of SEQ ID No. 36

<400> SEQUENCE: 43

```
agcaacagca acaaaattcg tctggagaag ggtcgcctgt atcagatcaa gatccagtat    60
cagcgcgaga atccgaccga gaaaggcctg gatttcaagc tgtactggac cgatagccag   120
aacaagaagg aagtgatcag ctctgataac ctgcaactgc cagaactgaa gcagaagagc   180
agcaacagcc gcaagaaacg cagcaccagc gcaggcccga ccgttccgga tcgtgacaac   240
```

```
gatggcattc cggacagcct ggaggttgaa ggttataccg tggatgtgaa gaacaaacgc    300
accttcctga gcccgtggat tagcaacatc catgaaaaga aaggcctgac caaatacaaa    360
agcagcccgg agaagtggtc taccgcgagc gacccataca gcgacttcga aaaagtgacg    420
ggccgcatcg ataagaacgt gagcccggaa gcacgtcacc cgctggttgc agcgtatccg    480
attgtgcatg tggacatgga gaacattatt ctgagcaaaa acgaagatca gagcacgcag    540
aacaccgata gccagacccg caccatcagc aagaacacca gcaccagccg cacccatacc    600
agcgaagtgc atggcaatgc agaagtgcat gcgagcttct ttgatattgg tggcagcgtg    660
agcgcgggct tcagcaacag caactctagc accgtggcga ttgatcatag cctgagcctg    720
gcgggcgaac gtacctgggc ggaaacgatg ggcctgaaca ccgcggatac cgcacgcctg    780
aacgcgaaca ttcgctacgt gaacaccggc accgcgccaa tctataacgt tctgccgacg    840
acgagcctgg ttctgggcaa gaatcagacc ctggcgacca tcaaagcgaa agagaaccag    900
ctgagccaaa tcctggcacc gaacaactac tatccgagca aaaacctggc accgattgcg    960
ctgaatgcgc aggatgattt tagcagcacc ccaattacca tgaactataa ccagttcctg   1020
gagctggaaa agaccaaaca gctgcgtctg gatacggatc aggtgtatgg caacattgcg   1080
acctacaact ttgagaacgg tcgcgttcgc gtggataccg gcagcaactg gtctgaagtg   1140
ctgccgcaga ttcaggaaac gaccgcgcgt atcatcttta cggtaaaga tctgaacctg   1200 gtggaacgcc gcattgcggc agtgaacccg tctgacccgc tggaaaccac caaaccggac   1260
atgaccctga agaagcgct gaagattgca tttggtttca cgaaccaaa tggcaacctg   1320 cagtatcagg gcaaagacat caccgagttc gatttcaact ttgatcagca gacctctcag   1380
aacatcaaga tcaactggcg agaactgaat gcgaccaaca tttacaccgt gctggacaag   1440
attaaactga acgcaaagat gaacattctg attcgtgaca aacgctttca ttatgatcgt   1500
aacaacatcg cggtgggcgc ggacgaaagc gttgtgaaag aggcgcaccg tgaggtgatt   1560
aactctagca cggagggcct gctgctgaac attgacaagg acatccgcaa gattctgtct   1620
ggctacattg tggaaattga agataccgaa ggtctgaaag aagtgattaa cgatcgctat   1680
gatatgctga atatcagcag cctgcgccag gacggcaaga ccttcatcga ctttaagaag   1740
tataacgaca aactg                                                   1755
```

<210> SEQ ID NO 44
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92%) of SEQ ID No. 36

<400> SEQUENCE: 44

```
agcaacagca acaaaatccg tctggagaag ggtcgcctgt atcagatcaa gatccagtat     60
cagcgcgaga atccgaccga gaaaggcctg gatttcaagc tgtactggac cgatagccag    120
aacaagaaag aagtgatcag cagcgataac ctgcagctgc agaactgaa gcagaagagc    180 agcaacagcc gcaagaaacg cagcacgagc gcaggcccga ccgttccgga tcgtgacaac    240
gatggcattc cggacagcct ggaggttgaa ggttataccg tggatgtgaa gaacaaacgc    300
accttcctga gcccgtggat tagcaacatc catgaaaaga aaggcctgac caaatacaaa    360
agcagcccgg agaagtggtc taccgcgagc gacccataca gcgacttcga aaaagtgacg    420
```

```
ggccgcatcg ataaaaacgt gagcccggaa gcacgtcatc cgctggttgc ggcgtatccg      480
attgtgcacg tggacatgga aacattatt  ctgagcaaga acgaagatca gagcacccag      540
aacaccgata gccagacccg caccatcagc aagaacacca gcaccagccg cacccatacc      600
agcgaagtgc atggcaacgc agaagtgcat gcgagcttct ttgatatcgg tggcagcgtg      660
agcgcgggct tcagcaacag caactcttct accgtggcga ttgatcacag cctgagcctg      720
gcgggcgaac gtacctgggc ggaaacgatg gccctgaaca ccgcggatac cgcacgcctg      780
aacgcgaaca ttcgctacgt gaacaccggc accgcgccaa tttataacgt tctgccgacg      840
acgagcctgg ttctgggcaa gaaccagacc ctggcgacca tcaaagcgaa agagaaccag      900
ctgagccaaa ttctggcacc gaacaactac tatccgagca aaaacctggc accgattgcg      960
ctgaatgcgc aggatgattt tagcagcacc ccaattacca tgaactataa ccagttcctg     1020
gagctggaaa agaccaaaca gctgcgtctg gatacggatc aggtgtatgg caacattgcg     1080
acctacaact tgagaacgg  tcgcgttcgc gtggataccg gcagcaattg gagcgaagtg     1140
ctgccgcaga ttcaggaaac gaccgcgcgt atcatcttta acggtaaaga cctgaacctg     1200
gtggaacgcc gcattgcggc agtgaatccg tctgacccgc tggaaacgac caaaccggac     1260
atgaccctga aggaagcgct gaagatcgca tttggtttca acgaaccaaa tggcaacctg     1320
cagtatcaag gcaaagacat caccgagttc gatttcaact ttgatcagca gacctctcag     1380
aacatcaaga atcaactggc agaactgaat gcgaccaaca tttacaccgt gctggacaag     1440
attaaactga acgcaaagat gaatattctg attcgtgaca aacgctttca ttatgatcgt     1500
aacaacatcg cagtgggcgc ggacgaaagc gttgtgaaag aggcgcatcg tgaggtgatt     1560
aactctagca ccgagggcct gctgctgaac attgacaagg acattcgcaa gattctgtct     1620
ggctacattg tggaaattga agataccgaa ggtctgaaag aagtgattaa cgatcgctat     1680
gatatgctga acatctctag cctgcgccag gacggcaaga ccttcatcga ttttaagaag     1740
tataacgaca aactg                                                      1755
```

<210> SEQ ID NO 45
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (91%) of SEQ ID No. 36

<400> SEQUENCE: 45

```
agcaacagca acaaaatccg tctggaaaag ggtcgcctgt atcagattaa gattcagtat       60
cagcgcgaga atccgaccga gaaaggcctg gatttcaagc tgtactggac cgatagccag      120
aacaagaaag aagtgatcag cagcgataac ctgcagctgc agaactgaa  gcagaagagc      180 agcaacagcc gcaagaaacg cagcaccagc gcaggcccga ccgttccgga tcgtgacaac      240
gatggcattc cggacagcct ggaggttgag ggttataccg tggacgtgaa gaacaaacgc      300
accttcctga gcccgtggat tagcaacatc catgaaaaga aaggcctgac caaatacaaa      360
agcagcccgg agaagtggtc taccgcgagc gacccataca gcgatttcga aaaagtgacg      420
ggccgtatcg ataaaaacgt gagcccggaa gcacgtcatc cgctggttgc ggcgtacccg      480
attgtgcacg tggacatgga aacattatc  ctgagcaaga acgaagatca gtctacccag      540
aacaccgata gccagacccg caccatcagc aaaaacacca gcaccagccg cacccatacg      600
agcgaagtgc atggcaacgc agaagtgcat gcgagctttt tcgatatcgg tggcagcgtg      660
```

```
agcgcaggct tcagcaacag caactctagc accgtggcga ttgatcacag cctgagcctg      720
gcgggcgaac gtacctgggc ggaaacgatg ggcctgaaca ccgcggatac cgcgcgcctg      780
aacgcgaaca ttcgctacgt taacaccggc accgcgccaa tttataacgt tctgccgacg      840
accagcctgg ttctgggcaa gaaccagacc ctggcgacca tcaaagcgaa agagaaccag      900
ctgagccaaa ttctggcacc gaacaactac tatccgagca aaaacctggc accgattgcg      960
ctgaatgcgc aggatgactt tagcagcacc ccaattacca tgaactataa ccagttcctg     1020
gagctggaaa agaccaaaca gctgcgtctg gatacggatc aggtgtatgg caacattgcg     1080
acctacaact ttgagaacgg tcgcgtgcgc gtggacaccg gcagcaattg gagcgaggtg     1140
ctgccgcaga ttcaggaaac gaccgcgcgc atcatcttta acggtaaaga tctgaacctg     1200
gtggaacgcc gcattgcggc agtgaatccg tctgacccgc tggaaacgac caaaccggac     1260
atgacactga aggaagcgct gaagatcgca tttggtttca cgaaccaaa tggcaacctg     1320 cagtatcaag gcaaggacat caccgagttc gatttcaact tgatcagca gacctctcag     1380 aacatcaaga tcaactggc agaactgaat gcgacgaaca tttataccgt gctggacaag     1440
attaaactga acgcaaagat gaatattctg attcgtgaca aacgctttca ttatgatcgt     1500
aacaacatcg cagtgggcgc ggacgaaagc gttgtgaaag aggcgcatcg tgaggtgatt     1560
aactctagca ccgagggcct gctgctgaac attgacaagg acattcgcaa gatcctgtct     1620
ggctacattg tggaaattga agataccgaa ggtctgaaag aagtgattaa cgatcgctat     1680
gatatgctga acatctctag cctgcgccag gatggcaaga ccttcatcga tttaagaag     1740 tataacgaca aactg                                                      1755
```

<210> SEQ ID NO 46
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No: 1 (bp. 202-2055)

<400> SEQUENCE: 46

```
ttcatcaaag tgaagaaaag cgatgagtat acctttgcga cgtctgcgga taaccatgtg      60
accatgtggg tggacgatca ggaagtgatc aacaaagcga gcaacagcaa caagattcgc     120
ctggagaagg gtcgcctgta tcagatcaag attcagtatc agcgcgagaa tccgaccgag     180
aaaggcctgg atttcaaact gtactggacc gatagccaga acaagaaaga agtgattagc     240
tctgataacc tgcaactgcc ggaactgaaa cagaagagca gcaacagccg caagaaacgc     300
agcacctctg caggcccgac cgttccagat cgcgacaacg atggcattcc ggacagcctg     360
gaagtggaag gttataccgt tgatgtgaag aacaaacgca cctttctgag cccgtggatt     420
agcaacattc atgagaagaa aggcctgacc aagtacaaaa gcagcccgga gaagtggagc     480
accgcgagcg atccgtatag cgactttgag aaagtgaccg ccgcattga taagaacgtg     540 agcccggaag cgcgtcaccc actggttgca gcgtatccga ttgtgcatgt tgacatggag     600
aacatcattc tgagcaagaa cgaagatcag agcacccaga cacgggatag ccagacccgc     660
acgatcagca gaacaccag cacgagccgt acccatacca gcgaagtgca tggcaatgcg     720
gaagtgcatg cgagcttctt tgacattggt ggcagcgtga gcgcgggctt cagcaacagc     780
aacagcagca ccgtggcgat tgatcatagc ctgagcctgg cgggcgaacg tacctgggcg     840
```

```
gaaaccatgg gcctgaacac ggcggatacg gcacgtctga atgcgaacat tcgctatgtg    900
aacaccggta ccgcgccaat ctataacgtt ctgccgacca cgagcctggt gctgggcaag    960
aatcagaccc tggcgaccat caaagcgaaa gagaaccagc tgtctcagat tctggcaccg   1020
aacaactact atccgagcaa gaacctggca ccgattgcac tgaatgcgca ggatgacttc   1080
agcagcaccc cgatcaccat gaactacaat cagtttctgg agctggagaa gaccaaacaa   1140
ctgcgcctgg ataccgatca ggtgtatggc aacattgcga cctacaactt tgagaacggc   1200
cgcgttcgcg tggataccgg tagcaactgg tctgaagtgc tgccgcagat tcaggaaacg   1260
accgcgcgca tcatcttcaa cggcaaagat ctgaacctgg tggaacgtcg catcgcggca   1320
gtgaacccat ctgatccact ggaaacgacc aaaccggaca tgaccctgaa agaagcgctg   1380
aagattgcat ttggcttcaa cgaaccgaat ggcaacctgc agtatcaggg caaagacatc   1440
accgagtttg acttcaactt tgatcaacag acctctcaga acatcaagaa ccagctggca   1500
gaactgaatg cgaccaacat ctacaccgtg ctggacaaga tcaaactgaa cgcaaagatg   1560
aacattctga ttcgtgacaa acgcttccac tatgatcgta acaacattgc ggtgggtgca   1620
gatgaaagcg ttgtgaaaga agcgcatcgt gaagtgatca actctagcac cgaaggcctg   1680
ctgctgaaca ttgacaaaga catccgtaag attctgagcg gctacattgt ggagattgaa   1740
gataccgaag gtctgaaaga agtgatcaac gatcgctatg acatgctgaa catctctagc   1800
ctgcgccagg atggcaagac cttcattgac ttcaagaagt acaacgacaa actg         1854
```

<210> SEQ ID NO 47
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99%) of SEQ ID No. 46

<400> SEQUENCE: 47

```
ttcatcaaag tgaagaaaag cgatgagtat acctttgcga cgtctgcgga taaccatgtg     60
accatgtggg tggacgatca ggaagtgatc aacaaagcga gcaacagcaa caaaattcgc    120
ctggagaagg gtcgcctgta tcagatcaag attcagtatc agcgcgagaa tccgaccgag    180
aaaggcctgg atttcaaact gtactggacc gatagccaga caagaaaga agtgattagc    240 tctgataacc tgcagctgcc ggaactgaaa cagaagagca gcaacagccg caagaaacgc    300
agcaccagcg caggcccgac cgttccagat cgcgacaacg atggcattcc ggacagcctg    360
gaagtggaag ttataccgt tgatgtgaag aacaaacgcc cctttctgag cccgtggatt    420
agcaacattc atgagaagaa aggcctgacc aagtacaaaa gcagcccgga agtggagc     480 accgcgagcg atccgtatag cgactttgaa aaagtgaccg gccgcattga taagaacgtg    540
agcccggaag cgcgtcaccc actggttgcg gcgtatccga ttgtgcatgt tgacatggag    600
aacatcattc tgagcaagaa cgaagatcag agcacccaga acacggatag ccagacccgc    660
acgatcagca agaacaccag cacgagccgt acccatacca gcgaagtgca tggcaatgcg    720
gaagtgcatg cgagcttctt tgacattggt ggcagcgtga gcgcgggctt cagcaacagc    780
aacagcagca ccgtggcgat tgatcatagc ctgagcctgg cgggcgaacg tacctgggca    840
gaaaccatgg gcctgaacac ggcggatacg gcacgtctga atgcgaacat tcgctatgtg    900
aacaccggta ccgcgccaat ctataacgtt ctgccgacca cgagcctggt gctgggcaag    960
```

```
aatcagaccc tggcgaccat caaagcgaaa gagaaccagc tgtctcagat tctggcaccg   1020
aacaactact atccgagcaa gaacctggca ccgattgcac tgaatgcgca ggatgacttc   1080
agctctaccc cgatcaccat gaactacaat caattcctgg agctggagaa gaccaagcaa   1140
ctgcgcctgg ataccgatca ggtgtatggc aacattgcga cctacaactt tgagaacggc   1200
cgcgttcgcg tggataccgg tagcaactgg tctgaagtgc tgccgcagat tcaggaaacg   1260
accgcgcgca tcatcttcaa cggcaaagat ctgaacctgg tggaacgtcg catcgcggca   1320
gtgaacccat ctgatccact ggaaacgacc aaaccggaca tgaccctgaa agaagcgctg   1380
aagattgcat ttggcttcaa cgaaccgaat ggcaacctgc agtatcaggg caaagacatc   1440
accgagtttg acttcaactt tgaccaacag acctctcaga acatcaagaa ccagctggca   1500
gaactgaatg cgaccaacat ctacaccgtg ctggacaaga tcaaactgaa cgcaaagatg   1560
aacattctga ttcgtgacaa acgcttccac tatgatcgta caacattgc ggtgggtgca   1620 gatgaaagcg ttgtgaaaga ggcgcatcgt gaagtgatca actctagcac cgaaggcctg   1680
ctgctgaaca ttgacaaaga tatccgtaag attctgagcg gctacattgt ggagattgaa   1740
gataccgaag gtctgaaaga agtgatcaac gatcgctatg acatgctgaa catctctagc   1800
ctgcgccagg atggcaagac ctttattgac ttcaagaagt acaacgacaa actg         1854
```

<210> SEQ ID NO 48
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98%) of SEQ ID No. 46

<400> SEQUENCE: 48

```
ttcatcaaag tgaagaaaag cgatgagtat acctttgcga cgtctgcgga taatcatgtg     60
accatgtggg tggacgatca ggaagtgatc aacaaagcga gcaacagcaa caaaattcgc    120
ctggagaagg tcgcctgta tcagatcaag attcagtatc agcgcgagaa tccgaccgag    180
aaaggcctgg acttcaaact gtactggacg gatagccaga caagaaaga agtgattagc    240 tctgataacc tgcagctgcc ggaactgaaa cagaagagca gcaacagccg caagaaacgt    300
agcaccagcg caggcccgac cgttccagat cgcgacaacg atggcattcc ggacagcctg    360
gaagtggaag ttataccgt tgatgtgaag aacaaacgca cctttctgag cccgtggatt    420
agcaacattc atgagaagaa aggcctgacc aagtacaaaa gcagcccgga aaagtggagc    480
accgcgagcg atccgtatag cgactttgaa aaagtgaccg gccgcatcga taagaacgtg    540
agcccggaag cgcgtcaccc actggtggcg gcgtatccga ttgtgcatgt tgacatggag    600
aacatcattc tgagcaagaa cgaagatcag agcacccaga acacggatag ccagacccgc    660
acgatcagca agaacaccag cacgagccgt acccatacca gcgaagtgca tggcaatgcg    720
gaagtgcatg cgagcttctt tgacattggt ggcagcgtga gcgcgggctt cagcaacagc    780
aacagcagca ccgtggcgat tgatcatagc ctgagcctgg cgggcgaacg cacctgggca    840
gaaaccatgg gcctgaacac ggcggatacg gcacgtctga atgcgaacat tcgctatgtg    900
aacaccggta ccgcgccaat ctataacgtt ctgccgacca cgagcctggt gctgggcaag    960
aaccagaccc tggcgaccat caaagcgaaa gagaaccagc tgtctcaaat tctggcaccg   1020
aacaactact atccgagcaa gaacctggca ccgattgcac tgaatgcgca ggatgacttc   1080
agctctaccc cgatcaccat gaactacaat cagttcctgg agctggagaa gaccaagcaa   1140
```

```
ctgcgcctgg ataccgatca ggtgtatggc aacattgcga cctacaactt tgagaacggc   1200
cgcgttcgcg tggacaccgg tagcaactgg tctgaagtgc tgccgcagat tcaggaaacc   1260
accgcgcgca tcatcttcaa cggcaaagat ctgaacctgg tggaacgtcg catcgcggca   1320
gtgaacccat ctgatccact ggaaacgacc aaaccggaca tgaccctgaa agaggcgctg   1380
aagattgcat ttggcttcaa cgaaccgaat ggcaacctgc agtatcaggg caaagacatc   1440
accgagtttg atttcaactt tgaccaacag acctctcaga acattaagaa ccagctggca   1500
gaactgaatg cgaccaacat ctacaccgtg ctggataaga tcaaactgaa cgcaaagatg   1560
aacattctga ttcgtgacaa acgcttccac tatgatcgta acaacattgc ggtgggtgca   1620
gatgaaagcg ttgtgaaaga ggcgcatcgc gaagttatca actctagcac cgaaggcctg   1680
ctgctgaaca ttgacaaaga tatccgtaag attctgagcg gctacattgt ggagattgaa   1740
gataccgaag gtctgaaaga agtgatcaac gatcgctatg acatgctgaa catctctagc   1800
ctgcgtcagg atggcaagac ctttattgac ttcaagaaat acaacgacaa gctg         1854

<210> SEQ ID NO 49
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97%) of SEQ ID No. 46

<400> SEQUENCE: 49
ttcatcaaag ttaagaaaag cgatgagtat acctttgcga cgtctgcgga taatcatgtg   60
accatgtggg tggacgatca ggaagtgatc aacaaagcga gcaacagcaa caaaattcgc   120
ctggagaagg gccgcctgta tcagatcaag attcagtatc agcgcgagaa tccgaccgag   180
aaaggcctgg acttcaaact gtactggacg gatagccaga caagaaaga agtgattagc   240 tctgataacc tgcagctgcc ggaactgaaa cagaagagca gcaacagccg taagaaacgt   300
agcaccagcg caggcccgac cgttccagat cgcgacaacg atggcattcc ggacagcctg   360
gaagtggaag gttataccgt tgatgtgaag aacaaacgca cctttctgag cccatggatt   420
agcaacattc atgagaagaa aggcctgacc aagtacaaaa gcagcccgga aaagtggagc   480
accgcgagcg atccgtatag cgactttgaa aaagtgaccg ccgcatcga taagaacgtg   540 agcccggaag cgcgccaccc actggtggca gcgtatccga ttgtgcatgt tgacatggag   600
aacatcattc tgagcaagaa cgaagatcag agcacccaga acacggatag ccagacccgc   660
acgatcagca gaacaccag cacgagccgt acccatacca gcgaagtgca tggcaatgcg   720
gaagtgcacg cgagcttctt tgacattggt ggcagcgtga gcgcgggctt cagcaacagc   780
aacagcagca ccgtggcgat tgatcatagc ctgagcctgg cgggcgaacg cacctgggca   840
gaaaccatgg gtctgaacac ggcggatacg gcacgtctga atgcgaacat cgctatgtg   900 aacaccggta ccgcgccaat ctataacgtg ctgccgacca cgagcctggt gctgggcaag   960
aaccagaccc tggcgaccat caaagcgaaa gagaaccagc tgtctcagat tctggcaccg   1020
aacaactact atccgagcaa gaacctggca ccgattgcac tgaatgcgca agatgacttc   1080
agctctaccc cgatcaccat gaactacaat cagttcctgg agctggagaa gaccaagcaa   1140
ctgcgcctgg ataccgatca ggtgtatggc aacatcgcga cctacaactt tgagaacggc   1200
cgcgttcgcg tggacaccgg tagcaactgg tctgaagtgc tgccgcagat tcaggaaacc   1260
```

```
accgcgcgca ttatcttcaa cggcaaggat ctgaacctgg tggaacgccg catcgcggca      1320
gtgaacccgt ctgatccact ggaaacgacc aaaccggaca tgaccctgaa agaggcgctg      1380
aagattgcat ttggcttcaa cgaaccgaat ggcaacctgc agtatcaggg caaagacatc      1440
accgagtttg atttcaactt tgaccaacag acctctcaga acattaaaaa ccagctggcg      1500
gaactgaatg cgaccaacat ctacaccgtg ctggataaga tcaaactgaa cgcaaagatg      1560
aacattctga ttcgtgacaa acgcttccat tatgatcgta acaacattgc ggtgggtgca      1620
gatgaaagcg ttgtgaaaga ggcgcatcgc gaagttatca actctagcac cgaaggcctg      1680
ctgctgaaca ttgacaaaga tatccgtaag attctgagcg gctacattgt ggagattgaa      1740
gataccgaag gtctgaaaga agtgatcaac gatcgttatg acatgctgaa catctctagc      1800
ctgcgtcagg atggcaagac ctttattgac ttcaagaaat acaacgacaa gctg            1854
```

<210> SEQ ID NO 50
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (96%) of SEQ ID No. 46

<400> SEQUENCE: 50

```
ttcattaaag ttaaaaaaag cgatgagtat accttttgcga cgtctgcgga taatcatgtg       60
accatgtggg tggacgatca ggaagtgatc aacaaagcga gcaacagcaa caaaatccgc      120
ctggagaagg gccgcctgta tcagatcaaa attcaatatc agcgcgagaa tccgaccgag      180
aaaggcctgg acttcaaact gtactggacg gatagccaga acaagaaaga agtgattagc      240
tctgataacc tgcagctgcc ggaactgaaa cagaagagca gcaacagccg taagaaacgt      300
agcaccagcg caggcccgac cgttccagat cgcgacaacg atggcattcc ggacagcctg      360
gaagtggaag gttataccgt tgatgtgaag aacaaacgca cctttctgag cccatggatt      420
agcaacattc atgagaagaa aggcctgacc aagtacaaga gcagcccgga aaagtggagc      480
accgcgagcg atccgtatag cgactttgag aaagttaccg gccgcatcga taagaacgtg      540
agcccggaag cacgccaccc actggtggca gcgtatccga ttgtgcatgt tgacatggag      600
aacatcattc tgagcaagaa cgaagatcag agcacccaga cacgcgatag ccagacccgc      660
acgatcagca gaacaccag cacgagccgt acccatacct ctgaagtgca tggcaatgcg      720
gaagttcatg cgagcttctt tgacattggt ggcagcgtga gcgcgggctt cagcaacagc      780
aacagcagca ccgtggcgat tgatcatagc ctgagcctgg cgggcgaacg cacctgggca      840
gaaaccatgg gtctgaacac cgcggatacg gcacgtctga atgcgaacat tcgctatgtg      900
aacaccggta ccgcgccaat ctataacgtg ctgccgacca cgagcctggt gctgggcaag      960
aaccagacgc tggcgaccat caaagcgaag gagaaccagc tgagccagat tctggcgccg     1020
aacaactact atccgagcaa gaacctggca ccgattgcac tgaatgcgca agatgacttc     1080
agctctaccc cgatcaccat gaactacaat cagttcctgg agctggaaaa gaccaagcaa     1140
ctgcgcctgg ataccgatca ggtgtatggc aacatcgcga cctacaactt tgagaacggc     1200
cgcgttcgcg tggacaccgg tagcaactgg tctgaagtgc tgccgcagat tcaggaaacc     1260
accgcgcgca ttatcttcaa cggcaaggat ctgaacctgg tggaacgccg catcgcggca     1320
gtgaacccgt ctgatccact ggaaacgacc aaaccggaca tgaccctgaa agaggcgctg     1380
aagattgcat ttggcttcaa cgaaccgaat ggcaacctgc agtatcaggg caaagacatc     1440
```

```
accgagtttg atttcaacttt tgaccagcag acctctcaga acattaaaaa ccagctggcg    1500
gaactgaatg cgaccaacat ctacaccgtg ctggataaga tcaaactgaa cgcaaagatg    1560
aacattctga ttcgtgacaa acgcttccac tatgatcgta acaacattgc ggtgggtgca    1620
gatgaaagcg tggtgaaaga ggcgcatcgc gaagtgatca actctagcac cgaaggcctg    1680
ctgctgaaca ttgacaaaga tatccgtaag attctgagcg gctacattgt ggagattgaa    1740
gataccgaag gtctgaaaga agtgatcaac gatcgttatg acatgctgaa catctctagc    1800
ctgcgtcagg atggcaagac ctttattgac ttcaagaaat acaacgacaa gctg          1854
```

<210> SEQ ID NO 51
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95%) of SEQ ID No. 46

<400> SEQUENCE: 51

```
ttcattaaag ttaaaaaaag cgatgagtac acctttgcga cgagcgcgga taatcatgtg    60
accatgtggg tggacgatca ggaagtgatc aacaaagcga gcaacagcaa caaaatccgc   120
ctggagaagg gccgcctgta tcagatcaaa attcaatatc agcgcgagaa tccgaccgag   180
aaaggcctgg acttcaaact gtactggacg gatagccaga acaagaaaga agtgattagc   240
tctgataacc tgcagctgcc ggaactgaaa cagaagagca gcaacagccg taagaaacgt   300
agcaccagcg caggcccgac cgttccagat cgcgacaacg atggcattcc ggacagcctg   360
gaagtggaag gttataccgt tgatgtgaag aacaaacgca cctttctgag cccatggatt   420
tctaacattc acgagaagaa aggcctgacc aagtataaga gcagcccgga aaagtggagc   480
accgcgagcg atccgtatag cgactttgaa aaagttaccg gccgcatcga taagaacgtg   540
agcccggaag cacgtcaccc actggtggca gcgtatccga ttgtgcatgt tgacatggag   600
aacatcattc tgagcaagaa cgaagaccag agcacccaga cacgggatag ccagacccgc   660
acgatcagca gaacaccag cacgagccgt acccatacct ctgaagtgca tggcaatgcg   720
gaagttcatg cgagcttctt tgacattggt ggcagcgtga gcgcgggctt cagcaacagc   780
aacagcagca ccgtggcgat tgatcatagc ctgagcctgg cgggcgaacg cacctgggca   840
gaaaccatgg tctgaacac cgcggatacg gcacgtctga atgcgaacat cgctacgtg   900 aacaccggta ccgcgccgat ctataacgtg ctgccgacca cgagcctggt gctgggcaag   960
aaccagacgc tggcgaccat caaagcgaag gagaaccagc tgagccagat tctggcgccg  1020
aacaactact atccgagcaa aaacctggca ccgattgcac tgaatgcgca agatgatttt  1080
agctctaccc cgatcaccat gaactacaat cagttcctgg agctggaaaa gaccaagcaa  1140
ctgcgcctgg ataccgatca ggtgtatggc aacatcgcga cctacaactt tgagaacggc  1200
cgcgttcgcg tggacaccgg tagcaactgg tctgaagtgc tgccgcagat tcaggaaacc  1260
accgcgcgca ttatcttcaa cggcaaggat ctgaacctgg tggaacgccg catcgcggca  1320
gtgaacccgt ctgatccact ggaaacgacc aagccggaca tgaccctgaa agaggcgctg  1380
aagattgcat tcggcttcaa cgaaccaaat ggcaacctgc agtatcaggg caaagacatc  1440
accgagtttg atttcaactt tgaccagcag acctctcaga acattaaaaa ccagctggcg  1500
gaactgaatg cgaccaacat ctataccgtg ctggataaga tcaaactgaa cgcaaagatg  1560
```

-continued

```
aacattctga ttcgtgacaa acgcttccat tatgatcgta acaacattgc ggtgggtgca      1620
gatgaaagcg tggtgaaaga ggcgcatcgc gaagtgatca actctagcac cgaaggcctg      1680
ctgctgaaca ttgacaaaga tatccgtaag attctgagcg gctacattgt ggagattgaa      1740
gataccgaag gtctgaaaga ggtgatcaac gatcgctatg acatgctgaa catctctagc      1800
ctgcgtcagg acggcaagac ctttattgat ttcaagaagt acaacgacaa actg            1854
```

<210> SEQ ID NO 52
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94%) of SEQ ID No. 46

<400> SEQUENCE: 52

```
ttcattaaag ttaaaaaaag cgatgagtac acctttgcga cgagcgcgga taatcatgtg       60
accatgtggg tggacgatca ggaagtgatc aacaaagcga gcaacagcaa caaaatccgc      120
ctggagaagg gccgcctgta tcagatcaaa attcaatatc agcgcgagaa tccgaccgag      180
aaaggcctgg acttcaaact gtactggacg gatagccaga caaaaaaga agtgattagc       240 tctgataacc tgcagctgcc ggaactgaaa cagaagagcg caacagccg taagaaacgt       300 agcaccagcg caggcccaac cgttccagat cgcgacaacg acggcattcc ggatagcctg      360
gaagtggaag ttataccgt tgatgtgaag aacaaacgca cctttctgag cccatggatt       420
tctaacattc acgagaagaa aggcctgacc aagtataaga gcagcccgga aaagtggagc      480
accgcgagcg atccgtatag cgactttgaa aaggttaccg ccgcatcga taagaacgtg       540 agcccggaag cacgtcaccc actggtggca gcgtatccga ttgtgcatgt tgacatggag      600
aacatcattc tgagcaagaa cgaagaccag agcacccaga cacggatag ccagacccgc      660 accatcagca agaacaccag cacgagccgt acccatacct ctgaggtgca tggcaatgcg      720
gaagttcatg cgagcttctt tgatattggt ggcagcgtga gcgcgggctt tagcaacagc      780
aacagcagca cggtggcgat tgatcatagc ctgagcctgg cgggcgaacg cacctgggca      840
gaaaccatgg gtctgaacac cgcggatacg gcgcgtctga atgcgaacat tcgctacgtg       900
aacaccggta ccgcgccgat ctacaacgtg ctgccgacca cgagcctggt gctgggcaag      960
aaccagaccc tggcgaccat caaagcgaag gagaaccagc tgagccagat tctggcgccg      1020
aacaactact atccgagcaa aaacctggca ccgattgcac tgaatgcaca agatgatttt      1080
agctctaccc cgatcaccat gaactacaat cagttcctgg agctggaaaa gaccaagcaa      1140
ctgcgcctgg acaccgatca ggtgtatggc aacatcgcga cctacaactt tgagaacggc      1200
cgcgttcgcg tggacaccgg tagcaactgg tctgaagtgc tgccgcagat tcaggaaacc      1260
accgcgcgca ttatcttcaa cggcaaggac ctgaacctgg tgaacgccg catcgcggca      1320 gtgaacccgt ctgatccgct ggaaacgacc aagccggaca tgaccctgaa agaggcgctg      1380
aagattgcat tcggcttcaa cgaaccaaat ggcaacctgc agtatcaggg caaagacatc      1440
accgaattcg atttcaactt tgaccagcag acctctcaga acattaaaaa ccagctggcg      1500
gaactgaatg cgaccaacat ctataccgtg ctggataaga tcaaactgaa cgcaaagatg      1560
aacattctga ttcgtgataa acgcttccat tatgatcgta acaacattgc ggtgggtgca      1620
gatgaaagcg tggtgaaaga ggcgcatcgc gaagtgatca actctagcac ggaaggcctg      1680
ctgctgaaca ttgacaaaga tatccgtaag attctgagcg gctacattgt ggagattgaa      1740
```

```
gataccgaag gtctgaaaga ggtgatcaac gatcgctatg acatgctgaa catctctagc   1800
ctgcgtcagg acggcaagac ctttattgat ttcaagaagt ataacgacaa actg         1854

<210> SEQ ID NO 53
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93%) of SEQ ID No. 46

<400> SEQUENCE: 53
ttcattaaag ttaaaaaaag cgacgagtac acctttgcga ccagcgcgga taatcatgtg     60
accatgtggg tggatgatca ggaagtgatc aacaaagcga gcaacagcaa caaaatccgc   120
ctggagaagg gccgcctgta tcagatcaaa attcagtatc agcgcgagaa tccgaccgag   180
aaaggcctgg atttcaaact gtactggacc gatagccaga acaaaaagga agtgattagc   240
tctgacaacc tgcagctgcc ggaactgaaa cagaaaagca gcaacagccg taagaaacgt   300
agcacctctg cgggcccaac cgttccggat cgcgacaacg acggcattcc ggatagcctg   360
gaagtggaag gttataccgt tgacgtgaag aacaagcgca cctttctgag cccgtggatt   420
agcaacattc acgaaagaa aggtctgacc aagtataaaa gcagcccgga aagtggagc    480 accgcgagcg atccatatag cgactttgaa aaggttacgg gccgcatcga taagaacgtg   540
agcccggaag cgcgtcaccc actggtggca gcgtatccaa ttgtgcatgt tgacatggag   600
aacatcattc tgagcaagaa cgaagaccag agcacccaga acacggatag ccagacgcgt   660
accattagca aaaacacgag cacgagccgt acccatacca gcgaggtgca tggcaatgcg   720
gaagtgcatg cgagcttctt tgacattggt ggcagcgtga gcgcgggctt tagcaacagc   780
aacagcagca cggtggcgat tgatcatagc ctgagcctgg cgggcgagcg cacctgggca   840
gaaaccatgg gtctgaacac cgcggatacg gcgcgtctga atgcaaacat ccgctacgtg   900
aacaccggca ccgcgccgat ctacaacgtg ctgccgacca ccagcctggt gctgggcaag   960
aaccaaaccc tggcgacgat caaagcgaag gagaaccagc tgtctcagat tctggcgccg  1020
aacaactact atccgagcaa aaacctggca ccgattgcgc tgaatgcaca ggatgacttt  1080
agctctaccc cgatcaccat gaactacaat cagttcctgg agctggaaaa gaccaagcaa  1140
ctgcgcctgg acaccgatca ggtgtatggc aacattgcga cctacaactt tgagaacggc  1200
cgcgttcgcg tggacaccgg tagcaactgg tctgaagtgc tgccgcagat tcaggaaacc  1260
accgcgcgca tcatttttcaa cggcaaggat ctgaacctgg tggaacgccg catcgcggca  1320
gtgaacccgt ctgatccgct ggaaaccacc aagccggaca tgaccctgaa agaggcactg  1380
aagattgcat tcggcttcaa cgaaccaaat ggcaacctgc agtatcaagg caaggatatc  1440
accgaattcg atttcaactt tgaccagcag acctctcaga acattaaaaa ccagctggca  1500
gaactgaacg cgaccaacat ctataccgtg ctggataaga ttaagctgaa tgcaaagatg  1560
aacattctga ttcgtgataa acgcttccat tatgatcgta acaacattgc ggtgggtgca  1620
gatgaaagcg ttgtgaaaga ggcgcatcgc gaagtgatca actctagcac ggaaggcctg  1680
ctgctgaaca tcgacaaaga tattcgcaag atcctgagcg gctacatcgt ggagatcgaa  1740
gataccgaag gtctgaaaga ggtgattaac gatcgctatg acatgctgaa catctctagc  1800
ctgcgtcagg atggcaagac ctttattgat ttcaagaaat ataacgacaa actg         1854
```

<210> SEQ ID NO 54
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92%) of SEQ ID No. 46

<400> SEQUENCE: 54

| | | | | | |
|---|---|---|---|---|---|
| ttcattaaag | tgaaaaaaag | cgacgagtac | acgtttgcga | ccagcgcgga | taatcatgtg | 60 |
| accatgtggg | tggatgatca | ggaagttatc | aacaaagcaa | gcaatagcaa | caagatccgc | 120 |
| ctggagaaag | gccgcctgta | tcagatcaaa | attcagtatc | agcgcgagaa | tccgaccgag | 180 |
| aaaggcctgg | atttcaaact | gtactggacc | gacagccaga | caaaaaagga | agtgatcagc | 240 |
| tctgacaacc | tgcagctgcc | ggaactgaag | cagaagagca | gcaacagccg | taagaaacgt | 300 |
| agcacctctg | cgggcccaac | cgttccggat | cgcgacaacg | acggcattcc | ggattctctg | 360 |
| gaagtggaag | ttataccgt | tgacgtgaaa | aacaagcgca | cctttctgag | cccgtggatt | 420 |
| agcaacattc | acgaaaagaa | gggtctgacc | aagtataaaa | gcagcccgga | aaagtggagc | 480 |
| accgcgagcg | atccatatag | cgactttgaa | aaggttaccg | gccgcatcga | taagaacgtg | 540 |
| agcccggaag | cgcgccaccc | actggtggca | gcgtatccaa | ttgtgcatgt | tgacatggag | 600 |
| aacattattc | tgagcaagaa | cgaagaccag | agcacccaga | acacggatag | ccagacgcgt | 660 |
| accattagca | aaaacacgag | cacgagccgt | acccatacca | gcgaggtgca | tggcaatgcg | 720 |
| gaagtgcatg | cgagcttctt | tgacattggt | ggcagcgtga | gcgcgggctt | tagcaacagc | 780 |
| aacagcagca | cggtggcgat | tgatcatagc | ctgagcctgg | cgggcgagcg | cacctgggca | 840 |
| gaaaccatgg | gtctgaacac | cgcggatacc | gcgcgtctga | atgcaaacat | ccgctacgtg | 900 |
| aacaccggca | ccgcgccgat | ctacaacgtg | ctgccgacca | ccagcctggt | gctgggcaag | 960 |
| aaccaaaccc | tggcgacgat | caaagcgaag | gagaaccagc | tgtctcagat | tctggcgccg | 1020 |
| aacaactatt | atccgagcaa | aaacctggca | ccgattgcgc | tgaacgcgca | ggatgacttt | 1080 |
| agcagcaccc | cgatcaccat | gaactacaac | cagttcctgg | agctggaaaa | gaccaagcaa | 1140 |
| ctgcgcctgg | acaccgatca | ggtgtacggg | aacattgcga | cctacaactt | tgagaacggc | 1200 |
| cgcgttcgcg | tggacaccgg | tagcaactgg | tctgaagtgc | tgccgcagat | tcaggaaacc | 1260 |
| accgcgcgca | tcattttcaa | cggcaaggat | ctgaacctgg | tggaacgccg | catcgcggca | 1320 |
| gtgaacccgt | ctgatccgct | ggaaaccacg | aagccggaca | tgaccctgaa | agaggcactg | 1380 |
| aagattgcat | tcggcttcaa | cgaaccaaat | ggcaacctgc | agtatcaggg | caaagatatc | 1440 |
| accgaattcg | atttcaactt | tgaccagcaa | acctctcaga | acattaaaaa | ccagctggca | 1500 |
| gaactgaacg | cgaccaacat | ctataccgtg | ctggataaga | ttaagctgaa | tgcaaagatg | 1560 |
| aatattctga | ttcgtgataa | acgtttccat | tatgatcgta | caacattgc | ggtgggtgca | 1620 |
| gatgaaagcg | ttgtgaaaga | ggcgcatcgc | gaagtgatca | actctagcac | ggaaggcctg | 1680 |
| ctgctgaaca | tcgacaaaga | tattcgcaag | atcctgagcg | gctacatcgt | ggagatcgaa | 1740 |
| gataccgaag | gtctgaaaga | ggtgattaac | gatcgctatg | acatgctgaa | catctctagc | 1800 |
| ctgcgtcagg | atggcaaaac | ctttattgat | ttcaagaaat | ataacgataa | actg | 1854 |

<210> SEQ ID NO 55
<211> LENGTH: 1854
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: Sequence variant (91%) of SEQ ID No. 46

<400> SEQUENCE: 55
ttcattaaag tgaaaaaaag cgacgaatac acgtttgcga ccagcgcgga taatcatgtt      60
accatgtggg tggacgatca ggaagtgatc aacaaagcaa gcaatagcaa caagatccgc     120
ctggagaaag gccgcctgta tcagatcaaa attcagtatc agcgcgagaa tccgaccgag     180
aaaggcctgg atttcaaact gtactggacc gacagccaga acaaaaagga agtgatcagc     240
agcgacaacc tgcagctgcc ggaactgaag cagaagagca gcaactctcg taagaaacgt     300
agcacctctg cgggcccaac cgttccggat cgcgataacg acggcattcc ggattctctg     360
gaagtggagg gttataccgt tgacgtgaaa aacaagcgca cctttctgag cccgtggatt     420
agcaacattc acgaaaagaa gggtctgacc aagtataaaa gcagcccgga aaagtggagc     480
accgcgagcg acccatatag cgactttgaa aaggtgaccg gccgcatcga caagaacgtg     540
agcccggaag cgcgccaccc actggtggca gcgtatccaa ttgtgcatgt tgacatggag     600
aacattattc tgagcaagaa cgaagaccag agcacccaga acaccgatag ccagacgcgt     660
accattagca aaaacacgag cacgagccgt acccatacct ctgaggtgca tggcaatgcg     720
gaagtgcatg cgagcttctt tgacattggc ggcagcgtga gcgcgggctt cagcaacagc     780
aacagcagca cggtggcgat tgatcatagc ctgagcctgg cgggcgagcg cacctgggca     840
gaaaccatgg gtctgaacac cgcggatacg gcgcgtctga atgcaaacat ccgctacgtg     900
aacaccggca ccgcgccgat ctacaacgtg ctgccgacca ccagcctggt gctgggcaag     960
aaccaaaccc tggcgacgat caaagcgaag gagaaccagc tgagccagat tctggcgccg    1020
aacaactatt atccgagcaa aaacctggca ccgattgcgc tgaacgcgca ggatgacttt    1080
agcagcaccc cgattaccat gaactacaac cagttcctgg agctggaaaa gaccaagcag    1140
ctgcgcctgg ataccgatca ggtgtacggc aacattgcga cctacaactt cgagaacggc    1200
cgcgttcgcg tggacaccgg tagcaactgg tctgaagtgc tgccgcagat tcaggaaacc    1260
accgcgcgca tcatttttaa cggcaaggat ctgaacctgg tggaacgccg catcgcggca    1320
gttaacccgt ctgatccgct ggaaaccacg aagccggaca tgaccctgaa agaggcactg    1380
aagattgcat ttggcttcaa cgaaccaaat ggtaacctgc agtatcaggg caaagatatc    1440
accgaattcg attttaactt cgatcagcaa acctctcaga acattaaaaa ccagctggca    1500
gaactgaacg cgaccaacat ctataccgtg ctggataaga ttaagctgaa tgcaaagatg    1560
aatattctga ttcgtgataa acgtttccat tatgatcgta acaacattgc ggtgggtgca    1620
gatgaaagcg ttgtgaaaga ggcgcatcgc gaagtgatca actctagcac ggaaggcctg    1680
ctgctgaaca tcgacaaaga tatccgcaag atcctgagcg gctacatcgt ggagatcgaa    1740
gataccgaag gtctgaaaga ggtgattaac gatcgctatg acatgctgaa catctctagc    1800
ctgcgtcaag atggcaaaac ctttattgat ttcaagaaat ataacgataa actg          1854

<210> SEQ ID NO 56
<211> LENGTH: 1953
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Truncated version of SEQ ID No. 1
```

(bp. 103-2055)

<400> SEQUENCE: 56

```
gtgacctcta gcacgaccgg cgatctgagc attccgagca gcgaactgga gaacattccg      60
agcgagaacc agtactttca gtctgcgatt tggagcggct tcatcaaagt gaagaaaagc     120
gatgagtata cctttgcgac gtctgcggat aaccatgtga ccatgtgggt ggacgatcag     180
gaagtgatca acaaagcgag caacagcaac aagattcgcc tggagaaggg tcgcctgtat     240
cagatcaaga ttcagtatca gcgcgagaat ccgaccgaga aaggcctgga tttcaaactg     300
tactggaccg atagccagaa caagaaagaa gtgattagct ctgataacct gcaactgccg     360
gaactgaaac agaagagcag caacagccgc aagaaacgca gcacctctgc aggcccgacc     420
gttccagatc gcgacaacga tggcattccg gacagcctgg aagtggaagg ttataccgtt     480
gatgtgaaga caaacgcac ctttctgagc ccgtggatta gcaacattca tgagaagaaa     540
ggcctgacca gtacaaaag cagcccggag aagtggagca ccgcgagcga tccgtatagc     600
gactttgaga agtgaccgg ccgcattgat aagaacgtga gcccggaagc gcgtcaccca     660
ctggttgcag cgtatccgat tgtgcatgtt gacatggaga acatcattct gagcaagaac     720
gaagatcaga gcacccagaa cacgatagc cagacccgca cgatcagcaa gaacaccagc     780
acgagccgta cccataccag cgaagtgcat ggcaatgcgg aagtgcatgc gagcttcttt     840
gacattggtg gcagcgtgag cgcgggcttc agcaacagca cagcagcac cgtggcgatt     900
gatcatagcc tgagcctggc gggcgaacgt acctgggcgg aaaccatggg cctgaacacg     960
gcggatacgg cacgtctgaa tgcgaacatt cgctatgtga acaccggtac cgcgccaatc    1020
tataacgttc tgccgaccac gagcctggtg ctgggcaaga atcagaccct ggcgaccatc    1080
aaagcgaaag agaaccagct gtctcagatt ctggcaccga caactacta tccgagcaag    1140
aacctggcac cgattgcact gaatgcgcag gatgacttca gcagcacccc gatcaccatg    1200
aactacaatc agtttctgga gctggagaag accaaacaac tgcgcctgga taccgatcag    1260
gtgtatggca acattgcgac ctacaacttt gagaacggcc gcgttcgcgt ggataccggt    1320
agcaactggt ctgaagtgct gccgcagatt caggaaacga ccgcgcgcat catcttcaac    1380
ggcaaagatc tgaacctggt ggaacgtcgc atcgcggcag tgaacccatc tgatccactg    1440
gaaacgacca aaccggacat gaccctgaaa gaagcgctga agattgcatt tggcttcaac    1500
gaaccgaatg caacctgca gtatcagggc aaagacatca ccgagtttga cttcaacttt    1560
gatcaacaga cctctcagaa catcaagaac cagctggcag aactgaatgc gaccaacatc    1620
tacaccgtgc tggacaagat caaactgaac gcaaagatga acattctgat tcgtgacaaa    1680
cgcttccact atgatcgtaa caacattgcg gtgggtgcag atgaaagcgt tgtgaaagaa    1740
gcgcatcgtg aagtgatcaa ctctagcacc gaaggcctgc tgctgaacat tgacaaagac    1800
atccgtaaga ttctgagcgg ctacattgtg gagattgaag ataccgaagg tctgaaagaa    1860
gtgatcaacg atcgctatga catgctgaac atctctagcc tgcgccagga tggcaagacc    1920
ttcattgact tcaagaagta caacgacaaa ctg                                   1953
```

<210> SEQ ID NO 57
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99%) of SEQ ID No. 56

<400> SEQUENCE: 57

```
gtgacctcta gcacgaccgg cgatctgagc attccgagca gcgaactgga gaacattccg    60
agcgagaacc agtactttca gagcgcgatt tggagcggct tcatcaaagt gaagaaaagc   120
gatgagtata cctttgcgac gtctgcggat aaccatgtga ccatgtgggt ggacgatcag   180
gaagtgatca acaaagcgag caacagcaac aagattcgcc tggagaaggg tcgcctgtat   240
cagatcaaga ttcagtatca gcgcgagaat ccgaccgaga aaggcctgga cttcaaactg   300
tactggaccg atagccagaa caagaaggaa gtgattagct ctgataacct gcaactgccg   360
gaactgaaac agaagagcag caacagccgc aagaaacgca gcacctctgc aggcccgacc   420
gttccagatc gcgacaacga tggcatcccg gacagcctgg aagtggaagg ttataccgtt   480
gatgtgaaga acaaacgcac cttcctgagc ccatggatta gcaacattca tgagaagaaa   540
ggcctgacca gtacaaaag cagcccggag aagtggagca ccgcgagcga tccgtatagc   600
gactttgaga aagtgaccgg ccgcattgat aagaacgtga gcccggaagc gcgtcaccca   660
ctggttgcag cgtatccgat tgtgcatgtt gacatggaga acatcattct gagcaagaac   720
gaagatcaga gcacccagaa cacgatagc cagacccgca cgatcagcaa gaacaccagc   780
acgagccgta cccataccag cgaagtgcat ggcaatgcgg aagtgcatgc gagcttcttt   840
gacattggtg gcagcgtgag cgcgggcttc agcaacagca acagcagcac cgtggcgatt   900
gatcatagcc tgagcctggc gggcgaacgt acctgggcgg aaaccatggg cctgaacacg   960
gcggatacgc cacgtctgaa tgcgaacatt cgctatgtga acaccggtac cgcgccaatt  1020
tataacgttc tgccgaccac cagcctggtg ctgggcaaga atcagaccct ggcgacgatc  1080
aaagcgaaag agaaccagct gtctcagatt ctggcaccga caactacta tccgtctaaa  1140
aacctggcac cgattgcact gaatgcgcag gatgacttca gcagcacccc gatcaccatg  1200
aactacaatc agtttctgga gctggagaag accaaacaac tgcgcctgga taccgatcag  1260
gtgtatggca acattgcgac ctacaacttt gagaacggcc gcgttcgcgt ggataccggt  1320
agcaactggt ctgaagtgct gccgcagatt caggaaacga ccgcgcgcat catcttcaac  1380
ggcaaagatc tgaacctggt ggaacgtcgc atcgcggcag tgaacccatc tgatccgctg  1440
gaaacgacca aaccggacat gaccctgaaa gaagcgctga agattgcatt tggctttaac  1500
gaaccgaatg caacctgca gtatcagggc aaagacatca ccgagtttga cttcaacttt  1560
gatcaacaga cctctcagaa catcaagaac cagctggcag aactgaatgc gaccaacatc  1620
tacaccgtgc tggataagat caaactgaac gcaaagatga acattctgat tcgtgacaaa  1680
cgcttccact atgatcgtaa caacattgcg gtgggtgcag atgaaagcgt tgtgaaagaa  1740
gcgcatcgtg aagtgatcaa ctctagcacc gaaggcctgc tgctgaacat tgacaaagac  1800
atccgtaaga ttctgagcgg ctacattgtg gagattgaag ataccgaagg tctgaaagaa  1860
gtgatcaacg atcgctatga catgctgaac atctctagcc tgcgccagga tggcaagacc  1920
ttcattgact tcaagaagta caacgacaaa ctg                                1953
```

<210> SEQ ID NO 58
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (98%) of SEQ ID No. 56

<400> SEQUENCE: 58

```
gtgacctcta gcacgaccgg cgatctgagc attccgagca gcgaactgga gaacattccg      60
agcgagaacc agtactttca gagcgcgatt tggagcggct tcatcaaagt gaagaaaagc     120
gatgagtata cctttgcgac gtctgcggat aaccatgtga ccatgtgggt ggacgatcag     180
gaagtgatca acaaagcgag caacagcaac aagattcgcc tggagaaggg tcgcctgtat     240
caaattaaga ttcagtatca gcgcgagaat ccgaccgaga aaggcctgga cttcaaactg     300
tactggaccg atagccagaa caagaaggaa gtgattagct ctgataacct gcagctgccg     360
gaactgaaac agaagagcag caacagccgc aagaaacgca gcacctctgc aggcccgacc     420
gttccagatc gcgacaacga tggcatcccg gacagcctgg aagtggaagg ttataccgtt     480
gatgtgaaga caaaacgcac cttcctgagc ccatggatca gcaacattca tgagaagaaa     540
ggcctgacca gtacaaaaag cagcccggag aagtggagca ccgcgagcga tccgtatagc     600
gactttgaga agtgaccgg ccgcattgat aagaacgtga gcccggaagc gcgtcaccca     660
ctggttgcag cgtatccgat tgtgcatgtt gacatggaga acatcattct gagcaagaac     720
gaagatcaga gcacccagaa cacggatagc cagaccccgca cgattagcaa gaacaccagc     780
acgagccgta cccataccag cgaggtgcat ggcaatgcgg aagtgcatgc gagcttcttt     840
gacattggtg gcagcgtgag cgcgggcttc tctaacagca acagcagcac cgtggcgatt     900
gatcatagcc tgagcctggc gggcgaacgt acctgggcgg aaaccatggg cctgaacacg     960
gcggatacgg cacgtctgaa tgcgaacatt cgctatgtga acaccggtac cgcgccaatt    1020
tataatgttc tgccgaccac cagcctggtg ctgggcaaga atcagaccct ggcgaccatc    1080
aaagcgaaag agaaccagct gtctcagatt ctggcaccga caactacta tccgtctaaa    1140
aacctggcac cgattgcact gaatgcgcag gatgacttca gcagccccc gatcaccatg    1200
aactacaacc agttcctgga actggagaag accaaacaac tgcgcctgga taccgatcag    1260
gtgtatggca acattgcgac ctacaacttt gaaaacggcc gtgttcgcgt ggataccggt    1320
agcaactggt ctgaagtgct gccgcagatt caggaaacga ccgcgcgcat catcttcaac    1380
ggcaaagatc tgaacctggt ggaacgtcgc atcgcggcga tgaacccatc tgatccgctg    1440
gaaacgacca aaccggacat gaccctgaaa gaagcgctga agattgcatt tggctttaac    1500
gagccgaatg gcaacctgca gtatcagggc aaagacatca ccgagtttga cttaacttt    1560
gatcaacaga cctctcagaa catcaagaac cagctggcag aactgaatgc gaccaacatc    1620
tacacggtgc tggataagat caaactgaac gcaaagatga acattctgat ccgtgacaaa    1680
cgcttccact atgatcgcaa caacattgcg gtgggtgcag atgaaagcgt tgtgaaagaa    1740
gcgcatcgtg aagtgatcaa cagcagcacc gaaggcctgc tgctgaacat tgacaaagac    1800
atccgtaaga ttctgagcgg ctacattgtg gagattgaag ataccgaagg tctgaaagaa    1860
gtgatcaacg atcgctatga catgctgaac atctctagcc tgcgccagga tggcaagacc    1920
ttcattgact tcaagaagta caacgacaaa ctg                                 1953
```

<210> SEQ ID NO 59
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (97%) of SEQ ID NO. 56

<400> SEQUENCE: 59

```
gtgacctcta gcacgaccgg cgatctgagc attccgagca gcgaactgga gaacattccg      60
agcgagaacc agtactttca gagcgcgatt tggagcggct tcatcaaagt gaagaaaagc     120
gatgagtata ccttcgcgac gtctgcggat aaccatgtga ccatgtgggt ggacgatcag     180
gaagtgatca acaaagcgag caacagcaac aaaattcgcc tggagaaggg tcgcctgtat     240
caaattaaga ttcagtatca gcgcgagaat ccgaccgaaa aaggcctgga ctttaagctg     300
tactggaccg atagccagaa caagaaggaa gtgattagct ctgataacct gcagctgccg     360
gaactgaaac agaagagcag caacagccgc aagaaacgca gcacctctgc aggcccgacc     420
gttccagatc gcgacaacga tggcatcccg gacagcctgg aagtggaagg ttataccgtg     480
gatgtgaaga caaacgcac cttcctgagc ccatggatca gcaacattca tgagaagaaa     540
ggcctgacca agtacaaaag cagcccggag aagtggagca ccgcgagcga tccgtatagc     600
gactttgaga agtgaccgg ccgcattgat aagaacgtga gcccggaagc gcgtcaccca     660
ctggttgcag cgtatccgat tgtgcatgtg gacatggaga acatcattct gagcaagaac     720
gaagatcaga gcacccagaa cacggattct cagacccgca cgattagcaa gaacaccagc     780
acgagccgta cccataccag cgaggtgcat ggcaatgcgg aagtgcatgc gagcttcttt     840
gacattggtg gcagcgtgag cgcgggcttc tctaacagca acagcagcac cgtggcgatt     900
gatcatagcc tgagcctggc gggcgaacgt acctgggcgg aaaccatggg cctgaacacg     960
gcggatacgg cacgtctgaa tgcgaacatt cgctatgtga acaccggtac cgcgccaatt    1020
tataatgttc tgccgaccac cagcctggtg ctgggcaaga atcagaccct ggcgaccatc    1080
aaagcgaaag agaaccagct gtctcagatt ctggcaccga caactacta tccgtctaaa    1140 aacctggcac cgattgcact gaatgcgcag gatgacttca gcagcacccc gatcaccatg    1200
aactacaacc agttcctgga actggagaag accaaacaac tgcgcctgga taccgatcag    1260
gtttatggca acattgcgac ctacaacttt gaaaacggcc gtgttcgcgt ggataccggt    1320
agcaactggt ctgaagtgct gccgcagatt caggaaacga ccgcgcgcat catcttcaac    1380
ggcaaagatc tgaacctggt ggaacgtcgc atcgcggcag ttaacccatc tgatccgctg    1440
gaaacgacca aaccggacat gaccctgaaa gaagcgctga agattgcatt tggctttaac    1500
gagccgaatg gcaacctgca gtatcagggc aaagacatca ccgagtttga ctttaacttt    1560
gatcaacaga cctctcagaa catcaagaac cagctggcag aactgaatgc gaccaacatc    1620
tacacggtgc tggataagat caaactgaac gcaaagatga acattctgat ccgtgacaaa    1680
cgcttccact atgatcgcaa caacattgcg gtgggtgcag atgaaagcgt ggttaaagaa    1740
gcgcatcgtg aagtgatcaa cagcagcacc gaaggcctgc tgctgaacat tgacaaagac    1800
atccgtaaga ttctgagcgg ctacattgtg agagattgaag ataccgaggg tctgaaagaa    1860
gtgatcaacg atcgctatga catgctgaac atcagcagcc tgcgccagga tggcaagacc    1920
ttcattgact tcaagaagta caacgacaaa ctg                                  1953
```

<210> SEQ ID NO 60
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 56

<400> SEQUENCE: 60

-continued

```
gtgacctcta gcacgaccgg cgatctgagc attccgagca gcgaactgga gaacattccg      60
agcgagaacc agtactttca gagcgcgatt tggagcggct tcatcaaagt gaagaaaagc     120
gatgagtata ccttcgcgac ctctgcggac aaccatgtga ccatgtgggt ggacgatcag     180
gaagtgatca caaagcgag caacagcaac aaaattcgcc tggagaaggg tcgcctgtat     240
caaattaaga ttcagtatca gcgcgagaat ccgaccgaaa aaggcctgga ctttaaactg     300
tactggaccg atagccagaa caagaaggaa gtgattagct ctgataacct gcagctgccg     360
gaactgaaac agaagagcag caacagccgc aagaaacgca gcaccagcgc aggcccgacc     420
gtgccagacc gcgacaacga tggcatcccg gatagcctgg aagtggaagg ttataccgtg     480
gatgtgaaga caaacgcac cttcctgagc ccatggatta gcaacattca tgagaagaaa     540
ggcctgacca gtacaaaag cagcccggag aagtggagca ccgcgagcga tccgtatagc     600
gactttgaga aagtgaccgg ccgcattgac aagaacgtga gcccggaagc gcgtcaccca     660
ctggttgcag cgtatccgat tgtgcatgtg gacatggaga acatcattct gagcaagaac     720
gaagatcaga gcacccagaa cacggattct cagacccgca cgattagcaa gaacaccagc     780
acgagccgca cccataccag cgaggtgcat ggcaatgcgg aagtgcatgc gagcttcttt     840
gacattggtg gcagcgtgag cgcgggcttc tctaacagca acagcagcac cgtggcgatt     900
gatcacagcc tgagcctggc gggcgaacgt acctgggcgg aaaccatggg cctgaacacg     960
gcggatacgg cacgcctgaa tgcgaacatt cgctatgtga acaccggtac cgcgccaatt    1020
tataatgttc tgccgaccac cagcctggtg ctgggcaaga atcagaccct ggcgaccatc    1080
aaagcgaaag agaaccagct gtctcagatt ctggcaccga caactacta tccgtctaaa    1140 aacctggcac cgattgcact gaatgcgcag gatgatttca gctctacccc gatcaccatg    1200
aactacaacc agttcctgga actggagaag acgaaacaac tgcgcctgga taccgatcag    1260
gtttatggca acattgcgac ctacaacttt gaaaacggcc gtgttcgcgt ggataccggt    1320
agcaactggt ctgaagtgct gccgcagatt caggaaacga ccgcgcgcat catcttcaac    1380
ggcaaagatc tgaacctggt ggaacgtcgc atcgcggcag ttaacccatc tgatccgctg    1440
gaaacgacca agccggacat gaccctgaaa gaagcgctga agattgcatt tggctttaac    1500
gagccgaatg gcaacctgca gtatcagggc aaagacatca ccgagtttga ctttaacttt    1560
gatcaacaga cctctcagaa catcaagaac cagctggcag aactgaatgc gaccaacatc    1620
tacacggttc tggataagat caaactgaac gcaaagatga acattctgat ccgtgacaaa    1680
cgtttccatt atgatcgtaa caacatcgcg gtgggtgcaa tgaaagcgt ggttaaagaa    1740 gcgcatcgtg aagtgatcaa cagcagcacc gaaggcctgc tgctgaacat tgacaaagac    1800
atccgtaaga ttctgagcgg ctacattgtg gagattgaag ataccgaggg tctgaaagaa    1860
gtgatcaacg atcgctatga tatgctgaac atcagcagcc tgcgccagga tggcaagacc    1920
ttcattgact tcaagaagta caacgacaaa ctg                                 1953
```

<210> SEQ ID NO 61
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95%) of SEQ ID No. 56

<400> SEQUENCE: 61

```
gtgacctcta gcacgaccgg cgatctgagc attccgagca gcgaactgga gaacattccg      60
```

```
agcgagaacc agtacttcca gagcgcgatt tggagcggct tcatcaaagt taagaaaagc    120
gatgagtata ccttcgcgac ctctgcggac aaccatgtga ccatgtgggt ggacgatcag    180
gaagtgatca acaaagcgag caacagcaac aaaattcgcc tggagaaggg tcgcctgtat    240
caaattaaga ttcagtatca gcgcgagaat ccaaccgaaa aaggcctgga ctttaaactg    300
tactggaccg atagccagaa taagaaggaa gtgatcagct ctgataacct gcagctgccg    360
gaactgaaac agaagagcag caacagccgc aagaaacgca gcaccagcgc gggcccgacc    420
gtgccagacc gcgacaacga tggcatcccg gatagcctgg aagtggaagg ttataccgtg    480
gatgtgaaga acaaacgcac cttcctgagc ccatggatta gcaacattca tgagaagaaa    540
ggcctgacca agtacaaaag cagcccggag aagtggagca ccgcgagcga tccgtatagc    600
gactttgaga aagtgacggg ccgcattgac aagaacgtga gcccggaagc gcgtcaccca    660
ctggttgcag cgtatccgat tgtgcatgtg gacatggaga acatcattct gagcaagaac    720
gaagatcaga gcacccagaa cacgattct cagacccgca cgattagcaa aaacaccagc    780
acgagccgca cccataccag cgaggtgcat ggcaatgcgg aagtgcatgc gagcttcttt    840
gacattggtg gcagcgtgag cgcgggcttc tctaacagca acagcagcac cgtggcgatt    900
gatcacagcc tgagcctggc gggcgaacgt acctgggcgg aaaccatggg cctgaacacc    960
gcggatacgc cacgcctgaa tgcgaacatt cgctatgtga acaccggtac cgcgccgatt   1020
tataatgttc tgccgaccac cagcctggtg ctgggcaaga atcagaccct ggcgaccatt   1080
aaagcgaaag agaaccagct gtctcagatt ctggcaccga caactacta tccgtctaaa   1140 aacctggcac cgattgcact gaatgcgcag gatgatttca gctctacccc gatcaccatg   1200
aactacaacc agttcctgga actggagaag acgaaacaac tgcgcctgga caccgatcag   1260
gtttatggca acattgcgac ctacaacttt gaaaacggcc gtgtgcgcgt ggataccggt   1320
agcaactggt ctgaagtgct gccgcagatt caggaaacga ccgcgcgcat catcttcaac   1380
ggcaaagatc tgaacctggt ggaacgtcgc atcgcggcag ttaacccatc tgatccgctg   1440
gaaacgacca gccggacat gaccctgaag gaagcgctga agattgcatt tggctttaac   1500
gagccgaatg gcaacctgca gtatcagggc aaagacatca ccgagtttga ttttaacttt   1560
gatcaacaga cctctcagaa catcaagaac cagctggcag aactgaacgc gaccaacatc   1620
tacacggttc tggataagat caaactgaac gcaaagatga acattctgat ccgtgacaaa   1680
cgttttcatt atgatcgtaa caacatcgca gtgggtgcag atgaaaagcgt ggttaaagaa   1740 gcgcatcgtg aagtgatcaa cagcagcacc gagggcctgc tgctgaacat tgacaaagac   1800
atccgtaaga ttctgagcgg ctacattgtg gaaattgaag ataccgaggg tctgaaagaa   1860
gtgatcaacg atcgctatga tatgctgaac atcagcagcc tgcgccagga tggcaagacc   1920
ttcattgact tcaagaagta caacgacaaa ctg                                1953
```

<210> SEQ ID NO 62
<211> LENGTH: 1953
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94%) of SEQ ID No. 56

<400> SEQUENCE: 62

```
gtgacctcta gcacgaccgg cgatctgagc attccgagca gcgaactgga gaacattccg     60
```

```
agcgagaacc agtacttcca gagcgcgatt tggagcggct tcatcaaagt taagaaaagc      120
gatgagtata ccttcgcgac ctctgcggac aaccatgtga ccatgtgggt ggacgaccag      180
gaagtgatca acaaagcgag caacagcaac aaaattcgcc tggagaaggg tcgcctgtat      240
caaattaaga ttcagtatca gcgcgagaat ccaaccgaaa aaggcctgga ctttaaactg      300
tactggaccg atagccagaa taagaaggaa gtgatcagct ctgacaacct gcagctgccg      360
gaactgaaac agaagtctag caacagccgc aagaaacgca gcaccagcgc gggcccgacc      420
gtgccagacc gcgacaacga tggcatcccg gatagcctgg aagtggaagg ttatacggtg      480
gatgtgaaga caaacgcac cttcctgagc ccatggatta gcaacattca tgagaagaaa      540
ggcctgacca agtacaaaag cagcccggag aagtggagca ccgcgagcga tccgtatagc      600
gactttgaga agtgacggg ccgcattgac aagaacgtga gcccggaagc acgtcaccca      660
ctggttgcag cgtatccgat tgtgcatgtg gacatggaga acatcattct gagcaagaac      720
gaagatcaga gcacccagaa cacgattct cagacccgca cgatcagcaa aaacaccagc      780
acgagccgca cccataccag cgaggtgcat ggcaatgcgg aagtgcatgc gagcttcttt      840
gacatcggcg gcagcgtgag cgcgggtttc tctaacagca acagcagcac cgtggcgatt      900
gatcacagcc tgagcctggc gggtgaacgt acctgggcgg aaaccatggg cctgaacacc      960
gcggatacgg cacgcctgaa tgcgaacatt cgctatgtga acaccggtac cgcgccgatt     1020
tataatgttc tgccgaccac cagcctggtg ctgggcaaga atcagaccct ggcgaccatt     1080
aaagcgaaag agaaccagct gtctcagatt ctggcaccga caactacta tccgagcaaa     1140 aacctggcac cgattgcact gaatgcgcag gatgatttca gctctacccc gattaccatg     1200
aactacaacc agttcctgga actggagaag accaagcaac tgcgcctgga caccgatcag     1260
gtttatggca acattgcgac ctacaacttt gaaaacggcc gtgtgcgcgt ggatacgggc     1320
agcaactggt ctgaagtgct gccgcagatc caggaaacga ccgcgcgcat catcttcaac     1380
ggcaaagatc tgaacctggt ggaacgtcgc atcgcggcag ttaacccatc tgatccgctg     1440
gaaacgacca gccggatat gaccctgaag gaagcactga agattgcgtt tggctttaac     1500
gagccgaatg gcaacctgca gtatcagggc aaagacatca ccgagtttga ttttaacttt     1560
gatcaacaga cctctcagaa cattaagaac cagctggcag aactgaacgc gaccaacatc     1620
tacaccgttc tggataaaat caaactgaac gcgaagatga cattctgat tcgtgataaa     1680 cgtttttcatt atgatcgtaa caacatcgca gtgggtgcag atgaaagcgt ggttaaagaa     1740
gcgcatcgtg aagtgatcaa cagcagcacc gagggcctgc tgctgaacat tgacaaggac     1800
atccgtaaaa ttctgagcgg ctacattgtg gaaattgaag ataccgaggg tctgaaagaa     1860
gtgatcaacg atcgctatga tatgctgaac atcagcagcc tgcgccagga tggcaagacc     1920
ttcattgact tcaagaagta caacgacaaa ctg                                  1953
```

<210> SEQ ID NO 63  
<211> LENGTH: 1953  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<223> OTHER INFORMATION: Sequence variant (93%) of SEQ ID No. 56

<400> SEQUENCE: 63

```
gtgacctctt ctacgaccgg cgatctgagc attccgagca gcgaactgga gaacattccg       60
agcgaaaacc agtactttca gagcgcgatt tggagcggct tcatcaaagt taagaaaagc      120
```

```
gatgagtata  ccttcgcgac  cagcgcggac  aaccatgtga  ccatgtgggt  ggacgaccag      180
gaagtgatca  acaaagcgag  caacagcaac  aaaattcgcc  tggagaaggg  tcgcctgtac      240
cagattaaga  ttcagtatca  gcgcgagaac  ccaaccgaaa  aaggcctgga  ctttaaactg      300
tactggaccg  atagccagaa  taagaaggaa  gtgatcagct  ctgacaacct  gcagctgccg      360
gaactgaaac  agaagtctag  caacagccgt  aagaaacgta  gcaccagcgc  gggcccgacc      420
gtgccagacc  gcgacaacga  tggcatcccg  gatagcctgg  aggtggaagg  ttatacggtg      480
gatgtgaaga  taaacgcac   cttcctgagc  ccatggatta  gcaacattca  tgagaagaaa      540
ggcctgacca  aatacaaaag  cagcccggag  aagtggagca  ccgcgagcga  tccgtattct      600
gactttgaga  agtgacgggc  cgcattgac   aagaacgtga  gcccggaagc  acgtcaccca      660
ctggtggcag  cgtatccgat  tgtgcatgtg  gacatggaga  acatcattct  gagcaagaac      720
gaagatcaga  gcacccagaa  cacggattct  cagacccgca  cgatcagcaa  aaacaccagc      780
acgagccgca  cccataccag  cgaagtgcat  ggcaatgcgg  aagttcatgc  gagcttcttt      840
gacattggcg  gcagcgttag  cgcgggtttc  tctaacagca  acagcagcac  cgtggcgatt      900
gatcacagcc  tgagcctggc  gggtgaacgt  acctgggcgg  aaaccatggg  cctgaacacc      960
gcggatacgg  cacgcctgaa  tgcgaacatt  cgctatgtga  acaccggtac  cgcgccgatt     1020
tacaatgtgc  tgccgaccac  cagcctggtg  ctgggcaaga  tcagaccct   ggcgaccatt     1080 aaagcgaaag  agaaccaact  gtctcagatt  ctggcaccga  caactacta   tccgagcaaa     1140 aacctggcac  cgattgcact  gaatgcgcag  gatgatttca  gcagcacccc  gattaccatg     1200
aactacaacc  agttcctgga  actggagaag  accaagcaac  tgcgcctgga  caccgatcag     1260
gtttatggca  acattgcgac  ctacaacttt  gaaaacggcc  gcgtgcgcgt  ggatacgggc     1320
agcaactggt  ctgaagtgct  gccgcagatc  caggaaacga  ccgcgcgcat  catcttcaac     1380
ggcaaagatc  tgaacctggt  ggaacgtcgc  atcgcggcag  ttaacccatc  tgatccgctg     1440
gaaacgacca  agccggatat  gaccctgaag  gaagcactga  agatcgcgtt  tggctttaac     1500
gagccgaatg  gcaacctgca  gtatcagggc  aaagacatca  ccgagtttga  ttttaacttt     1560
gatcaacaga  cctctcagaa  cattaagaac  cagctggcag  aactgaacgc  gaccaacatc     1620
tacaccgttc  tggataaaat  caaactgaac  gcgaagatga  acattctgat  tcgtgataag     1680
cgtttccatt  atgatcgtaa  caacatcgca  gtgggtgcag  atgaaagcgt  ggttaaagaa     1740
gcgcatcgcg  aagtgatcaa  cagcagcacc  gagggcctgc  tgctgaacat  tgacaaggac     1800
atccgtaaaa  ttctgagcgg  ctatattgtg  gaaattgaag  ataccgaggg  tctgaaagag     1860
gtgatcaacg  atcgctatga  tatgctgaac  atcagcagcc  tgcgccagga  tggcaagacc     1920
ttcattgact  tcaagaagta  taacgacaaa  ctg                                    1953
```

<210> SEQ ID NO 64
<211> LENGTH: 1953
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92%) of SEQ ID No. 56

<400> SEQUENCE: 64

```
gtgacctctt  ctacgaccgg  cgatctgagc  attccgagca  gcgaactgga  gaacattccg       60
agcgaaaacc  agtacttcca  gagcgcgatt  tggtctggct  tcatcaaagt  taagaaaagc      120
```

```
gatgagtaca ccttcgcgac cagcgcggac aaccatgtga ccatgtgggt ggacgaccag    180
gaagtgatca acaaagcgag caacagcaac aaaattcgcc tggagaaggg tcgtctgtat    240
cagattaaga ttcagtatca gcgcgaaaac ccgaccgaaa aaggcctgga ctttaaactg    300
tactggaccg atagccagaa taagaaggaa gtgatcagct ctgacaacct gcagctgccg    360
gaactgaaac agaagtctag caacagccgt aagaaacgta gcaccagcgc gggcccgacc    420
gtgccagacc gcgacaacga tggcatcccg gatagcctgg aggtggaagg ttatacggtg    480
gatgtgaaga ataagcgcac cttcctgagc ccatggatta gcaacattca tgagaagaaa    540
ggcctgacca aatacaaaag cagcccggag aagtggagca ccgcgagcga tccatattct    600
gattttgaga agtgaccgg ccgcattgac aagaacgtga gcccggaagc acgtcaccca     660
ctggtggcag cgtatccgat tgtgcatgtg gacatggaga acatcattct gagcaagaac    720
gaagatcaga gcacccagaa caccgattct cagacccgta cgatcagcaa aaataccagc    780
acgagccgca cccataccag cgaagtgcat ggcaatgcgg aagttcatgc gagcttcttt    840
gacattggcg gcagcgttag cgcgggtttt agcaacagca cagcagcac cgtggcgatt     900 gatcacagcc tgagcctggc gggtgaacgt acgtgggcgg aaaccatggg cctgaacacc    960
gcggatacgg cacgcctgaa cgcgaacatt cgctatgtga ataccggtac cgcgccgatt   1020
tacaacgtgc tgccgaccac cagcctggtg ctgggcaaga atcagaccct ggcgaccatt   1080
aaagcgaaag agaaccaact gtctcagatt ctggcaccga caactacta tccgagcaaa   1140 aacctggcac cgattgcact gaatgcgcag gatgatttca gcagcacccc gattaccatg   1200
aactacaacc agttcctgga actggagaaa accaagcaac tgcgcctgga caccgaccag   1260
gtttatggca acattgcgac ctacaacttt gaaaacggcc gcgtgcgcgt ggatacgggc   1320
agcaactggt ctgaagtgct gccgcagatc caggaaacga ccgcgcgtat catcttcaac   1380
ggcaaggatc tgaacctggt ggaacgccgc atcgcggcag ttaacccatc tgatccgctg   1440
gaaacgacca agccggatat gaccctgaag gaagcactga gatcgcgtt tggctttaac    1500 gagccgaatg gcaacctgca gtatcagggc aaagacatca ccgagtttga ttttaacttt   1560
gatcaacaga cctctcagaa cattaagaac cagctggcgg agctgaacgc aaccaacatc   1620
tacaccgttc tggataaaat caaactgaac gcgaagatga acattctgat tcgcgataag   1680
cgtttccatt atgatcgtaa caacatcgca gtgggtgcag atgaaagcgt ggttaaagaa   1740
gcgcatcgcg aagtgatcaa cagcagcacc gaaggcctgc tgctgaacat tgacaaagac   1800
atccgcaaaa ttctgagcgg ctatattgtg gaaattgagg atacggaggg tctgaaagag   1860
gtgatcaacg atcgctatga tatgctgaac atcagcagcc tgcgccagga tggcaagacc   1920
ttcattgact tcaagaagta taacgacaaa ctg                                 1953
```

<210> SEQ ID NO 65
<211> LENGTH: 1953
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (91%) of SEQ ID No. 56

<400> SEQUENCE: 65

```
gtgacctctt ctacgaccgg tgatctgagc attccgagca gcgaactgga gaacattccg    60
agcgaaaacc agtacttcca gagcgcgatt tggtctggtt tcatcaaagt taagaaaagc   120
gatgagtaca cgttcgcgac cagcgcggac aaccatgtga ccatgtgggt ggacgaccag   180
```

| | |
|---|---|
| gaagtgatca acaaagcgag caacagcaac aaaattcgcc tggagaaggg tcgtctgtat | 240 |
| cagattaaga tccagtatca gcgcgaaaac ccgaccgaaa aaggcctgga ctttaaactg | 300 |
| tactggaccg atagccagaa taagaaggaa gtgatcagct ctgacaacct gcagctgccg | 360 |
| gaactgaaac agaagtctag caacagccgt aagaaacgta gcaccagcgc gggcccgacc | 420 |
| gtgccagacc gtgacaacga tggcatcccg gatagcctgg aggtggaagg ctataccgtg | 480 |
| gacgtgaaga ataagcgtac cttcctgagc ccatggatta gcaacattca tgagaagaaa | 540 |
| ggcctgacca aatacaaaag cagcccggag aagtggagca ccgcgagcga tccatattct | 600 |
| gattttgaga aagtgaccgg ccgcattgac aagaacgtga gcccggaagc acgccacccg | 660 |
| ctggtggcag cgtatccgat tgtgcatgtg gacatggaga acatcattct gagcaagaac | 720 |
| gaagatcaga gcacccagaa caccgattct cagacccgta cgattagcaa aaataccagc | 780 |
| acgagccgca cgcataccag cgaagtgcat ggcaatgcgg aagttcatgc gagcttcttt | 840 |
| gacattggcg gcagcgttag cgcgggtttt agcaacagca cagcagcac ggtggcgatt | 900 |
| gatcacagcc tgagcctggc gggtgaacgt acgtgggcgg aaaccatggg cctgaacacc | 960 |
| gcggatacgc cacgcctgaa cgcgaacatt cgctatgtga ataccggtac cgcgccgatc | 1020 |
| tacaacgtgc tgccgaccac cagcctggtg ctgggcaaga atcagaccct ggcgaccatt | 1080 |
| aaagcgaaag agaaccaact gtctcagatt ctggcaccga caactacta tccaagcaaa | 1140 |
| aacctggcac cgattgcact gaatgcgcag gatgatttca gcagcacccc gattaccatg | 1200 |
| aactacaacc agttcctgga actggagaaa accaagcaac tgcgcctgga caccgaccag | 1260 |
| gtttatggca acattgcgac ctacaacttt gaaaacggcc gcgtgcgcgt ggatacgggc | 1320 |
| agcaactggt ctgaagtgct gccgcagatc caggagacca ccgcgcgtat cattttcaac | 1380 |
| ggcaaggatc tgaacctggt ggaacgccgc atcgcggcag ttaacccatc tgatccgctg | 1440 |
| gaaacgacca gccggatat gaccctgaag gaagcactga agatcgcgtt tggctttaac | 1500 |
| gagccgaatg gcaacctgca gtatcagggc aaagatatca ccgaatttga ttttaacttt | 1560 |
| gatcaacaga cctctcagaa cattaagaac cagctggcgg agctgaacgc aaccaacatc | 1620 |
| tacaccgttc tggataaaat caaactgaac gcgaagatga acattctgat ccgcgataag | 1680 |
| cgcttccatt atgatcgtaa caacatcgca gtgggtgcag atgaaagcgt ggttaaggaa | 1740 |
| gcgcatcgcg aagtgattaa cagcagcacc gaaggcctgc tgctgaacat tgataaagac | 1800 |
| atccgcaaaa ttctgagcgg ctatattgtg gaaattgagg ataccgaggg cctgaaagag | 1860 |
| gtgatcaacg atcgctatga catgctgaac atcagcagcc tgcgccagga tggcaagacc | 1920 |
| ttcattgact caaaaagta taacgacaaa ctg | 1953 |

<210> SEQ ID NO 66
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Truncated version of SEQ ID No. 1 (bp 301-2106)

<400> SEQUENCE: 66

| | |
|---|---|
| agcaacagca acaagattcg cctggagaag ggtcgcctgt atcagatcaa gattcagtat | 60 |
| cagcgcgaga atccgaccga gaaaggcctg gatttcaaac tgtactggac cgatagccag | 120 |
| aacaagaaag aagtgattag ctctgataac ctgcaactgc cggaactgaa acagaagagc | 180 |

| | |
|---|---|
| agcaacagcc gcaagaaacg cagcacctct gcaggcccga ccgttccaga tcgcgacaac | 240 |
| gatggcattc cggacagcct ggaagtggaa ggttataccg ttgatgtgaa gaacaaacgc | 300 |
| acctttctga gcccgtggat tagcaacatt catgagaaga aaggcctgac caagtacaaa | 360 |
| agcagcccgg agaagtggag caccgcgagc gatccgtata gcgactttga gaaagtgacc | 420 |
| ggccgcattg ataagaacgt gagcccggaa gcgcgtcacc cactggttgc agcgtatccg | 480 |
| attgtgcatg ttgacatgga gaacatcatt ctgagcaaga acgaagatca gagcacccag | 540 |
| aacacggata gccagacccg cacgatcagc aagaacacca gcacgagccg tacccatacc | 600 |
| agcgaagtgc atggcaatgc ggaagtgcat gcgagcttct ttgacattgg tggcagcgtg | 660 |
| agcgcgggct tcagcaacag caacagcagc accgtggcga ttgatcatag cctgagcctg | 720 |
| gcgggcgaac gtacctgggc ggaaaccatg ggcctgaaca cggcggatac ggcacgtctg | 780 |
| aatgcgaaca ttcgctatgt gaacaccggt accgcgccaa tctataacgt tctgccgacc | 840 |
| acgagcctgg tgctgggcaa gaatcagacc ctggcgacca tcaaagcgaa agagaaccag | 900 |
| ctgtctcaga ttctggcacc gaacaactac tatccgagca agaacctggc accgattgca | 960 |
| ctgaatgcgc aggatgactt cagcagcacc ccgatcacca tgaactacaa tcagtttctg | 1020 |
| gagctggaga agaccaaaca actgcgcctg gataccgatc aggtgtatgg caacattgcg | 1080 |
| acctacaact ttgagaacgg ccgcgttcgc gtggataccg gtagcaactg gtctgaagtg | 1140 |
| ctgccgcaga ttcaggaaac gaccgcgcgc atcatcttca cggcaaaga tctgaacctg | 1200 |
| gtggaacgtc gcatcgcggc agtgaaccca tctgatccac tggaaacgac caaaccggac | 1260 |
| atgaccctga agaagcgct gaagattgca tttggcttca cgaaccgaa tggcaacctg | 1320 |
| cagtatcagg gcaagacat caccgagttt gacttcaact ttgatcaaca gacctctcag | 1380 |
| aacatcaaga accagctggc agaactgaat gcgaccaaca tctacaccgt gctggacaag | 1440 |
| atcaaactga cgcaaagat gaacattctg attcgtgaca aacgcttcca ctatgatcgt | 1500 |
| aacaacattg cggtgggtgc agatgaaagc gttgtgaaag aagcgcatcg tgaagtgatc | 1560 |
| aactctagca ccgaaggcct gctgctgaac attgacaaag acatccgtaa gattctgagc | 1620 |
| ggctacattg tggagattga agataccgaa ggtctgaaag aagtgatcaa cgatcgctat | 1680 |
| gacatgctga acatctctag cctgcgccag gatggcaaga ccttcattga cttcaagaag | 1740 |
| tacaacgaca aactgccgct gtacatcagc aatccgaact caaagtgaa cgtgtatgcg | 1800 |
| gtgacc | 1806 |

<210> SEQ ID NO 67
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99%) of SEQ ID No. 66

<400> SEQUENCE: 67

| | |
|---|---|
| agcaacagca acaagattcg cctggagaag ggtcgcctgt atcagatcaa gattcagtat | 60 |
| cagcgtgaga atccgaccga gaaaggcctg gatttcaaac tgtactggac cgatagccag | 120 |
| aacaagaaag aagtgattag ctctgataat ctgcaactgc cggaactgaa acagaagagc | 180 |
| agcaacagcc gcaagaaacg cagcacctct gcgggcccga ccgttccaga tcgcgacaac | 240 |
| gatggcattc cggacagcct ggaagtggaa ggttataccg ttgatgtgaa gaacaaacgc | 300 |
| acctttctga gcccgtggat tagcaacatt catgagaaga aaggcctgac caagtataaa | 360 |

```
agcagcccgg agaagtggag caccgcgagc gatccgtata gcgacttcga gaaagtgacc    420
ggccgcattg ataagaacgt gagcccggaa gcacgccacc cactggttgc agcgtatccg    480
attgtgcatg ttgacatgga gaacatcatt ctgagcaaga acgaagatca gagcacccag    540
aacacggata gccagacccg cacgatcagc aaaaacacca gcacgagccg tacccatacc    600
agcgaagtgc atggcaatgc ggaagtgcat gcgagcttct ttgacattgg tggcagcgtg    660
agcgcgggct tcagcaacag caacagcagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggt accgcgccaa tctacaacgt tctgccgacc    840
acgagcctgg tgctgggcaa gaatcagacc ctggcgacca tcaaagcgaa agagaaccag    900
ctgtctcaga ttctggcacc gaacaactac tatccgagca gaacctggc accgattgca    960 ctgaatgcgc aggatgactt cagcagcacc ccgatcacca tgaactacaa ccagtttctg   1020
gagctggaga agaccaaaca actgcgcctg gataccgatc aggtgtatgg caacattgcg   1080
acctacaact ttgagaacgg ccgcgttcgc gtggataccg gtagcaactg gtctgaagtg   1140
ctgccgcaga ttcaggaaac gaccgcgcgc atcattttca acggcaaaga tctgaacctg   1200
gtggaacgtc gcatcgcggc agtgaaccca tctgatccac tggaaacgac caaaccggac   1260
atgaccctga agaagcgct gaagattgca tttggcttca acgaaccgaa tggcaacctg   1320
cagtatcagg gtaaggacat caccgagttt gactttaact ttgatcaaca gacctctcag   1380
aacattaaga accagctggc agaactgaat gcgaccaaca tctacaccgt gctggacaag   1440
atcaaactga acgcaaagat gaacattctg attcgtgaca aacgcttcca ctatgatcgt   1500
aacaacattg cggtgggcgc agatgaaagc gttgtgaaag aagcgcatcg tgaagtgatc   1560
aactctagca ccgaaggcct gctgctgaac attgacaaag acatccgtaa gatcctgagc   1620
ggctacattg tggagatcga agataccgaa ggtctgaaag aagtgatcaa cgatcgctat   1680
gacatgctga acatctctag cctgcgccag gatggcaaga ccttcattga cttcaagaag   1740
tacaacgaca aactgccgct gtacatcagc aatccgaact acaaagtgaa cgtgtatgcg   1800
gtgacc                                                              1806
```

<210> SEQ ID NO 68
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98%) of SEQ ID No. 66

<400> SEQUENCE: 68

```
agcaacagca acaagattcg cctggagaag ggtcgcctgt atcagatcaa gattcagtat     60
cagcgtgaga atccgaccga gaaaggcctg gatttcaaac tgtactggac cgatagccag    120
aacaagaagg aagtgattag ctctgataat ctgcaactgc cggaactgaa acagaagagc    180
agcaacagcc gcaagaaacg cagcacctct gcgggcccga ccgttccaga tcgcgacaac    240
gatggcattc cggacagcct ggaggtggaa ggttataccg ttgatgtgaa gaacaaacgc    300 accttttctga gccgtggat tagcaacatt catgagaaga aaggcctgac caagtataaa    360
agcagcccgg agaagtggag caccgcgagc gatccgtata gcgacttcga gaaagtgacc    420
ggccgcattg ataagaacgt gagcccggaa gcacgccacc cactggttgc agcgtatccg    480
```

```
attgtgcatg tggacatgga gaacatcatt ctgagcaaga acgaagatca gagcacccag    540
aacacggata gccagacccg cacgatcagc aaaaacacca gcacgagccg tacccatacc    600
agcgaagttc atggcaacgc ggaagtgcat gcgagcttct ttgacattgg tggcagcgtg    660
agcgcgggct tcagcaacag caactctagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggt accgcgccaa tctacaacgt tctgccgacc    840
acgagcctgg tgctgggcaa gaatcagacc ctggcgacca tcaaagcgaa agagaaccag    900
ctgtctcaga ttctggcacc gaataactac tatccgagca agaacctggc accgattgca    960
ctgaacgcgc aggatgactt cagcagcacc ccgatcacca tgaactacaa ccagtttctg    1020
gagctggaaa agaccaaaca actgcgcctg gataccgatc aggtgtatgg caacattgcg    1080
acctacaact ttgagaacgg ccgcgttcgc gtggataccg gtagcaactg gtctgaagtg    1140
ctgccgcaga ttcaggaaac gaccgcgcgc atcattttca cggcaaaaga tctgaacctg    1200
gtggaacgtc gcatcgcggc agtgaaccca agcgatccac tggaaaccac caaaccggac    1260 atgacccctga aagaagcgct gaagattgca tttggcttca cgaaccgaa tgcaacctg    1320 cagtatcagg gtaaggacat caccgagttt gactttaact ttgatcaaca gacgtctcag    1380
aacattaaga accagctggc agaactgaat gcgaccaaca tctacaccgt gctggacaag    1440
atcaaactga acgcaaagat gaacattctg attcgtgaca aacgcttcca ctatgatcgt    1500
aacaacattg cggtgggcgc agatgaaagc gttgtgaaag aagcgcatcg tgaagtgatc    1560
aactctagca ccgaaggtct gctgctgaac attgacaaag acatccgtaa gatcctgagc    1620
ggctacattg tggagatcga agataccgaa ggcctgaaag aagtgatcaa tgatcgctat    1680
gacatgctga acatctctag cctgcgccag gatggcaaga ccttcattga cttcaaaaag    1740
tacaacgaca aactgccgct gtacatcagc aatccgaact acaaagtgaa cgtgtatgcg    1800
gtgacc                                                              1806
```

<210> SEQ ID NO 69
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97%) of SEQ ID No. 66

<400> SEQUENCE: 69

```
agcaacagca acaagattcg cctggagaag ggtcgcctgt atcagatcaa gattcagtat    60
cagcgtgaga atccgaccga gaaaggcctg gatttcaaac tgtactggac cgatagccag    120
aacaagaagg aagtgattag ctctgataat ctgcaactgc cggaactgaa acagaagagc    180
agcaacagcc gcaagaaacg cagcaccctct gcgggcccga ccgttccaga tcgcgacaac    240
gatggcattc cggatagcct ggaggtggaa ggttataccg ttgatgtgaa gaacaaacgc    300 accttctctga gcccgtggat tagcaacatt catgagaaga aaggcctgac caagtataaa    360
agcagcccgg agaagtggag cacggcgagc gatccgtata gcgacttcga gaaagtgacc    420
ggccgcattg ataagaacgt gagcccgaa gcacgccacc cactggttgc agcgtatccg    480
attgtgcatg tggacatgga gaacatcatt ctgagcaaga acgaagatca gagcacccag    540
aacacggata gccagacccg cacgatcagc aaaaacacca gcacgagccg tacccatacc    600
agcgaagttc atggcaacgc ggaagtgcat gcgagcttct ttgacattgg tggcagcgtg    660
```

-continued

```
agcgcgggct tcagcaacag caactctagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggt accgcaccaa tctacaacgt tctgccgacc    840
acgagcctgg tgctgggcaa gaatcagacc ctggcgacca tcaaagcgaa agagaaccag    900
ctgtctcaga ttctggcacc gaataactac tatccgagca gaacctggc accgattgca     960
ctgaacgcgc aggatgactt cagcagcacc ccgatcacca tgaactacaa ccagtttctg   1020
gagctggaaa agaccaaaca actgcgcctg gataccgatc aggtgtatgg caacattgcg   1080
acctacaact ttgagaacgg ccgcgttcgc gtggataccg tagcaactg gtctgaagtg    1140
ctgccgcaga ttcaggaaac gaccgcgcgt atcattttca acggcaaaga tctgaacctg   1200
gtggaacgtc gcatcgcggc agtgaatccg agcgatccac tggaaaccac caaaccggac   1260
atgacccctga aagaagcgct gaagattgca tttggcttca cgaaccgaa cggcaacctg   1320
cagtatcagg gtaaggacat caccgagttc gactttaact tgatcaaca gacgtctcag   1380
aacattaaga accagctggc agaactgaat gcgaccaaca tctacaccgt gctggacaag   1440
atcaaactga acgcaaagat gaacattctg attcgtgaca aacgcttcca ctatgatcgt   1500
aacaacattg cggtgggcgc ggatgaaagc gttgtgaaag aagcgcatcg tgaagtgatt   1560
aactctagca ccgaaggtct gctgctgaac attgacaaag acatccgcaa gatcctgagc   1620
ggctacattg tggagatcga agacaccgaa ggcctgaaag aagtgatcaa tgatcgctat   1680
gacatgctga acatctctag cctgcgccag gatggcaaga ccttcatcga ctttaaaaag   1740
tacaacgaca aactgccact gtacatcagc aatccgaact acaaagtgaa cgtgtatgcg   1800
gtgacc                                                             1806
```

<210> SEQ ID NO 70
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 66

<400> SEQUENCE: 70

```
agcaacagca acaagattcg cctggagaaa ggtcgcctgt atcagatcaa gattcagtat     60
cagcgtgaga atccgaccga gaaaggcctg gatttcaaac tgtactggac cgatagccag   120
aacaagaagg aagtgattag ctctgacaat ctgcaactgc cggaactgaa acagaagagc   180
agcaacagcc gcaagaagcg cagcacctct gcgggcccaa ccgttccaga tcgcgacaac   240
gatggcattc cggatagcct ggaagtggaa ggttataccg ttgatgtgaa gaacaaacgc   300
acctttctga gcccgtggat tagcaacatt catgagaaga aaggcctgac caagtataaa   360
agcagcccgg agaagtggag caccgcgagc gatccgtata gcgatttcga aaagtgacc   420
ggccgcattg ataagaacgt gagcccggaa gcacgccacc cactggttgc agcgtatccg   480
attgtgcatg tggacatgga gaacatcatt ctgagcaaga acgaagacca gagcacccag   540
aacaccgata gccagacgcg cacgatcagc aaaaacacca gcacgagccg tacccatacc   600
agcgaagttc atggcaacgc ggaagtgcat gcgagcttct ttgacattgg tggcagcgtg   660
agcgcgggct ttagcaacag caactctagc accgtggcga ttgatcatag cctgagcctg   720
gcgggcgaac gtacctgggc ggaaaccatg ggcctgaaca cggcggacac ggcacgtctg   780
```

```
aatgcgaaca ttcgctatgt gaacaccggt accgcaccaa tctacaacgt tctgccgacc      840
acgagcctgg tgctgggcaa gaatcagacc ctggcgacca tcaaagcgaa agagaaccag      900
ctgtctcaga ttctggcacc gaataactac tatccgagca agaacctggc accgattgca      960
ctgaacgcgc aagatgactt cagcagcacc ccgatcacca tgaactacaa ccagtttctg     1020
gagctggaaa agacgaaaca actgcgcctg gataccgatc aggtgtatgg caacattgcg     1080
acctacaact tcgagaacgg ccgcgttcgc gtggacaccg gtagcaactg gtctgaagtg     1140
ctgccgcaga ttcaggaaac caccgcgcgt atcattttca acggcaaaga tctgaacctg     1200
gtggagcgtc gcatcgcggc agtgaatcca agcgatccgc tggaaaccac caaaccggac     1260
atgaccctga agaagcgct gaagattgca tttggcttca cgaaccgaa cggcaacctg      1320 cagtatcagg gtaaggacat caccgagttc gattttaact ttgatcagca gacgtctcag     1380
aacattaaga accagctggc agaactgaat gcgaccaaca tctacaccgt gctggacaag     1440
atcaaactga acgcaaagat gaacattctg attcgtgaca aacgcttcca ctatgatcgt     1500
aacaacattg cggtgggcgc ggatgaaagc gttgtgaaag aagcgcatcg tgaagtgatt     1560
aactctagca ccgaaggtct gctgctgaac attgataaag acatccgcaa gatcctgagc     1620
ggctacattg tggagatcga agacaccgaa ggcctgaaag aagtgatcaa tgatcgctat     1680
gacatgctga acatctctag cctgcgccag gatggcaaga ccttcatcga tttttaaaaag    1740 tacaacgaca aactgccgct gtacatcagc aatccgaact acaaagtgaa cgtgtatgcg     1800
gtgacc                                                               1806
```

<210> SEQ ID NO 71
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95%) of SEQ ID No. 66

<400> SEQUENCE: 71

```
agcaacagca acaagattcg cctggagaaa ggtcgcctgt atcagatcaa gattcagtat       60
cagcgtgaga atccgaccga gaaaggcctg gatttcaaac tgtactggac cgatagccag      120
aacaagaagg aagtgattag ctctgacaat ctgcaactgc cggaactgaa acagaagagc      180
agcaacagcc gcaagaagcg cagcacctct gcgggcccga ccgttccaga tcgcgacaac      240
gatggcattc cggatagcct ggaagtggaa ggttataccg ttgatgtgaa gaacaagcgc      300
acctttctga gcccgtggat tagcaacatt catgagaaga aaggcctgac caagtataaa      360
agcagcccgg agaagtggag caccgcgagc gatccgtata gcgatttcga gaaagtgacc     420
ggccgcattg ataagaacgt gagcccggaa gcacgccatc cactggttgc agcgtatccg     480
attgtgcatg tggacatgga gaacatcatt ctgagcaaga acgaagacca gagcacccag     540
aacaccgatt ctcagacgcg cacgatcagc aaaaacacca gcacgagccg tacccacacc     600
agcgaagttc atggcaacgc ggaagtgcat gcgtctttct ttgacattgg tggcagcgtg     660
agcgcgggct ttagcaacag caactctagc accgtggcga ttgatcatag cctgagcctg     720
gcgggcgaac gtacctgggc ggaaaccatg gcctgaaca cggcggacac ggcacgtctg     780
aacgcgaaca ttcgctatgt gaacaccggt accgcaccaa tctacaacgt tctgccgacc      840
acgagcctgg tgctgggcaa gaatcagacc ctggcgacca tcaaagcgaa agagaaccag      900
ctgtctcaga ttctggcacc gaataactac tatccgagca agaacctggc accgattgca      960
```

```
ctgaacgcgc aagatgactt cagcagcacc ccgatcacca tgaactacaa ccagtttctg   1020
gagctggaaa agaccaaaca actgcgcctg ataccgatc aggtgtatgg caacattgcg   1080
acctacaact tcgagaacgg ccgcgttcgc gtggacaccg gtagcaactg gtctgaagtg   1140
ctgccgcaga tccaggaaac caccgcgcgt atcattttca acggcaaaga tctgaacctg   1200
gtggagcgtc gcatcgcggc agtgaatcca agcgatccgc tggaaaccac caaaccggac   1260
atgaccctga aagaagcgct gaagattgca tttggcttca cgaaccgaa cggcaacctg   1320 cagtatcagg gtaaggacat caccgagttc gattttaact ttgatcagca gacgagccag   1380
aacattaaga accagctggc agaactgaat gcgaccaaca tctacaccgt gctggacaag   1440
atcaaactga acgcaaaaat gaacattctg attcgtgaca aacgcttcca ctatgatcgt   1500
aacaacattg cggtgggcgc ggatgaaagc gttgtgaaag aagcgcatcg tgaagtgatt   1560
aactctagca ccgaaggtct gctgctgaac attgataaag acatccgcaa gatcctgagc   1620
ggctacattg tggagatcga agacacgaa ggcctgaaag aagtgattaa tgatcgctat   1680
gacatgctga atatcagcag cctgcgccag gatggcaaga ccttcatcga tttaaaaag   1740 tacaacgaca aactgccact gtacatcagc aatccgaact acaaagtgaa cgtgtatgcg   1800
gtgacc                                                             1806

<210> SEQ ID NO 72
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94%) of SEQ ID No. 66

<400> SEQUENCE: 72
agcaacagca acaagattcg cctggagaaa ggtcgcctgt atcagatcaa gattcagtat     60
cagcgtgaga tccgaccga gaaaggcctg gatttcaaac tgtactggac cgatagccag    120
aacaagaagg aagtgattag ctctgacaat ctgcaactgc cggaactgaa acagaagagc    180
agcaacagcc gtaagaagcg cagcacctct gcgggtccga ccgttccaga tcgcgacaac    240
gatggcattc cggatagcct ggaagtggaa ggctataccg ttgatgtgaa gaacaagcgc    300
acctttctga gcccgtggat tagcaacatt catgagaaga aaggcctgac caaatataaa    360
agcagcccgg agaagtggag caccgcgagc gatccgtata gcgatttcga gaaagtgacc    420
ggccgtattg ataagaacgt gagcccggaa gcacgccacc cactggttgc agcgtatccg    480
attgtgcatg tggacatgga gaacatcatt ctgagcaaga acgaagacca gagcacccag    540
aacaccgatt ctcagacgcg cacgatcagc aaaaacacca gcacgagccg tacccatacc    600
agcgaagttc atggcaacgc ggaagtgcat gcgtctttct ttgacattgg cggcagcgtg    660
agcgcgggtt tcagcaacag caactctagc accgtggcga ttgatcatag cctgagcctg    720
gcgggcgaac gcacctgggc ggaaaccatg gccctgaaca cggcggacac ggcacgtctg    780
aacgcgaaca tccgctacgt gaacaccggt accgcaccaa tctataacgt tctgccgacc    840
acgagcctgg ttctgggcaa gaatcagacc ctggcgacca tcaaagcgaa ggagaaccag    900
ctgtctcaga ttctggcgcc gaacaactac tatccgagca agaacctggc accgattgca    960
ctgaacgcgc aagatgactt cagcagcacc ccgatcacca tgaactataa tcagtttctg   1020
gagctggaaa agaccaaaca actgcgcctg ataccgaccg aggtgtatgg caacattgca   1080
```

```
acctacaact tcgagaacgg ccgcgttcgc gtggacaccg gtagcaactg gtctgaagtg    1140
ctgccgcaga ttcaggaaac caccgcgcgc atcattttta acggcaaaga tctgaatctg    1200
gtggagcgtc gcatcgcggc agtgaatcca agcgatccgc tggaaaccac caaaccggac    1260
atgaccctga agaagcgct gaagattgca ttcggcttca acgaaccgaa cggcaacctg    1320
cagtaccagg gtaaggacat caccgagttc gattttaact ttgatcagca gacgagccag    1380
aacattaaaa accagctggc agaactgaat gcgaccaaca tctacaccgt gctggacaag    1440
atcaaactga acgcaaaaat gaacattctg attcgtgaca aacgctttca ctatgatcgt    1500
aataacattg cggtgggcgc ggatgaaagc gtggtgaaag aagcgcatcg tgaagtgatt    1560
aactctagca ccgaaggtct gctgctgaac attgataaag acatccgcaa gatcctgagc    1620
ggctacattg tggagatcga agacacggaa ggcctgaagg aagtgattaa tgatcgctat    1680
gacatgctga acatcagcag cctgcgccag gatggcaaga ccttcatcga ttttaaaaag    1740
tacaacgata aactgccact gtacatcagc aacccgaact acaaagtgaa cgtgtatgcg    1800
gtgacc                                                              1806

<210> SEQ ID NO 73
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93%) of SEQ ID No. 66

<400> SEQUENCE: 73
agcaacagca acaagattcg cctggagaag ggtcgcctgt atcagatcaa gattcagtat      60
cagcgtgaga atccgaccga gaaaggcctg gatttcaaac tgtactggac cgatagccag     120
aacaagaagg aagtgattag ctctgacaat ctgcaactgc cggaactgaa acagaagagc     180
agcaacagcc gtaagaagcg cagcacctct gcgggcccga cggttccaga tcgcgacaac     240
gatggcattc cggatagcct ggaagtggaa ggttataccg ttgatgtgaa aaacaagcgc     300 accttttctgt ctccgtggat tagcaacatt catgagaaga aaggcctgac caaatataaa     360
agcagcccgg agaagtggag caccgcgagc gatccgtata gcgatttcga aaagtgacc     420 ggccgtattg ataagaacgt gagcccggaa gcacgccacc cactggttgc agcgtatccg     480
attgtgcatg tggacatgga aacatcatt ctgagcaaga acgaagacca gagcaccccag     540 aacaccgata gccagacgcg cacgatcagc aaaaacacct ctacgagccg tacccatacc     600
agcgaagttc atggcaacgc ggaagtgcat gcaagcttct ttgacattgg cggcagcgtg     660
agcgcgggtt tcagcaacag caactctagc accgtggcga ttgatcattc tctgagcctg     720
gcgggcgaac gcacctgggc ggaaaccatg ggtctgaaca ccgcggacac ggcacgtctg     780
aacgcgaaca tccgctacgt gaacaccggc accgcaccaa tctataacgt tctgccgacc     840
acgagcctgg ttctgggcaa gaatcagacc ctggcgacca tcaaagcgaa ggagaaccag     900
ctgtctcaga ttctggcgcc gaacaactac tatccgagca agaacctggc accgattgca     960
ctgaacgcgc aagatgactt cagcagcacc ccgatcacca tgaactataa tcagtttctg    1020
gagctggaaa aaccaaaca actgcgcctg gataccgacc aggtgtatgg caacattgca    1080
acctacaact tcgagaacgg ccgcgttcgc gtggacaccg gtagcaactg gtctgaagtg    1140
ctgccgcaga ttcaggaaac caccgcgcgc atcattttta acggcaaaga tctgaatctg    1200
gtggagcgtc gcatcgcggc ggtgaatcca agcgatccgc tggagaccac caagccggac    1260
```

```
atgaccctga agaagcgct gaagattgca ttcggcttca acgaaccgaa cggcaacctg    1320
cagtaccagg gtaaggacat caccgagttc gattttaact ttgaccagca gacgagccag    1380
aacattaaaa accagctggc agaactgaat gcgaccaaca tctacaccgt gctggataag    1440
atcaaactga acgcaaaaat gaacattctg attcgtgaca aacgctttca ctatgatcgt    1500
aataacattg cggtgggcgc ggatgaaagc gtggtgaaag aagcgcatcg tgaagtgatt    1560
aacagcagca ccgaaggtct gctgctgaac attgataaag acatccgcaa gatcctgagc    1620
ggctacattg tggaaatcga agacacggaa ggcctgaagg aagtgattaa tgatcgctat    1680
gatatgctga acatcagcag cctgcgccag gacggcaaga ccttcatcga ttttaaaaag    1740
tacaacgata aactgccact gtacatcagc aaccccgaact acaaagtgaa cgtgtatgcg    1800
gtgacc                                                               1806
```

<210> SEQ ID NO 74
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92%) of SEQ ID No. 66

<400> SEQUENCE: 74

```
agcaacagca acaagattcg cctggagaag ggtcgcctgt atcagattaa gattcagtat     60
cagcgtgaga atccgaccga gaaaggcctg gatttcaaac tgtactggac cgatagccag    120
aacaagaagg aagtgattag ctctgacaat ctgcaactgc cggaactgaa acagaagagc    180
agcaacagcc gtaagaaacg cagcacctct gcgggcccga cggttccaga tcgcgacaac    240
gatggcatcc cggatagcct ggaagtggaa ggttacaccg tggatgtgaa aaacaagcgc    300
acctttctgt ctccgtggat tagcaacatt catgagaaga aaggcctgac caaatataaa    360
agcagcccgg agaagtggag caccgcgagc gatccgtata gcgatttcga gaaagtgacc    420
ggtcgtattg ataagaacgt gagcccggaa gcacgccatc cactggttgc agcgtatccg    480
attgtgcacg tggacatgga gaacatcatt ctgagcaaga acgaggacca gagcacccag    540
aacaccgata gccagacgcg cacgatcagc aaaaacacct ctacgagccg tacccatacc    600
agcgaagttc atggcaacgc ggaagtgcat gcaagcttct ttgacatcgg cggcagcgtg    660
agcgcgggtt tcagcaacag caactctagc accgtggcga ttgatcattc tctgagcctg    720
gcgggcgaac gcacctgggc ggaaaccatg ggtctgaaca ccgcggacac ggcacgtctg    780
aacgcgaata ttcgctacgt gaacaccggc accgcgccaa tctataacgt tctgccgacg    840
acgagcctgg ttctgggcaa gaatcagacc ctggcgacca ttaaagcgaa ggagaaccag    900
ctgtctcaga ttctggcacc gaacaactac tatccgagca aaaacctggc accgattgca    960
ctgaacgcgc aagatgactt cagcagcacc ccgatcacca tgaactataa tcagtttctg   1020
gagctggaaa aaccaaaaca actgcgcctg gataccgacc aggtgtatgg caacatcgca   1080
acctacaact tcgaaaacgg ccgcgttcgc gtggacaccg gcagcaactg gtctgaagtg   1140
ctgccgcaga tccaggagac caccgcgcgc atcattttta acggcaaaga tctgaacctg   1200
gtggagcgtc gcattgcggc ggtgaatcca agcgatccgc tggagaccac caagccggac   1260
atgaccctga agaagcgct gaagattgca ttcggcttca acgaaccgaa cggcaacctg    1320
cagtatcagg gtaaggacat caccgaattc gattttaact ttgaccagca gaccagccag    1380
```

```
aacattaaaa accagctggc agaactgaat gcgaccaaca tctacaccgt gctggataag    1440
atcaaactga acgcaaaaat gaacattctg attcgtgaca agcgctttca ctatgatcgt    1500
aataacattg cggtgggcgc ggatgaaagc gtggttaaag aagcgcatcg tgaagtgatt    1560
aacagcagca ccgaaggtct gctgctgaac attgataagg acatccgcaa gatcctgagc    1620
ggctacatcg tggaaatcga agacacggaa ggcctgaagg aagtgattaa tgatcgctat    1680
gatatgctga acatcagcag cctgcgccag gacggcaaga ccttcatcga ttttaaaaag    1740
tacaacgata aactgccact gtacattagc aacccgaact acaaagtgaa cgtgtatgcg    1800
gtgacc                                                              1806
```

<210> SEQ ID NO 75
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (91%) of SEQ ID No. 66

<400> SEQUENCE: 75

```
agcaacagca ataagattcg cctggagaag ggtcgcctgt atcagattaa gattcagtat      60
cagcgcgaga atccgaccga gaaaggcctg gatttcaaac tgtactggac cgatagccag     120
aacaagaaag aggtgattag ctctgacaac ctgcaactgc cggaactgaa acagaagagc     180
agcaacagcc gtaagaaacg cagcacctct gcgggcccga cggttccaga tcgcgacaac     240
gatggcattc cggatagcct ggaagtggaa ggttataccg tggatgtgaa gaacaagcgc     300
acctttctgt ctccgtggat tagcaacatt catgagaaga aaggcctgac gaagtataaa     360
agcagcccgg agaagtggag cacggcgagc gatccgtata gcgatttcga aaaggtgacc     420
ggtcgtattg acaagaacgt gagcccggaa gcacgccatc cactggttgc agcgtatccg     480
attgtgcacg tggacatgga gaatatcatc ctgtctaaga acgaggacca gagcacccag     540
aacaccgata gccagacccg cacgattagc aaaaacacca gcacgagccg tacccatacg     600
agcgaagttc atggcaacgc ggaagtgcat gcgagcttct ttgacatcgg cggcagcgtg     660
agcgcgggtt tcagcaacag caactctagc accgtggcaa ttgatcattc tctgagcctg     720
gcgggcgaac gcacgtgggc ggaaaccatg ggtctgaaca ccgcggacac cgcacgtctg     780
aacgcgaata ttcgctacgt gaacaccggc accgcgccga tctataacgt gctgccgacc     840
accagcctgg ttctgggcaa gaaccagacc ctggcgacca tcaaagcaaa ggagaaccag     900
ctgtctcaga ttctggcgcc gaacaactac tatccgagca aaaacctggc accaattgca     960
ctgaacgcgc aagatgactt cagcagcacc ccgatcacca tgaactataa tcagtttctg    1020
gagctggaaa aaaccaagca actgcgcctg gataccgacc aggtttatgg caacatcgcg    1080
acctacaact ttgaaaacgg ccgcgtgcgc gtggacaccg gcagcaactg gtctgaagtg    1140
ctgccgcaga tccaggagac caccgcgcgc atcatttttca acggcaaaga tctgaacctg    1200
gtggagcgtc gtattgcagc ggtgaatcca agcgatccgc tggagaccac caagccggac    1260
atgaccctga agaagcgct gaagattgca ttcggcttca acgaaccgaa cggcaacctg    1320
cagtatcagg gtaaggacat taccgaattc gattttaact tgaccagca gaccagccag    1380 aacattaaaa accagctggc agaactgaac gcgaccaaca tctacaccgt gctggataag    1440
attaaactga acgcaaaaat gaacatcctg attcgtgaca agcgctttca ctatgatcgt    1500
aataacattg cggtgggcgc ggacgaaagc gtggttaaag aagcgcatcg tgaagtgatc    1560
```

| | |
|---|---|
| aacagcagca ccgaaggtct gctgctgaac attgataaag atattcgcaa aatcctgagc | 1620 |
| ggctacatcg tggaaatcga agatacggaa ggcctgaaag aagtgatcaa tgatcgctac | 1680 |
| gatatgctga atatcagcag cctgcgccag gacggcaaga ccttcatcga ttttaaaaag | 1740 |
| tacaacgata aactgccact gtacattagc aacccgaact acaaagtgaa cgtttatgcg | 1800 |
| gtgacc | 1806 |

<210> SEQ ID NO 76
<211> LENGTH: 1857
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Truncated version of SEQ ID No. 1
    (bp. 301-2157)

<400> SEQUENCE: 76

| | |
|---|---|
| agcaacagca acaagattcg cctggagaag ggtcgcctgt atcagatcaa gattcagtat | 60 |
| cagcgcgaga atccgaccga gaaaggcctg gatttcaaac tgtactggac cgatagccag | 120 |
| aacaagaaag aagtgattag ctctgataac ctgcaactgc cggaactgaa acagaagagc | 180 |
| agcaacagcc gcaagaaacg cagcacctct gcaggcccga ccgttccaga tcgcgacaac | 240 |
| gatggcattc cggacagcct ggaagtggaa ggttataccg ttgatgtgaa gaacaaacgc | 300 |
| acctttctga gcccgtggat tagcaacatt catgagaaga aaggcctgac caagtacaaa | 360 |
| agcagcccgg agaagtggag caccgcgagc gatccgtata gcgactttga gaaagtgacc | 420 |
| ggccgcattg ataagaacgt gagcccggaa gcgcgtcacc cactggttgc agcgtatccg | 480 |
| attgtgcatg ttgacatgga gaacatcatt ctgagcaaga acgaagatca gagcacccag | 540 |
| aacacggata gccagacccg cacgatcagc aagaacacca gcacgagccg tacccatacc | 600 |
| agcgaagtgc atggcaatgc ggaagtgcat gcgagcttct ttgacattgg tggcagcgtg | 660 |
| agcgcgggct tcagcaacag caacagcagc accgtggcga ttgatcatag cctgagcctg | 720 |
| gcgggcgaac gtacctgggc ggaaaccatg ggcctgaaca cggcggatac ggcacgtctg | 780 |
| aatgcgaaca ttcgctatgt gaacaccggt accgcgccaa tctataacgt tctgccgacc | 840 |
| acgagcctgg tgctgggcaa gaatcagacc ctggcgacca tcaaagcgaa agagaaccag | 900 |
| ctgtctcaga ttctggcacc gaacaactac tatccgagca agaacctggc accgattgca | 960 |
| ctgaatgcgc aggatgactt cagcagcacc ccgatcacca tgaactacaa tcagtttctg | 1020 |
| gagctggaga gaccaaaaca actgcgcctg gataccgatc aggtgtatgg caacattgcg | 1080 |
| acctacaact ttgagaacgg ccgcgttcgc gtggataccg gtagcaactg gtctgaagtg | 1140 |
| ctgccgcaga ttcaggaaac gaccgcgcgc atcatcttca cggcaaaaga tctgaacctg | 1200 |
| gtggaacgtc gcatcgcggc agtgaaccca tctgatccac tggaaacgac caaaccggac | 1260 |
| atgaccctga agaagcgct gaagattgca tttggcttca cgaaccgaa tggcaacctg | 1320 |
| cagtatcagg gcaaagacat caccgagttt gacttcaact ttgatcaaca gacctctcag | 1380 |
| aacatcaaga accagctggc agaactgaat gcgaccaaca tctacaccgt gctggacaag | 1440 |
| atcaaactga acgcaaagat gaacattctg attcgtgaca aacgcttcca ctatgatcgt | 1500 |
| aacaacattg cggtgggtgc agatgaaagc gttgtgaaag aagcgcatcg tgaagtgatc | 1560 |
| aactctagca ccgaaggcct gctgctgaac attgacaaag acatccgtaa gattctgagc | 1620 |
| ggctacattg tggagattga agataccgaa ggtctgaaag aagtgatcaa cgatcgctat | 1680 |

```
gacatgctga acatctctag cctgcgccag gatggcaaga ccttcattga cttcaagaag    1740
tacaacgaca aactgccgct gtacatcagc aatccgaact acaaagtgaa cgtgtatgcg    1800
gtgaccaaag agaacaccat cattaaccca agcgagaatg gcgataccag caccaac      1857
```

<210> SEQ ID NO 77
<211> LENGTH: 1857
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Sequence variant (99%) of SEQ ID No. 76

<400> SEQUENCE: 77

```
agcaacagca acaagattcg cctggagaag ggtcgcctgt atcagatcaa gattcagtat      60
cagcgcgaga atccgaccga gaaaggcctg gatttcaaac tgtactggac cgatagccag     120
aacaagaaag aagtgattag ctctgataac ctgcaactgc cggaactgaa acagaagagc     180
agcaacagcc gcaagaaacg cagcaccctct gcaggcccga ccgttccaga tcgcgacaac    240
gatggcattc cggacagcct ggaagttgaa ggttataccg ttgatgtgaa gaacaaacgc    300
acctttctga gcccgtggat cagcaacatt catgagaaga aaggcctgac caagtacaaa    360
agcagcccgg agaagtggag caccgcgagc gatccgtata gcgactttga gaaagtgacc    420
ggccgcattg ataagaacgt gagcccggaa gcgcgtcacc cactggttgc agcgtatccg    480
attgtgcatg ttgacatgga gaacatcatt ctgagcaaga acgaagatca gagcacccag    540
aacacggata gccagacccg cacgatcagc aagaacacca gcacgtctcg tacccatacc    600
agcgaagtgc atggcaatgc ggaagtgcat gcgagcttct ttgacattgg tggcagcgtg    660
agcgcgggct tcagcaacag caacagcagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggt accgcgccaa tctataacgt tctgccgacc    840
acgagcctgg tgctgggcaa gaatcagacc ctggcgacca tcaaagcgaa agagaaccag    900
ctgtctcaga ttctggcacc gaacaactac tatccgagca agaacctggc accgattgca    960
ctgaatgcgc aggatgactt cagcagcacc ccgatcacca tgaactacaa tcagtttctg   1020
gagctggaga agaccaaaca actgcgcctg gataccgatc aggtgtatgg caacattgcg   1080
acctacaact ttgagaacgg ccgcgttcgc gtggataccg gtagcaactg gagcgaagtg   1140
ctgccgcaga ttcaggaaac gaccgcgcgc attatcttca cggcaaaga tctgaacctg   1200 gtggaacgtc gcatcgcggc agtgaaccca tctgatccac tggaaacgac caaaccggac   1260
atgaccctga agaagcgct gaagattgca tttggcttca cgaaccgaa tggcaacctg    1320 cagtatcagg gcaaagacat caccgagttt gacttcaact ttgatcaaca gacctctcag   1380
aacatcaaga accagctggc agaactgaat gcgaccaaca tctacaccgt gctggacaag   1440
atcaaactga acgcaaagat gaacatcctg attcgtgaca aacgcttcca ctatgatcgt   1500
aacaacattg cggtgggtgc agatgaaagc gtggtgaaag aagcgcatcg tgaagtgatc   1560
aacagcagca ccgaaggcct gctgctgaac attgacaaag acattcgtaa gattctgagc   1620
ggctacattg tggagattga agataccgaa ggtctgaaag aagtgatcaa cgatcgctat   1680
gacatgctga acatctctag cctgcgccag gatggcaaga ccttcattga cttcaagaag   1740
tacaacgaca aactgccgct gtacatctct aatccgaact acaaagtgaa cgtgtatgcg   1800
```

```
gtgaccaaag agaacaccat cattaaccca agcgagaatg gcgataccag caccaac      1857
```

<210> SEQ ID NO 78
<211> LENGTH: 1857
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98%) of SEQ ID No. 76

<400> SEQUENCE: 78

```
agcaacagca acaagattcg cctggagaag ggtcgcctgt atcagatcaa gattcagtat      60
cagcgcgaga atccgaccga gaaaggcctg gatttcaaac tgtactggac cgatagccag     120
aacaagaaag aagtgattag ctctgataac ctgcaactgc cggaactgaa acagaagagc     180
agcaacagcc gcaagaaacg cagcacctct gcaggcccga ccgttccaga tcgcgacaac     240
gatggcattc cggacagcct ggaagttgaa ggttataccg ttgatgtgaa gaacaaacgc     300
acctttctga gcccgtggat cagcaacatt catgagaaga aaggcctgac caagtacaaa     360
agcagcccgg agaagtggag caccgcgagc gatccgtata gcgactttga aaaagtgacc     420
ggccgcattg ataagaacgt gagcccggaa gcgcgtcacc cactggttgc ggcgtatccg     480
attgtgcatg ttgacatgga gaacatcatt ctgagcaaga acgaggatca gagcacccag     540
aacacggata gccagacccg caccatcagc aagaacacca gcacgtctcg tacccatacc     600
agcgaagtgc atggcaatgc ggaagtgcat gcgagcttct ttgacattgg tggcagcgtg     660
agcgcaggct tcagcaacag caacagcagc accgtggcga ttgatcatag cctgagcctg     720
gcgggcgaac gtacctgggc ggaaaccatg ggcctgaaca cggcagatac ggcacgtctg     780
aatgcgaaca ttcgctatgt gaacaccggt accgcgccaa tttataacgt tctgccgacc     840
acgagcctgg tgctgggcaa gaatcagacc ctggcgacca tcaaagcgaa agagaaccag     900
ctgtctcaga ttctggcacc gaacaactac tatccgagca agaacctggc accgattgca     960
ctgaatgcgc aggatgactt cagcagcacg ccgatcacca tgaactacaa tcagtttctg    1020
gagctggaaa agaccaaaca actgcgcctg gataccgatc aggtgtatgg caacattgcg    1080
acctacaact ttgagaacgg ccgcgttcgt gtggataccg gtagcaactg gagcgaagtg    1140
ctgccgcaga tccaggaaac gaccgcgcgc attatcttca cggcaaaga tctgaacctg    1200
gtggaacgtc gcatcgcggc agtgaaccca tctgatccac tggaaacgac caaaccggac    1260
atgaccctga agaggcgctg aagattgca tttggcttca cgaaccgaa tggcaacctg     1320
cagtatcagg gcaaagacat taccgagttt gacttcaact ttgatcaaca gacctctcag    1380
aacatcaaga accagctggc agaactgaat gcgaccaaca tctacaccgt gctggacaag    1440
atcaaactga acgcgaagat gaacatcctg attcgcgaca aacgcttcca ctatgatcgt    1500
aacaacattg cggtgggtgc agatgaaagc gtggtgaaag aagcgcatcg tgaagtgatc    1560
aacagcagca ccgaaggcct gctgctgaac attgacaaag acattcgtaa gatcctgagc    1620
ggctacattg tggagattga agacaccgaa ggtctgaaag aagtgatcaa cgatcgctat    1680
gatatgctga acatctctag cctgcgccag gatggcaaga ccttcattga cttcaagaag    1740
tacaacgaca aactgccgct gtacatctct aatccgaact acaaagtgaa cgtgtatgcg    1800
gtgaccaaag agaacaccat cattaaccca agcgagaatg gcgataccag caccaac      1857
```

<210> SEQ ID NO 79
<211> LENGTH: 1857

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97%) of SEQ ID No. 76

<400> SEQUENCE: 79
```

| | | | | |
|---|---|---|---|---|
| agcaacagca | acaagattcg | cctggagaag | ggtcgcctgt atcagatcaa gattcagtat | 60 |
| cagcgcgaga | atccgaccga | gaaaggcctg | gatttcaagc tgtactggac cgatagccag | 120 |
| aacaagaaag | aagtgattag | ctctgataac | ctgcaactgc cggaactgaa acagaagagc | 180 |
| agcaacagcc | gcaagaaacg | cagcacctct | gcaggcccga ccgttccaga tcgcgacaac | 240 |
| gatggcattc | cggacagcct | ggaggttgaa | ggttataccg ttgatgtgaa gaacaaacgc | 300 |
| accttcctga | gcccgtggat | ctctaacatt | catgagaaga aaggcctgac caagtacaaa | 360 |
| agcagcccgg | agaagtggag | caccgcgagc | gatccgtata gcgactttga aaaagtgacc | 420 |
| ggccgcattg | ataagaacgt | gagcccggaa | gcacgtcacc cactggttgc ggcgtacccg | 480 |
| attgtgcatg | ttgacatgga | gaacatcatt | ctgagcaaga acgaagatca gagcacccag | 540 |
| aacacggata | gccagacccg | taccatcagc | aagaacacca gcacgtctcg tacccatacc | 600 |
| agcgaagtgc | atggcaatgc | ggaagtgcat | gcgagctttt ttgacattgg tggcagcgtg | 660 |
| agcgcaggct | tcagcaacag | caacagcagc | accgtggcga ttgatcatag cctgagcctg | 720 |
| gcgggcgaac | gtacctgggc | ggaaaccatg | ggcctgaaca cggcagatac ggcacgtctg | 780 |
| aatgcgaaca | ttcgctatgt | gaacaccggt | accgcgccaa tttataacgt tctgccgacc | 840 |
| acgagcctgg | tgctgggcaa | gaatcagacc | ctggcgacca tcaaagcgaa agagaaccag | 900 |
| ctgagccaga | ttctggcacc | gaacaactac | tatccgagca agaacctggc gccgattgca | 960 |
| ctgaatgcgc | aggatgactt | cagcagcacg | ccgattacca tgaactacaa tcagtttctg | 1020 |
| gagctggaaa | agaccaaaca | actgcgcctg | gataccgatc aggtgtatgg caacattgcg | 1080 |
| acctacaact | ttgagaacgg | ccgcgttcgc | gtggataccg gtagcaactg gagcgaagtg | 1140 |
| ctgccgcaga | tccaggaaac | gaccgcgcgc | attatcttta cggcaaagga tctgaacctg | 1200 |
| gtggaacgtc | gcatcgcggc | agtgaaccca | tctgatccac tggaaacgac caaaccggac | 1260 |
| atgaccctga | agaggcgct | gaagattgca | ttcggcttca cgaaccgaa tggcaacctg | 1320 |
| cagtatcagg | gcaaagacat | taccgagttt | gacttcaact ttgatcaaca gacctctcag | 1380 |
| aacatcaaga | accagctggc | agaactgaat | gcgaccaaca tctacaccgt gctggacaag | 1440 |
| atcaaactga | acgcgaaaat | gaacatcctg | attcgcgaca aacgcttcca ctatgatcgt | 1500 |
| aacaacattg | cggtgggtgc | agatgaaagc | gtggtgaaag aagcgcatcg cgaagtgatc | 1560 |
| aacagcagca | ccgaaggcct | gctgctgaac | attgacaaag acatccgtaa gatcctgagc | 1620 |
| ggctacatcg | tggagattga | agacaccgaa | ggtctgaaag aagtgattaa cgatcgctat | 1680 |
| gatatgctga | acatctctag | cctgcgtcag | gatggcaaga ccttcattga cttcaagaag | 1740 |
| tacaacgaca | aactgccgct | gtacatctct | aatccgaact ataaagtgaa cgtgtatgcg | 1800 |
| gtgaccaaag | agaacaccat | cattaaccca | agcgagaatg gcgataccag caccaac | 1857 |

```
<210> SEQ ID NO 80
<211> LENGTH: 1857
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<223> OTHER INFORMATION: Sequence variant (96%) of SEQ ID No. 76

<400> SEQUENCE: 80

```
agcaacagca acaagattcg cctggagaag ggtcgcctgt atcagatcaa gatccagtat      60
cagcgcgaga atccgaccga gaaaggcctg gatttcaagc tgtactggac cgatagccag     120
aacaagaaag aagtgattag ctctgacaac ctgcaactgc cggaactgaa gcagaaaagc     180
agcaacagcc gcaagaaacg cagcaccctct gcaggcccga ccgttccgga tcgcgacaac    240
gatggcattc cggacagcct ggaggttgaa ggctataccg ttgatgtgaa gaacaaacgc     300
accttcctga gcccgtggat ctctaacatt catgagaaga aaggcctgac caagtacaaa     360
agcagcccgg agaagtggag caccgcgagc gatccgtata gcgactttga aaaagtgacc     420
ggccgcattg ataagaacgt gagcccggaa gcacgtcacc cactggttgc ggcgtacccg     480
attgtgcatg ttgacatgga aacatcatt ctgagcaaga acgaagatca gagcacccag      540
aacacggata gccagacccg taccatcagc aagaacacca gcacgtctcg tacccatacc     600
agcgaagtgc atggtaatgc ggaagtgcat gcgagctttt ttgacattgg tggcagcgtg     660
agcgcaggct ttagcaacag caacagcagc acggtggcga ttgatcatag cctgagcctg     720
gcgggcgaac gtacctgggc ggaaaccatg ggcctgaaca cggcagatac cgcacgtctg     780
aatgcgaaca ttcgctatgt gaacaccggt accgcgccaa tttataacgt tctgccgacc     840
acgagcctgg tgctgggcaa gaatcagacc ctggcgacca tcaaagcgaa agagaaccag     900
ctgagccaga ttctggcacc gaacaactac tatccaagca aaaacctggc gccgattgca     960
ctgaatgcgc aggatgactt cagcagcacg ccgattacca tgaactacaa tcagtttctg    1020
gagctggaaa agaccaagca actgcgcctg gataccgatc aggtgtatgg caacattgcg    1080
acctacaact ttgagaacgg ccgcgttcgc gtggataccg gtagcaactg gagcgaagtg    1140
ctgccgcaga tccaggaaac gaccgcgcgc attatcttta cggcaaagaa tctgaacctg    1200
gtggaacgtc gcatcgcggc agtgaaccca tctgatccac tggaaaccac caaaccggac    1260
atgaccctga agaggcgct gaagattgca ttcggcttca cgaaccgaa tggcaacctg      1320
cagtatcagg gcaaagacat taccgagttt gatttcaact tcgatcaaca gacctctcag    1380
aacatcaaga accagctggc agaactgaat gcgaccaaca tctacaccgt gctggacaag    1440
atcaaactga acgcgaaaat gaacatcctg attcgcgaca aacgcttcca ctatgatcgt    1500
aacaacattg cggtgggtgc agatgaaagc gtggtgaaag aagcgcatcg cgaagtgatc    1560
aacagcagca ccgaaggcct gctgctgaac attgacaaag acatccgtaa gatcctgagc    1620
ggctacatcg tggagattga agacaccgaa ggtctgaaag aagtgattaa cgatcgctat    1680
gatatgctga acatctctag cctgcgtcag gatggcaaga ccttcattga cttcaagaag    1740
tacaacgaca aactgccgct gtacatttct aatccgaact ataaagtgaa cgtgtatgcg    1800
gtgaccaaag agaacacgat cattaaccca agcgagaatg cgataccag cacccaac      1857
```

<210> SEQ ID NO 81
<211> LENGTH: 1857
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Sequence variant (95%) of SEQ ID No. 76

<400> SEQUENCE: 81

-continued

| | |
|---|---|
| agcaacagca acaagatccg cctggagaag ggtcgcctgt atcagatcaa gatccagtat | 60 |
| cagcgcgaaa atccgaccga aaaggcctg gatttcaagc tgtactggac cgatagccag | 120 |
| aacaagaaag aagtgattag ctctgacaac ctgcaactgc cggaactgaa gcagaaaagc | 180 |
| agcaacagcc gcaagaaacg cagcacctct gcaggcccga ccgtgccgga tcgcgacaac | 240 |
| gatggcattc cggacagcct ggaggttgaa ggctataccg ttgatgtgaa gaacaaacgc | 300 |
| accttcctga gcccgtggat ctctaacatt cacgagaaga aaggcctgac caagtacaaa | 360 |
| agcagcccgg agaagtggag caccgcgagc gatccgtatt ctgactttga aaaagtgacc | 420 |
| ggccgcattg ataagaacgt gagcccggaa gcacgtcacc cactggttgc ggcgtacccg | 480 |
| attgtgcatg tggacatgga gaacatcatt ctgagcaaga acgaagatca gagcacccag | 540 |
| aatacggata gccagacccg taccatcagc aagaacacca gcacgagccg tacccatacc | 600 |
| agcgaagtgc atggtaatgc ggaagtgcat gcgagcttt ttgacattgg tggcagcgtg | 660 |
| agcgcaggct ttagcaacag caacagcagc acggtggcga ttgatcatag cctgagcctg | 720 |
| gcgggcgaac gtacctgggc ggaaaccatg ggcctgaaca cggcagatac cgcacgtctg | 780 |
| aatgcgaaca ttcgctatgt taacaccggt accgcaccaa tttataacgt tctgccgacc | 840 |
| acgagcctgg tgctgggcaa gaatcagacc ctggcgacca tcaaagcgaa agagaaccag | 900 |
| ctgagccaga ttctggcacc gaacaactac tatccaagca aaaacctggc gccgattgca | 960 |
| ctgaatgcgc aggatgactt cagcagcacg ccgattacca tgaactacaa ccagtttctg | 1020 |
| gagctggaaa agaccaagca actgcgcctg gataccgatc aggtttatgg caacattgcg | 1080 |
| acctacaact ttgagaacgg ccgcgtgcgc gtggataccg tagcaactg gagcgaagtg | 1140 |
| ctgccgcaga tccaggaaac gaccgcgcgc attatcttta cggcaaaaga tctgaacctg | 1200 |
| gtggaacgtc gcatcgcggc agtgaaccca tctgatccac tggaaaccac caaaccggac | 1260 |
| atgaccctga agaggcgct gaagattgca ttcggcttca tgaaccgaa tggcaacctg | 1320 |
| cagtatcagg gcaaagacat taccgagttt gacttcaact tcgatcaaca gacctctcag | 1380 |
| aacatcaaga accagctggc ggaactgaac gcgaccaaca tctacaccgt gctggacaag | 1440 |
| atcaaactga acgcgaaaat gaacatcctg attcgcgaca aacgcttcca ttatgatcgt | 1500 |
| aacaacattg cggtgggtgc agatgaaagc gtggttaaag aagcgcatcg cgaagtgatc | 1560 |
| aacagcagca ccgaaggcct gctgctgaac attgacaaag acattcgtaa gatcctgagc | 1620 |
| ggctacatcg tggaaattga agataccgag ggtctgaaag aggtgattaa cgatcgctat | 1680 |
| gatatgctga acatctctag cctgcgtcag gatggcaaga ccttcattga cttcaagaag | 1740 |
| tacaacgaca aactgccgct gtacatttct aatccgaact ataaagtgaa cgtgtatgcg | 1800 |
| gtgaccaaag agaacacgat cattaaccca agcgagaatg gcgataccag caccaac | 1857 |

<210> SEQ ID NO 82
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94%) of SEQ ID No. 76

<400> SEQUENCE: 82

| | |
|---|---|
| agcaacagca acaagattcg tctggagaag ggtcgcctgt atcagatcaa gatccagtat | 60 |
| cagcgcgaaa atccgaccga aagggcctg gatttcaagc tgtactggac cgatagccag | 120 |
| aacaagaaag aagtgattag ctctgacaac ctgcagctgc cggaactgaa gcagaaaagc | 180 |

| | |
|---|---|
| agcaacagcc gcaagaaacg cagcacctct gcaggcccga ccgtgccgga tcgcgacaac | 240 |
| gatggcattc cggacagcct ggaggttgaa ggctataccg ttgatgtgaa gaacaaacgc | 300 |
| accttcctga gcccgtggat ctctaacatt cacgagaaga aaggcctgac caagtacaaa | 360 |
| agcagcccgg agaagtggag caccgcgagc gatccgtatt ctgactttga aaaagtgacc | 420 |
| ggccgcattg ataagaacgt gagcccggaa gcacgccacc cactggtggc ggcgtacccg | 480 |
| attgtgcatg tggacatgga gaacatcatt ctgagcaaga acgaagatca gagcacccag | 540 |
| aatacggata gccagacccg taccatcagc aaaaacacca gcaccagccg tacgcatacc | 600 |
| agcgaagttc atggtaatgc ggaagtgcat gcgagctttt ttgatattgg tggcagcgtg | 660 |
| agcgcaggct ttagcaacag caacagcagc acggtggcga ttgatcatag cctgagcctg | 720 |
| gcgggcgaac gtacctgggc ggaaaccatg ggcctgaaca cggcagatac cgcgcgtctg | 780 |
| aatgcgaaca ttcgctacgt taacaccggt accgcaccaa tttataacgt tctgccgacc | 840 |
| accagcctgg tgctgggcaa gaatcagacc ctggcaacca tcaaagcgaa agagaaccag | 900 |
| ctgagccaga ttctggcacc gaacaactac tatccaagca aaaacctggc gccgattgca | 960 |
| ctgaatgcgc aggatgactt cagcagcacg ccgattacca tgaactacaa ccagtttctg | 1020 |
| gagctggaaa agaccaagca actgcgcctg gatacggatc aggtgtatgg caacatcgcg | 1080 |
| acctataact ttgagaacgg ccgcgtgcgc gtggataccg gtagcaactg gagcgaagtg | 1140 |
| ctgccgcaga tccaggaaac gaccgcgcgc attatcttta acggcaaaga tctgaacctg | 1200 |
| gtggaacgtc gcatcgcagc ggtgaaccca tctgatccac tggaaaccac caaaccggat | 1260 |
| atgaccctga agaggcgct gaagattgcg ttcggcttca tgaaccgaa tggcaacctg | 1320 |
| cagtatcaag gcaaagacat taccgagttt gacttcaact cgaccaaca gacctctcag | 1380 |
| aacatcaaga accagctggc ggaactgaac gcgaccaaca tctacaccgt gctggacaag | 1440 |
| atcaaactga cgcgaaaat gaacatcctg attcgcgaca aacgcttcca ttatgatcgt | 1500 |
| aacaacattg cggtgggtgc agatgaaagc gtggttaaag aagcgcatcg cgaagtgatc | 1560 |
| aacagcagca ccgaaggcct gctgctgaac attgacaaag acattcgtaa gattctgagc | 1620 |
| ggctacattg tggaaattga agataccgag ggtctgaaag aggtgatcaa cgatcgctat | 1680 |
| gacatgctga acatctctag cctgcgtcag gatggcaaga ccttcatcga cttcaagaag | 1740 |
| tacaacgaca aactgccgct gtacatttct aatccgaact ataaagttaa cgtgtatgca | 1800 |
| gtgaccaaag agaacacgat cattaaccca agcgagaatg cgataccag caccaac | 1857 |

<210> SEQ ID NO 83
<211> LENGTH: 1857
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93%) of SEQ ID No. 76

<400> SEQUENCE: 83

| | |
|---|---|
| agcaacagca acaagattcg tctggagaag ggccgcctgt atcagatcaa gatccagtac | 60 |
| cagcgcgaaa atccgaccga aagggcctg gatttcaagc tgtactggac cgatagccag | 120 |
| aataagaaag aagtgattag ctctgataac ctgcagctgc cggaactgaa gcagaaaagc | 180 |
| agcaacagcc gcaagaaacg cagcacctct gcaggcccga ccgtgccgga tcgcgacaac | 240 |
| gatggcattc cagacagcct ggaggtggaa ggctacaccg ttgatgtgaa gaacaaacgc | 300 |

```
accttcctga gcccgtggat ctctaacatt cacgagaaga aaggcctgac caagtataaa      360
agcagcccgg agaagtggag caccgcgagc gacccgtata gcgactttga aaaagtgacc      420
ggccgcattg ataagaacgt gagcccggaa gcacgccacc cactggtggc ggcgtacccg      480
attgtgcatg tggacatgga aaacatcatt ctgagcaaga acgaagacca gagcacccag      540
aacacggata gccagacccg taccatcagc aaaaacacca gcacctctcg tacgcatacc      600
agcgaagttc atggtaatgc ggaagtgcat gcgagctttt tcgatattgg tggcagcgtg      660
agcgcaggct ttagcaacag caacagcagc acggtggcga ttgatcatag cctgagcctg      720
gcgggcgaac gtacctgggc ggaaaccatg ggcctgaaca cggcagatac cgcgcgtctg      780
aatgcgaaca ttcgctacgt taacaccggt accgcaccaa tttataacgt tctgccgacc      840
accagcctgg tgctgggcaa gaatcagacc ctggcaacca tcaaagcgaa agagaaccag      900
ctgagccaga ttctggcgcc gaacaactac tatccaagca aaaacctggc gccgattgca      960
ctgaatgcgc aggatgactt cagcagcacg ccgattacca tgaactacaa ccagtttctg     1020
gagctggaaa agaccaagca actgcgcctg gatacggatc aggtgtatgg caacatcgca     1080
acctataact ttgagaacgg ccgcgtgcgc gttgataccg gtagcaactg gagcgaagtg     1140
ctgccgcaga tccaggaaac gaccgcgcgc attattttta acggcaaaga tctgaacctg     1200
gtggagcgtc gcatcgcagc ggttaaccca tctgatccac tggaaaccac caaaccggat     1260
atgaccctga agaggcgct gaagattgcg ttcggcttca tgaaccgaa tggcaacctg     1320 cagtatcaag gcaaagacat caccgagttc gacttcaact tgaccagca gacctctcaa     1380 aacatcaaga accagctggc ggaactgaac gcgaccaaca tctacaccgt gctggacaag     1440
atcaaactga cgcgaaaat gaacatcctg attcgcgaca aacgcttcca ttatgatcgt     1500
aacaacattg cggtgggtgc agatgaaagc gtggtgaaag aagcgcatcg cgaagtgatc     1560
aacagcagca ccgaaggcct gctgctgaac attgacaaag acattcgtaa gattctgagc     1620
ggctacattg tggaaattga agataccgag ggtctgaaag aggtgatcaa cgatcgctat     1680
gatatgctga acatctctag cctgcgtcag gatggtaaga ccttcatcga ctttaagaag     1740
tacaacgaca aactgccgct gtatatttct aatccgaact ataaagttaa cgtgtatgca     1800
gtgaccaaag agaacacgat cattaaccc agcgagaatg gcgataccag caccaac     1857
```

<210> SEQ ID NO 84
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92%) of SEQ ID No. 76

<400> SEQUENCE: 84

```
agcaacagca acaagattcg tctggagaag ggccgcctgt atcagatcaa gatccagtac       60
cagcgcgaaa atccgaccga aagggcctg gatttcaagc tgtactgac cgatagccag      120 aataagaaag aagtgattag ctctgataac ctgcagctgc cggaactgaa gcagaaaagc      180
agcaacagcc gcaaaaaacg cagcacctct gcaggcccga ccgtgccgga tcgcgacaac      240
gatggcattc cggacagcct ggaggtgaa ggctacaccg ttgatgtgaa gaacaaacgc      300
accttcctga gcccgtggat ctctaacatt cacgagaaga aaggcctgac caagtataaa      360
agcagcccgg agaagtggag caccgcgagc gacccgtata gcgattttga aaaagtgacc      420
ggccgcattg ataagaacgt gagcccggaa gcacgccatc cactggtggc ggcgtaccca      480
```

```
attgtgcacg tggacatgga aaacatcatt ctgagcaaga acgaagacca gagcacgcag    540
aacaccgata gccagacccg caccatcagc aagaacacca gcacctctcg tacgcatacc    600
agcgaagttc atggtaatgc ggaagtgcat gcgagctttt tcgatattgg tggcagcgtg    660
agcgcaggct ttagcaacag caacagcagc accgtggcga ttgatcatag cctgagcctg    720
gcgggcgaac gtacctgggc ggaaaccatg ggcctgaaca cggcagatac cgcgcgtctg    780
aacgcgaaca ttcgctacgt taacaccggt accgcaccaa tttataacgt tctgccgacc    840
accagcctgg tgctgggcaa gaatcagacc ctggcaacca tcaaagcgaa agagaatcag    900
ctgagccaga ttctggcgcc gaacaactac tatccaagca aaaacctggc gccgattgca    960
ctgaacgcgc aggacgactt cagcagcacg ccgattacca tgaactacaa ccagtttctg   1020
gagctggaaa agaccaagca actgcgcctg gacacggatc aagtgtatgg caacatcgca   1080
acctataatt ttgagaacgg ccgcgtgcgc gttgataccg gtagcaactg gagcgaagtg   1140
ctgccgcaga tccaggaaac gacggcgcgt attattttta acggcaaaga tctgaacctg   1200
gtggagcgtc gcatcgcagc ggttaaccca tctgatccac tggaaaccac caaaccggat   1260
atgaccctga agaggcgct gaagattgcg ttcggcttca tgaaccgaa tggcaacctg   1320 cagtatcagg gcaaagacat caccgagttc gacttcaact ttgaccagca gacctctcaa   1380
aacattaaga accagctggc ggaactgaac gcgaccaaca tctataccgt gctggacaag   1440
atcaaactga acgcgaaaat gaacatcctg attcgcgaca aacgcttcca ttatgatcgt   1500
aacaacattg cggtgggcgc agatgaaagc gtggtgaaag aagcgcatcg cgaagtgatc   1560
aacagcagca ccgaaggcct gctgctgaac atcgacaaag acattcgtaa gattctgagc   1620
ggctacattg tggaaattga agataccgag ggtctgaaag aggtgatcaa cgatcgctat   1680
gatatgctga acatctctag cctgcgtcag gatggtaaga ccttcatcga ttttaagaag   1740
tacaacgaca aactgccgct gtatatttct aatccgaact ataaagttaa cgtgtacgca   1800
gtgaccaaag agaacacgat cattaacccg agcgagaatg gtgataccag caccaac     1857
```

<210> SEQ ID NO 85
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91%) of SEQ ID No. 76

<400> SEQUENCE: 85

```
agcaacagca acaagattcg tctggagaaa ggccgcctgt atcagatcaa gatccagtac     60
cagcgcgaaa atccgaccga gaagggcctg gatttcaagc tgtactggac cgatagccag    120
aataagaaag aagtgattag ctctgataac ctgcagctgc cggaactgaa gcagaaaagc    180
agcaacagcc gcaaaaaacg tagcacctct gcaggcccga ccgtgccgga tcgcgacaac    240
gatggcattc cagacagcct ggaggtggaa ggctacaccg ttgatgtgaa gaacaaacgc    300
accttcctga gcccgtggat ctctaacatt cacgagaaga agggcctgac caagtataaa    360
agctctccgg agaagtggag caccgcgagc gacccgtata gcgattttga aaaagtgacc    420
ggccgtattg ataaaaatgt gagcccggaa gcacgccatc cactggtggc ggcgtacccg    480
attgtgcacg tggacatgga aaacatcatt ctgagcaaga acgaagacca gagcacgcaa    540
aacaccgata gccagacccg caccatcagc aagaacacca gcaccagccg tacgcatacc    600
```

```
agcgaagtgc atggtaatgc ggaagtgcat gcgagctttt ttgatattgg tggcagcgtg      660
agcgcgggct ttagcaacag caacagcagc accgtggcga ttgatcatag cctgagcctg      720
gcgggcgaac gtacctgggc ggaaaccatg ggcctgaaca ccgcagatac cgcgcgtctg      780
aacgcgaaca ttcgctacgt taacaccggc accgcaccaa tttataacgt tctgccgacc      840
accagcctgg tgctgggtaa gaatcagacc ctggcaacca tcaaagcgaa agagaaccag      900
ctgagccaga ttctggcgcc gaacaactat tatccaagca aaaacctggc gccgattgca      960
ctgaacgcgc aggacgactt cagcagcacg ccgattacca tgaactacaa ccagtttctg     1020
gagctggaaa agaccaaaca gctgcgcctg gacacggacc aagtgtatgg caacatcgca     1080
acctacaatt ttgagaacgg ccgtgtgcgc gtggataccg gtagcaactg gagcgaagtg     1140
ctgccgcaga tccaggaaac cacggcgcgc attatcttca acggcaagga tctgaacctg     1200
gtggagcgcc gcatcgcagc ggttaaccca tctgatccac tggaaaccac gaaaccggat     1260
atgaccctga agaggcact  gaagattgcg ttcggcttca tgaaccgaa  tgcaacctg      1320 cagtatcagg gcaaggacat caccgagttc gatttcaact ttgaccagca gacctctcaa     1380
aacattaaaa accagctggc ggaactgaac gcgaccaaca tctatacggt tctggacaag     1440
attaaactga acgcgaagat gaacattctg attcgcgata aacgcttcca ttatgatcgc     1500
aacaacattg cggtgggcgc agatgaaagc gtggtgaaag aagcgcatcg cgaagttatc     1560
aacagcagca ccgaaggcct gctgctgaac atcgacaaag acattcgtaa gattctgtct     1620
ggctacattg ttgaaattga agataccgag ggtctgaaag aggtgatcaa cgatcgctac     1680
gatatgctga acatctctag cctgcgtcag gacggtaaga ccttcatcga ttttaaaaaa     1740
tacaacgaca gctgccgct gtatatcagc aatccgaact ataaagtgaa cgtgtatgca      1800
gtgaccaagg agaacacgat cattaacccg agcgagaatg tgataccag  caccaac        1857

<210> SEQ ID NO 86
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Truncated version of SEQ ID No. 1
      (bp. 202-2106)

<400> SEQUENCE: 86
ttcatcaaag tgaagaaaag cgatgagtat acctttgcga cgtctgcgga taaccatgtg       60
accatgtggg tggacgatca ggaagtgatc aacaaagcga gcaacagcaa caagattcgc      120
ctggagaagg tcgcctgta  tcagatcaag attcagtatc agcgcgagaa tccgaccgag      180
aaaggcctgg atttcaaact gtactggacc gatagccaga caagaaaga agtgattagc       240 tctgataacc tgcaactgcc ggaactgaaa cagaagagca gcaacagccg caagaaacgc      300
agcacctctg caggcccgac cgttccagat cgcgacaacg atggcattcc ggacagcctg      360
gaagtggaag gttataccgt tgatgtgaag aacaaacgca cctttctgag cccgtggatt      420
agcaacattc atgagaagaa aggcctgacc aagtacaaaa gcagcccgga agtggagc       480 accgcgagcg atccgtatag cgactttgag aaagtgaccg gccgcattga taagaacgtg      540
agcccggaag cgcgtcaccc actggttgca gcgtatccga ttgtgcatgt tgacatggag      600
aacatcattc tgagcaagaa cgaagatcag agcacccaga cacggatag  ccagacccgc      660 acgatcagca agaacaccag cacgagccgt acccatacca gcgaagtgca tggcaatgcg      720
```

| | |
|---|---|
| gaagtgcatg cgagcttctt tgacattggt ggcagcgtga gcgcgggctt cagcaacagc | 780 |
| aacagcagca ccgtggcgat tgatcatagc ctgagcctgg cgggcgaacg tacctgggcg | 840 |
| gaaaccatgg gcctgaacac ggcggatacg gcacgtctga atgcgaacat tcgctatgtg | 900 |
| aacaccggta ccgcgccaat ctataacgtt ctgccgacca cgagcctggt gctgggcaag | 960 |
| aatcagaccc tggcgaccat caaagcgaaa gagaaccagc tgtctcagat tctggcaccg | 1020 |
| aacaactact atccgagcaa gaacctggca ccgattgcac tgaatgcgca ggatgacttc | 1080 |
| agcagcaccc cgatcaccat gaactacaat cagtttctgg agctggagaa gaccaaacaa | 1140 |
| ctgcgcctgg ataccgatca ggtgtatggc aacattgcga cctacaactt tgagaacggc | 1200 |
| cgcgttcgcg tggataccgg tagcaactgg tctgaagtgc tgccgcagat tcaggaaacg | 1260 |
| accgcgcgca tcatcttcaa cggcaaagat ctgaacctgg tggaacgtcg catcgcggca | 1320 |
| gtgaacccat ctgatccact ggaaacgacc aaaccggaca tgaccctgaa agaagcgctg | 1380 |
| aagattgcat ttggcttcaa cgaaccgaat ggcaacctgc agtatcaggg caaagacatc | 1440 |
| accgagtttg acttcaactt tgatcaacag acctctcaga acatcaagaa ccagctggca | 1500 |
| gaactgaatg cgaccaacat ctacaccgtg ctggacaaga tcaaactgaa cgcaaagatg | 1560 |
| aacattctga ttcgtgacaa acgcttccac tatgatcgta caacattgc ggtgggtgca | 1620 |
| gatgaaagcg ttgtgaaaga gcgcatcgt gaagtgatca actctagcac cgaaggcctg | 1680 |
| ctgctgaaca ttgacaaaga catccgtaag attctgagcg gctacattgt ggagattgaa | 1740 |
| gataccgaag gtctgaaaga agtgatcaac gatcgctatg acatgctgaa catctctagc | 1800 |
| ctgcgccagg atggcaagac cttcattgac ttcaagaagt acaacgacaa actgccgctg | 1860 |
| tacatcagca atccgaacta caaagtgaac gtgtatgcgg tgacc | 1905 |

<210> SEQ ID NO 87
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (99%) of SEQ ID No. 86

<400> SEQUENCE: 87

| | |
|---|---|
| ttcatcaaag tgaagaaaag cgatgagtat acctttgcga cgtctgcgga taaccatgtg | 60 |
| accatgtggg tggacgatca ggaagtgatc aacaaagcga gcaacagcaa caagattcgc | 120 |
| ctggagaagg gccgcctgta tcagatcaag attcagtatc agcgcgagaa tccgaccgag | 180 |
| aaaggcctgg atttcaaact gtactggacc gatagccaga acaagaaaga agtgattagc | 240 |
| tctgataacc tgcaactgcc ggaactgaaa cagaagagca gcaacagccg caagaaacgc | 300 |
| agcacctctg caggcccgac cgttccagat cgcgacaacg atggcattcc ggacagcctg | 360 |
| gaagtggaag gttataccgt tgatgtgaag aacaaacgca cctttctgag cccgtggatt | 420 |
| agcaacattc atgagaagaa aggcctgacc aagtacaaaa gcagcccgga aaagtggagc | 480 |
| accgcgagcg atccgtatag cgactttgag aaagtgaccg gccgcattga taagaacgtg | 540 |
| agcccggaag cgcgtcaccc actggttgca gcgtatccga ttgtgcatgt tgacatggag | 600 |
| aacatcattc tgagcaagaa cgaagatcag agcacccaga cacgatag ccagacccgc | 660 |
| acgatcagca agaacaccag cacgagccgt acccatacca gcgaggtgca tggcaatgcg | 720 |
| gaagtgcatg cgagcttctt tgacattggt ggcagcgtga gcgcgggctt cagcaatagc | 780 |
| aacagcagca ccgtggcgat tgatcatagc ctgagcctgg cgggcgaacg tacctgggcg | 840 |

```
gaaaccatgg gcctgaacac ggcggatacc gcacgtctga acgcgaacat tcgctatgtg    900
aacaccggta ccgcgccgat ctataacgtt ctgccgacca cgagcctggt gctgggtaaa    960
aatcagaccc tggcgacgat caaagcgaaa gagaaccagc tgtctcagat tctggcaccg   1020
aacaactact atccgagcaa gaacctggca ccgattgcac tgaatgcaca ggatgacttt   1080
agcagcaccc cgatcaccat gaactacaat cagtttctgg aactggagaa gaccaaacaa   1140
ctgcgcctgg ataccgatca ggtgtatggc aacattgcga cctacaactt tgagaacggc   1200
cgcgttcgcg tggataccgg tagcaactgg tctgaagtgc tgccgcagat tcaggaaacg   1260
accgcgcgca tcatcttcaa cggcaaagat ctgaacctgg tggaacgtcg catcgcggca   1320
gtgaacccat ctgatccact ggaaacgacc aaaccggaca tgaccctgaa agaagcgctg   1380
aagattgcat ttggcttcaa cgagccaaat ggcaacctgc agtatcaggg caaagacatc   1440
accgagttcg acttcaactt tgatcaacag acctctcaga acatcaagaa ccagctggca   1500
gaactgaatg cgaccaacat ctacaccgtg ctggacaaga tcaaactgaa cgcgaagatg   1560
aacattctga ttcgtgacaa acgcttccac tatgatcgta caacattgc ggtgggtgca   1620 gatgaaagcg ttgtgaagga agcgcatcgt gaagtgatca actctagcac cgaaggcctg   1680
ctgctgaaca tcgacaaaga catccgtaag attctgagcg gctacattgt ggagattgaa   1740
gataccgaag gtctgaaaga agtgatcaac gatcgctatg acatgctgaa catttctagc   1800
ctgcgccagg atggcaagac cttcattgac ttcaagaagt acaacgacaa actgccgctg   1860
tacatcagca atccgaacta caaagtgaac gtgtatgcgg tgacc                   1905

<210> SEQ ID NO 88
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98%) of SEQ ID No. 86

<400> SEQUENCE: 88
ttcatcaaag tgaagaaaag cgatgagtat acctttgcga cgagcgcgga taaccatgtg     60
accatgtggg tggacgatca ggaagtgatc aacaaagcga gcaacagcaa caagattcgc    120
ctggagaagg gccgcctgta tcagatcaag attcagtatc agcgcgagaa tccgaccgag    180
aaaggcctgg atttcaaact gtactggacc gatagccaga caagaaaga agtgattagc    240 tctgataacc tgcaactgcc ggaactgaaa cagaagagca gcaacagccg caagaaacgc    300
agcacctctg caggcccgac cgttccagat cgtgacaacg atggcatccc ggacagcctg    360
gaagtggaag gttataccgt tgatgtgaag aacaaacgca ccttctgag cccgtggatt    420 agcaacattc atgagaagaa aggcctgacc aagtataaaa gcagcccgga aaagtggagc    480
accgcgagcg atccgtatag cgactttgag aaagtgaccg gccgcattga taagaacgtg    540
agcccggaag cgcgccaccc actggttgca gcgtatccga ttgtgcatgt tgacatggag    600
aacatcattc tgagcaagaa cgaggatcag agcacccaga acacgatag ccagacgcgc    660 acgatcagca gaacaccag cacgagccgt acccatacca gcgaggtgca tggcaatgcg    720
gaagtgcatg cgagcttctt tgacattggt ggcagcgtga gcgcgggctt cagcaattct    780
aacagcagca ccgtggcgat tgatcatagc ctgagcctgg cgggcgaacg tacctgggcg    840
gaaaccatgg gcctgaacac ggcggatacc gcacgtctga acgcgaacat tcgctatgtg    900
```

```
aacaccggta ccgcgccgat ctataacgtt ctgccgacca cgagcctggt gctgggtaaa      960
aatcagaccc tggcgaccat caaagcgaaa gaaaaccagc tgtctcagat tctggcaccg     1020
aacaactact atccgagcaa gaacctggca ccgattgcac tgaatgcaca ggatgacttt     1080
agcagcaccc cgatcaccat gaactacaat cagtttctgg agctggagaa gaccaaaacaa   1140 ctgcgcctgg ataccgatca ggtgtatggc aacattgcga cctacaactt tgagaacggc    1200
cgcgttcgcg tggataccgg tagcaactgg tctgaagtgc tgccgcagat tcaggaaacg    1260
accgcgcgca tcatcttcaa cggcaaagat ctgaacctgg tggaacgtcg catcgcggca    1320
gtgaacccat ctgatccact ggaaacgacc aaaccggaca tgaccctgaa agaagcgctg    1380
aagattgcat ttggcttcaa cgagccaaat ggcaacctgc agtaccaggg caaagacatc    1440
accgagttcg acttcaactt tgatcaacag acctctcaga acatcaaaaa ccagctggca    1500
gaactgaatg cgaccaacat ctacaccgtg ctggacaaga tcaaactgaa cgcgaagatg    1560
aacattctga ttcgtgacaa acgcttccac tatgatcgta caacattgc ggtgggtgca    1620 gatgaaagcg tggtgaagga agcgcatcgt gaagtgatca actctagcac cgaaggcctg    1680
ctgctgaaca tcgacaaaga cattcgtaag attctgagcg gctacattgt ggaaattgaa    1740
gataccgaag gtctgaagga agtgatcaac gatcgctatg acatgctgaa catttctagc    1800
ctgcgccagg atggcaagac cttcattgac ttcaagaagt acaacgacaa actgccgctg    1860
tacatcagca atccgaacta caaagtgaac gtttatgcgg tgacc                    1905
```

<210> SEQ ID NO 89
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97%) of SEQ ID No. 86

<400> SEQUENCE: 89

```
ttcatcaaag tgaagaaaag cgatgagtat acctttgcga cgagcgcgga taaccatgtg       60
accatgtggg tggacgatca ggaagtgatc aacaaagcga gcaacagcaa caagattcgc      120
ctggagaagg gccgcctgta tcagatcaag attcagtatc agcgcgagaa tccgaccgag      180
aaaggcctgg atttcaaact gtactggacc gatagccaga caagaaaga agtgattagc       240 tctgataacc tgcaactgcc ggaactgaag cagaagagca gcaacagccg caagaaacgc      300
agcacctctg caggcccgac cgtgccagat cgtgacaacg atggcatccc agacagcctg      360
gaagtggaag ttataccgt tgatgttaag aacaaacgca cctttctgag cccgtggatt       420
agcaacattc atgagaagaa aggcctgacc aagtataaaa gcagcccgga aaagtggagc      480
accgcaagcg atccgtatag cgactttgag aaagtgaccg gccgcattga caagaacgtg     540
agcccggaag cgcgccaccc actggttgca gcgtatccga ttgtgcatgt tgacatggag      600
aacatcattc tgagcaagaa cgaggatcag agcacccaga acacggatag ccagacgcgc     660
acgatcagca agaacaccag cacgagccgt acccatacca gcgaggtgca tgcaatgcg       720 gaagtgcatg cgagcttctt tgacattggc ggcagcgtga gcgcaggctt cagcaattct     780
aacagcagca ccgtggcgat tgatcatagc ctgagcctgg cgggcgaacg tacctgggcg     840
gaaaccatgg gcctgaacac ggcggatacc gcacgtctga acgcgaacat tcgctatgtg     900
aacaccggta ccgcgccgat ctataacgtt ctgccgacca cgagcctggt tctgggtaaa     960
aatcagaccc tggcgaccat caaagcgaaa gaaaaccagc tgtctcagat tctggcaccg    1020
```

```
aacaactact atccgagcaa gaacctggca ccgattgcac tgaatgcaca ggatgacttt   1080
agcagcaccc cgatcaccat gaactacaat cagtttctgg agctggaaaa gaccaaacaa   1140
ctgcgcctgg ataccgatca ggtgtatggt aacattgcga cctacaactt tgagaacggc   1200
cgcgttcgcg tggataccgg tagcaactgg tctgaagtgc tgccgcagat tcaggaaacg   1260
accgcgcgca tcattttcaa cggcaaagat ctgaacctgg tggaacgtcg catcgcggcg   1320
gtgaacccgt ctgatccact ggaaacgacc aaaccggata tgaccctgaa agaagcgctg   1380
aagattgcgt ttggcttcaa cgagccaaat ggcaacctgc agtaccaggg caaagacatc   1440
accgagttcg acttcaactt tgatcaacag acctctcaga acatcaaaaa ccagctggca   1500
gaactgaatg cgaccaacat ctacaccgtg ctggacaaga tcaaactgaa cgcgaagatg   1560
aacattctga ttcgtgacaa acgcttccac tatgatcgta acaacattgc ggtgggtgca   1620
gatgaaagcg tggtgaagga agcgcatcgt gaggtgatca actctagcac cgaaggcctg   1680
ctgctgaaca tcgacaaaga cattcgtaaa atcctgagcg gctacattgt ggaaattgaa   1740
gataccgaag gtctgaagga agtgatcaac gatcgctatg acatgctgaa catttctagc   1800
ctgcgccagg atggcaagac cttcattgac ttcaagaagt acaacgacaa actgccgctg   1860
tacatcagca atccgaacta caaagtgaac gtttatgcgg tgacc               1905
```

<210> SEQ ID NO 90
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 86

<400> SEQUENCE: 90

```
ttcatcaaag tgaagaaaag cgatgagtat acctttgcga cgagcgcgga taaccatgtg    60
accatgtggg tggacgatca ggaagtgatc aacaaagcga gcaacagcaa caagattcgc   120
ctggagaagg gccgcctgta tcagatcaag attcagtatc agcgcgagaa tccgaccgag   180
aaaggcctgg atttcaaact gtactggacc gatagccaga caagaaaga ggtgattagc    240 tctgataacc tgcaactgcc ggaactgaag cagaagagcc gcaacagccg caagaaacgc   300
agcacctctg caggcccgac cgtgccagat cgtgacaacg atggcatccc agacagcctg   360
gaagtggaag gttataccgt tgatgttaag aacaaacgca cctttctgag cccatggatt   420
agcaacattc atgagaagaa aggcctgacc aagtataaaa gcagcccgga aaagtggagc   480
accgcaagcg atccgtatag cgactttgag aaagtgaccg gccgcattga caaaaacgtg   540
agcccggaag cgcgccatcc actggttgca gcgtacccga ttgtgcatgt tgacatggag   600
aacatcattc tgagcaagaa cgaggatcag agcacccaga acacggatag ccagacgcgc   660
acgatcagca agaacaccag cacgagccgt acccacacca gcgaggtgca tggcaatgcg   720
gaagtgcatg cgagccttctt tgacattggc ggcagcgtga gcgcaggctt tagcaattct   780
aacagcagca ccgtggcgat tgatcatagc ctgagcctgg cgggcgaacg tacctgggcg   840 gaaccatgg gcctgaacac ggcggatacc gcacgtctga cgcgaacat tcgctatgtg    900 aacaccggta ccgcgccgat ctacaacgtg ctgccgacca cgagcctggt tctgggtaaa   960
aatcagaccc tggcgaccat caaagcgaaa gaaaaccagc tgtctcagat tctggcaccg  1020
aacaactact atccgagcaa gaacctggca ccgattgcac tgaatgcaca ggatgacttt  1080
```

```
agcagcaccc cgatcaccat gaactataat cagtttctgg agctggaaaa gaccaaacaa    1140
ctgcgcctgg ataccgatca ggtgtatggt aacattgcga cctacaactt cgagaacggc    1200
cgtgttcgcg tggataccgg cagcaactgg tctgaagtgc tgccgcagat tcaggaaacg    1260
accgcgcgca tcattttcaa cggcaaagat ctgaacctgg tggaacgtcg catcgcggcg    1320
gtgaacccgt ctgatccgct ggaaacgacc aaaccggata tgaccctgaa agaagcgctg    1380
aagattgcgt ttggttttca cgagccaaat ggcaacctgc agtaccaggg caaagacatc    1440
accgaattcg acttcaactt tgatcaacag acctctcaga acatcaaaaa ccagctggca    1500
gaactgaatg cgaccaacat ctacaccgtg ctggacaaga tcaaactgaa cgcgaagatg    1560
aacattctga ttcgtgacaa gcgcttccac tatgatcgta caacattgc ggtgggtgca    1620 gatgaaagcg tggtgaagga gcgcatcgc gaggtgatca actctagcac cgaaggcctg    1680
ctgctgaaca tcgacaaaga cattcgtaaa atcctgagcg ctatattgt ggaaattgaa    1740 gataccgaag gtctgaagga agtgatcaac gatcgctatg acatgctgaa catttctagc    1800
ctgcgccagg atggcaagac cttcattgac ttcaagaagt acaacgacaa actgccgctg    1860
tacatcagca atccgaacta caaagtgaac gtttatgcgg tgacc                    1905

<210> SEQ ID NO 91
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95%) of SEQ ID No. 86

<400> SEQUENCE: 91
ttcatcaaag tgaagaaaag cgatgagtat acctttgcga cgagcgcgga taaccatgtg      60
accatgtggg tggacgatca ggaagtgatc aacaaagcga gcaacagcaa caaaattcgc     120
ctggagaagg gccgcctgta tcaaatcaag attcagtatc agcgcgagaa tccgaccgag     180
aaaggcctgg atttcaaact gtactggacc gatagccaga acaagaaaga ggtgattagc     240
tctgacaacc tgcagctgcc ggaactgaag cagaagagca gcaacagccg caagaaacgc     300
agcacctctg caggcccgac cgtgccagat cgtgacaacg atggcatccc agacagcctg     360
gaagtggaag gttataccgt tgatgttaag aacaaacgca cctttctgag cccatggatt     420
agcaacattc atgagaaaaa aggcctgacc aagtataaaa gcagcccgga aaagtggagc     480
accgcaagcg atccgtatag cgattttgag aaagtgaccg gccgcattga caaaaacgtg     540
agcccggaag cgcgccatcc actggttgca gcgtacccga ttgtgcatgt tgatatggag     600
aacatcattc tgagcaagaa cgaggatcag agcacccaga cacgcgatag ccagacgcgc     660
acgatcagca agaacaccag cacgagccgt acccacacca gcgaggtgca tgcaatgca     720 gaagtgcatg cgagcttctt cgacattggc ggcagcgtga gcgcaggctt tagcaattct     780
aacagcagca ccgtggcgat tgatcatagc ctgagcctgg cgggcgaacg tacctgggcg     840
gaaaccatgg gcctgaacac ggcggatacc gcgcgtctga cgcgaacat cgctatgtg      900 aacacgggta ccgcgccgat ctacaacgtg ctgccgacca ccagcctggt tctgggtaaa     960
aatcagaccc tggcgaccat caaagcgaaa gaaaaccagc tgtctcagat tctggcaccg    1020
aacaactact atccgagcaa gaacctggca ccgattgcgc tgaatgcaca ggatgacttt    1080
agcagcaccc cgatcaccat gaactataat cagtttctgg agctggaaaa gaccaagcaa    1140
ctgcgcctgg ataccgatca ggtgtatggt aacattgcga cctacaactt cgagaacggc    1200
```

```
cgtgttcgcg tggataccgg cagcaactgg tctgaagtgc tgccgcagat tcaagaaacg   1260
accgcgcgca tcatcttcaa cggcaaagat ctgaacctgg tggaacgtcg catcgcggcg   1320
gtgaacccgt ctgatccgct ggaaacgacc aaaccggaca tgaccctgaa agaagcactg   1380
aagattgcgt ttggtttcaa cgagccaaat ggcaacctgc agtaccaggg caaagacatc   1440
accgaattcg acttcaactt tgatcagcag acctctcaga acatcaaaaa ccagctggca   1500
gaactgaacg cgaccaacat ctacaccgtg ctggacaaga tcaagctgaa cgcgaagatg   1560
aacattctga ttcgtgacaa gcgctttcac tatgatcgta acaacattgc ggtgggtgca   1620
gatgaaagcg tggtgaagga agcgcatcgc gaggtgatca actctagcac cgaaggcctg   1680
ctgctgaaca tcgacaaaga cattcgtaaa atcctgagcg gctatattgt ggaaattgaa   1740
gataccgaag gtctgaagga agtgatcaac gatcgctatg acatgctgaa catttctagc   1800
ctgcgccagg atggcaagac cttcattgac ttcaagaagt acaacgacaa actgccgctg   1860
tacattagca atccgaacta caaagtgaat gtttatgcgg tgacc                  1905
```

<210> SEQ ID NO 92
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94%) of SEQ ID No. 86

<400> SEQUENCE: 92

```
ttcattaaag tgaagaaaag cgatgagtat acctttgcaa cgagcgcgga taaccatgtg    60
accatgtggg tggacgatca ggaagtgatc aacaaagcga gcaacagcaa caaaattcgc   120
ctggaaaagg gccgcctgta tcaaatcaag attcagtatc agcgcgagaa tccgaccgag   180
aaaggcctgg atttcaaact gtactggacc gatagccaaa acaagaaaga ggtgatttct   240
tctgacaacc tgcagctgcc ggaactgaag cagaagagca gcaacagccg caagaaacgc   300
agcacctctg caggcccgac cgtgccagat cgtgacaacg atggcatccc ggacagcctg   360
gaagtggaag gttataccgt tgatgttaag aacaaacgca cctttctgag cccatggatt   420
agcaacattc atgagaaaaa aggcctgacc aagtataaaa gcagcccgga aaagtggagc   480
accgcgagcg atccgtatag cgattttgag aaagtgaccg gccgcattga caaaacgtg   540 agcccggaag cgcgccatcc actggttgca gcgtacccga ttgtgcatgt tgatatggag   600
aacatcatcc tgagcaagaa cgaggatcag agcacccaga atacggatag ccagacgcgc   660
acgatcagca gaacaccag cacgagccgt acccacacca gcgaggtgca tgcaatgca   720 gaagtgcatg cgagcttctt cgacattggc ggcagcgtga gcgcaggctt tagcaacagc   780
aacagcagca ccgtggcaat tgatcacagc ctgtctctgg cgggcgaacg tacctgggcg   840
gaaaccatgg gcctgaacac ggcggatacc gcgcgtctga cgcgaacat tcgttatgtg   900 aacacgggta ccgcgccgat ctacaacgtg ctgccgacca ccagcctggt gctgggtaaa   960
aatcagaccc tggcgaccat caaagcgaaa gaaaccagc tgtctcagat tctggcgccg  1020
aataactact atccgagcaa gaacctggca ccaattgcgc tgaatgcaca ggatgacttt  1080
agcagcaccc cgatcaccat gaactataat cagtttctgg agctggaaaa gaccaagcaa  1140
ctgcgcctgg ataccgatca ggtgtatggt aacattgcga cctacaactt cgagaacggc  1200
cgtgttcgcg tggataccgg cagcaactgg tctgaagtgc tgccgcagat tcaggaaacg  1260
```

```
accgcgcgca tcatcttcaa cggcaaagat ctgaacctgg tggaacgtcg catcgcggcg    1320
gtgaacccga gcgatccgct ggaaacgacc aaaccggaca tgaccctgaa agaagcactg    1380
aagattgcgt ttggtttcaa cgagccaaat ggcaacctgc agtaccaggg caaagacatc    1440
accgaattcg acttcaactt tgatcagcag acctctcaga acatcaaaaa ccagctggca    1500
gaactgaacg cgaccaacat ctacaccgtg ctggacaaga tcaagctgaa cgcgaagatg    1560
aacattctga ttcgcgacaa gcgctttcat tatgatcgta acaacattgc ggtgggtgca    1620
gatgaaagcg tggtgaagga agcgcatcgc gaggtgatca actctagcac cgaaggcctg    1680
ctgctgaaca tcgacaaaga cattcgtaaa atcctgagcg gctatattgt tgaaattgag    1740
gataccgaag gtctgaagga agtgatcaac gatcgctatg acatgctgaa catttctagc    1800
ctgcgccagg atggcaagac cttcattgac ttcaagaagt acaacgacaa actgccgctg    1860
tacattagca acccgaacta caaagtgaat gtttatgcgg tgacc                    1905

<210> SEQ ID NO 93
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93%) of SEQ ID No. 86

<400> SEQUENCE: 93
ttcattaaag tgaagaaaag cgatgagtat acctttgcaa cgagcgcgga taaccatgtg      60
accatgtggg tggacgatca ggaagtgatc aacaaagcga gcaacagcaa caaaattcgc    120
ctggaaaagg gccgcctgta tcaaatcaag attcagtatc agcgcgagaa tccgaccgag    180
aaaggcctgg atttcaaact gtactggacc gatagccaaa acaagaaaga ggtgatttct    240
tctgataacc tgcagctgcc ggagctgaag cagaagagca gcaacagccg caagaaacgc    300
agcaccagcg caggcccgac cgtgccggat cgtgacaacg atggcatccc ggacagcctg    360
gaagtggaag ttataccgt tgatgtgaag aacaaacgca cctttctgag cccatggatt    420
agcaacattc acgaaaaaaa aggcctgacc aagtataaaa gcagcccgga aaagtggagc    480
accgcgagcg atccgtatag cgattttgag aaagtgaccg gccgcattga caaaaacgtg    540
agcccggaag cgcgccatcc actggttgca gcgtacccga ttgtgcatgt ggatatggag    600
aacatcatcc tgagcaaaaa cgaggatcag agcacccaga atacggatag ccagacgcgc    660
acgatcagca aaaacaccag cacgagccgt acccacacca gcgaggtgca tggcaatgca    720
gaagtgcatg cgagcttctt cgacattggc ggcagcgtga gcgcaggctt tagcaacagc    780
aacagcagca ccgtggcaat tgatcatagc ctgtctctgg cgggcgaacg tacctgggcg    840
gaaaccatgg gcctgaacac ggcggatacc gcgcgtctga cgcgaacat tcgttatgtg    900 aacacgggta ccgcgccgat ctacaacgtt ctgccgacca ccagcctggt gctgggtaaa    960
aatcaaaccc tggcgaccat caaagcgaaa gaaaaccagc tgtctcagat cctggcgcca   1020
aacaactact atccgtctaa gaacctggca ccaattgcgc tgaatgcaca ggatgacttt   1080
agcagcaccc cgatcaccat gaactataat cagtttctgg agctggaaaa gaccaagcag   1140
ctgcgcctgg ataccgatca ggtgtatggt aacattgcga cctacaactt cgagaacggc   1200
cgtgttcgcg tggataccgg cagcaactgg tctgaagtgc tgccgcagat tcaggaaacg   1260
accgcgcgca tcatcttcaa cggcaaagat ctgaacctgg tggaacgtcg catcgcggcg   1320
gtgaacccga gcgacccgct ggaaaccacc aaaccggaca tgaccctgaa agaagcactg   1380
```

```
aagattgcgt tggtttcaa cgagccaaat ggcaacctgc agtaccaggg caaagacatc    1440
accgaattcg acttcaattt tgatcagcag acctctcaga acatcaaaaa ccagctggca    1500
gaactgaacg cgaccaacat ttacaccgtg ctggacaaga tcaagctgaa cgcgaagatg    1560
aacattctga ttcgcgacaa gcgctttcat tatgatcgta acaacattgc ggtgggtgca    1620
gatgaaagcg tggtgaagga agcgcatcgc gaggttatca actctagcac ggaaggcctg    1680
ctgctgaaca tcgacaaaga cattcgtaaa atcctgagcg gctatattgt tgaaattgag    1740
gataccgaag gtctgaagga agtgatcaac gatcgctatg acatgctgaa catttctagc    1800
ctgcgccagg atggcaagac cttcattgac ttcaagaagt acaacgacaa gctgccgctg    1860
tacattagca acccgaacta caaggtgaat gtttatgcgg tgacc                    1905
```

<210> SEQ ID NO 94
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92%) of SEQ ID No. 86

<400> SEQUENCE: 94

```
ttcattaaag tgaagaaaag cgatgagtat acctttgcaa cgagcgcgga taaccatgtg    60
accatgtggg tggacgatca ggaggtgatc aacaaagcga gcaacagcaa caaaattcgc    120
ctggaaaaag gccgcctgta tcagatcaag attcagtatc aacgcgagaa cccgaccgaa    180
aaaggcctgg atttcaaact gtactggacc gatagccaga acaagaaaga ggtgatttct    240
tctgataacc tgcaactgcc ggagctgaag cagaagagca gcaacagccg caagaaacgc    300
agcaccagcg caggcccgac cgtgccggac cgcgacaacg atggcattcc ggatagcctg    360
gaagtggaag gttataccgt tgatgttaag aacaaacgta cgtttctgag cccatggatc    420
agcaacattc acgaaaaaaa aggcctgacc aagtataaaa gcagcccgga aaagtggagc    480
accgcgagcg atccgtatag cgattttgaa aaagtgaccg gccgcattga taaaaacgtg    540
agcccggaag cacgccatcc gctggttgcg gcgtacccga ttgtgcatgt ggatatggag    600
aatatcatcc tgagcaagaa cgaggatcag agcacgcaga ataccgatag ccagacgcgt    660
acgatcagca aaaacaccag cacgagccgt acccacacca gcgaggtgca tggcaacgcg    720
gaagtgcatg cgagcttctt cgacattggc ggcagcgtga gcgcgggctt tagcaacagc    780
aacagcagca ccgttgcaat tgatcatagc ctgtctctgg caggcgaacg tacctgggcg    840
gagaccatgg gcctgaacac ggcggatacc gcgcgcctga acgcgaacat tcgttatgtg    900
aacaccggta ccgcgccgat ctacaacgtg ctgccgacca ccagcctggt gctgggtaaa    960
aatcagaccc tggcgaccat caaagcgaaa gaaaaccagc tgtctcagat cctggcacca    1020
aacaactact atccgagcaa gaacctggca ccaattgcgc tgaatgcaca ggatgacttt    1080
agcagcaccc cgatcacgat gaactataac cagtttctgg agctggaaaa gaccaagcag    1140
ctgcgcctgg ataccgatca ggtgtatggt aacattgcaa cctacaactt cgagaacggc    1200
cgtgttcgcg tggataccgg cagcaactgg tctgaagtgc tgccgcagat tcaggaaacc    1260
accgcgcgca tcatcttcaa cggcaaagat ctgaacctgg tggaacgtcg catcgcggcg    1320
gtgaacccga cgacccgct ggaaaccacc aaaccggaca tgaccctgaa agaagcgctg    1380
aagattgcgt ttggtttcaa tgagccgaat ggcaacctgc agtaccaggg caaagacatc    1440
```

```
accgaattcg acttcaattt tgatcaacag acctctcaga acatcaaaaa ccagctggca    1500
gagctgaacg cgaccaacat ttacaccgtg ctggacaaga tcaagctgaa cgcgaagatg    1560
aatattctga ttcgcgacaa gcgctttcat tatgatcgta acaacattgc ggtgggtgca    1620
gatgaaagcg tggtgaagga agcgcatcgc gaggtgatca actctagcac ggaaggcctg    1680
ctgctgaaca tcgacaaaga cattcgtaaa atcctgagcg gctacattgt tgaaattgaa    1740
gacaccgaag gtctgaagga agtgatcaac gatcgctatg acatgctgaa catttctagc    1800
ctgcgccagg atggcaagac cttcattgac ttcaagaagt acaacgacaa gctgccactg    1860
tatatttcta acccaaacta caaggtgaat gtttatgcgg tgacc                    1905
```

<210> SEQ ID NO 95
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (91%) of SEQ ID No. 86

<400> SEQUENCE: 95

```
ttcattaaag tgaagaaaag cgacgagtac acctttgcaa cgagcgcgga taaccatgtg      60
accatgtggg ttgacgatca ggaggttatt aataaagcga gcaacagcaa caaaattcgt    120
ctggaaaaag gccgcctgta tcagatcaag attcagtatc aacgtgagaa cccgaccgaa    180
aaaggcctgg attttaaact gtactggacc gatagccaga acaagaaaga ggtgatttct    240
tctgataacc tgcagctgcc ggagctgaag cagaagagca gcaacagccg caagaaacgc    300
agcaccagcg cgggcccgac cgtgccggat cgcgacaacg atggcattcc ggacagcctg    360
gaagtggaag gttataccgt tgatgttaag aacaaacgca ccttttctgag cccatggatc    420 agcaacattc acgaaaaaaa aggcctgacc aagtataaaa gcagcccgga aaagtggagc    480
accgcgtctg atccgtatag cgattttgaa aaagtgaccg gccgcattga taaaaacgtg    540
agcccggaag cacgccatcc gctggttgcg gcgtatccga ttgtgcatgt ggatatggaa    600
aatatcatcc tgagcaagaa cgaggatcag agcacccaga taccgatagc cagacgcgt     660 acgatcagca aaaacaccag cacgagccgt acccatacca gcgaggtgca cggcaacgcg    720
gaagtgcatg cgagcttctt cgacattggc ggcagcgtga gcgcgggctt tagcaacagc    780
aacagcagca cggtggcaat tgatcatagc ctgtctctgg caggcgaacg tacctgggcg    840
gagaccatgg gcctgaacac ggcggatacc gcgcgcctga acgcaaacat tcgttatgtg    900
aacaccggta ccgcgccgat ctataacgtg ctgccgacca ccagcctggt gctgggtaaa    960
aatcagacgc tggcgaccat caaagcgaaa gaaaaccagc tgtctcagat cctggcacca   1020 acaactact atccgagcaa gaacctggca ccaatcgcgc tgaatgcgca ggatgatttc   1080
agcagcaccc cgatcacgat gaactataac cagtttctgg agctggaaaa gaccaagcag   1140
ctgcgcctgg ataccgatca ggtgtacggt aacattgcga cctataactt cgagaacggc   1200
cgcgttcgcg tggataccgg cagcaactgg tctgaagtgc tgccgcagat tcaggaaacc   1260
accgcgcgca tcatcttcaa cggcaaagat ctgaacctgg tggaacgtcg catcgcagcg   1320
gtgaacccga gcgacccgct ggaaaccacc aaaccggaca tgaccctgaa agaagcactg   1380
aagattgcgt ttggtttcaa cgagccgaat ggcaacctgc agtaccaagg caaagacatc   1440
accgaattcg attttaattt cgatcaacag acctctcaga acatcaaaaa ccagctggca   1500
gagctgaacg cgaccaacat ttacaccgtg ctggacaaga tcaagctgaa cgcgaagatg   1560
```

```
aatattctga ttcgcgacaa gcgttttcat tacgatcgta acaacatcgc ggtgggtgca    1620
gatgaaagcg tggtgaagga agcgcatcgc gaggtgatca actctagcac ggagggcctg    1680
ctgctgaaca tcgacaaaga cattcgcaaa attctgagcg gctacattgt tgaaattgaa    1740
gacaccgaag gtctgaagga agtgatcaac gatcgctatg acatgctgaa cattagcagc    1800
ctgcgccagg acggcaagac cttcattgac ttcaagaagt acaacgacaa gctgccactg    1860
tatatttcta atccaaacta caaggtgaac gtgtatgcgg tgacc                    1905
```

<210> SEQ ID NO 96
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No. 1 (bp. 103-2157)

<400> SEQUENCE: 96

```
gtgacctcta gcacgaccgg cgatctgagc attccgagca gcgaactgga gaacattccg    60
agcgagaacc agtactttca gtctgcgatt tggagcggct tcatcaaagt gaagaaaagc    120
gatgagtata cctttgcgac gtctgcggat aaccatgtga ccatgtgggt ggacgatcag    180
gaagtgatca acaaagcgag caacagcaac aagattcgcc tggagaaggg tcgcctgtat    240
cagatcaaga ttcagtatca gcgcgagaat ccgaccgaga aaggcctgga tttcaaactg    300
tactggaccg atagccagaa caagaaagaa gtgattagct ctgataacct gcaactgccg    360
gaactgaaac agaagagcag caacagccgc aagaaacgca gcacctctgc aggcccgacc    420
gttccagatc gcgacaacga tggcattccg gacagcctgg aagtggaagg ttataccgtt    480
gatgtgaaga acaaacgcac ctttctgagc ccgtggatta gcaacattca tgagaagaaa    540
ggcctgacca agtacaaaag cagcccggag aagtggagca ccgcgagcga tccgtatagc    600
gactttgaga agtgaccgg ccgcattgat aagaacgtga gcccggaagc gcgtcaccca    660
ctggttgcag cgtatccgat tgtgcatgtt gacatggaga acatcattct gagcaagaac    720
gaagatcaga gcacccagaa cacggatagc cagacccgca cgatcagcaa gaacaccagc    780
acgagccgta cccataccag cgaagtgcat ggcaatgcgg aagtgcatgc gagcttcttt    840
gacattggtg gcagcgtgag cgcgggcttc agcaacagca acagcagcac cgtggcgatt    900
gatcatagcc tgagcctggc gggcgaacgt acctgggcgg aaaccatggg cctgaacacg    960
gcggatacgg cacgtctgaa tgcgaacatt cgctatgtga acaccggtac cgcgccaatc    1020
tataacgttc tgccgaccac gagcctggtg ctgggcaaga atcagaccct ggcgaccatc    1080
aaagcgaaag agaaccagct gtctcagatt ctggcaccga acaactacta tccgagcaag    1140
aacctggcac cgattgcact gaatgcgcag gatgacttca gcagcccccc gatcaccatg    1200
aactacaatc agtttctgga gctggagaag accaaacaac tgcgcctgga taccgatcag    1260
gtgtatggca acattgcgac ctacaacttt gagaacggcc gcgttcgcgt ggataccggt    1320
agcaactggt ctgaagtgct gccgcagatt caggaaacga ccgcgcgcat catcttcaac    1380
ggcaaagatc tgaacctggt ggaacgtcgc atcgcggcag tgaacccatc tgatccactg    1440
gaaacgacca aaccggacat gaccctgaaa gaagcgctga gattgcatt tggcttcaac    1500 gaaccgaatg gcaacctgca gtatcagggc aaagacatca ccgagtttga cttcaacttt    1560
gatcaacaga cctctcagaa catcaagaac cagctggcag aactgaatgc gaccaacatc    1620
```

```
tacaccgtgc tggacaagat caaactgaac gcaaagatga acattctgat tcgtgacaaa    1680
cgcttccact atgatcgtaa caacattgcg gtgggtgcag atgaaagcgt tgtgaaagaa    1740
gcgcatcgtg aagtgatcaa ctctagcacc gaaggcctgc tgctgaacat tgacaaagac    1800
atccgtaaga ttctgagcgg ctacattgtg gagattgaag ataccgaagg tctgaaagaa    1860
gtgatcaacg atcgctatga catgctgaac atctctagcc tgcgccagga tggcaagacc    1920
ttcattgact tcaagaagta caacgacaaa ctgccgctgt acatcagcaa tccgaactac    1980
aaagtgaacg tgtatgcggt gaccaaagag aacaccatca ttaacccaag cgagaatggc    2040
gataccagca ccaac                                                    2055
```

<210> SEQ ID NO 97
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99%) of SEQ ID No. 96

<400> SEQUENCE: 97

```
gtgacctcta gcacgaccgg cgatctgagc attccgtcta gcgaactgga gaacattccg    60
agcgagaacc agtactttca gtctgcgatt tggagcggct tcatcaaagt gaagaaaagc    120
gatgagtata cctttgcgac gtctgcggat aaccatgtga ccatgtgggt ggacgatcag    180
gaagtgatca acaaagcgag caacagcaac aagattcgcc tggagaaggg tcgcctgtat    240
cagatcaaga ttcagtatca gcgcgagaat ccgaccgaga aaggcctgga tttcaaactg    300
tactggaccg atagccagaa caagaaggaa gtgattagct ctgataacct gcaactgccg    360
gaactgaaac agaagagcag caacagccgc aagaaacgca gcacctctgc aggcccgacc    420
gttccagatc gcgataacga tggcattccg gacagcctgg aagtggaagg ttataccgtt    480
gatgtgaaaa acaaacgcac ctttctgagc ccgtggatta gcaacattca tgaagaaaa    540 ggcctgacga agtacaaaag cagcccggag aagtggagca ccgcgagcga tccgtatagc    600
gactttgaga agtgaccgg ccgcattgat aagaacgtga gcccggaagc gcgtcaccca    660
ctggttgcag cgtatccgat tgtgcatgtt gacatggaga acatcattct gagcaagaac    720
gaagatcaga gcacccagaa cacggatagc cagacccgca cgatcagcaa gaacaccagc    780
acgagccgta cccataccag cgaagtgcat ggcaacgcgg aagtgcatgc gagcttcttt    840
gacattggtg gcagcgtgag cgcgggcttc agcaatagca acagcagcac cgtggcgatt    900
gaccatagcc tgagcctggc gggcgaacgt acctgggcag aaaccatggg cctgaacacg    960
gcggatacgg cacgtctgaa tgcgaacatt cgctatgtga ataccggtac cgcgccaatc    1020
tataacgttc tgccgaccac gagcctggtg ctgggcaaga accagaccct ggcgaccatc    1080
aaagcgaaag agaaccagct gtctcagatt ctggcaccga caactacta tccgagcaag    1140 aacctggcgc cgattgcact gaatgcgcag gatgacttca gcagcacccc gatcaccatg    1200
aactacaatc agtttctgga gctggagaag accaaacaac tgcgcctgga taccgatcag    1260
gtgtatggca acattgcgac ctacaacttt gagaacggcc gcgttcgcgt ggataccggt    1320
agcaactggt ctgaagtgct gccgcagatt caggaaacca ccgcgcgcat catcttcaac    1380
ggcaaagacc tgaacctggt ggaacgtcgc atcgcggcag tgaacccatc tgatccactg    1440
gaaacgacca aaccggacat gaccctgaaa gaagcgctga gattgcatt tggcttcaac    1500
```

```
gaaccgaatg gcaacctgca gtatcagggc aaagacatca ccgagtttga cttcaacttt    1560
gatcaacaga ccagccagaa catcaagaac cagctggcag aactgaatgc gaccaacatc    1620
tacaccgtgc tggacaagat caaactgaac gcaaagatga acattctgat tcgtgataaa    1680
cgcttccact atgatcgtaa caacattgcg gtgggtgcag atgaaagcgt tgtgaaagaa    1740
gcgcatcgtg aagtgatcaa ctctagcacc gaaggcctgc tgctgaacat tgacaaagac    1800
atccgtaaga ttctgagcgg ctacattgtg gagattgaag ataccgaagg tctgaaagaa    1860
gtgatcaacg atcgctatga catgctgaac atctctagcc tgcgccagga tggcaagacc    1920
ttcattgact tcaagaagta caacgacaaa ctgccgctgt acatcagcaa tccgaactac    1980
aaagtgaacg tgtatgcggt gaccaaagag aacaccatca ttaacccaag cgagaatggc    2040
gataccagca ccaac                                                    2055
```

<210> SEQ ID NO 98
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (98%) of SEQ ID No. 96

<400> SEQUENCE: 98

```
gtgacctcta gcacgaccgg cgatctgagc attccgtcta gcgaactgga gaacattccg    60
agcgagaacc agtactttca gtctgcaatt tggagcggct tcatcaaagt gaagaaaagc    120
gatgagtata cctttgcgac gtctgcggat aaccatgtga ccatgtgggt ggacgatcag    180
gaagtgatca acaaagcgag caacagcaac aagattcgcc tggagaaggg tcgcctgtat    240
cagattaaga ttcagtatca gcgcgagaat ccgaccgaga aaggcctgga ttttaaactg    300
tattggaccg atagccagaa caagaaggaa gtgattagca gcgataacct gcaactgccg    360
gaactgaaac aaaagagcag caacagccgc aagaaacgca gcacctctgc aggcccgacc    420
gttccagatc gcgataacga tggcattccg gacagcctgg aagtggaagg ttataccgtt    480
gatgtgaaaa acaaacgcac ctttctgagc ccgtggatta gcaacattca tgaaaagaaa    540
ggcctgacga agtacaaaag cagcccggag aagtggagca ccgcgagcga tccgtacagc    600
gactttgaga agtgaccgg ccgcattgat aagaacgtga gcccggaagc gcgtcaccca    660
ctggttgcag cgtatccgat tgtgcatgtt gacatggaga acatcattct gagcaagaac    720
gaagatcagt ctacccagaa cacggatagc cagacccgca cgatcagcaa gaacaccagc    780
acgagccgta cccataccag cgaagtgcat ggcaacgcgg aagtgcatgc gagcttcttc    840
gacattggtg gcagcgtgag cgcgggcttc agcaatagca acagcagcac cgtggcgatt    900
gaccatagcc tgagcctggc gggcgaacgt acctgggcag aaaccatggg cctgaacacg    960
gcggatacgg cacgtctgaa tgcgaacatt cgctatgtga ataccggtac cgcgccaatc    1020
tataacgttc tgccgaccac gagcctggtg ctgggcaaga accagaccct ggcgaccatc    1080
aaagcgaaag agaaccagct gtctcagatt ctggcaccga caactacta tccgagcaag    1140 aacctggcgc cgattgcgct gaatgcgcag gatgacttca gcagcacccc gatcaccatg    1200
aactacaatc agtttctgga gctggagaag accaaacagc tgcgcctgga caccgatcag    1260
gtgtatggca acattgcgac ctacaacttt gagaacggcc gcgttcgcgt ggataccggt    1320
agcaactggt ctgaagtgct gccgcagatt caggaaacca ccgcgcgcat catcttcaac    1380
ggcaaagacc tgaacctggt ggaacgtcgc atcgcggcag tgaacccatc tgatccactg    1440
```

```
gagacgacca aaccggatat gaccctgaaa gaagcgctga agattgcatt tggcttcaac    1500
gaaccgaatg gcaacctgca gtatcagggc aaagacatca ccgagtttga cttcaacttt    1560
gatcaacaga ccagccagaa catcaagaac cagctggcag aactgaatgc gaccaacatc    1620
tacaccgtgc tggacaagat caaactgaac gcaaagatga acatcctgat tcgtgataaa    1680
cgcttccact atgatcgtaa caacattgcg gtgggtgcag atgaaagcgt tgtgaaagaa    1740
gcgcatcgtg aagtgatcaa ctctagcacc gaaggcctgc tgctgaacat tgacaaagac    1800
atccgtaaga ttctgagcgg ctacattgtg gagattgaag ataccgaagg tctgaaagaa    1860
gtgatcaacg atcgctatga tatgctgaac atctctagcc tgcgccagga cggcaagacc    1920
ttcattgact tcaagaagta caacgacaaa ctgccgctgt acatcagcaa tccgaactac    1980
aaagtgaacg tgtatgcggt gaccaaagag aacaccatca ttaacccaag cgagaatggc    2040
gataccagca ccaac                                                     2055
```

<210> SEQ ID NO 99
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (97%) of SEQ ID No. 96

<400> SEQUENCE: 99

```
gtgacctcta gcacgaccgg cgatctgagc attccgagca gcgaactgga gaacattccg     60
tctgagaacc agtactttca gtctgcaatt tggagcggct tcatcaaagt gaagaagagc    120
gatgagtata cctttgcgac ctctgcggat aaccatgtga ccatgtgggt ggacgatcag    180
gaagtgatca acaaagcgag caacagcaac aagattcgcc tggagaaggg tcgcctgtat    240
cagattaaga ttcagtacca gcgcgagaat ccgaccgaga agggcctgga ttttaaactg    300
tattggaccg atagccagaa caagaaggag gtgattagca gcgataaccct gcaactgccg    360 gaactgaaac aaaagagcag caacagccgc aagaaacgca gcacctctgc aggcccgacc    420
gttccagatc gcgataacga tggcattccg gacagcctgg aagtggaggg ttataccgtt    480
gatgtgaaaa acaaacgcac ctttctgagc ccgtggatta gcaacattca tgaaaaaaaa    540
ggcctgacga agtacaaaag cagcccggag aagtggagca ccgcaagcga tccgtacagc    600
gactttgaaa aagtgaccgg ccgcattgat aagaacgtga gcccggaagc gcgtcaccca    660
ctggttgcag cgtatccgat tgtgcatgtt gacatggaga acattattct gagcaagaac    720
gaagatcagt ctacccagaa cacggatagc cagacccgca cgatcagcaa gaacaccagc    780
acgagccgta cccataccag cgaagtgcat ggcaacgcgg aagtgcatgc gagcttcttc    840
gacattggtg gcagcgtgag cgcgggcttc agcaatagca acagcagcac cgtggcgatt    900
gaccatagcc tgagcctggc gggcgaacgt acctgggcag aaaccatggg cctgaacacg    960
gcggataccg cacgtctgaa tgcgaacatt cgctatgtga atcgggtac cgcgccaatc   1020 tataacgttc tgccgaccac gagcctggtg ctgggcaaga ccagacgct ggcgaccatc   1080 aaagcgaaag agaaccagct gtctcagatt ctggcaccga caactacta tccgagcaag   1140 aacctggcgc cgattgcgct gaatgcgcag gatgacttca gcagcacccc gatcaccatg   1200
aactacaatc agtttctgga gctggagaag accaaacagc tgcgcctgga caccgatcag   1260
gtgtatggca acatcgcgac ctataacttt gaaaacggcc gcgttcgcgt ggataccggt   1320
```

| | |
|---|---|
| agcaactggt ctgaagtgct gccgcagatt caggaaacca ccgcgcgcat catcttcaac | 1380 |
| ggcaaagacc tgaacctggt ggaacgtcgc atcgcggcag tgaacccatc tgatccactg | 1440 |
| gagacgacca aaccggatat gaccctgaaa gaagcgctga agattgcatt tggcttcaac | 1500 |
| gaaccgaatg gcaacctgca gtatcagggc aaagacatca ccgagtttga cttcaacttt | 1560 |
| gatcaacaga ccagccagaa catcaaaaac cagctggcgg aactgaatgc gaccaacatc | 1620 |
| tacaccgtgc tggacaagat caaactgaac gcaaagatga acatcctgat tcgtgataaa | 1680 |
| cgcttccact atgatcgtaa caacattgcg gtgggtgcag atgagagcgt tgtgaaagaa | 1740 |
| gcgcatcgtg aagtgatcaa ctctagcacc gaaggcctgc tgctgaacat tgacaaagac | 1800 |
| atccgtaaga ttctgagcgg ctacattgtg gagattgaag ataccgaagg tctgaaagaa | 1860 |
| gtgatcaacg atcgctatga tatgctgaac atctctagcc tgcgccagga cggcaagacc | 1920 |
| ttcattgact tcaagaagta caacgacaaa ctgccgctgt acatcagcaa tccgaactac | 1980 |
| aaagtgaacg tgtatgcggt gaccaaagaa aacaccatca ttaacccaag cgagaatggc | 2040 |
| gataccagca ccaac | 2055 |

<210> SEQ ID NO 100
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (96%) of SEQ ID No. 96

<400> SEQUENCE: 100

| | |
|---|---|
| gtgacgtcta gcacgaccgg cgatctgagc attccgagct ctgaactgga gaacattccg | 60 |
| tctgagaacc agtactttca gtctgcaatt tggagcggct tcatcaaagt gaagaaaagc | 120 |
| gatgaatata cctttgcgac ctctgcggat aaccatgtga ccatgtgggt ggacgatcag | 180 |
| gaagtgatca acaaagcgag caacagcaac aagattcgcc tggagaaggg tcgcctgtat | 240 |
| caaattaaga ttcagtacca gcgcgagaac ccgaccgaga agggcctgga ttttaaactg | 300 |
| tattggaccg atagccagaa caagaaggag gtgattagca gcgataacct gcaactgccg | 360 |
| gagctgaaac agaaaagcag caacagccgc aagaaacgca gcacctctgc aggcccgacc | 420 |
| gttccagatc gcgataacga tggcattccg gacagcctgg aagtggaggg ttataccgtt | 480 |
| gacgtgaaga caaacgcac ctttctgagc ccgtggatca gcaacattca tgaaaaaaaa | 540 |
| ggcctgacca agtacaaaag cagcccggag aagtggagca ccgcaagcga tccgtacagc | 600 |
| gattttgaaa aagtgaccgg ccgcattgat aagaacgtga gcccggaagc gcgtcaccca | 660 |
| ctggttgcag cgtatccgat tgtgcatgtt gacatggaga acattattct gagcaagaac | 720 |
| gaagatcagt ctacccagaa cacggatagc cagacccgca cgattagcaa gaacaccagc | 780 |
| acgagccgta cccataccag cgaagtgcat ggcaacgcgg aagtgcatgc gagcttcttc | 840 |
| gacattggtg gcagcgtgag cgcgggcttc agcaatagca acagcagcac cgtggcgatt | 900 |
| gatcatagcc tgagcctggc gggcgaacgt acctgggcag aaaccatggg cctgaacacg | 960 |
| gcggataccg cacgtctgaa tgcgaacatt cgctatgtga acgggtac cgcgccaatc | 1020 |
| tataacgttc tgccgaccac gagcctggtg ctgggcaaga accagacgct ggcgaccatc | 1080 |
| aaagcgaaag agaaccagct gtctcagatt ctggcaccga caactacta tccgagcaag | 1140 |
| aacctggcgc cgattgcgct gaatgcgcag gacgacttca gcagcacccc gatcaccatg | 1200 |
| aactacaacc agtttctgga gctggagaag accaaacagc tgcgcctgga caccgatcag | 1260 |

```
gtgtatggca acatcgcgac ctataacttt gaaaacggcc gcgttcgcgt ggataccggt    1320
agcaactgga gcgaagtgct gccgcagatt caggaaacca ccgcgcgcat catcttcaac    1380
ggcaaagacc tgaatctggt ggaacgtcgc atcgcggcag tgaatccatc tgatccactg    1440
gagacgacca aaccggatat gaccctgaaa gaggcgctga agattgcatt tggcttcaac    1500
gaaccgaacg gcaacctgca gtatcagggc aaagacatca ccgagtttga cttcaatttt    1560
gatcaacaga ccagccagaa catcaaaaac cagctggcgg aactgaatgc gaccaacatc    1620
tacaccgtgc tggacaagat caaactgaac gcaaagatga acatcctgat tcgtgataaa    1680
cgcttccact atgatcgtaa caatattgcg gtgggtgcag atgaaagcgt tgtgaaagaa    1740
gcgcatcgtg aagtgatcaa ctctagcacc aaggcctgc tgctgaacat tgacaaggac    1800
atccgtaaga ttctgagcgg ctacattgtg agattgaag ataccgaagg tctgaaagaa    1860
gtgatcaacg atcgctatga tatgctgaac atctctagcc tgcgccagga cggcaagacc    1920
ttcattgact tcaagaagta caacgacaaa ctgccgctgt acatcagcaa cccgaattac    1980
aaagtgaacg tgtatgcggt gaccaaagaa aacaccatca ttaacccaag cgagaatggc    2040
gataccagca ccaac                                                     2055

<210> SEQ ID NO 101
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95%) of SEQ ID No. 96

<400> SEQUENCE: 101
gtgacgtcta gcacgaccgg cgatctgagc attccgagct ctgaactgga gaacattccg    60
tctgagaacc agtactttca gtctgcaatt tggagcggct tcatcaaagt gaagaaaagc    120
gatgaatata cctttgcgac ctctgcggat aaccatgtga ccatgtgggt ggacgatcag    180
gaagttatca caaagcgag caacagcaac aagattcgcc tggagaaggg tcgcctgtat    240
caaattaaga ttcagtacca gcgcgagaac ccgaccgaga agggcctgga ttttaaactg    300
tattggaccg atagccagaa caagaaggag gtgattagca gcgataacct gcaactgccg    360
gagctgaaac agaaaagcag caacagccgt aagaaacgca gcacctctgc aggcccgacc    420
gttccagatc gcgataacga tggcattccg gacagcctgg aagtggaggg ttataccgtt    480
gacgtgaaga acaaacgcac ctttctgagc ccgtggatca gcaacattca tgagaaaaaa    540
ggcctgacca agtacaaaag cagcccggaa aagtggagca ccgcaagcga tccgtacagc    600
gactttgaaa aagtgaccgg ccgcattgac aagaacgtga gcccggaagc gcgtcaccca    660
ctggttgcgg cgtatccgat tgtgcatgtg gatatggaaa acattattct gagcaagaac    720
gaagatcagt ctacccaaaa cacggatagc cagacccgca cgattagcaa gaacaccagc    780
acgagccgta cccataccag cgaagtgcat ggcaacgcgg aagtgcatgc gagcttcttc    840
gacattggtg gcagcgtgag cgcgggcttc agcaatagca acagcagcac cgtggcgatt    900
gatcatagcc tgagcctggc gggcgaacgt acctgggcag aaaccatggg cctgaacacg    960
gcggataccg cacgcctgaa tgcgaacatt cgctatgtga acacgggtac cgcgccaatc    1020
tataacgttc tgccgaccac gagcctggtg ctgggcaaga accagacgct ggcgaccatc    1080
aaagcaaaag agaaccagct gtctcagatt ctggcaccga acaactacta tccgagcaag    1140
```

-continued

```
aacctggcgc cgattgcgct gaatgcgcag gatgacttta gcagcacccc gatcaccatg    1200
aactacaacc agtttctgga gctggagaag accaaacagc tgcgcctgga caccgatcag    1260
gtgtatggca acatcgcgac ctataacttt gaaaacggcc gcgttcgcgt ggataccggt    1320
agcaactgga gcgaagtgct gccacagatt caggaaacca ccgcgcgcat catcttcaac    1380
ggcaaagacc tgaatctggt ggaacgtcgc atcgcggcag tgaatccatc tgatccgctg    1440
gagacgacca aaccggatat gaccctgaag gaggcgctga agattgcatt tggcttcaac    1500
gaaccgaacg gcaacctgca gtatcagggc aaagacatca ccgagttcga tttcaatttt    1560
gatcagcaga ccagccagaa catcaaaaac cagctggcgg agctgaatgc gaccaacatc    1620
tacaccgtgc tggacaagat caaactgaac gcaaagatga acatcctgat tcgtgataaa    1680
cgcttccact atgatcgcaa caatattgcg gtgggtgcag atgaaagcgt tgtgaaagaa    1740
gcgcatcgtg aagtgatcaa ctctagcacc gaaggcctgc tgctgaacat tgacaaggac    1800
atccgtaaga ttctgagcgg ctacattgtg gagattgaag ataccgaagg tctgaaagaa    1860
gtgatcaacg accgttatga tatgctgaac atctctagcc tgcgccagga cggcaagacc    1920
ttcattgact tcaaaaagta caacgacaaa ctgccgctgt acatcagcaa cccgaattac    1980
aaagtgaacg tgtatgcggt gaccaaagaa aacaccatca ttaacccaag cgagaatggc    2040
gataccagca ccaac                                                    2055
```

<210> SEQ ID NO 102
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94%) of SEQ ID No. 96

<400> SEQUENCE: 102

```
gtgacgtcta gcacgaccgg cgatctgagc attccgagct ctgaactgga aaatattccg     60
agcgagaacc agtactttca gtctgcaatt tggagcggct ttatcaaagt gaagaaaagc    120
gatgaatata cctttgcgac cagcgcggat aaccatgtga ccatgtgggt ggacgatcag    180
gaagttatca acaaagcgag caacagcaac aagattcgcc tggagaaggg tcgcctgtat    240
caaattaaga ttcagtacca gcgtgagaac ccgaccgaga agggcctgga ttttaaactg    300
tattggaccg atagccagaa caagaaggag gtgattagca gcgataacct gcaactgccg    360
gagctgaaac agaaaagcag caacagccgt aagaaacgca gcaccagcgc aggcccgacc    420
gttccagatc gcgataacga tggcattccg gatagcctgg aagtggaggg ttataccgtg    480
gacgtgaaga acaaacgcac ctttctgtct ccgtggatca gcaacattca tgagaaaaaa    540
ggcctgacca gtacaaaag cagcccggaa aagtggtcta ccgcaagcga tccgtactct    600
gactttgaaa agtgaccgg ccgcattgac aagaacgtga gcccggaagc gcgtcaccca    660
ctggttgcgg cgtatccgat tgtgcatgtt gatatggaga acatcattct gagcaagaac    720
gaagatcaga gcacccaaaa cacgatagc cagcccgca cgatttctaa gaacaccagc    780
acgagccgta cccataccag cgaagtgcat ggcaacgcgg aagtgcatgc gagcttcttc    840
gacattggtg gcagcgtgag cgcgggcttc agcaatagca acagcagcac cgtggcgatt    900
gatcatagcc tgagcctggc gggcgaacgc acctgggcag aaaccatggg cctgaacacg    960
gcggataccg cacgcctgaa tgcgaacatt cgctatgtga acacgggtac cgcgccaatc   1020
tataacgttc tgccgaccac cagcctggtg ctgggcaaga accagacgct ggcgaccatc   1080
```

```
aaagcaaaag agaaccagct gtctcagatt ctggcaccga acaactacta tccgagcaag    1140
aacctggcgc cgattgcgct gaatgcgcag gatgacttta gcagcacccc gatcaccatg    1200
aactacaacc agttcctgga gctggagaag accaaacagc tgcgcctgga caccgatcag    1260
gtgtatggca acatcgcgac ctataacttt gaaaacggcc gcgttcgcgt ggataccggt    1320
agcaactgga gcgaagtgct gccacagatt caggaaacca ccgcgcgcat catcttcaac    1380
ggcaaagacc tgaatctggt ggaacgtcgc atcgcggcag tgaacccatc tgacccgctg    1440
gagacgacca aaccggatat gaccctgaag gaggcgctga agattgcgtt tggcttcaac    1500
gaaccgaacg gcaacctgca gtatcagggc aaagacatca ccgagttcga tttcaatttt    1560
gatcagcaga cgagccagaa tatcaaaaac cagctggcgg agctgaatgc gaccaacatc    1620
tacaccgtgc tggacaagat caaactgaac gcaaagatga acatcctgat tcgtgataaa    1680
cgcttccact atgatcgcaa caatattgca gtgggtgcag atgaaagcgt tgtgaaagaa    1740
gcgcatcgtg aagtgatcaa ctctagcacc gaaggcctgc tgctgaacat tgacaaggac    1800
atccgtaaga ttctgagcgg ctacattgtg gagattgaag ataccgaagg tctgaaagaa    1860
gtgattaacg accgttatga tatgctgaac atctctagcc tgcgccagga cggcaagacc    1920
ttcattgact caaaaagta caacgacaaa ctgccgctgt acatcagcaa cccgaactac    1980
aaagtgaacg tgtatgcggt gaccaaagaa aacaccatca ttaacccaag cgagaatggc    2040
gataccagca ccaac                                                    2055
```

<210> SEQ ID NO 103
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93%) of SEQ ID No. 96

<400> SEQUENCE: 103

```
gtgacgagca gcacgaccgg cgatctgagc attccgagct ctgaactgga aaacattccg      60
agcgagaacc agtactttca gtctgcaatc tggagcggct tcatcaaagt gaagaaaagc     120
gatgaatata ccttcgcgac cagcgcggat aaccatgtga ccatgtgggt ggacgatcag     180
gaagttatca caaaagcgag caacagcaac aagattcgcc tggagaaagg tcgtctgtat     240
cagattaaga ttcagtacca gcgtgagaac ccgaccgaga agggcctgga ttttaaactg     300
tattggaccg atagccagaa caagaaggag gtgattagca gcgataacct gcaactgccg     360
gagctgaaac agaaaagcag caacagccgc aagaaacgta gcaccagcgc aggcccgacc     420
gttccagatc gcgataacga tggcattccg gatagcctgg aagtggaggg ttataccgtg     480
gacgtgaaga taaacgcac ctttctgtct ccgtggatca gcaacatcca tgagaaaaaa     540
ggcctgacca agtacaagag cagcccggaa aagtggtcta ccgcaagcga cccgtattct     600
gactttgaaa aagtgaccgg ccgcatcgat aagaacgtga gccgggaagc gcgtcaccca     660
ctggttgcgg cgtatccgat tgtgcatgtt gatatggaga acattattct gagcaagaac     720
gaagatcaga gcacccaaaa cacgatagc cagaccccgca cgattctaa gaataccagc     780 acgagccgta cccataccag cgaagtgcat ggcaacgcgg aagtgcatgc gagcttcttc     840
gacattggtg gcagcgtgtc tgcgggcttc agcaatagca acagcagcac cgtgcgcgatt     900 gatcatagcc tgagcctggc gggcgaacgc acctgggcag aaaccatggg cctgaacacg     960
```

```
gcggataccg cacgcctgaa tgcgaacatt cgctatgtga acacgggtac cgcgccaatc    1020
tataacgttc tgccgaccac cagcctggtg ctgggcaaga accagacgct ggcgaccatc    1080
aaagcaaaag aaaatcagct gtctcagatt ctggcaccga caactacta tccgagcaag     1140 aacctggcgc cgattgcgct gaacgcgcag gatgacttta gcagcacccc gatcaccatg    1200
aactacaacc agttcctgga gctggagaag accaaacagc tgcgcctgga caccgatcag    1260
gtgtatggca acatcgcgac ctataacttt gagaacggcc gcgttcgcgt ggataccggt    1320
agcaactgga gcgaagtgct gccacagatt caggaaacca ccgcgcgcat tatctttaac    1380
ggcaaagacc tgaatctggt ggaacgtcgc atcgcggcag tgaacccatc tgacccgctg    1440
gagacgacca accggatat gaccctgaag gaggcgctga agattgcgtt cggcttcaac    1500
gaaccgaacg gcaacctgca atatcagggc aaagacatca ccgagtttga tttcaatttt    1560
gatcagcaga cgagccagaa tatcaaaaac cagctggcgg agctgaacgc gaccaacatc    1620
tacaccgtgc tggacaagat caaactgaac gcaaagatga cattctgat cgtgataaa     1680 cgctttcact atgatcgcaa caatattgca gtgggtgcag atgaaagcgt tgtgaaagaa    1740
gcgcatcgcg aagtgatcaa ctctagcacc gaaggcctgc tgctgaacat tgacaaggac    1800
atccgtaaga ttctgagcgg ctacattgtg gagattgaag ataccgaagg tctgaaagaa    1860
gtgattaacg accgttacga tatgctgaac atctctagcc tgcgccagga cggcaagacc    1920
ttcattgact tcaaaaagta caacgacaaa ctgccgctgt acatcagcaa cccgaactac    1980
aaagtgaacg tgtatgcggt gaccaaagaa aacaccatca ttaacccaag cgagaatggc    2040
gataccagca ccaac                                                    2055
```

<210> SEQ ID NO 104
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92%) of SEQ ID No. 96

<400> SEQUENCE: 104

```
gtgacgagca gcacgaccgg cgatctgagc attccgagct ctgaactgga gaatattccg      60
agcgagaacc agtactttca gtctgcaatc tggagcggct tcattaaagt gaagaagagc     120
gatgaatata ccttcgcgac cagcgcggat aaccatgtga ccatgtgggt ggatgaccag     180
gaagttatca acaaagcgag caacagcaac aagattcgcc tggaaaaagg tcgtctgtat     240
cagattaaga ttcagtacca gcgtgagaac ccgaccgaga agggcctgga ttttaaactg     300
tattggacgg atagccagaa caagaaggaa gtgattagca gcgataaccct gcagctgccg     360 gagctgaaac agaaaagctc taacagccgc aagaaacgta gcaccagcgc aggcccgacc     420
gttccagatc gcgataacga tggcattccg gatagcctgg aagtggaggg ttataccgtg     480
gacgtgaaga ataaacgcac ctttctgtct ccgtggatca gcaacatcca tgagaaaaaa     540
ggcctgacca agtacaaaag cagcccggaa aagtggtcta cggcaagcga cccgtattct     600
gactttgaaa aagtgaccgg ccgcatcgat aagaacgtga gcccggaagc gcgtcatcca     660
ctggttgcgg cgtatccgat tgtgcatgtt gatatggaga cattattct gagcaagaac     720 gaagatcaga gcacccaaaa cacggatagc cagaccccgca cgatttctaa aaataccagc     780
acgagccgta cccataccag cgaagtgcac ggcaacgcgg aagtgcatgc gagcttcttc     840
gatattggtg gcagcgtgtc tgcgggcttc agcaatagca acagcagcac cgtggcgatt     900
```

```
gatcatagcc tgagcctggc gggcgaacgc acctgggcag aaaccatggg cctgaacacc    960
gcggataccg cacgcctgaa tgcgaacatt cgctatgtga cacgggcac cgcgccaatc   1020 tataacgttc tgccgaccac cagcctggtg ctgggtaaga accagacgct ggcgaccatc   1080
aaggcaaaag aaaatcagct gtctcagatt ctggcaccga caactacta tccgagcaag   1140 aacctggcgc cgattgcgct gaacgcgcag gatgacttta gcagcacccc gatcaccatg   1200
aactacaacc agttcctgga actggagaag accaaacaac tgcgcctgga caccgatcag   1260
gtgtatggca acatcgcgac ctataacttt gagaacggcc gcgttcgcgt ggataccggt   1320
agcaactgga gcgaagtgct gccacagatt caggaaacca ccgcgcgcat tatctttaac   1380
ggcaaagacc tgaatctggt ggaacgtcgc atcgcggcag tgaacccaag cgacccgctg   1440
gagacgacca aaccggatat gaccctgaag gaggcgctga aaattgcgtt cggcttcaac   1500
gagccgaacg gcaacctgca atatcagggc aaagacatca ccgagtttga tttcaatttt   1560
gatcagcaga ccagccagaa tatcaaaaac cagctggcgg agctgaacgc gaccaacatc   1620
tacaccgtgc tggacaagat caaactgaac gcaaagatga acattctgat tcgtgataaa   1680
cgctttcact atgatcgcaa caacattgca gtgggtgcag atgaaagcgt tgtgaaagaa   1740
gcgcatcgcg aagtgatcaa ctctagcacc gaaggcctgc tgctgaacat cgacaaggac   1800
atccgtaaga ttctgagcgg ctacattgtg gagattgagg ataccgaagg tctgaaagaa   1860
gtgattaacg accgttacga catgctgaac atctctagcc tgcgccagga cggcaagacc   1920
ttcattgact tcaagaagta caacgacaaa ctgccgctgt acatcagcaa cccgaactac   1980
aaagtgaacg tgtatgcggt gaccaaagaa aacaccatca ttaacccaag cgagaatggc   2040
gataccagca ccaac                                                   2055
```

<210> SEQ ID NO 105
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91%) of SEQ ID No. 96

<400> SEQUENCE: 105

```
gtgacgagca gcacgaccgg cgacctgagc attccgagct ctgaactgga gaatattccg     60
agcgagaacc agtactttca gtctgcgatc tggagcggct tcattaaagt gaagaaaagc    120
gatgaatata ccttcgcgac cagcgcggat aaccatgtga ccatgtgggt ggatgaccag    180
gaagttatca caaagcgag caacagcaac aagattcgtc tggaaaaagg tcgtctgtat    240
cagattaaga ttcagtacca gcgtgaaaac ccgaccgaga agggcctgga tttcaaactg    300
tattggacgg atagccagaa caagaaggag gtgattagca gcgataacct gcagctgccg    360
gagctgaaac agaaaagctc taacagccgc aagaaacgta gcacctctgc aggcccgacc    420
gttccagacc gcgataacga tggcattccg gatagcctgg aagtggaggg ctataccgtg    480
gacgtgaaga ataaacgcac ctttctgtct ccgtggatca gcaacatcca tgagaaaaaa    540
ggcctgacca agtacaaaag cagcccgaaa agtggagca ccgcaagcga cccgtattct    600
gattttgaaa aggtgaccgg ccgcatcgat aagaacgtga gcccggaagc gcgtcatcca    660
ctggttgcgg cgtatccgat tgtgcatgtt gatatggaga acattattct gagcaagaac    720
gaagatcaga gcacccaaaa cacggatagc cagacgcgca cgatttctaa aaataccagc    780
```

| | |
|---|---|
| accagccgta cccataccag cgaagtgcac ggcaacgcgg aggtgcatgc gagcttcttt | 840 |
| gatattggtg gcagcgtgtc tgcgggtttc agcaacagca acagcagcac cgtggcgatt | 900 |
| gatcatagcc tgtctctggc gggcgaacgt acctgggcag aaaccatggg cctgaacacc | 960 |
| gcggataccg cacgcctgaa tgcgaacatt cgctatgtga acacgggcac cgcgccaatc | 1020 |
| tataacgttc tgccgaccac cagcctggtg ctgggtaaga accagacgct ggcgaccatc | 1080 |
| aaggcaaaag aaaatcagct gtctcagatt ctggcaccga caactatta tccgagcaag | 1140 |
| aacctggcgc cgattgcgct gaacgcgcag gatgacttta gcagcacccc gatcaccatg | 1200 |
| aactacaacc agttcctgga actggagaag accaaacaac tgcgcctgga caccgatcag | 1260 |
| gtgtatggca acatcgcgac ctacaacttt gagaacggcc gcgttcgcgt ggataccggt | 1320 |
| agcaactgga gcgaagtgct gccacagatt caggaaacca ccgcgcgcat catctttaac | 1380 |
| ggcaaagatc tgaatctggt ggaacgccgc attgcagcag tgaacccaag cgacccgctg | 1440 |
| gagacgacca aaccggatat gaccctgaag gaggcgctga aaattgcgtt cggcttcaac | 1500 |
| gaaccgaacg gcaacctgca atatcagggc aaagacatca cggagtttga tttcaatttt | 1560 |
| gatcagcaga ccagccagaa tattaaaaac cagctggcgg agctgaacgc aaccaacatc | 1620 |
| tacaccgtgc tggataagat caaactgaac gcgaagatga acatcctgat tcgcgataaa | 1680 |
| cgctttcact atgatcgcaa caatattgca gtgggtgcag acgaaagcgt tgtgaaagaa | 1740 |
| gcgcatcgcg aagtgatcaa cagcagcacc gaaggcctgc tgctgaacat cgacaaggac | 1800 |
| atccgtaaga ttctgagcgg ctacattgtg gagattgagg acaccgaagg tctgaaagaa | 1860 |
| gtgattaacg accgttacga catgctgaac atctctagcc tgcgccagga cggcaagacc | 1920 |
| ttcattgact tcaagaagta caacgataaa ctgccgctgt acatcagcaa cccgaactac | 1980 |
| aaagtgaacg tgtatgcggt gaccaaagaa aacaccatca ttaatccaag cgagaacggc | 2040 |
| gataccagca ccaac | 2055 |

<210> SEQ ID NO 106
<211> LENGTH: 2211
<212> TYPE: DNA
<213> ORGANISM: Artificial Sequence
<220> FEATURE:
<223> OTHER INFORMATION: Description of Artificial Sequence: Synthetic consensus polynucleotide

<400> SEQUENCE: 106

| | |
|---|---|
| atggaagtta aacaggagaa ccgtttgttg aatgaatgcg aatctagttc tcagggggttg | 60 |
| ctgggctact attttagtga tttgaatttt caggcaccga tggttgttac ctcttgtact | 120 |
| accggggatt tgtgtattcc tagttgtgag ttggagaata ttccgtggga gaaccagtat | 180 |
| tttcagtctg ctatttggtg cggctttatc aaagttaaga gagtgatga gtataccttt | 240 |
| gctacttctg ctgataatca tgtgaccatg tgggtggatg atcaggaagt gattaataaa | 300 |
| gcttgtaatt gtaacaagat tcgcttggag aagggtcgct tgtatcagat caagattcag | 360 |
| tatcagcgcg agaatcctac tgagaaaggc ttggatttca gttgtactg gaccgattgt | 420 |
| cagaataaga agaagtgat tgttgtgat aacttgcaat tgccggaatt gaaacagaag | 480 |
| tgttggaact gccgcaagaa gcgcagtacc tgtgctggcc ctacggttcc agatcgtgac | 540 |
| aatgatggca ttcctgattg cttggaggtg aaggttata cggttgatgt gaagaataaa | 600 |
| cgcactttc tttgcccgtg gatttgtaat attcatgaga agaaaggctt gaccaagtat | 660 |
| aaatgctgtc ctgagaagtg gagcacggct tgtgatccgt atagtgattt tgagaaggtt | 720 |
| accggccgga ttgataagaa tgtgtgcccg gaggcgcgtc accccttgt tgcagcttat | 780 |

```
ccgattgtgc atgttgatat ggagaatatt attctgtgca agaatgagga tcagtgcacc    840
cagaatactg atagtcagac gcgcacgatc agtaagaata cttgtacgag tcgtacccat    900
actagtgaag tgcatggcaa tgcggaagtg catgcgtggt tctttgatat tggtgggagt    960
gtgtgtgcgg gctttagtaa ttggaattgc agtacggtgg cgattgatca ttgcctgtgt   1020
ctggcggggg aacgtacttg ggctgaaacc atgggtttga atacggctga tacggcacgt   1080
ttgaatgcga atattcgcta tgtgaatact ggtacggctc caatctataa cgttttgccg   1140
acgacttggt tggtgttggg caagaatcag accctggcga ccattaaagc taaggagaac   1200
cagttgtgtc agattcttgc acctaataat tattatcctt gtaagaactt ggcgccgatt   1260
gcattgaatg cgcaggatga tttcagttgt actccgatta ccatgaatta caatcagttt   1320
cttgagttgg agaagacgaa acaattgcgc ttggatacgg atcaggtgta tgggaatatt   1380
gcgacctaca atttttgagaa tggccgcgtt cgggtggata ccggttggaa ctggtgtgaa   1440
gtgttgccgc agattcagga aacgactgcg cgtatcattt ttaatggcaa agatttgaat   1500
ctggtggaac gtcggatcgc ggcggttaat ccttgtgatc cattggaaac gactaaaccg   1560
gatatgacct tgaaagaagc gcttaagatt gcatttggct ttaacgaacc gaatggcaac   1620
ttgcagtatc aggggaaaga catcaccgag tttgattta attttgatca acagacctct    1680
cagaatatca gaatcagtt ggcggaattg aatgcgacta catctatac tgtgttggat     1740 aagatcaaat tgaatgcaaa gatgaatatt ttgattcgtg ataaacgttt tcattatgat   1800
cgtaataaca ttgcggttgg tgcggatgag tgcgttgtta aggaggctca tcgtgaagtg   1860
attaattctt gcaccgaggg cttgttgttg aatattgata aggatatccg taagattttg   1920
tgcggttata ttgtggagat tgaagatact gaaggtctta agaagttat caatgatcgc    1980 tatgatatgt tgaatatttc tagtttgcgg caggatggca agaccttat tgattttaag    2040 aagtataatg ataaattgcc gttgtatatc agtaatccga attataaggt gaatgtgtat   2100
gctgttacta agagaacac tattattaat cctagtgaga atggggatac tagtaccaac    2160
gggatcaaga gattttgat cttttgtaag aaaggctatg agattggcta a             2211
```

<210> SEQ ID NO 107
<211> LENGTH: 21
<212> TYPE: PRT
<213> ORGANISM: Homo sapiens

<400> SEQUENCE: 107

Ile Lys Leu Asn Ala Lys Met Asn Ile Leu Ile Arg Asp Lys Arg Phe
1               5                   10                  15

His Tyr Asp Arg Asn
            20

<210> SEQ ID NO 108
<211> LENGTH: 9
<212> TYPE: PRT
<213> ORGANISM: Macaca fascicularis

<400> SEQUENCE: 108

Pro Leu Tyr Ile Ser Asn Pro Asn Tyr
1               5

<210> SEQ ID NO 109
<211> LENGTH: 21
<212> TYPE: PRT
<213> ORGANISM: Homo sapiens

```
<400> SEQUENCE: 109

Pro Ile Tyr Asn Val Leu Pro Thr Thr Ser Leu Val Leu Gly Lys Asn
1               5                   10                  15

Gln Thr Leu Ala Thr
            20

<210> SEQ ID NO 110
<211> LENGTH: 12
<212> TYPE: PRT
<213> ORGANISM: Homo sapiens

<400> SEQUENCE: 110

Ser Leu Val Leu Gly Lys Asn Gln Thr Leu Ala Thr
1               5                   10

<210> SEQ ID NO 111
<211> LENGTH: 16
<212> TYPE: PRT
<213> ORGANISM: Homo sapiens

<400> SEQUENCE: 111

Arg Leu Tyr Gln Ile Lys Ile Gln Tyr Gln Arg Glu Asn Pro Thr Glu
1               5                   10                  15
```

```

PREPARATION OF PROTECTIVE ANTIGEN

CROSS REFERENCE TO RELATED APPLICATION

This application is a divisional application of co-pending U.S. application Ser. No. 13/246,659, filed Sep. 27, 2011, which is a divisional application of co-pending U.S. application Ser. No. 12/042,150, filed Mar. 4, 2008, (now U.S. Pat. No. 8,101,735), which is a continuation-in-part application of U.S. application Ser. No. 11/153,865, filed Jun. 15, 2005, entitled "BACILLUS ANTHRACIS PROTECTIVE ANTIGEN", (now U.S. Pat. No. 7,355,027), which claims the benefit of U.S. Provisional Application 60/579,687, filed Jun. 16, 2004, entitled "PREPARATION OF PROTECTIVE ANTIGEN".

SEQUENCE LISTING INCORPORATION BY REFERENCE

A sequence listing in an ASCII text file, having the name "MSQ01-010-DIVY-US_SEQUENCE_LISTING.txt", created on 26 Sep. 2011, and having a size of 307,748 bytes, is hereby incorporated by reference in its entirety.

The present invention relates to polynucleotides and vectors encoding recombinant *Bacillus anthracis* protective antigen (rPA), methods of producing rPA, and uses thereof in antigenic compositions, such as vaccines.

*Bacillus anthracis* is a Gram positive, spore-forming bacterium and the causative agent of anthrax. Anthrax is a disease of domestic and land animals, and can affect humans through contact with infected animal products. In the lungs, anthrax can cause massive fluid build-up, tissue decay, toxic shock and death.

Anthrax vaccine has been manufactured by the present Applicant for over 40 years and, since 1979, has been the subject of a UK Product Licence (PL1511/0037) held by the Secretary of State for Health. However, within that time there has been little product development or advance in its manufacturing process.

The above vaccine preparation is now described in more detail. Cultures of the toxigenic, non-capsulating *B. anthracis* 34F2 "Sterne" strain [see Sterne, M. (1939) Onderstepoort J. of Veterinary Science and Animal Industry, 13, pp 307-312] are grown in multiple 500 mL volumes in a partially defined medium in Thompson bottles at 37° C. until the pH of selected culture bottles falls below pH 7.4.

At the end of the growth period (approximately 24-28 hours) the cultures are harvested by aspiration, and the pooled supernatant fluids sterilised by filtration. Potassium aluminium sulphate solution is added, and the resulting solution mixed. The pH is then adjusted to 5.8-6.2, and the resulting flocculant ('alum-precipitation') allowed to settle under gravity for up to one week at 5° C.

The precipitate is then concentrated 20-fold (by volume) by aspiration, and diluted 1:4 with a saline solution to provide a '5-fold' concentrate of anthrax vaccine precipitate (AVP). This is the antigenic composition that is used for vaccine formulation. Although the vaccine is subjected to animal tests for potency and safety prior to human use, there is no separate routine biochemical characterisation.

One further cell-free anthrax vaccine is available for human use. This vaccine is produced in the United States of America and is broadly similar to that available under PL1511/0037, except that a different *B. anthracis* strain is used and grown anaerobically. The process is fermenter-based, and the culture filtrate is absorbed on to an aluminium hydroxide suspension.

Other available vaccines comprise live, attenuated spore suspensions. However, because of the inherent risks associated with attenuated pathogens, these vaccines are usually restricted to non-human use.

Anthrax toxin consists of three distinct polypeptides known as protective antigen (PA), oedema factor (EF), and lethal factor (LF). The toxin components act in specific binary combinations of PA and EF to form oedema toxin (ET), which causes tissue oedema, and of PA and LF to form lethal toxin (LT), which is lethal to laboratory animals and causes lysis of monocyte and macrophage cells. Lethal toxin is considered to be the principal cause of anthrax-associated death as a consequence of its cytotoxic effects on peripheral macrophages and other cells.

PA acts as a target cell-binding moiety and, after a site-specific N-terminal activation by a cell-associated protease (furin), oligomerises and provides a high-affinity binding component for which EF and LF compete. Following binding of EF or LF to activated PA, the resulting ET or LT complexes become internalised by an acidic endosome compartment, and the toxin factors EF and LF are thereby delivered into the cytosol of the target cell.

EF is a calcium- and calmodulin-dependent adenylyl cyclase that catalyses the conversion of intracellular ATP to cAMP. EF is active in a variety of intracellular signalling pathways, and is thereby capable of disrupting a range of cellular processes.

LF is a $Zn^{2+}$-dependent metalloprotease that cleaves and inactivates the dual specificity, mitogen-activated protein kinase kinases MAPKK/1 and 2, MEK-1 and MEK-2, and probably other proteins.

A survey of in vitro or in vivo published data on anthrax vaccines for human use indicates the following:—

1. to date, all effective anthrax vaccines contain or produce PA (i.e. either the 83 kDa pro-form, or its activated 63 kDa derivative). In fact, the current dogma is that PA is necessary and sufficient alone to produce an effective anthrax vaccine, and efforts are underway to develop such a vaccine [see, for example, Baillie, L. (2001), 91, pp 609-613]:
2. the non-capsulated, toxigenic live-spore vaccines effect a higher degree of protection against all *B. anthracis* strains so far tested than do the licensed cell-free vaccines [see Little, S. F. (1986) Inf. and Immunol. vol. 52, No. 2, pp 509-512]:
3. the current cell-free vaccines are generally poorly defined and may vary significantly in effectiveness on a batch-by-batch basis. Accordingly, each batch must be individually tested for efficacy in an animal model prior to human use;
4. the current cell-free anthrax vaccine manufacturing process is evaluated only on completion of the production process and packaging of the final product. Thus, in the event that any one batch of vaccine material should not meet the validation test criteria, the contributing factors cannot be identified readily. Such factors may differ between manufactured batches and the lack of understanding exacerbates any difficulties encountered in the manufacturing process;
5. as a result of the poorly defined nature of current cell-free vaccines, these vaccines may contain quantities of PA together with LF and/or EF which, upon in vivo (or in vitro) activation of PA to the 63 kDa form, may form LT and ET and exert adverse effects on the recipient of the vaccine. Such vaccines may, of course, also contain other *B. anthra-* cis proteins, both secreted and lysis products, peptidoglycan, nucleic acid and carbohydrate, which may compromise protective efficacy;

6. the current cell-free vaccine compositions are highly variable in terms of LF, PA, and EF concentrations, so much so that EF may be absent from some preparations; and 7. the current cell-free compositions are highly variable in terms of total protein content. Thus, the concentration of toxin components present in a given composition may vary significantly. This, in turn, may affect efficacy and potential toxicity in humans.

Over the last few years there has been notable academic research in the anthrax field. Sharma et al. (1996) describe the expression of native PA from *E. coli*. The signal sequence of the outer membrane protein A (OmpA) was added to the 5'-end of the PA gene and allowed the purification of the protein from the *E. coli* periplasmic space. Further research has allowed identification of the native binding sites and translocation domain of PA [see Bhatnagas, R. (2001) Critical Rev. in Microbiol., 27(3), pp 167-200; and Batra, S. (2001) Biochem. and Biophys. Res. Comm., 281, pp 186-192]. Thus, the structure and binding/translocation domains of PA have been well documented.

Recently, a second-generation "recombinant" anthrax vaccine has been proposed by The Ohio State University Research Foundation [see WO 01/45639; and Price, B. M. (2001) Inf. and Immun., vol. 69, No. 7, pp 4509-4515]. The described vaccine is based on PA and LF, wherein the LF molecule has been modified so as to be zinc metalloprotease negative. Thus, the described PA and LF components are fully capable of binding to one another to form an LT molecule, but the resulting LT molecule is not cytotoxic as there is no active zinc metalloprotease function present with the LF component.

Ahuja Nidhi et al., Biochem. and Biophys. Research Communications, Vol. 287, No. 2, 21 Sep. 2001, pp 542-549, describes PA mutants having impaired oligomerization and their potential as vaccine candidates.

Batra Smriti et al., Biochem. and Biophys. Research Communications, Vol. 281, No. 1, 16 Feb. 2001, pp 186-192 describes PA mutants having mutant residues that may have a role in membrane insertion of PA and/or translocation of LF/EF into the cytosol.

WO 02/04646 describes PA polypeptide domains capable of producing an immune response. The PA polypeptide is produced in *E. coli* and accumulates in the form of inclusion bodies.

DNA-based anthrax vaccine compositions are described in WO 20041024067. The vaccine compositions contain anthrax nucleic acids that have been modified to optimise expression in a eukaryotic host—e.g. the patient to whom the vaccine composition is administered.

In view of the increasing threats of bio-terrorism and biological warfare, there is a need for alternative anthrax vaccines, and for vaccines that address one or more of the above-identified problems.

Thus, according to a first aspect of the present invention, there is provided a polynucleotide sequence comprising a nucleic acid sequence having at least 75% identity to SEQ ID NO: 1, wherein said nucleic acid sequence encodes recombinant *Bacillus anthracis* Protective Antigen (rPA); or a fragment of said nucleic acid sequence wherein said fragment encodes a fragment of recombinant *Bacillus anthracis* Protective Antigen (rPA).

In this regard, SEQ ID NO: 1 represents a modified nucleic acid that encodes rPA. The sequence of SEQ ID NO: 1 is approximately 70% identical to the wild-type *Bacillus anthracis* nucleic acid sequence encoding PA, provided herein as SEQ ID NO: 2.

The present inventors have found that by modifying the wild-type PA nucleic acid sequence (SEQ ID NO: 2), expression levels of rPA protein may be significantly improved. Thus, the present invention relates to non-natural nucleic acid sequences which encode for the rPA polypeptide. Particularly, the non-natural nucleic acid sequences are selected to increase expression levels of rPA expressed in heterologous systems, such as heterologous bacterial systems, e.g. *E. coli*. Preferably, the rPA polypeptide or fragment thereof, which is expressed from the modified, non-natural nucleic acid sequence (or fragment thereof) of the invention, is expressed at a level that is at least 110%, at least 120%, at least 150%, at least 200%, at least 250%, at least 300%, at least 400%, or at least 500% higher than that expressed from the wild-type nucleic acid sequence under equivalent conditions.

The polynucleotide of the invention comprises a nucleic acid sequence (or fragment thereof) that encodes rPA (or a fragment thereof). This rPA encoding nucleic acid sequence (or fragment thereof) is referred to herein as the rPA nucleic acid (or fragment thereof). Thus, the polynucleotide of the present invention may comprise the rPA nucleic acid, plus other coding and/or non-coding sequences. By way of example, non-coding sequences that may be comprised in the polynucleotide of the present invention include promoter sequences and transcription/translation initiation and termination sequences.

In this regard, the rPA nucleic acid sequence of the present invention may embrace a number of modifications, which result in the same translated amino acid sequence of the encoded polypeptide. Numerous factors should be taken into account when modifying a nucleic acid sequence, for example, the degree of degeneracy available, codon usage, and predicted RNA secondary structure considerations. For example, many amino acids are designated by more than one codon, due to the "degeneracy" of the genetic code. In more detail, alanine is coded for by 4 different triplets, and serine is coded for by 6 different triplets. This degeneracy allows for DNA base composition to vary over a wide range without altering the amino acid sequence of the protein encoded by the DNA.

The wild-type polypeptide sequence of *Bacillus anthracis* UM44 PA is provided in SEQ ID NO: 5 (see also, Vodkin, M., et al., Cell, 34:693 (1983); and Welkos, S., et al., Gene, 69(2): 287 (1988)).

For sequence comparison, typically one sequence acts as a reference sequence, to which test sequences may be then compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat. Acad. Sci. USA 85: 2444 (1988)], by computer implementations of these algorithms (GAP, BESTFIT, FASTA, and TFASTA—Sequence Analysis Software Package of the Genetics Computer Group University of Wisconsin Biotechnology Center, 1710 University Avenue, Madison, Wis. 53705), or by visual inspection [see Current Protocols in Molecular Biology, F. M. Ausubel et al., eds, Current Protocols, a joint venture between Greene Publishing Associates, in. and John Wiley & Sons, Inc. (1995 Supplement) Ausubel].

Examples of algorithms suitable for determining percent sequence similarity are the BLAST and BLAST 2.0 algorithms [see Altschul (1990) J. Mol. Biol. 215: pp. 403-410; and www.ncbi.nlm.nih.gov of the National Center for Biotechnology Information].

In one embodiment of a polypeptide homology comparison, the identity exists over a region of the sequences that is at least 10 amino acids, preferably at least 20 amino acids, more preferably at least 35 amino acids in length, in a preferred polypeptide homology comparison, the identity exists over a region of the sequences that is at least 100 amino acids, preferably at least 200 amino acids, more preferably at least 350 amino acids in length.

The terms "peptide" or "polypeptide" throughout this specification are synonymous with the term "protein", and do not refer to a specific length of the product. These terms may embrace post-translational modifications such as glycosylation, acetylation, and phosphorylation.

Reference throughout the present application to rPA polypeptides, polynucleotides and nucleic acids embraces fragments, variants and derivatives thereof. In particular, reference throughout the present application to rPA polypeptides embraces fragments, variants and derivatives thereof that have a common antigenic cross-reactivity with wild-type Bacillus anthracis PA (SEQ ID NO: 5). Similarly, reference throughout the present application to rPA polynucleotides and nucleic acids embraces fragments, variants and derivatives thereof that encode peptides having a common antigenic cross-reactivity with wild-type Bacillus anthracis PA (SEQ ID No. 5).

In one embodiment, the above-mentioned fragments, variants and derivatives may have a common antigenic cross-reactivity with one or more of the four domains of the mature 735 amino acid monomer (see SEQ ID NO: 5) described below:

DOMAIN 1: amino acids 1-258. This domain binds two $Ca^{2+}$ ions and is the cleavage site for proteases to activate the PA protein. The product of this cleavage is the amino terminal fragment a20 (20K fragment). A furin cleavage site is located at amino acids 164-167.

DOMAIN 2: amino acids 259-487. This domain is involved in the formation of hexamer and has flexible loop which aids membrane insertion, DOMAIN 3: amino acids 488-595. This domain currently has no known function.

DOMAIN 4: amino acids 596-735. This domain is involved in receptor binding.

In preferred embodiments, polypeptide "fragments" of the invention comprise at least one of the four domains identified above. More preferably, they comprise at least two, at least three, or all four of these domains in any combination. In a particular embodiment, they comprise at least domains 2 & 3 identified above.

Each of the four domains identified above is considered to comprise important epitope(s) of wild-type Bacillus anthracis PA. In addition, PA epitopes have been identified as shown in the two tables below (the "B Cell" table and the "T Cell" table).

In a preferred embodiment of the invention, polynucleotides are provided that encode one or more epitopes or partial epitopes of PA. By way of example, SEQ ID NOs: 36-105 encode all or part of the first, and the third to the sixth, epitopes listed in the "B Cell" table, and all three of the epitopes listed in the "T Cell" table. SEQ ID NOs: 66-105 further encode the second epitope listed in the "B-Cell" table.

| B-Cell Epitopes from Human and Non Human Primates (NHPs) | | Epitope Position | |
|---|---|---|---|
| Immunized Species | Epitope Sequence | in rPA protein | Reference |
| H. sapiens | IKLMAKMNILIRDKRFHYDRD (SEQ ID NO: 107) | 581-601 | Les Baillie et al., "Characterisation of the human immune response to the UK anthrax vaccine". FEMS Immunol. Med. Microbial. 2004 |
| M. fascicularis | PLYISNPNY (SEQ ID NO: 108) | 686-694 | Laffy et al., "Selection of a macaque Fab with framework regions like those in humans, high affinity, and ability to neutralize the protective antigen of Bacillus anthracis by binding to the segment of PA between residues 686 and 694". Antimicrob. Agents Chemother. 2005 |
| M. mulatta | — | 486-735 | E D Williamson, et al. Infect. Immun. 2005 |
| M. mulatta | — | 596-735 | " |
| M. mulatta | — | 1-258 | " |
| P. trogiodytes | — | 614-735 | Chen et al., Efficient neutralization of anthrax toxin by chimpanzee monoclonal antibodies against protective antigen, J. Infect. Dis. 2006 |

| T-Cell Epitopes from Human and Non Human Primates (NHPs) | | Epitope Position | |
|---|---|---|---|
| Immunized Species | Epitope Sequence | in rPA protein | Reference |
| H. sapiens | PIYNVLPTTSLVLQKNQTLAT (SEQ ID NO: 109) | 373-393 | Laughlin et al., Antigen-specific CD4+ T cells recognize epitopes of protective antigen following vaccination. infect. immun. 1007 |
| H. sapiens | SLYLGFNGTLAT (SEQ ID NO: 110) | 381-392 | Laughlin et al., Antigen-specific CD4+ T cells recognize epitopes of protective antigen following vaccination. infect. immun. 1007 |
| H. sapiens | RLYQIKTQYQRENPTE (SEQ ID NO: 111) | 112-127 | Laughlin et al., Antigen-specific CD4+ T cells recognize epitopes of protective antigen following vaccination. infect. immun. 1007 |

The term "fragment" of a polypeptide means a peptide consisting of at least 5, preferably at least 10, more preferably at least 20, and most preferably at least 35 amino acid residues of the full-length polypeptide that is the product of the polynucleotide in question. The fragment preferably includes at least one epitope of the corresponding full-length polypeptide. The fragment may result from enzymatic break-down of the corresponding full-length polypeptide. Alternatively, a fragment of the corresponding full-length polypeptide may be produced by expressing a polynucleotide that is fragment of the corresponding full-length polynucleotide.

In preferred embodiments, the polypeptide "fragment" has an amino acid length which is at least 10%, preferably at least 20%, preferably at least 30%, preferably at least 40%, preferably at least 50%, preferably at least 70%, and more preferably at least 80%, or at least 90%, that of the length of the amino acid sequence of the corresponding full-length polypeptide. For example, the polypeptide fragment may comprise at least 100, preferably at least 150, preferably at least 200, preferably at least 300, most preferably at least 400, or at least 500, or at least 600, or at least 700, amino acid residues, of the wild-type PA polypeptide sequence (SEQ ID NO: 5).

The present invention embraces "variants". An example of a "variant" is a peptide or peptide fragment that contains one or more analogs of an amino acid (e.g. an unnatural amino acid), or a substituted linkage. In a further embodiment, a "variant" may be a mimic of the peptide or peptide fragment, which mimic reproduces at least one epitope of the peptide or peptide fragment. The mimic may be, for example, a nucleic acid mimic, preferably a DNA mimic.

The present invention also embraces "derivatives", meaning a protein comprising the peptide (or fragment, or variant thereof) in question. Thus, a derivative may include the peptide in question, and a further peptide sequence that may introduce one or more additional epitopes. The further sequence should preferably not interfere with the basic folding and thus conformational structure of the peptide in question.

Examples of a "derivative" are a fusion protein, a conjugate, and a graft. Thus, two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polyketide components may be included in a derivative.

All of the molecules "fragment", "variant" and "derivative" have a common antigenic cross-reactivity and/or substantially the same in vitro or in vivo biological activity as the product of the polynucleotide in question from which they are derived. By way of example, an antibody capable of binding to a fragment, variant or derivative would be also capable of binding to the product of the polynucleotide in question. it is a preferred feature that the fragment, variant and derivative each possess the active site of the peptide in question. Alternatively, all of the above embodiments of a peptide of the present invention share a common ability to induce a "recall response" of a T-lymphocyte which has been previously exposed to an antigenic component of a Bacillus anthracis infection.

An rPA peptide fragment, variant or derivative preferably has one or more of the following properties—a) able to bind to the PA receptor on a cell membrane; b) able to bind to EF and/or LF; and c) able to be cleaved by furin protease. Thus, in one embodiment, a fragment, variant or derivative of a peptide of the present invention may be identified by carrying out simple tests for the above-mentioned properties, as described in WO 03/037370 which is incorporated by reference herein.

The terms DNA "fragment", polynucleotide "fragment" and nucleic acid "fragment" used in this application refer to a polynucleotide that will usually comprise at least about 5 codons (15 nucleotides), more usually at least about 7 to 15 codons, and most preferably at least about 35 codons. This number of nucleotides is usually about the minimal length required for a successful probe that would hybridize specifically (e.g. under selective hybridization conditions) with such a sequence.

Preferably, the DNA "fragment" of the invention comprises nucleotides encoding at least one of the four PA protein domains identified above. More preferably, the DNA "fragment" comprises nucleotides encoding at least two, at least three, or all four of the domains identified above in any combination. The corresponding DNA base numbering for the four PA protein domains is as follows:
DOMAIN 1: bp 1-774 (774 bp)
DOMAIN 2: bp 775-1461 (687 bp)
DOMAIN 3: bp 1462-1785 (324 bp)
DOMAIN 4: bp 1786-2205 (420 bp)

In a particular embodiment, the DNA "fragment" comprises DNA encoding protein at least domains 2 & 3 as identified above. Examples of such fragments are given in SEQ ID Nos: 36-105, which relate to truncated versions of SEQ ID NO: 1. These truncated sequences encode domains 2 & 3 in their entirety and substantial portions of both domains 1 & 4.

In preferred embodiments, the DNA "fragment" has a nucleotide length which is at least 10%, preferably at least 20%, preferably at least 30%, preferably at least 40%, preferably at least 50%, preferably at least 70%, and more preferably at least 80% or at least 90% that of the coding sequence of the corresponding gene. For example, the fragment may comprise at least 200, 300, 400, 500 or 600, preferably at least 900, most preferably at least 1200, or at least 1500, or at least 1700, or at least 1900, or at least 2100 nucleotides of the full-length rPA nucleic acid sequence of the present invention. In particular embodiments, the DNA fragments have at least 1755, or at least 1806, or at least 1854, or at least 1857, or at least 1905, or at least 1953, or at least 2055 nucleotides of the full-length rPA sequence of the present invention.

The present invention embraces DNA "variants". A DNA variant is a DNA sequence that has substantial homology or substantial similarity to a reference sequence, such as the coding sequence (or a fragment thereof) of the corresponding wild-type (natural) gene. A nucleic acid or fragment thereof is "substantially homologous" (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 to 99% of the nucleotide bases. Homology determination is performed as described supra for peptides.

Alternatively, a DNA "variant" is substantially homologous (or substantially similar) with the coding sequence (or a fragment thereof) of a wild-type (natural) gene when it is capable of hybridizing under selective hybridization conditions. Nucleic acid hybridization will be affected by such conditions as salt concentration (e.g. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. However, the combination of parameters is much more important than the measure of any single parameter. See, for example, Wetmur and Davidson (1968) J. Mol. Biol. 31:349-370.

Selectivity of hybridization exists when hybridization occurs which is substantially more selective than total lack of specificity. Typically, selective hybridization will occur when there is at least about 65% homology over a stretch of at least about 14 nucleotides, preferably at least about 70%, more preferably at least about 75%, and most preferably at least about 90% (see, Kanehisa (1984) Nuc. Acids Res. 12: 203-213). The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides. In a preferred embodiment, the length of homology comparison is over a stretch of at least about 170 nucleotides, usually at least about 200 nucleotides, more usually at least about 240 nucleotides, typically at least about 280 nucleotides, more typically at least about 320 nucleotides, and preferably at least about 360 or more nucleotides.

The present invention embraces DNA "derivatives", meaning a DNA polynucleotide which comprises a DNA sequence (or a fragment, or variant thereof) corresponding to the coding sequence of the reference gene, e.g. the wild-type *Bacillus anthracis* PA gene, and an additional DNA sequence which is not naturally associated with the DNA sequence corresponding to the coding sequence. The comments on peptide derivatives supra also apply to DNA "derivatives". A "derivative" may, for example, include two or more coding sequences of an operon. Thus, depending on the presence or absence of a non-coding region between the coding sequences, the expression product(s) of such a "derivative" may be a fusion protein, or separate peptide products encoded by the individual coding regions.

The above terms DNA "fragment", "variant", and "derivative" have in common with each other that the resulting peptide products have cross-reactive antigenic properties, which are substantially the same as those of the corresponding wild-type peptide. Preferably all of the peptide products of the above DNA molecule embodiments of the present invention bind to an antibody which also binds to the wild-type peptide. Alternatively, all of the above peptide products are capable of inducing a "recall response" of a T lymphocyte, which has been previously exposed to an antigenic component of a *Bacillus anthracis* infection.

Thus, a DNA fragment, variant or derivative may be identified by way of its encoded peptide product—for example, by carrying out the simple tests mentioned above (and described in WO 03/037370).

Polynucleotides of the present invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 1; or a fragment of said nucleic acid.

Specific polynucleotides having between 91 and 99% identity to SEQ ID NO: 1 (minus the terminal "TAA" stop codon) are provided in SEQ ID NOs: 9 to 35 as shown in the table below.

| SEQ ID NO | % Identity to SEQ ID No. 1 | No. of bases differing from SEQ ID No. 1 |
|---|---|---|
| SEQ ID No. 9 | 99.00 | 22 |
| SEQ ID No. 10 | 99.00 | 22 |
| SEQ ID No. 11 | 99.00 | 22 |
| SEQ ID No. 12 | 98.00 | 44 |
| SEQ ID No. 13 | 98.00 | 44 |
| SEQ ID No. 14 | 98.00 | 44 |
| SEQ ID No. 15 | 97.01 | 66 |
| SEQ ID No. 16 | 98.00 | 66 |
| SEQ ID No. 17 | 98.00 | 66 |
| SEQ ID No. 18 | 96.01 | 88 |
| SEQ ID No. 19 | 96.01 | 88 |
| SEQ ID No. 20 | 96.01 | 88 |
| SEQ ID No. 21 | 95.01 | 110 |
| SEQ ID No. 22 | 95.01 | 110 |
| SEQ ID No. 23 | 95.01 | 110 |
| SEQ ID No. 24 | 94.01 | 132 |
| SEQ ID No. 25 | 94.01 | 132 |

-continued

| SEQ ID NO | % Identity to SEQ ID No. 1 | No. of bases differing from SEQ ID No. 1 |
|---|---|---|
| SEQ ID No. 26 | 94.01 | 132 |
| SEQ ID No. 27 | 93.02 | 154 |
| SEQ ID No. 28 | 93.02 | 154 |
| SEQ ID No. 29 | 93.02 | 154 |
| SEQ ID No. 30 | 92.02 | 176 |
| SEQ ID No. 31 | 92.02 | 176 |
| SEQ ID No. 32 | 92.02 | 176 |
| SEQ ID No. 33 | 91.02 | 198 |
| SEQ ID No. 34 | 91.02 | 198 |
| SEQ ID No. 35 | 91.02 | 198 |

In one embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 36, SEQ ID NO: 36 is a truncated version of SEQ ID NO: 1 and comprises base pairs 301-2055 of SEQ ID NO: 1. Specific polynucleotides having between 91 and 99% identity to SEQ ID NO: 36 are provided in SEQ ID NOs: 37 to 45 as shown in the table below.

| SEQ ID NO | % Identity to SEQ ID No. 36 | No. of bases differing from SEQ ID No. 36 |
|---|---|---|
| SEQ ID No. 37 | 98.97 | 18 |
| SEQ ID No. 38 | 98.06 | 34 |
| SEQ ID No. 39 | 97.04 | 52 |
| SEQ ID No. 40 | 95.90 | 72 |
| SEQ ID No. 41 | 94.99 | 88 |
| SEQ ID No. 42 | 93.96 | 106 |
| SEQ ID No. 43 | 93.16 | 120 |
| SEQ ID No. 44 | 92.02 | 140 |
| SEQ ID No. 45 | 91.00 | 158 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 46. SEQ ID NO: 46 is a truncated version of SEQ ID NO: 1 and comprises base pairs 202-2055 of SEQ ID NO: 1. Specific polynucleotides having between 91 and 99% identity to SEQ ID NO: 46 are provided in SEQ ID NOs: 47-55 as shown in the table below.

| SEQ ID NO | % Identity to SEQ ID No. 46 | No. of bases differing from SEQ ID No. 46 |
|---|---|---|
| SEQ ID No. 47 | 99.03 | 18 |
| SEQ ID No. 48 | 97.95 | 38 |
| SEQ ID No. 49 | 97.09 | 54 |
| SEQ ID No. 50 | 96.12 | 72 |
| SEQ ID No. 51 | 95.04 | 92 |
| SEQ ID No. 52 | 93.96 | 112 |
| SEQ ID No. 53 | 92.99 | 130 |
| SEQ ID No. 54 | 92.13 | 146 |
| SEQ ID No. 55 | 91.05 | 166 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 56. SEQ ID NO: 56 is a truncated version of SEQ ID NO: 1 and comprises base pairs 103-2055 of SEQ ID NO: 1. Specific polynucleotides having between 91 and 99% identity to SEQ ID NO: 56 are provided in SEQ ID NOs: 57-65 as shown in the table below.

| SEQ ID NO | % Identity to SEQ ID No. 56 | No. of bases differing from SEQ ID No. 56 |
|---|---|---|
| SEQ ID No. 57 | 99.08 | 18 |
| SEQ ID No. 58 | 97.95 | 40 |
| SEQ ID No. 59 | 97.03 | 58 |
| SEQ ID No. 60 | 96.01 | 78 |
| SEQ ID No. 61 | 94.98 | 98 |
| SEQ ID No. 62 | 94.06 | 116 |
| SEQ ID No. 63 | 93.04 | 136 |
| SEQ ID No. 64 | 92.01 | 156 |
| SEQ ID No. 65 | 90.99 | 176 |

In another embodiment, polynucleotides of the invention comprise a nucleic acid having at least 75%, preferably at least 80%, more preferably at least 85%, more preferably at least 90%. even more preferably at least 91%, 92%, 93%, 94%, 95%, 96%, 97%, 98% and most preferably 99% or 100% identity to SEQ ID NO: 66. SEQ ID NO: 66 is a truncated version of SEQ ID NO: 1 and comprises base pairs 301-2106 of SEQ ID NO: 1. Specific polynucleotides having between 91 and 99% identity to SEQ ID NO: 66 are provided in SEQ ID NOs: 67-75 as shown in the table below.

| SEQ ID NO | % Identity to SEQ ID No. 66 | No. of bases differing from SEQ ID No. 66 |
|---|---|---|
| SEQ ID No. 67 | 99.00 | 18 |
| SEQ ID No. 68 | 97.90 | 38 |
| SEQ ID No. 69 | 97.01 | 54 |
| SEQ ID No. 70 | 96.12 | 70 |
| SEQ ID No. 71 | 95.02 | 90 |
| SEQ ID No. 72 | 94.02 | 108 |
| SEQ ID No. 73 | 93.02 | 126 |
| SEQ ID No. 74 | 92.03 | 144 |
| SEQ ID No. 75 | 91.03 | 162 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 76. SEQ ID NO: 76 is a truncated version of SEQ ID NO: 1 and comprises base pairs 301-2157 of SEQ ID NO: 1. Specific polynucleotides having between 91 and 99% identity to SEQ ID NO: 76 are provided in SEQ ID NOs: 77-85 as shown in the table below.

| SEQ ID NO | % Identity to SEQ ID No. 76 | No. of bases differing from SEQ ID No. 76 |
|---|---|---|
| SEQ ID No. 77 | 99.03 | 18 |
| SEQ ID No. 78 | 98.06 | 36 |
| SEQ ID No. 79 | 96.98 | 56 |
| SEQ ID No. 80 | 96.02 | 74 |

-continued

| SEQ ID NO | % Identity to SEQ ID No. 76 | No. of bases differing from SEQ ID No. 76 |
|---|---|---|
| SEQ ID No. 81 | 95.05 | 92 |
| SEQ ID No. 82 | 93.97 | 112 |
| SEQ ID No. 83 | 93.00 | 130 |
| SEQ ID No. 84 | 92.03 | 148 |
| SEQ ID No. 85 | 90.95 | 168 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 86. SEQ ID NO: 86 is a truncated version of SEQ ID NO: 1 and comprises base pairs 202-2106 of SEQ ID NO: 1. Specific polynucleotides having between 91 and 99% identity to SEQ ID NO: 86 are provided in SEQ ID NOs: 87-95 as shown in the table below.

| SEQ ID NO | % Identity to SEQ ID No. 86 | No. of bases differing from SEQ ID No. 86 |
|---|---|---|
| SEQ ID No. 87 | 98.95 | 20 |
| SEQ ID No. 88 | 98.01 | 38 |
| SEQ ID No. 89 | 96.96 | 58 |
| SEQ ID No. 90 | 96.01 | 76 |
| SEQ ID No. 91 | 94.96 | 96 |
| SEQ ID No. 92 | 94.02 | 114 |
| SEQ ID No. 93 | 92.97 | 134 |
| SEQ ID No. 94 | 92.02 | 152 |
| SEQ ID No. 95 | 90.97 | 172 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 96. SEQ ID NO: 96 is a truncated version of SEQ ID NO. 1 and comprises base pairs 103-2157 of SEQ ID NO: 1. Specific polynucleotides having between 91 and 99% identity to SEQ ID NO: 96 are provided in SEQ ID NOs: 97-105 as shown in the table below.

| SEQ ID NO | % Identity to SEQ ID No. 96 | No. of bases differing from SEQ ID No. 96 |
|---|---|---|
| SEQ ID No. 97 | 99.03 | 20 |
| SEQ ID No. 98 | 97.96 | 42 |
| SEQ ID No. 99 | 96.98 | 62 |
| SEQ ID No. 100 | 96.01 | 82 |
| SEQ ID No. 101 | 95.04 | 102 |
| SEQ ID No. 102 | 93.97 | 124 |
| SEQ ID No. 103 | 93.00 | 144 |
| SEQ ID No. 104 | 92.02 | 164 |
| SEQ ID No. 105 | 91.15 | 182 |

In one embodiment, polynucleotide sequences of the present invention further comprise a polynucleotide encoding a secretion sequence. The polynucleotide encoding the secretion sequence is preferably cloned upstream of the rPA nucleic acid sequence, or fragment thereof, and is most preferably operatively linked to said nucleic acid sequence, or fragment thereof.

Secretion sequences may allow the encoded protein to cross and/or lodge in cell membranes, and thus attain its functional topology or be secreted from a host cell. In this regard, the secretion sequence may be for extracellular translocation of the expressed polypeptide from a host cell (e.g. a bacterial host cell) into the extracellular environment. Alternatively, the secretion sequence may be for periplasmic translocation of the expressed polypeptide from a bacterial host cell cytoplasm into the periplasmic space.

It is particularly preferred that the secretion sequence is cleavable from the expressed polypeptide during periplasmic translocation or during extracellular translocation, in which case the periplasmic/extracellular polypeptide is free of this sequence. One example of such a 'cleavable' sequence is a cpg leader sequence encoded by SEQ ID NO: 3.

The cpg leader sequence illustrated in SEQ ID NO: 3 is designed such that it has a 5'-NdeI restriction site for inserting into an expression vector at a NdeI site, and a 3'-MscI site for fusion with a rPA nucleic acid sequence, or fragment thereof, where a similar MscI site has preferably been engineered. Thus, the cpg leader is cleaved from the expressed rPA protein (or protein fragment) as it passes through a host cell membrane, leaving the 'trimmed' mature rPA protein, or fragment thereof, in the extracellular environment or periplasmic space accordingly.

Other suitable secretion sequences for use in the present invention are described in Watson (1984) Proc. Nat. Acad. Sci. USA. vol. 12: 5145; and Makrides (1996) Microbiological Reviews 60: 512-538; and include, ompA (Denefle et al. (1989) Gene 85: 4990-510; and Ghrayeb et al. (1984) EMBO J. 3: 2437-2442); peIB (Better et alt (1988) Science 240: 1041-1043; and Lei et al. (1987) J. Bacteriol. 169: 4379-4383); including a degenerate version thereof—see Le Calvez et al. (1996) Gene 170: 51-55; phoA (Denefle at al. (1989) Gene 85: 499-510; and Oka et al. (1985) Proc. Nat. Acad. Sci. USA. 82: 7212-7216); ompT (Johnson et al. (1996) Protein Expression Purif. 7: 104-1123); lamB (Hoffman & Wright (1985) Proc. Nat. Acad. Sci. USA. 82: 5107-5111); ompF (Hoffman & Wright (1985)); beta lactamase (Kadonaga et al. (1984) J. Biol. Chem. 259: 2149-2154; and VIIIa-Komaroff et al. (1977) Proc. Nat. Acad. Sci. USA. 75: 3727-3731); *Staphylococcus aureus* protein A (Abrahmsen (1986) Nucl. Acids Res. 14: 7487-7500; and Macyntyre & Henning (1990) Biochimmie 72: 157-167); *Bacillus subtilis* endoglucanase (Proudfoot et al. (1996) J. Biol. Chem. 271: 2599-2603); murine RNAse (Schein et al. (1992) Biochem. J. 283: 137-144); human growth hormone (Gray et al. (1985) Gene 39: 247-254); and enterotoxins ST-II, LT-A and LT-B (Fujimoto et al (1988) J. Biotechnol. 8: 77-86; and Morioka-Fujimoto et al. (1991) J. Biol. Chem. 266: 1728-1732).

In one embodiment, the polynucleotide sequence of the present invention comprises a nucleic acid of the present invention, or a fragment thereof, having a 3' and a 5' end, and said nucleic acid or fragment thereof has a codon encoding a methionine residue cloned to the 5' end. By way of example, the nucleic acid may be SEQ ID NO: 7 (or a fragment of SEQ ID NO: 7 that includes the 5' terminal, met-encoding codon of SEQ ID NO: 5). This methionine-encoding codon is added in order to increase stability of the final (signal-less) protein when expressed in *E. coli*. Thus, rPA protein encoded by the polynucleotide of this particular embodiment of the invention is distinguished from wild-type PA protein naturally produced in *Bacillus anthracis* by the addition of an extra methionine residue to the N-terminus.

The present invention thus also provides a polypeptide or polypeptide fragment encoded by the polynucleotide of the present invention. Polypeptides of the present invention may therefore comprise an amino acid sequence encoding rPA, or a fragment thereof, with an extra methionine residue added at the N-terminus of the rPA amino acid sequence.

In a related aspect, the present invention also provides an isolated RNA molecule that is encoded by a DNA polynucleotide sequence of the present invention, or a fragment or variant or derivative of said DNA sequence.

Also contemplated within the invention are expression vectors comprising a polynucleotide of the present invention. Expression vectors are useful for the expression of heterologous nucleic acid sequences in a host cell. As used herein, the term "heterologous" means that the polynucleotide or polypeptide sequence concerned does not naturally exist in the cell, but has been introduced into it, for example by transformation, transfection, injection etc.

Expression vectors generally are replicable polynucleotide constructs that include coding regions for a peptide, operably linked to suitable transcriptional and translational regulatory elements. Examples of regulatory elements usually included in expression vectors are promoters, enhancers, ribosomal binding sites, and transcription and translation initiation and termination sequences. These regulatory elements are operably linked to the sequence to be translated. A nucleic acid sequence is operably linked when it is placed into a functional relationship with another nucleic acid sequence. For instance, a promoter is operably linked to a coding sequence if the promoter affects its transcription or expression. Generally, "operably linked" means that the DNA sequences being linked are contiguous and, where necessary to join two protein coding regions, contiguous and in reading frame. The regulatory elements employed in the expression vectors containing a polynucleotide encoding a virulence factor are functional in the host cell used for expression.

It is preferred that the expression vector expresses the polynucleotide in the absence of a chemical inducer—i.e. a chemical inducer is not required for induction of expression from the expression vector. In one embodiment, the vector expresses the polynucleotide constitutively, with no induction of gene expression needed. In another embodiment, the vector expresses the polynucleotide in response to an environmental stimulus or stimuli—such as starvation, or limitation of nutrients or oxygen, such as when a component or components become exhausted in the growth medium.

The term "promoter" is well known in the art, encompasses relatively simple, minimal promoters to complex promoters having upstream elements and enhancers. Suitable promoters for expression in prokaryotic and eukaryotic host cells are well known in the art, and are described in, for example, Molecular Cloning. A laboratory Manual (Sambrook et al., Second edition, 1989) and Current Protocols in Molecular Biology (Ausubel et al., eds., 1994).

Appropriate promoter and other necessary vector sequences are selected so as to be functional in the host. By way of example, promoters such as the trp, lac and phage promoters (e.g. T7, T4, lambda, fd), tRNA promoters and glycolytic enzyme promoters may be used in prokaryotic hosts. It is preferred that the expression vector comprises a "strong" promoter,—i.e. a promoter that is selected so as to ensure that the encoded rPA polypeptide (or fragment thereof) is highly expressed. Examples of strong promoters include recA, malate dehydrogenase, T7, tac, etc. In this regard, a polypeptide is said to be "highly expressed" if it is expressed at levels above 20% of total host cell soluble protein, preferably above 30%, more preferably above 40% and most preferably above 50% total host cell soluble protein. A preferred "strong promoter" for use in accordance with the invention is the malate dehydrogenase (mdh) promoter (proprietary to CAMR; U.S. Pat. No. 5,670,333).

Expression vectors may contain a selectable marker—i.e. a gene encoding a protein necessary for the survival or growth of a host cell transformed with the vector. The presence of this gene ensures the growth on a selective medium of only those host cells that contain the desired vector and that express the selectable marker. Typical selection genes encode proteins that: (a) confer resistance to antibiotics or other toxic substances, e.g. ampicillin, tetracycline, neomycin, methotrexate, etc.; (b) complement auxotrophic deficiencies; or (c) supply critical nutrients not available from complex media. The selection of an appropriate vector and an appropriate selectable marker will depend on the host cell, and is well within the capabilities of an ordinary person of skill in the art.

Expression vectors typically contain all of the additional elements that are necessary for efficient expression of the nucleic acid in a host cell. Examples of suitable vectors for expression of heterologous proteins in bacterial include pET vectors (for example pET26b-Novagen), and pTrKHis (Invitrogen). Both these vectors achieve high-level expression of nucleic acid in *E. coli.* pMTL expression vectors are advantageous because they are capable of yielding high levels of recombinant protein, and can be very stable, even in the absence of selective pressure using antibiotics. Furthermore, those pMTL vectors based on the very strong *E. coli* malate dehydrogenase (mdh) promoter are particularly advantageous because induction of expression using exogenous inducer chemicals is not required (Alldread et al. (1992) Gene 14: 139-143). It is an advantage not to require an exogenous chemical inducer for regulatory reasons, since any chemical inducer may have to be rigorously and successfully removed from the final product before administration to patients.

In a particularly preferred embodiment, the expression vector is also a high copy number plasmid, such as pMTL1015 (Chambers et al. (1988) Gene 68: 139-149). pMTL1015 is a derivative of pMTL4, it replicates from a mutant of the ColE1 replicon (600 copies per cell; Minton et al. (1988) Focus 10: 56) and is encoded by SEQ ID NO: 4. Plasmid pMTL1015 is essentially identical to pMTL1003 as described by Brehm et al. (1991) Appl. Microbiol. Biotechnol 36: 358-363, and has numerous advantageous features. By way of example, pMTL1015 differs from pMTL1003 in that the trp promoter has been replaced with the very powerful mdh promoter (Alldread et al. (1992) Gene 14: 139-143), and the ampicillin resistance gene has been replaced with the tetracycline resistance gene of pBR322 (Bolivar et al. (1977) Gene 2: 95). The plasmid also incorporates the pSC101 partition function (par; Miller et al. (1983) Gene 24: 309-315), the rmrnB double terminator (Brosius et al. (1981) J. Mol. Biol. 148: 107-127) and the pMTL20 polylinker cloning region (Chambers et al., 1988). The par locus endows the plasmid with good segregational stability enabling antibiotic-free fermentations without plasmid loss and the tetracycline resistance marker is a biopharmaceutically acceptable drug.

An example of an expression vector suitable for use in the present invention is the vector deposited under ECACC No: 04061401.

An example of an expression vector comprising a polynucleotide according to the present invention is pMTL1015-cpg-PA-synt, deposited under ECACC No: 04052501.

The vectors containing the nucleic acids of interest can be transcribed in vitro and the resulting RNA introduced into the host cell (e.g. by injection), or the vectors can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). The term "host cells" is meant to embrace the progeny of such cells.

The present application thus also provides a host cell comprising an expression vector as described above. It is preferred that the host cell is a bacterial cell, in particular an *E. coli* cell, such as *E. coli* strains DH5, BL21 and HMS174 (invitrogen).

It is particularly preferred that the bacterial cell e.g. *E. coli* strain is a protease-deficient strain, since rPA protein is generally considered to be a protease-sensitive protein. One example of a protease-deficient strain of *E. coli* is *E. coli* RV308 (ATCC No: 31608).

Also provided by the present invention are methods for producing rPA comprising expressing the polynucleotide of the present invention.

In one embodiment, the polynucleotide is expressed—i.e. transcribed and translated, in a host cell. In another embodiment, the polynucleotide is DNA, which is transcribed into RNA in vitro. and then the RNA is then translated into protein in a host cell. The host cell may be a bacterial cell, such as an *E. coli* host cell. The *E. coli* host cell is preferably a protease-deficient strain, such as *E. coli* RV308 (deposited under ATCC No: 31608).

In a preferred embodiment, rPA is expressed in a host cell from the expression vector of the present invention, as described above. In this embodiment, the method may incorporate at least one, preferably two, most preferably all of the following features—(i) the expression vector comprises the cpg leader sequence encoded by SEQ ID NO: 3; (ii) the vector is the plasmid pMTL1015, encoded by SEQ ID NO: 4; and (iii) the vector is expressed in an *E. coli* host cell such as *E. coli* RV308 (ATCC No: 31608).

In one embodiment, the method comprises the initial steps of transforming an expression vector comprising the polynucleotide of interest into a host cell, such as *E. coli* host cell and culturing the transformed host cell in a suitable growth medium.

Optionally, the culture is carried out under selective pressure, such as in the presence of an antibiotic, e.g. tetracycline, in which case it is an advantage for the expression vector to comprise a selectable marker that confers resistance to the antibiotic.

Culture parameters may be controlled, in order to control nutrients, pH and/or oxygen levels (dissolved oxygen tension—DOT) in the culture. For example, DOT may be controlled by agitation, back pressure, sparged airflow and/or oxygen supplementation. It is preferred that DOT is maintained at above 40%.

The temperature at which host cells are grown can have an effect on the level of protein that can be purified from the culture. For example, protein expression rate and protein degradation rate (such as due to protease activity) can both affect the amount of protein that can be extracted. Growing the cultured host cells comprising the claimed polynucleotide at a reduced temperature of less than, for example 40° C., has been found to give acceptable levels of rPA expression and stability. Thus, in one embodiment of the invention, host cells containing polynucleotides of the invention (e.g. expression vectors) are cultured at less than 40° C.; preferably at less than 37° C.; more preferably at less than 35° C.; more preferably at about 30° C., and most preferably at 25-30° C., such as 29° C., 28° C., 27° C., 26° C. and 25° C. Culturing host cells at these reduced temperatures may slow down the rate of rPA expression, but this may be useful if a high-level expression vector, such as the plasmid pMTL1015, is used for expression.

It is preferred that a growth medium is used that is free of animal products (i.e. products derived from animals), since this is advantageous for meeting the regulations for injectable products. Examples of suitable media include phytone peptone—based Terrific Broth, and soy peptone-based L-broth.

If a secretion sequence is used that enables extracellular secretion of the polypeptide into the growth medium then the growth medium may be harvested and undergo further purification steps to extract the polypeptide.

Alternatively, if the secretion sequence enables secretion of the polypeptide into the bacterial periplasm then the polypeptide product will be intracellular. In this case, the cells must be harvested from the culture medium (e.g. by centrifugation as a cell paste) and undergo further processing to extract the polypeptide from the cells.

Suitable protocols for the harvesting of cell cultures, such as bacterial cultures, for the purification of polypeptides are well known in the art, and can be found in common laboratory manuals such as Sambrook et al. (1989) Molecular Cloning: A Laboratory Manual, Second Edition, Cold Spring Harbor Laboratory Press; and Sambrook and Russell (2001) Molecular Cloning: A Laboratory Manual, Third Edition, Cold Spring Harbor Laboratory Press.

Typically, bacterial cells can be harvested by centrifugation for extraction of either nucleic acids or polypeptides. For protein purification the conditions selected for the harvesting of cultured cells by centrifugation are generally gentler than for the extraction of nucleic acid, so as not to damage the target protein. For example, the harvesting of bacterial cells for extraction of a target polypeptide may be carried out at 4° C., by centrifugation at 4,000-5,000 g for 10-15 minutes.

It is an option for the method to further comprise testing steps, to identify the presence and/or yield of desired polypeptide, prior to further processing, in one embodiment, an ELISA-based test is carried out.

Following the fermentation (bacterial growth and harvesting) and optional testing protocols, the method may further comprise downstream processing steps in order to obtain isolated, purified, rPA protein.

The downstream processing steps employed in the present invention preferably achieve one or more of the following aims:— reduction in the number of chromatography steps required, compared to prior art methods;

use of step elution rather than gradient elution for some, preferably all, chromatography steps;

increase in the level of primary processing prior to chromatography, compared to prior art methods;

removal of the need for the addition of conditioning agents (e.g. nucleases) where possible;

use of techniques capable of scaling-up to at least 100 L fermentation scale; and use of techniques that are compatible with cGMP.

It is preferred that the purification procedure has reduced process times and volumes and/or has increased process efficiency in comparison to prior art methods. In the present invention, the number of dialysis/buffer exchange steps is preferably minimised, for example, by linking steps that generate a process stream of high conductivity with those that require a high conductivity starting material (e.g. ammonium sulphate precipitation or ion-exchange chromatography may be followed by hydrophobic interaction chromatography).

The downstream processing protocol commences with a crude mixture containing rPA polypeptide. If the rPA polypeptide is located within the host cell (e.g. within a bacterial host cell periplasm) then the cells must be treated to extract the rPA polypeptide, for example by homogenisation.

It is preferred that the method further comprises at least one separation step, carried out on the extracted rPA polypeptide. Examples of separation steps that may be included in the method are filtration steps such as diafiltration steps, and chromatography steps. In one embodiment, the method comprises at least one chromatography step and at least one filtration step.

In a particularly preferred embodiment of the present method, the extracted rPA polypeptide (together with unwanted components such as nucleic acids, other proteins, and cell debris) is subjected to diafiltration, such as tangental flow diafiltration. The purpose of this step is to alter the load of charged molecules, in preparation for subsequent separation steps, such as chromatography steps. Diafilters retain molecules of above a certain molecular weight (e.g. above 30 kDa, kDa or 50 kDa) and allow dissolved substances and those below the specified molecular weight to pass through the filter. Thus, it is preferred that the method includes at least one filtration step that is a diafiltration step.

Chromatography steps may include ion-exchange chromatography (e.g. using a Q-sepharose anion exchange column) and hydrophobic charge chromatography (e.g. using a mercaptoethyl pyridine hypercel column). Other examples of suitable chromatographic techniques are known in the art and would be routinely available to a skilled person. Thus, the present method may include at least one ion-exchange chromatography step and at least one hydrophobic charge chromatography step.

In one embodiment, when the rPA polypeptide has been expressed in an *E. coli* host cell, there may be residual *E. coli* endotoxin associated with the rPA polypeptide and this can be separated from the rPA polypeptide by a (further) separation step, if necessary. In one embodiment, separation of endotoxin may be achieved by filtration, using a charged filter to which the toxin adheres.

Thus, in a specific embodiment, a method of producing rPA comprises the steps of obtaining host cells that express the polypeptide of the present invention; extracting the expressed rPA from the host cells; subjecting the extracted rPA to a diafiltration step (e.g. tangential flow diafiltration at 30 kDa); followed by at least one chromatography step selected from ion exchange chromatography and hydrophobic charge chromatography; then a further diafiltration step (which may be at a higher molecular weight cut-off e.g. 40 kDa or 50 kDa); and an optional further filtration step to remove any residual protein and/or bacterial endotoxin.

In one embodiment of the present invention, the combination of high-level gene expression (plasmid containing strong promoter), periplasmic translocation (secretion sequence), nucleic acid sequence modification (rPA nucleic acid sequence) and efficient downstream processing, results in an increase of rPA protein yields that are 10 to 20-fold above yields previously available in the prior art.

Furthermore, the downstream processing steps of the present invention allow rPA protein to be obtained that has greater than 70%, preferably greater than 80%, greater than 90%, or greater than 95%, and more preferably greater than 98% purity.

Polypeptide purity or homogeneity may be indicated by, for example, polyacrylamide gel electrophoresis of a protein sample, followed by visualizing a single polypeptide band upon staining the gel. Alternatively, higher resolution may be provided by using, for example, HPLC.

If desirable, the amino acid sequence of the polypeptides of the present invention may be determined by protein sequencing methods.

The present invention thus also provides an rPA polypeptide or fragment thereof produced by the method of the present invention. In one embodiment, the polypeptide may be identical to wild-type PA produced by *Bacillus anthracis*. In another embodiment, as described above, the polypeptide or fragment thereof may be distinguished from wild-type PA (or a fragment thereof) by the presence of an extra residue, such as a methionine residue, at the N-terminus of the rPA amino-acid sequence. For example, the polypeptide may be SEQ ID NO: 6, or a fragment thereof comprising the N-terminal methionine residue of SEQ ID NO: 6

Also envisaged by the present invention is a kit, which may comprise one or more of a polynucleotide, an expression vector, a host cell, and a polypeptide of the present invention.

Also provided by the present invention are antigenic compositions, such as vaccine compositions, comprising a polypeptide according to the present invention.

The invention also provides methods of inducing an immune response against infection by *Bacillus anthracis* comprising administering a polypeptide of the present invention or an antigenic composition of the present invention.

Also provided by the present invention is use of a polypeptide of the present invention for manufacture of a medicament for inducing an immune response against infection by *Bacillus anthracis*.

In this regard, "inducing an immune response" may embrace protecting against infection by *Bacillus anthracis*. The protection conferred by the method and/or use of the present invention may be 100%, or may be less than 100%. Preferably, "protecting against infection by *Bacillus anthracis*" provides protection against at least 50%, preferably at least 70%, more preferably at least 80%, most preferably at least 90%, 91%, 92%, 93%, 94%, 95%, 96%, 97%, 98% or 99% of *Bacillus anthracis* infections. Preferably, "protecting against infection by *Bacillus anthracis*" provides a level of protection that is at least 50%, preferably at least 70%, more preferably at least 80%, most preferably at least 90%, 91%, 92%, 93%, 94%, 95%, 96%, 97%, 98% or 99% effective against a *Bacillus anthracis* infection.

Furthermore, the term "protecting against infection" may embrace preventing infection and treating infection. In this regard, the term "preventing" includes reducing the severity/intensity of, or initiation of, a *Bacillus anthracis* infection. The term "treating" includes post-infection therapy and amelioration of a *Bacillus anthracis* infection.

The antigenic composition may be administered by conventional routes, e.g. intravenous, subcutaneous, intraperitoneal, and mucosal routes using methods well known in the art.

Typically, such antigenic compositions are prepared as injectables, either as liquid solutions or suspensions; solid forms suitable for solution in, or suspension in, liquid prior to injection may also be prepared. The preparation may also be emulsified, or the peptide encapsulated in liposomes or microcapsules.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L- threonyl-D-isoglutamine (thr-M DP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy phosphory loxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The active components may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The antigenic compositions are conventionally administered parenterally, by injection, for example, either subcutaneously or intramuscularly.

The antigenic compositions are for administration in a manner compatible with the dosage formulation, and in such amount as will be prophylactically and/or therapeutically effective. The quantity to be administered, which is generally in the range of 5 micrograms to 250 micrograms of antigen per dose, preferably about 50-100 μg per dose, depends on the subject to be treated, capacity of the subject's immune system to synthesize antibodies, and the degree of protection desired. Precise amounts of the active ingredient that is required to be administered may depend on the judgment of the practitioner and may be particular to each subject.

The antigenic composition may be given in a single dose schedule, or optionally in a multiple dose schedule. A multiple dose schedule is one in which a primary course of vaccination may be with 1-6 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the antigenic composition containing the immunogenic antigen(s) may be administered in conjunction with other immunoregulatory agents, for example, immunoglobulins, as well as antibiotics.

Additional formulations which are suitable for other modes of administration include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

In one embodiment the medicament may be administered intranasally (i.n.). An intranasal composition may be administered in droplet form having approximate diameters in the range of 100-5000 μm, which in terms of volume would have droplet sizes in the approximate range of 0.001-100 μl.

Intranasal administration may be achieved by way of applying nasal droplets or via a nasal spray. In the case of nasal droplets, the droplets may typically have a diameter of approximately 1000-3000 μm and/or a volume of 1-25 μl, whereas in the case of a nasal spray, the droplets may typically have a diameter of approximately 100-1000 μm and/or a volume of 0.001-1 μl.

It is possible that, following i.n. delivery of antibodies, their passage to the lungs may be facilitated by a reverse flow of mucosal secretions.

In a different embodiment, the medicament may be delivered in an aerosol formulation. The aerosol formulation may take the form of a powder, suspension or solution.

The size of aerosol particles is one factor relevant to the delivery capability of an aerosol. Thus, smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli.

The aerosol particles may be delivered by way of a nebulizer or nasal spray.

In the case of aerosol delivery of the medicament, the particles may have diameters in the approximate range of 0.1-50 μm, preferably 1-5 μm.

The aerosol formulation of the medicament of the present invention may optionally contain a propellant and/or surfactant.

By controlling the size of the droplets which are to be administered to a patient to within the defined range of the present invention, it is possible to avoid/minimise inadvertent antigen delivery to the alveoli and thus avoid alveoli-associated pathological problems such as inflammation and fibrotic scarring of the lungs.

Intranasal vaccination engages both T and B cell mediated effector mechanisms in nasal and bronchus associated mucosal tissues, which differ from other mucosae-associated lymphoid tissues.

Intranasal delivery of antigens allows targeting of the antigens to submucosal B cells of the respiratory system. These B cells are the major local IgA-producing cells in mammals and intranasal delivery facilitates a rapid increase in IgA production by these cells against the anthrax antigens.

In one embodiment administration of the medicament comprising an anthrax antigen stimulates IgA antibody production, and the IgA antibody binds to the anthrax antigen. In another embodiment, a mucosal and/or Th2 immune response is stimulated.

In one embodiment, the vaccine composition comprises rPA protein adsorbed to ALHYDROGEL™ adjuvant. In one embodiment, the vaccine is delivered by intramuscular injection.

The invention also provides a vector having the sequence SEQ ID NO:4.

The invention also provides a vector as deposited under ECACC No: 04061401.

The invention also provides a vector comprising a polynucleotide according to the present invention, as deposited under ECACC NO: 04052501, Referring to the Figures of the present application:—

FIG. 1 depicts HPA clone pMTL1015-cpg-rPA-synt—i.e. the modified rPA nucleic acid sequence fused to the $cpg_2$ leader in pMTL1015 ($Tc^R$). Manipulations required to generate this plasmid are as follows: (1) sub-clone synthetic 'mature' rPA sequence from sequence verified PCR product TOPO vector (i.e. without any leader) into HPA pET22bcpg vector; (2) sub-clone cpg-SynPA from pET22bcpgSynPA into pMTL1015.

FIG. 2 demonstrates SDS-PAGE of pMTL1015 clones expressing rPA after 16 hr Shake-flask culture in phytone peptone-based Terrific Broth. The key is as follows:—
1. Blank.
2. rPA Standard (DEV0301P; 100 µg/mL)
3, pMTL1015 vector only
4. pMTL1015-ompA-PA-wt
5. pMTL1015-cpg-PA-wt
6. pMTL1015-pelB-PA-wt
7. pMTL1015-ompA-PA-synt
8. pMTL1015-cpg-PA-synt
9, pMTL1015-pelB-PA-synt
10. Molecular weight markers FIG. 3 shows a Western blot of pMTL1015 clones expressing rPA after 16 hrs Shake-flask culture in phytone peptone-based Terrific Broth. The key is as described above for FIG. 2.

Figure 9:
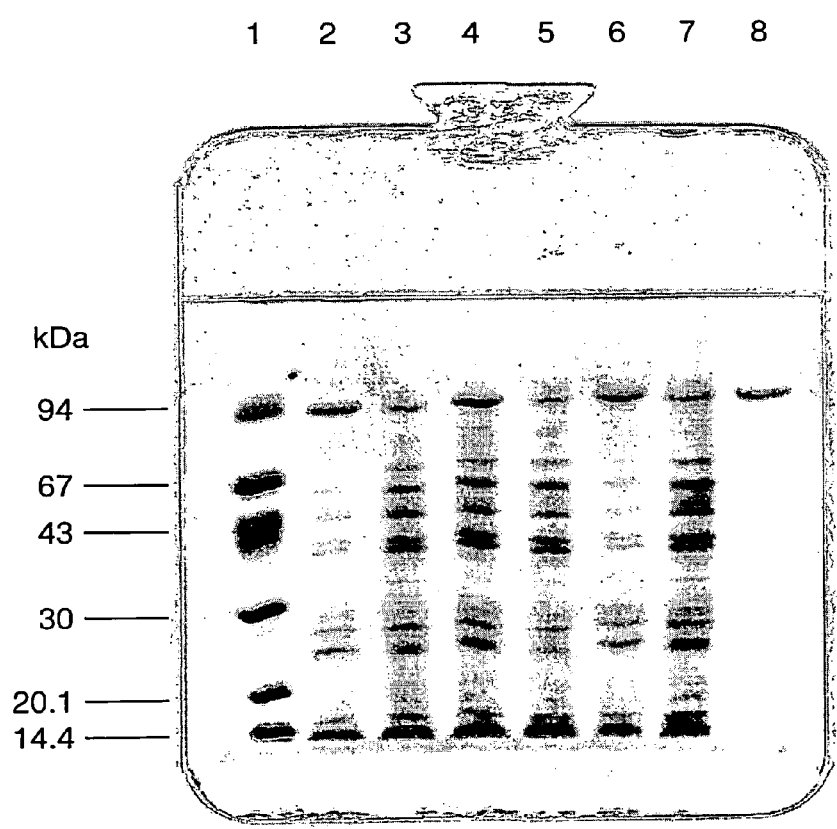

FIG. 9 shows SDS-PAGE (12.5% PHAST-GEL) of pMTL1015 clones expressing rPA in Shake-flask culture using Hy-soy based semi-defined medium. The key is as follows:—
1: Molecular Weight Markers
2: RV308 pMTL1015 ompA-PA-synt
3: RV308 pMTL1015 ompA-PA-wt
4: RV308 pMTL1015 pelB-PA-synt
5: RV308 pMTL1015 pelB-PA-wt
6: RV308 pMTL1015 cpg-PA-synt
7: RV308 pMTL1015 cpg-PA-wt
8: Reference DEV03031P (100 µg/mL)

Figure 10:
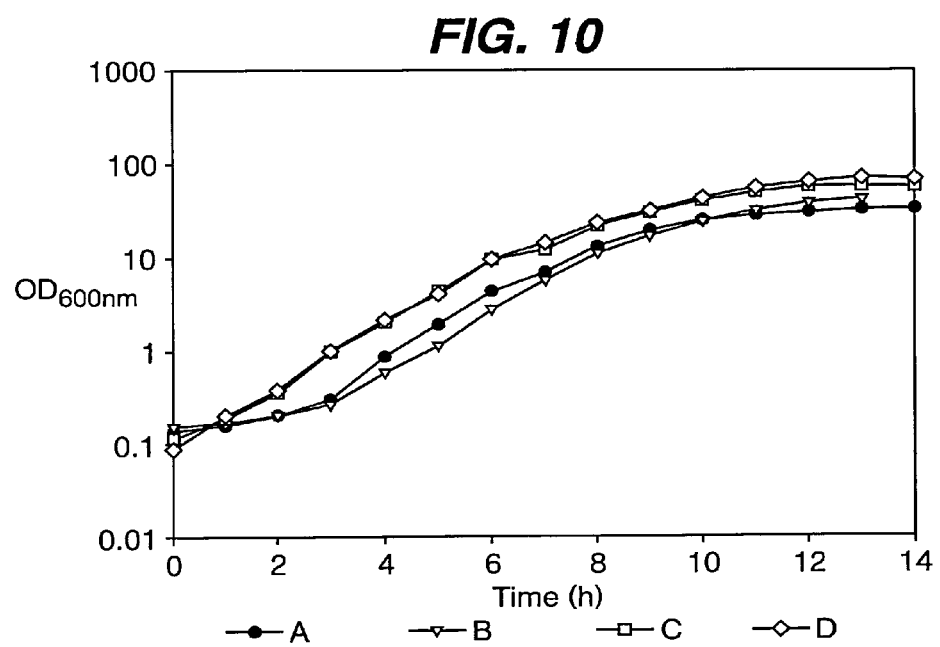
Figure 11:
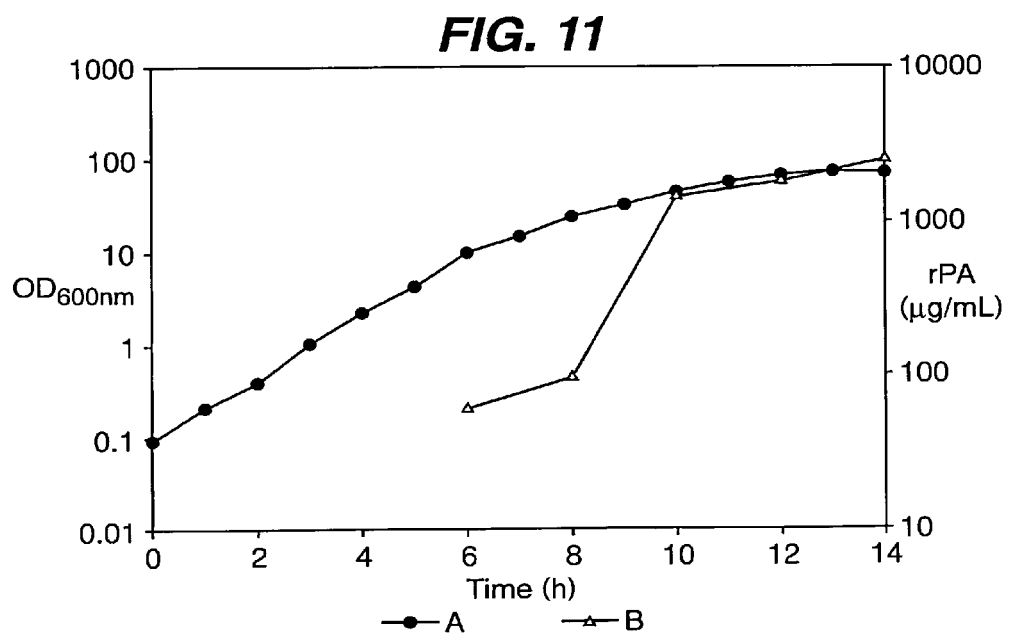

FIG. 10 shows growth of *E. coli* RV308 pMTL1015-cpg-PA-synt in production medium (Phytone peptone 12 g/L, Bacto yeast extract 60 g/L, glucose 25 g/L, magnesium sulphate heptahydrate 2 g/L, $K_2HPO_4$ 12.54 g/L, $KH_2PO_4$ 2.31 g/L and tetracycline 1.5 mg/L. pH 7.0-7.2), with varying levels of Yeast Extract, as follows:—
A 1× yeast extract
B 1.5× yeast extract
C 2× yeast extract
D 2.5× yeast extract FIG. 11 shows growth curves (A) and rPA production curves (B) for *E. coli* RV308 pMTL1015-cpg-PA-synt in production medium.

Figure 12:
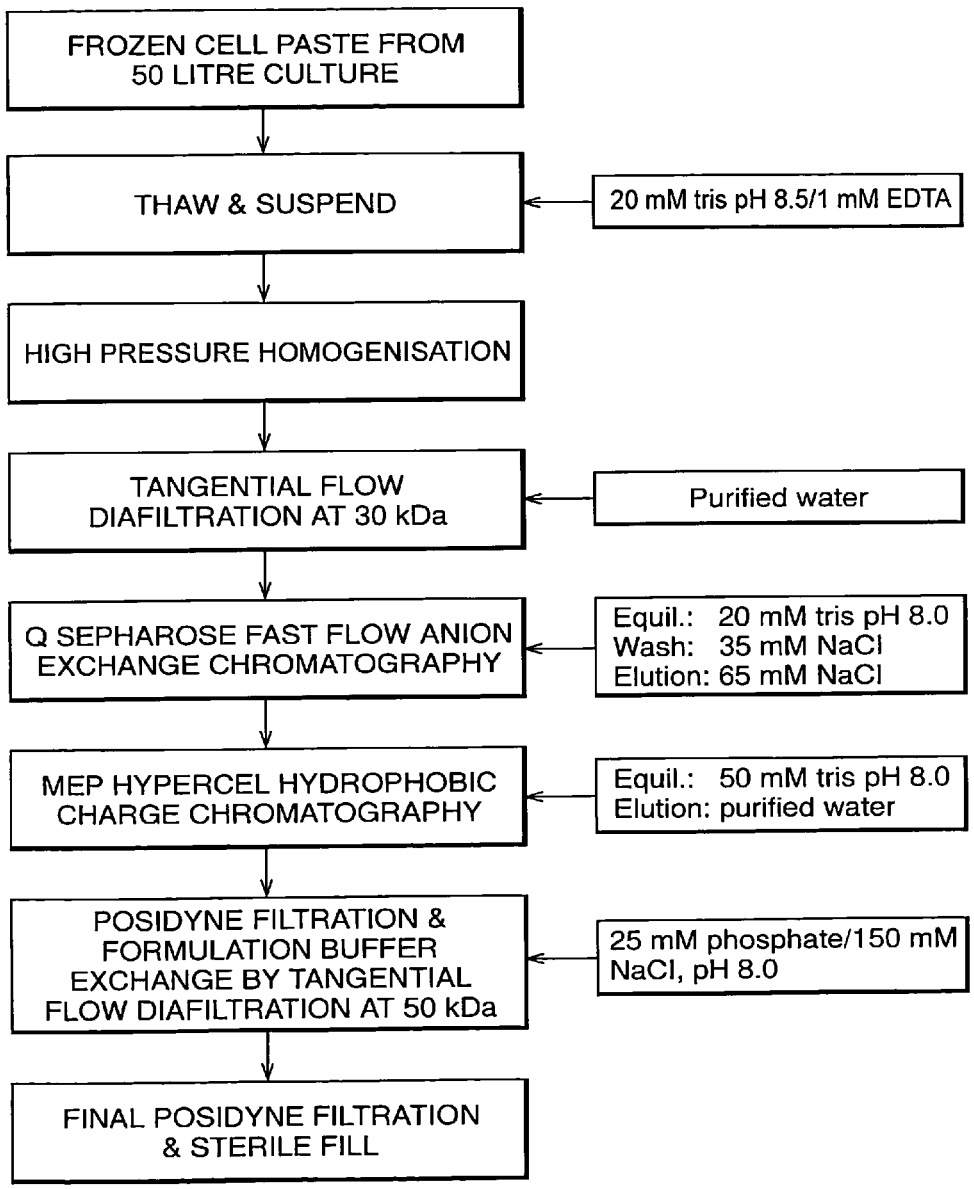

FIG. 12 is a flow chart showing the downstream processing steps for isolation of rPA.

Figure 13:
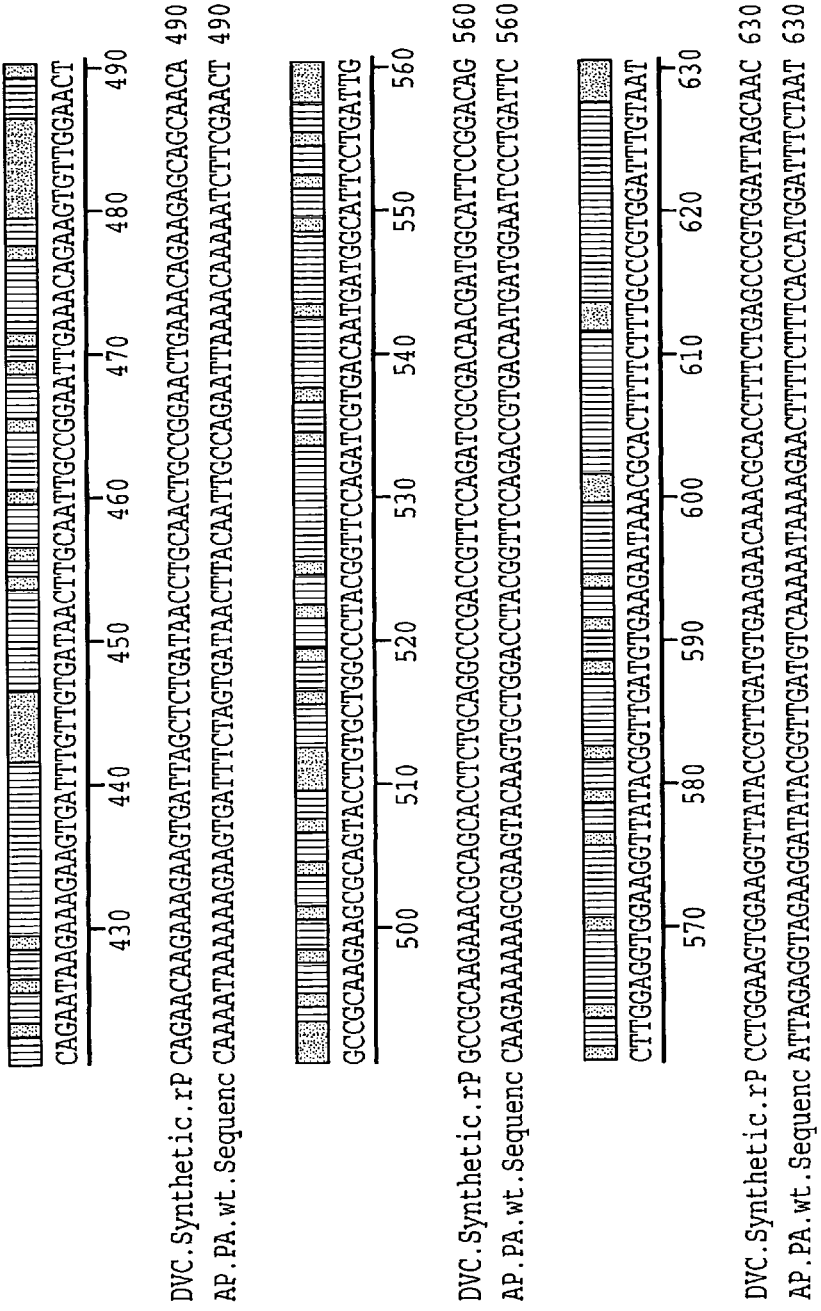
Figure 13:
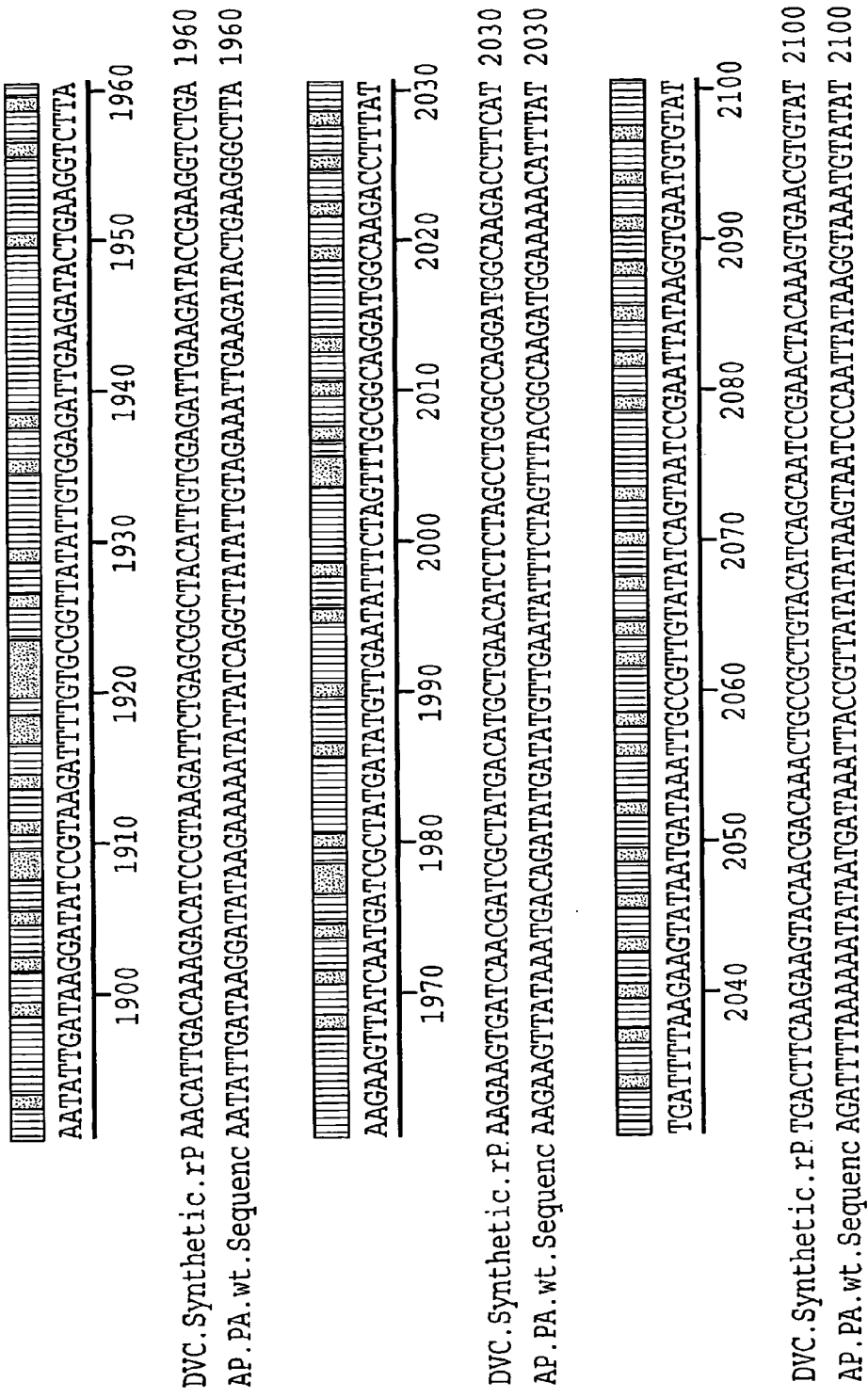
Figure 13:
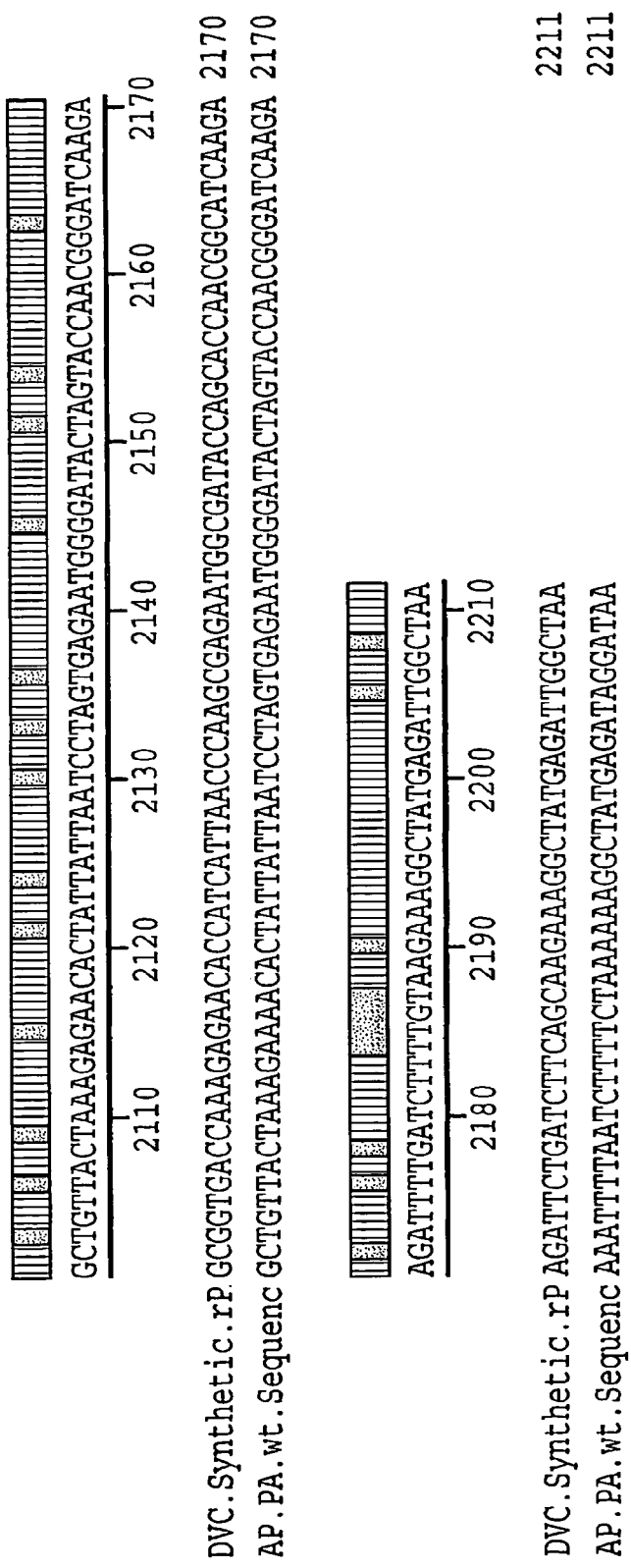

FIG. 13 (A-D) shows the sequence alignment between SEQ ID NO: 8—"DVC.Synthetic. rP" (i.e. the wild-type PA gene sequence, SEQ ID NO: 2, plus a 5' codon encoding a methionine residue), and SEQ ID NO: 7—"AP.PA.wt Sequenc" (i.e. the modified rPA gene sequence of the present invention, SEQ ID NO: 1, plus a 5' codon encoding a methionine residue). The sequence identity is 71.2%. (The consensus sequence is disclosed as SEQ. ID NO: 106.)

The invention is now described by reference to the following Examples.

EXAMPLE 1 rPA Expression Systems pMTL expression vector constructs were generated, directing expression of either the wild-type PA gene sequence or the modified rPA gene sequence, fused to either the *Erwinia carotovora* pelB or the pseudomonad carboxypeptidase $G_2$ ($cpg_2$) leader sequences. The latter sequence is described in European Patent 0 121 352, and has been shown to be efficiently processed in *E. coli*, directing soluble protein into the periplasmic space. These rPA expression constructs were compared with Dynport Vaccine Company (DVC)'s pET26b and Invitrogen pTrk vector-based constructs for evaluation.

Generation of novel rPA pMTL-based expression clones was as follows:

1. PCR amplification of the two PA-encoding nucleotide sequences (wild type and modified) fused to both the pelB, ompA and $cpg_2$ leader sequences. This generated six rPA sequence options,
2. Primary clones were constructed in a PCR product cloning vector system (e.g. Invitrogen TA Cloning).
3. Primary clones were authenticated by DNA sequence analysis of the composite PA/leader sequences.
4. The six rPA sequences were sub-cloned into pMTL1015 expression vector and the recombinant plasmids were authenticated.
5. Plasmid DNA derived from the four authenticated clones was used to transform a protease-deficient expression strain, *E. coli* RV308 (ATCC 31608).

Strategy for Comparison of rPA Expression Systems

The six clones based on the pMTL expression plasmid were evaluated in shake-flask culture in the current production medium. The existing DVC production organism was used as a control. Growth conditions and induction initiation/duration (where applicable) were standardised as much as possible to allow a true comparison of expression levels to be made under the given experimental conditions. For example, a standard cell density was used for inoculation. Production levels were compared by sampling cultures throughout growth and following chemical cell lysis using BugBuster™ (Novagen) of harvested cells, by densitometric analysis of SDS-PAGE. Western blotting was used to confirm the identity of the rPA protein band.

Media Selection Strategy

In addition to increasing the expression level of rPA by genetic manipulation, the final yield of product was raised by growing cultures to a higher cell density using a medium containing higher nutrient levels.

The strains showing the most promise in terms of rPA production levels in the current production medium were examined further, initially in shake-flask culture, using a range of potential production media. The analytical techniques used by DVC (SDS-PAGE, RP-HPLC) were used to estimate product levels throughout growth and at harvest.

EXAMPLE 2

Shake-Flask Comparisons of rPA Expression

EXAMPLE 2.1

Phytone Peptone-Based Terrific Broth

An experiment was performed to compare the expression of rPA by six pMTL1015 clones in phytone peptone-based Terrific Broth using shake-flask culture. Since previous work using the pMTL1015 expression system at CAMR had shown that low oxygenation rates may favour product expression, cultures were set up in both baffled flasks (high oxygenation) and non-baffled flasks (low oxygenation).

The 10 mL cultures prepared as primary seed cultures for the cell banking were used to prepare seed cultures for this study. A 50 µL aliquot of the 10 mL culture was used to inoculate 50 mL of phytone peptone-based Terrific Broth in 250 mL baffled flasks.

These seed cultures were incubated at 30° C. at 150 rpm for 17 h and then used to inoculate duplicate 200 mL cultures of the same medium in 1000 mL baffled flasks and single cultures of 250 mL in 500 mL non-baffled flasks. The inoculum for each culture was calculated to give a starting $OD_{600}$ of 0.1-0.2. The cultures were incubated at 30° C. and 150 rpm for 24 h. Samples (2.5 mL) were removed at 2 hourly intervals for rPA assay when the $OD_{600}$ reached 5-7. Samples were centrifuged at 4,000 rpm in a Clandon T-52 bench top centrifuge for 15 min, the supernatant decanted and the pellets stored frozen at −20° C. After 24 h growth, the duplicate baffled flask cultures were bulked and the cell mass harvested by centrifugation (Sorvall RC-3, 5000 rpm for 15 min) and the cell paste stored frozen at −20° C.

Figure 1:
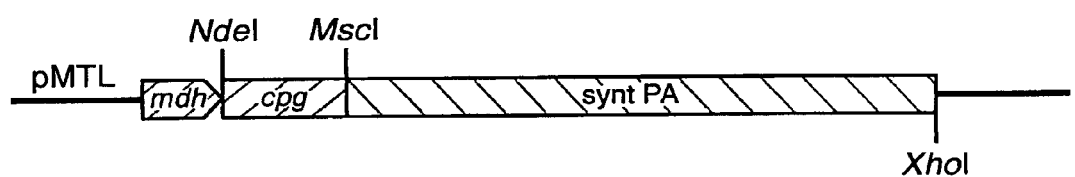
Figure 2:
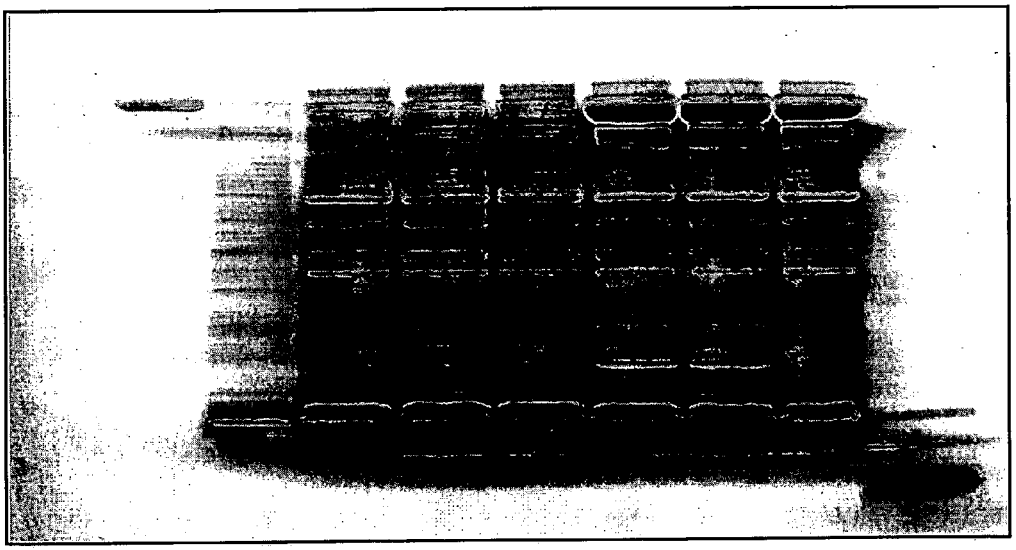
Figure 3:
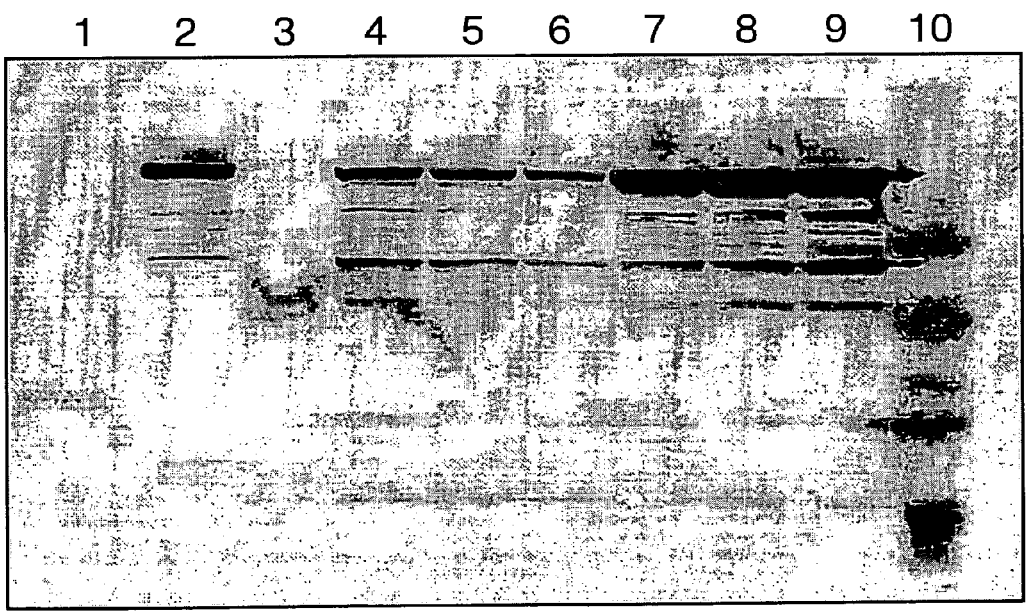

FIGS. 2 and 3 show SDS-PAGE and Western blot analysis of the 16 h samples from each of the pMTL1015 clones grown in phytone peptone-based Terrific Broth under conditions of high oxygenation (baffled flasks) following treatment with BugBuster™. It can be seen that strong protein bands are present at the expected rPA molecular mass following SDS-PAGE for the three clones expressing the synthetic gene product, with weaker bands for those clones expressing the wild type gene (FIG. 2). The amount of rPA present was estimated by comparison with the intensity of the rPA standard and confirmed by ELISA (Table 1). The Western blot analysis demonstrated the presence of some immuno-reactive material at lower molecular weights than the rPA (FIG. 3). The amount of this material relative to intact rPA was similar for all clones. It is not known at present whether this represents proteolytic degradation products or truncated expression.

TABLE 1

Comparison of rPA expression of all 12 E. coli clones following growth in phytone peptone-based Terrific Broth.

| | | | | | rPA (µg/mL culture) |
|---|---|---|---|---|---|
| Clone | Name | E. coli host | $OD_{600}$ culture | *Gel estimate | ELISA |
| 1 | pET26b-PA | BL21 (DE3) | 5.5 | <100 | 24 |
| 2 | pET26b-PA-synt | BL21 (DE3) | 3.6 | <100 | 11 |
| 3 | pTrck-pelB-PA | DH5a | 9.7 | <100 | 57 |

TABLE 1-continued

Comparison of rPA expression of all 12 E. coli clones following growth in phytone peptone-based Terrific Broth.

| | | | | | rPA (µg/mL culture) |
|---|---|---|---|---|---|
| Clone | Name | E. coli host | $OD_{600}$ culture | *Gel estimate | ELISA |
| 4 | pTrck-ompA-PA | DH5α | 9.7 | <100 | 74 |
| 5 | pMTL1015-pelB-PA-wt | RV308 | 17.3 | <100 | 58 |
| 6 | pMTL1015-ompA-PA-wt | RV308 | 19.7 | <100 | 135 |
| 7 | pMTL1015-cpg-PA-wt | RV308 | 20.4 | <100 | 67 |
| 8 | pMTL1015-pelB-PA-synt | RV308 | 21.1 | >>100 | 394 |
| 9 | pMTL1015-cpg-PA-synt | RV308 | 23.3 | >>100 | 496 |
| 10 | pMTL1015-ompA-PA-synt | RV308 | 25.3 | >>100 | 476 |
| 11 | pTrck-pelB-PA-synt | DH5α | 8.2 | >100 | 304 |
| 12 | pTrck-ompA-PA-synt | DH5α | 11 | >100 | 252 |

*estimate of rPA concentration from SDS-PAGE by comparison with 100 µg/mL rPA standard.

Figure 4A:
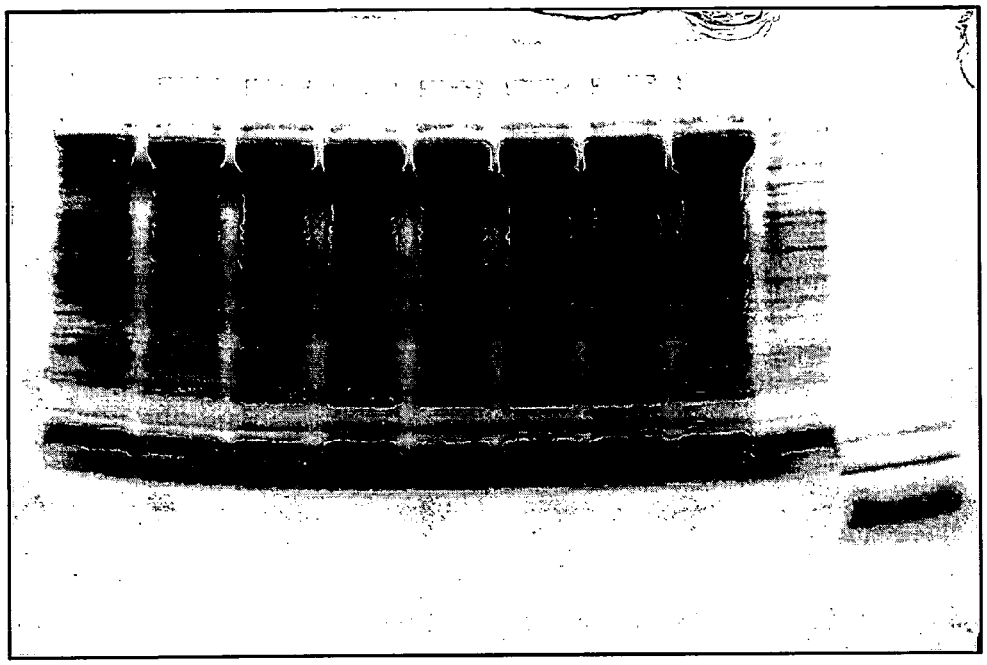
FIG. 4 shows time course analysis by (A) SDS-PAGE and (B) Western Blot of samples from Shake-flask culture of *E. coli* (pMTL1015-cpg-PA-synt) in phytone peptone-based Terrific Broth. The negative control was *E. coli* RV308 (pMTL1015).
Figure 4B:
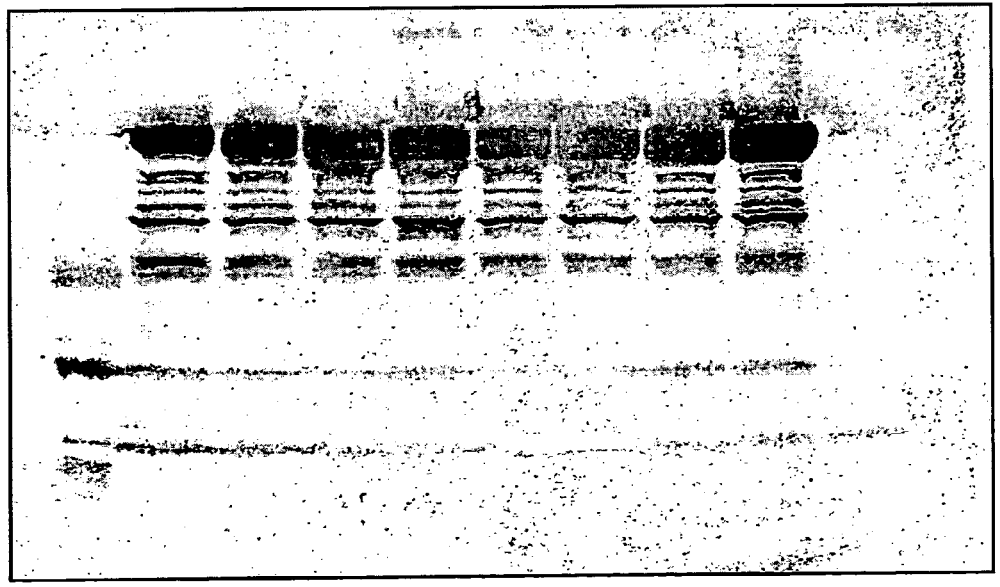

Time course samples from the pMTL1015-cpg-PA-synt clone were analysed by SDS-PAGE (Phast-gel), Western Blot (FIG. 4) and ELISA (Table 2) to determine; (a) the point at which rPA expression was maximal, and (b) whether prolonged incubation resulted in loss of product due to proteolytic activity. It can be seen that rPA expression by ELISA was optimal after 14-16 h incubation and did not change appreciably with further incubation up to 24 h (Table 2). Western blot analysis (FIG. 4) showed that the level of lower molecular weight immuno-reactive material relative to intact rPA did not change significantly with extended incubation time.

TABLE 2

Time course analysis by ELISA of samples from shake flask culture of E. coli (pMTL1015-cpg-PA-synt) in phytone peptone based Terrific Broth.

| Time (h) | rPA (µg/mL culture) |
|---|---|
| 10 | 107 |
| 12 | 313 |
| 14 | 507 |
| 16 | 532 |
| 18 | 488 |
| 20 | 491 |
| 22 | 487 |
| 24 | 525 |

Figure 5:
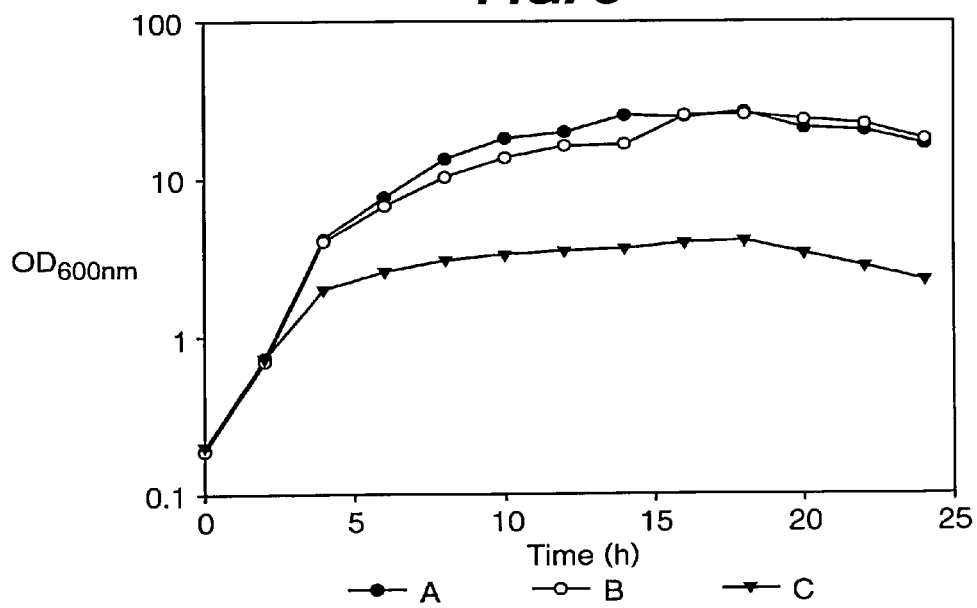
FIG. 5 shows growth curves of *E. coli* RV308 pMTL1015-ompA-PA-synt in phytone peptone-based Terrific Broth, Shake-flask culture, in baffled flasks (A and B) or non-baffled flasks (C).

FIG. 5 shows the growth curves obtained for E. coli RV308 (pMTL1015-ompA-PA-synt) when grown in phytone peptone-based Terrific Broth using baffled (high oxygenation) and non-baffled (low oxygenation) flasks. It can be seen that growth was substantially better in the baffled flasks. Cultures grown in non-baffled flasks reached a much lower final cell density compared with the baffled flask cultures. rPA expression was considerably lower in the cultures grown in non-baffled flasks (data not shown).

EXAMPLE 2.2

Hy-Soy-Based Semi-Defined Medium

Figure 6:
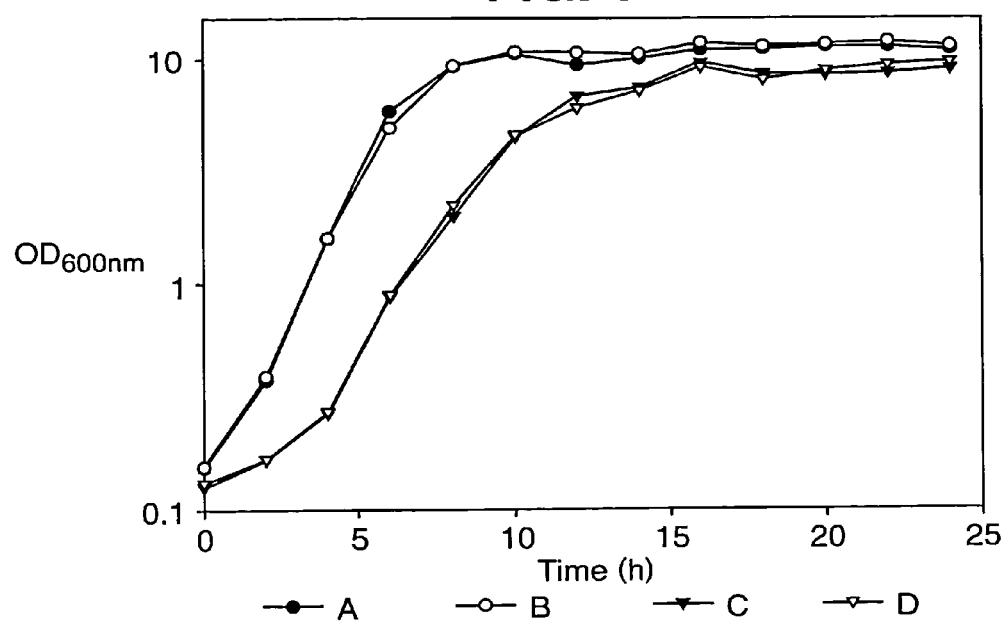
FIG. 6 shows growth curves of *E. coli* RV308 pMTL1015-ompA-PA-wt (A and B) and pMTL1015-ompA-PA-synt [C and D) in Hy-soy based semi-defined medium, Shake-flask culture.
Figure 7:
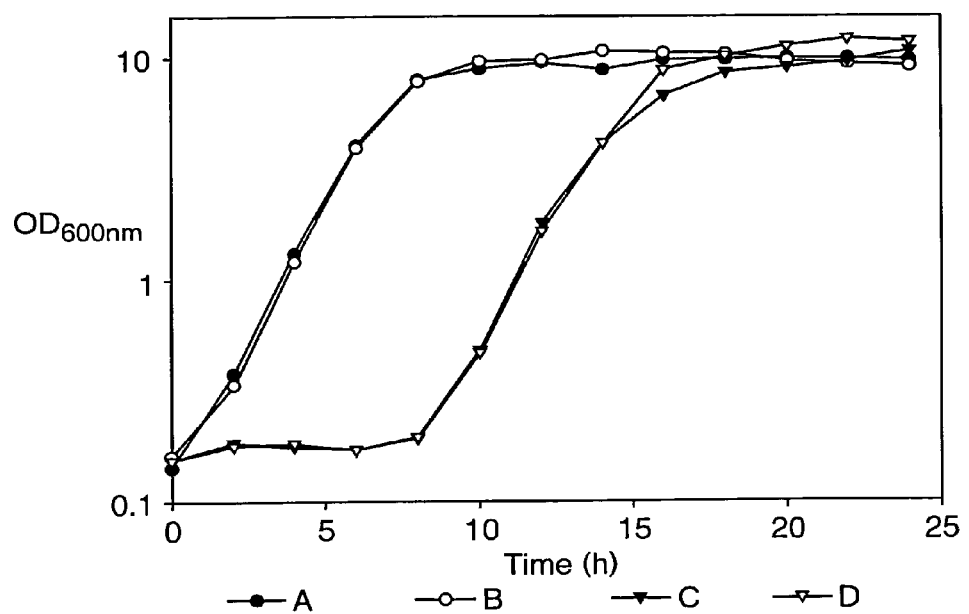
FIG. 7 shows growth curves of *E. coli* RV308 pMTL1015-pelB-PA-wt (A and B) and pMTL1015-pelB-PA-synt [C and D) in Hy-soy based semi-defined medium, Shake-flask culture.
Figure 8:
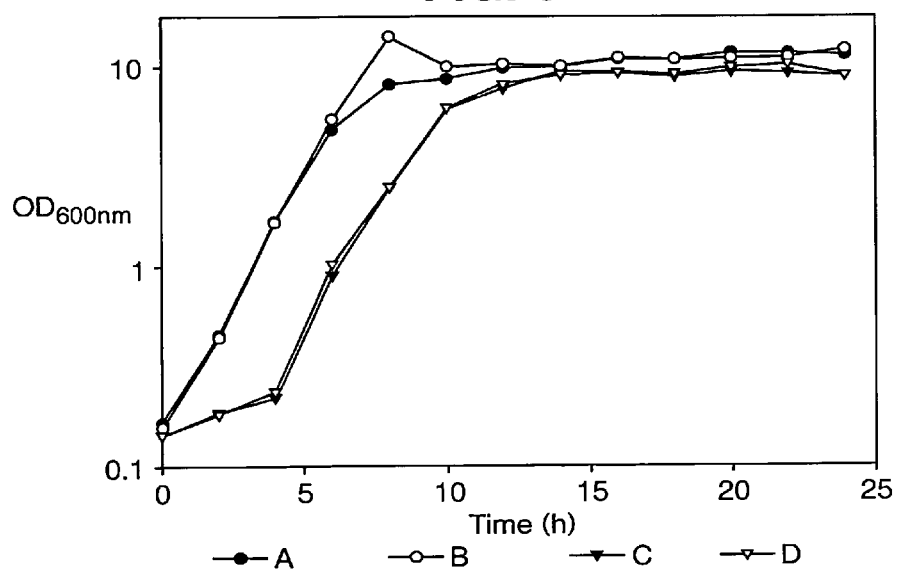
FIG. 8 shows the growth curve of *E. coli* RV308 pMTL1015-cpg-PA-wt (A and B) and pMTL1015-cpg-PA-synt [C and D) in Hy-soy based semi-defined medium, Shake-flask culture.

The experiment described above (Example 2.1) was repeated using Hy-Soy based semi-defined medium in baffled flasks only. The growth curves (FIGS. 6, 7 & 8) show that lower growth rates and final cell densities were obtained in this medium compared to Terrific Broth and a lag phase of up to 8 h was obtained for the clones expressing the synthetic gene. rPA expression levels were generally lower than observed in phytone peptone-based Terrific Broth; however, a similar pattern of superior expression levels with clones expressing the synthetic gene compared with the wild-type gene was observed by SDS-PAGE (FIG. 9) and ELISA (Table 3).

TABLE 3

Comparison of rPA expression of E. coli pMTL1015 clones following growth in Hy-soy-based semi-defined medium.

| | | | | rPA (µg/mL culture) | |
|---|---|---|---|---|---|
| | Clone Name | E. coli host | Sample time (h) | *Gel estimate | ELISA |
| 5 | pMTL1015-pelB-PA-wt | RV308 | 16 | <100 | 50 |
| 6 | pMTL1015-ompA-PA-wt | RV308 | 16 | <100 | 64 |
| 7 | pMTL1015-cpg-PA-wt | RV308 | 16 | <100 | 56 |
| 8 | pMTL1015-pelB-PA-synt | RV308 | 20 | >100 | 224 |
| 9 | pMTL1015-cpg-PA-synt | RV308 | 20 | >100 | 170 |
| 10 | pMTL1015-ompA-PA-synt | RV308 | 20 | >100 | 189 |

*estimate of rPA concentration from SDS-PAGE by comparison with 100 µg/mL rPA standard

EXAMPLE 3

Fermenter Level Comparisons of rPA Expression

Evaluation of the following four down-selected clones in fermenter culture was continued:
E. coli RV308 pMTL1015-cpg-PA-synt
E. coli RV308 pMTL1015-ompA-PA-synt
E. coli RV308 pMTL1015-ompA-PA-wt
E. coli DH.5 pTrcK-pelB-PA-synt
Medium Selection 8 L fermentations were performed in each medium under conditions as previously described with DOT and pH control.

The growth curves obtained were similar to those seen previously with the same media (see FIG. 10), but the rPA yield from production medium (Run No: PRECRV0034: Table 4) was 2500 µg/mL by ELISA. This culture was fed with 80 mL of 50% glucose solution prior to glucose depletion in the culture. A growth curve for PRECRV0034 showing rPA production can be seen in FIG. 11, but data does not indicate whether the yield has reached a maximum when the culture was harvested, in order to determine whether the improved rPA yields obtained for E. coli RV308 pMTL1015-cpg-PA-synt when cultured in production also occurred in the other two down-selected pMTL1015 clones, parallel fermentations were set up for all three strains under these conditions. However, the 80 mL of 50% glucose fed to the previous cultures was included from the start, raising the initial glucose concentration to 25 g/L.

E. coli RV308 pMTL1015-cpg-PA-synt again gave a yield of 2500 µg/mL and E. coli RV308 pMTL1015-ompA-PA-synt yielded 2000 µg/mL (see PRECRV0038 and 0037, Table 4).

E. coli DH5a pTrcK-pelB-PA-synt was grown in PPTBgly at 8 L scale (see Table 4, PRECDH0013) with the exception that the $OD_{600}$ at induction was raised to 15. The rPA yield was not improved significantly over previous results although more biomass was produced with a higher final $OD_{600}$ of 26 at four hours post induction with IPTG.

Effect of Growth Temperature

Previous development programs incorporating the E. coli RV308 pMTL1015-cpg-host/vector system have indicated that expression of product is most efficient at temperatures between 25 and 30° C.

Assessment of the effect on yield and product stability of growth at lower temperatures of E. coli RV308 pMTL1015-cpg-PA-synt was made by culturing the strain in production medium, under conditions described above, at 30, 28 and 25° C. (see Table 4, PRECRV0039, 0040 and 0041 respectively).

The yields from production at the lower temperatures were lower than when grown at 30° C. The quality of the material produced did not improve with the reduction in temperature, with little or no reduction in minor impurity bands on SDS-PAGE/Western Blot.

Effect of Antibiotic Concentration

As a confirmation of the stability of the plasmid under reduced antibiotic selective pressure, E. coli RV308 pMTL1015-cpg-PA-synt was cultured in production medium, under conditions described above, with varying tetracycline concentration levels in the medium (see Table 4, PRECRV0042-0044). The tetracycline concentrations were 15 µg/mL (100%), 1.5 µg/mL (10%) and 0. The 2° seed cultures contained 15, 1.5 and 15 µg/mL respectively. Thus the fermenter with no added antibiotic relied on carryover from the secondary seed to supply any selective pressure, assuming no degradation of the tetracycline during the seed growth. The volume of seed transferred to the fermenter was 124 mL giving a nominal 0.23 µg/mL tetracycline in the fermentation medium at inoculation.

The yields in terms of final $OD_{600}$ and biomass were within the expected range, but the yield of rPA was slightly lower than expected for the 15 µg/mL control. The levels for the reduced antibiotic cultures were slightly higher. The stability of the pMTL1015-cpg-PA-synt plasmid was confirmed by tooth-picking final fermentation sample colony isolates onto selective (L-agar with 15 µg/mL tetracycline) and non-selective media. The results of 100, 98 and 96% growth on selective medium for 15, 1.5 and 0 µg/mL tetracycline fermentations respectively, indicate good stability under the conditions used. The viable count results for PPTBgluc2.5xYE fermentations are in the $2 \times 10^{10}$-$5 \times 10^{10}$ cfu/mL range.

TABLE 4

Summary Table of fermentations.

| Run no. | Clone | Medium (No.) | Seed $OD_{600}$ | Fermenter $OD_{600}$ | SDS-PAGE (mg/L) | ELISA (mg/L) |
|---|---|---|---|---|---|---|
| PRECRV 0031 | pMTL1015-cpg-PA-synt | PPTBgluc | 12.6 | 34.8 | 100+ | 320 |

TABLE 4-continued

Summary Table of fermentations.

| Run no. | Clone | Medium (No.) | Seed $OD_{600}$ | Fermenter $OD_{600}$ | SDS-PAGE (mg/L) | ELISA (mg/L) |
|---|---|---|---|---|---|---|
| PRECRV 0032 | pMTL1015-cpg-PA-synt | PPTBgluc YEx1.5 | 13.0 | 44.2* | 100* | 84* |
| PRECRV 0033 | pMTL1015-cpg-PA-synt | PPTBgluc YEx2 | 14.7 | 59.8 | 500++ | 1630 |
| PRECRV 0034 | PMTL1015-cpg-PA-synt | PPTBgluc YEx2.5 | 14.2 | 71.6 | 500++ | 2500 |
| PRECDH 0013 | pTrcK-pelB-PA-synt | PPTBgly | 2.67 | 26.2 | 100++ | 360-465 |
| PRECRV 0036 | pMTL1015-ompA-PA-wt | PPTBgluc YEx2.5 | 14.8 | 43.9* | <100* | 90* |
| PRECRV 0037 | pMTL1015-ompA-PA-synt | PPTBgluc YEx2.5 | 8.7 | 56.6 | 500++ | 2000 |
| PRECRV 0038 | pMTL1015-cpg-PA-synt | PPTBgluc YEx2.5 | 14.7 | 62.6 | 500++ | 2500 |
| PRECRV 0039 | pMTL1015-cpg-PA-synt | PPTBgluc YEx2.5 | 15.6 | 62.4 | 500++ | 2300 |
| PRECRV 0040 | PMTL1015-cpg-PA-synt | PPTBgluc YEx2.5 | 15.6 | 62.2 | 500++ | 1600 |
| PRECRV 0041 | pMTL1015-cpg-PA-synt | PPTBgluc YEx2.5 | 15.6 | 63.6 | 500++ | 1500 |
| PRECRV 0042 | PMTL1015-cpg-PA-synt | PPTBgluc YEx2.5 | 12.9 | 62.4 | 500++ | 1720 |
| PRECRV 0043 | PMTL1015-cpg-PA-synt | PPTBgluc YEx2.5 | 13.2 | 66.4 | 500++ | 1800 |
| PRECRV 0044 | PMTL1015-cpg-PA-synt | PPTBgluc YEx2.5 | 12.9 | 63.8 | 500++ | 2120 |

PPTB—Phytone Peptone-based Terrific Broth; gluc—glucose; YE—Yeast Extract

Selection of Production Strain

The results obtained to date for the clones investigated after the initial down-selection have shown that of the four, *E. coli* RV308 pMTL1015-cpg-PA-synt has, in most cases, shown the highest yield when compared with the other pMTL1015 clones under equivalent conditions.

The largest proportion of information generated has been from the *E. coli* RV308 pMTL1015-cpg-PA-synt clone, for both fermentation and DSP development and with yields in the 1.5-2.5 mg/mL range when production medium has been used. This has allowed the present applicant to select this clone as their preferred production organism for all future work.

Table 5 shows a summary of all cultures grown to date in production medium. The figures indicate that although 2500 μg/mL is achievable, a more realistic value for the yield is 2000 μg/mL.

TABLE 5

Comparison of rPA levels relative to cell wet weight and optical density at harvest for cultures of *E. coli* RV308 pMTL1015-cpg-PA-synt containing 2.5x yeast extract.

| Run No. | Culture $OD_{600}$ | Cell Weight (g/L) | rPA Yield (mg/L) | mg rPA/ OD unit | mg rPA/g wet weight |
|---|---|---|---|---|---|
| PRECRV0030 | 69.8 | 85.8 | 1900 | 27.2 | 22.1 |
| PRECRV0034 | 71.6 | 102 | 2500 | 34.9 | 24.5 |
| PRECRV0038 | 62.6 | 86.5 | 2500 | 39.9 | 28.9 |
| PRECRV0039 | 62.4 | 77.5 | 2300 | 36.9 | 29.7 |
| PRECRV0040 | 62.2 | 80.4 | 1600 | 25.7 | 19.9 |
| PRECRV0041 | 63.6 | 98.5 | 1500 | 23.5 | 15.2 |
| PRECRV0042 | 62.4 | 89.1 | 1720 | 27.6 | 19.3 |
| PRECRV0043 | 66.4 | 88.8 | 1800 | 27.1 | 20.3 |
| PRECRV0044 | 63.8 | 83.9 | 2120 | 33.2 | 25.3 |
| MEAN | 65.0 | 88.1 | 1993 | 30.7 | 22.8 |

EXAMPLE 4

Upstream Process for rPA Production

Seed Banks for Clone of Interest—Clone pMTL1015-cpq-PA-synt Transformed into *E. Coli* RV308 (ATCC 31608).

After sequence confirmation, a research seed bank was prepared by growth under selective pressure of tetracycline (15 mg/L) in soy peptone based L-broth (Phytone peptone 15 g/L, Bacto yeast extract 5 g/L, NaCl 5 g/L, pH 6.8-7.0). A single colony from a nutrient agar plate with tetracycline was inoculated into 100 mL medium in 500 mL baffled shake flasks and incubated at 30° C. and 150 rpm in a shaking incubator until $OD_{600}$ reached 1.5. The culture was then mixed with sterile 50% glycerol in growth medium (see above) to give a final glycerol concentration of 10%, and stored frozen at −80° C. as 1 mL aliquots in 1.8 mL cryovials.

A working research cell bank (WRCB) of 250 vials was prepared from above seed bank using the same conditions and medium for growth, however 250 μL of thawed vial contents were inoculated into 200 mL medium in 1000 mL baffled shake flasks.

Primary Seed Culture.

1 vial of WRCB was thawed and 100 μL inoculated into 10 mL soy peptone based L-Broth (see above) containing tetracycline at 15 mg/L in a 25 mL universal bottle, incubated at 30° C. with shaking at 150 rpm for 7-9 hours. This was a recovery step to ensure that the organism is viable and to give a more consistent seed production process. The final $OD_{600}$ of this step was 0.7-1.0.

Secondary Seed Culture.

This step produces the inoculum for the fermentation, and with a reasonably sized shaking incubator is capable of producing inocula sufficient for 5-250 L cultures in shake flasks. At 50 L scale, 200 μL of primary seed was inoculated into 200 mL of production medium in each of 5×1000 mL baffled shake flasks. The cultures were incubated with shaking at 150 rpm and 30®C for 11-12 hours giving a final $OD_{600}$ of 13-16.

To prevent precipitation and caramelisation of some components during sterilisation by autoclaving, production medium is prepared by sterilising the complex component as a bulk and then adding the glucose, phosphate, magnesium and tetracycline aseptically as sterile solutions when the temperature of the components has fallen to lower than 25° C.

Production Fermentation

The seed cultures were then bulked and a volume sufficient to give a starting $OD_{600}$ of 0.2 in the fermenter was inoculated into 50 L production medium (see above) in a 72 L Applikon stirred tank fermenter. The complex medium components were sterilised, as a 40 L bulk, in situ at 121-123° C. for 30 minutes, cooled to below 25° C. and then supplemented with the remaining components to bring the total volume to 50 L.

The culture was then grown as a batch at a temperature of 30(±0.5)° C., pH 7.0 controlled by addition of sodium hydroxide and phosphoric acid. Dissolved oxygen tension was maintained at >40% by cascade step control of the following parameters: agitation (200-800 rpm), backpressure (3-7 psi), sparged airflow (25-50 Lpm) and oxygen supplementation (0-20 Lpm), in the order described.

When growth had ceased (12-14 hours), as measured by OD ($OD_{600}$ 60-65), the culture was chilled to below 15° C. and harvested by batch centrifugation (Sorvall RC-3B, H6000A rotor, 5000 rpm for 15 minutes). The harvested cell paste was stored at −20° C. until required for downstream processing. Product expression was assessed by ELISA assay from samples removed hourly from the culture.

EXAMPLE 5

Downstream Processing Steps

Cell Breakage

Approximately 4.5 kg of frozen cell paste harvest were suspended into a smooth paste with, initially, a minimum volume of 20 mM tris/1 mM EDTA pH 8.5. Further buffer was added to give an overall suspended volume of 16 L.

The suspended cells were broken by passing twice through an 'APV Gaulin' high-pressure homogeniser at a pressure of 7000 psi. The homogenate was then centrifuged for 1 hour at 5000 rpm in a 'Sorval' RC3 centrifuge. The pellet was discarded, and the supernatant (16 L approx) was retained.

Diafiltration

The centrifuged homogenate was diafiltered with 3 times its volume of purified water using a 'Millipore Pellicon' concentrator fitted with two 'Pall' OS030F07 0.5 m² 'Centrasette 2 Omega' suspended screen channel 30 kDa membranes. The concentrator was operated at a flow-rate of 17 L/min with a trans-membrane pressure of 1.6 Bar. The pH was adjusted to 8.0 and the conductivity to 2 mS/cm.

Anion Exchange and Chromatography

A 25 cm diameter chromatography column was packed with 5 L of 'Amersham' 'Q-Sepharose Fast Flow' anion exchanger to give a bed height of 10 cm. An industrial UV monitor was then connected to the effluent line. The column was operated at a flow-rate of 330 mL/min throughout. The packed column was washed with 10 L of water, then 5 L of 0.5 M sodium hydroxide, followed by purified water. 10 L of 0.5 M tris, pH 8.0, was pumped, and the column was then equilibrated with start buffer (20 mM tris, pH 8.0).

The diafiltrate was loaded, and then the loaded column was washed to baseline resolution with start buffer. The bound rPA was eluted with increasing salt steps of 10, 20, and 65 mM sodium chloride in start buffer, and the eluted peaks were collected in separate appropriately sized vessels. The eluates were assayed by SDS-PAGE and SEC-HPLC, and the fractions containing rPA at a purity of >40% were retained.

The column was regenerated by passing sequentially 10 L of 2 M sodium chloride, followed by 10 L of 1 M sodium acetate, 10 L of 0.5 M sodium hydroxide, then 10 L of 50 mM sodium hydroxide for storage.

Hydrophobic Charge Induction Chromatography

A 30 cm diameter column connected to UV monitor was packed with 20 L of 'Ciphergen' 'MEP HyperCel' at a flow rate of 7 L/min. Once packed, all further steps were performed at 800 mL/min. The column was washed with 5 L of 1 M sodium hydroxide with a contact time of no more than 40 min. The column was then washed with water, and then equilibrated with 20 L loading buffer (50 mM tris, pH 8.0). The Q pool (i.e. the pool from the previous Q chromatography step) was loaded, the column was washed with loading buffer to baseline, then the bound rPA was eluted with purified water. The collected product was assayed by SDS-PAGE and SEC-HPLC. The MEP pool (i.e. the pool from the MEP Hypercel column) was filtered through a 0.22 μm, 2000 cm² Pall 'Posidyne' filter. The column was regenerated with 10 L of 1 M sodium hydroxide, washed with purified water, and then stored in 0.2 μm filtered 50 mM sodium hydroxide.

Diafiltration and Formulation

The purified rPA was diafiltered using a 'Pall Centramate' medium screen 'Omega' 50 kDa cartridge (part No. OS0350C12, 0.093 m²). A flow-rate of 800 mL/min, and a trans-membrane pressure of 1.6 Bar were used. The diafiltration was performed versus 5 L of formulation buffer; 25 mM sodium phosphate, 150 mM sodium chloride, pH 8.0. A further filtration was perfomled using a 0.22 μm Pall 'Posidyne' filter of 5000 cm² area, and then the final product was dispensed into appropriate vials.

EXAMPLE 6

Construction of Variant Synthetic rPA Gene Constructs

The variant sequences set out in SEQ ID NOS: 9-105 are synthesized using solid phase chemical synthesis using nucleoside phosphoramidites. This is a well-established method in the field (see Brown T, Brown DJS. 1991. in Oligonucleotides and Analogues. A Practical Approach, ed. F Eckstein, pp. 1-24. Oxford: IRL). Typically, the synthetic gene sequences are constructed from a number of oligonucleotide sequences (40-80 bp in length) that have been generated using this chemical synthesis methodology. These oligonucleotide sequences represent both strands of the gene sequence and have their termini designed such that, post hybridization of complementary oligonucleotide pairs, the double stranded elements are bound by unique complementary overhanging sequences that enable their correct ordered assembly to generate the rPA gene "sub-fragment" sequences, typically ~500 base pairs in length. This is performed by mixing the hybridized oligonucleotide pairs with an appropriately cleaved plasmid vector (for example, a PUC or Invitrogen TOPO vector) with the addition of bacteriophage T4 ligase; both plasmid and rPA sub-fragments having compatible restriction site termini. These ligation products are used to transform competent *E. coli* host cells, generating Ecoli clones for screening. Screening of clones is carried out using restriction enzyme analysis of isolated plasmid DNA, and selected clones authenticated by DNA sequence analysis of the cloned insert of the plasmid.

The final rPA-encoding gene product is then assembled via the isolation of the plasmid-borne "sub-fragment" DNA segments as specifically bound restriction fragments, which are then ligated together with an appropriately cleaved plasmid vector (for example, a PUC or Invitrogen TOPO vector) and the ligation mixture used to transform competent *E. coli* cells. The *E. coli* clones generated are then screened by restriction analysis and the entire cloned rPA-encoding gene sequence verified by DNA sequence analysis.

The synthetic rPA-encoding gene sequence may be generated with or without a 5'-leader sequence DNA moiety. If generated without a leader sequence, a unique MscI restriction site is engineered at the 5'-end of the coding sequence as this will enable "in-frame" cloning to some leader sequences (e.g., ompA, pelB) which already reside in some commercially available *E. coli* expression plasmids. More typically, the choice of a larger range of leader sequences (e.g., cpg2, ompA, pelB, phoA, ompT, lamb, omp F, beta lactamase, *Staphylococcus aureus* Protein A, *Bacillus subtilis* endoglucanase, murine RNAase, human growth hormone, enterotoxins ST-II, LT-A and LT-B) is incorporated in the original design and DNA synthesis strategy. This way, the leader sequence-rPA "cassette" is generated as a single genetic element that can then be sub-cloned into a variety of *E. coli* expression vectors for production of the rPA polypeptide product. By virtue of engineering a unique MscI restriction site at the leader sequence-rPA-encoding gene sequence, different leader sequences may be substituted via simple sub-cloning procedures (Sambrook, J., Fritsch, E. F., Maniatis, T. Molecular Cloning: a Laboratory Manual, $2^{nd}$ Ed. 1989. Cold Spring Harbour Laboratory Press).

EXAMPLE 7

Expression of Variant Synthetic rPA Gene Constructs

The rPA gene encoding sequences depicted in SEQ ID NOs: 9 to 105 are cloned as leader sequence-rPA sequence "cassettes" into *E. coli* expression plasmids.

Cloning of these leader sequence-rPA sequence "cassettes" is facilitated by virtue of unique restriction sites engineered at the 5'- and 3'-ends for compatibility with the *E. coli* expression vector of choice. Typically, this would be either a NdeI or NcoI restriction site at the 5-end as this facilitates optimal positioning of the ATG initiation (metheionine) codon to the vector borne ribosome binding site (RBS) to enable efficient translation initiation of the RNA message originating from the expression vector moiety of the constructs. Restriction enzyme sites at the 3'-ends of the leader sequence-rPA sequence "cassettes" are variable and engineered to be compatible with choice of *E. coli* expression vector. The choice of available *E. coli* expression vectors is varied and examples include: pMTL series of vectors (proprietary to HPA), pET series (Novagen), pRSET, pET and pBAD series (Invitrogen), pQE series (Qiagen), pMal series (New England Biolabs), pPROTet series (Clontech), pGEX series (GE Healthcare), pEK/LIC series (EMD Biosciences), pIVEX series for cell-free expression (Roche) and bacteriophage Lambda gt11 and Lambda ZAP expression vectors (Stratagene).

Expression of the rPA polypeptides elaborated from rPA-coding sequences SEQ ID Nos 9 to 105 is conducted in shake flasks or in fermenter bioreactors as described in Examples 2 and 3. The latter of these (i.e. the fermenter) attains levels of periplasmically located rPA polypeptide product at levels typically exceeding 2 grams per liter. Particularly good levels of rPA polypeptide (in the range 2.1-2.4 grams per liter) are achieved using SEQ ID NQs: 36, 46, 56, 66, 76, 86 and 96. SEQ ID NO: 36, for example, achieves a typical yield of at least 2.2 grams per liter.

Purification of the rPA polypeptide is achieved using the methods described in Example 5.

REFERENCES

Abrahmsen (1986). Nucl. Acids Res. 14: 7487-7500
Alldread et al. (1992). Gene 14: 139-143
Altschul (1990) J. Mol. Biol. 215: pgs. 403-410
Ausubel F. M. et al., Current Protocols in Molecular Biology, eds, Current Protocols, a joint venture between Greene Publishing Associates, In. And John Wiley & Sons, Inc. (1995 Supplement) Ausubel
Baillie, L. (2001), 91, pgs 609-613
Batra, S. (2001) Biochem. and Biophys. Res. Comm., 281, pgs 186-192
Better et al. (1988) Science 240:1041-1043
Bhatnagas, R. (2001) Critical Rev. in Microbiol., 27(3), 167-200
Bolivar et al. (1977) Gene 2: 95
Brehm et at (1991) Appl. Microbiol Biotechnol 36: 358-363
Brosius eta. (1981) J Mol Biol 148: 107-127
Chambers et al. (1988) Gene 68: 139-149
Chambers et al. (1992) FEMS Microbiol Letters 91: 277-284
Denefle et al (1989) Gene 85: 499-510
Fujimoto et al. (1988) J. Biotechnol. 8: 77-86
Ghrayeb et al. (1984) EMBO J. 3: 2437-2442
Gray et al. (1985) Gene 39: 247-254
Hoffman & Wright (1985) Proc. Nat. Acad. Sci. USA. 82: 5107-5111
Johnson et al (1996) Protein Expression Purif. 7: 104-1123
Kadonaga et al. (1984) J Biol. Chem. 259: 2149-2154
Kanehisa (1984) Nuc. Acids Res 12:203-213
Le Calvez et al. (1996) Gene 170: 51-55
Lei et al. (1987) J. Bacteriol. 169: 4379-4383
Little, S. F. (1986) Inf. and Immunol vol. 52, No. 2, 509-512
Macyntyre & Henning (1990). Biochimmie 72: 157-167
Makrides (1996) Microbiological Reviews 60: 512-538
Maniatis et al. (1991) Molecular Cloning: A laboratory Manual. Cold Spring Harbor, N.Y., Cold Spring Harbor Laboratory Press
Michael et al. (1994) FEMS Microbiol. Letters 124: 195-202
Miller et al. (1983) Gene 24: 309-315
Minton et al. (1988) Focus 10: 56
Morioka-Fujimoto et a (1991) J. Biol. Chem. 266: 1728-1732
Needleman & Wunsch (1970) J. Mol. Biol. 48: 443
Oka et al., (1985) Proc. Nat. Acad. Sci. USA. 82: 7212-7216
Pearson & Lipman (1988) Proc. Nat. Acad. Sci. USA 85: 2444
Price, B. M. (2001) Inf. and Immun., vol. 69, No. 7, 4509-4515
Proudfoot et al. (1996) J. Biol. Chem. 271: 2599-2603
Sambrook et al. (1989) Molecular Cloning: A laboratory Manual. Second Edition. Cold Spring Harbor Laboratory Press
Sambrook and Russell (2001) Molecular Cloning: A laboratory Manual. Third Edition. Cold Spring Harbor Laboratory Press
Schein et al. (1992) Biochem. J. 283: 137-144
Sharma at al. (1996) Protein Expression and Purification. 7, 33-38
Smith and Waterman (1981) Adv. Appl. Math. 2: 484
Sterne, M. (1939) Onderstepoort J. of Veterinary Science and Animal industry, 13, 307-312
Tucker et al (1983) Gene 24: 309-15

Villa-Komaroff et al. (1977) Proc. Nat. Acad. Sci. USA. 75: 3727-3731

Vodkin, M. et al. (1983) Cell, 34:693

Watson, (1984) Proc. Nat. Acad. Sci. USA. vol. 12: 5145

Welkos, S., et al. (1988) Gene, 69(2): 287

Wetmur and Davidson (1968) J. Mol. Biol. 31:349-370

```

The invention claimed is:

1. A method for producing rPA comprising expressing a polynucleotide comprising the nucleic acid sequence of SEQ ID NO: 1,
wherein said polynucleotide encodes a recombinant *Bacillus anthracis* Protective Antigen (rPA).

2. A method according to claim 1, wherein said polynucleotide is expressed in a host cell.

3. A method according to claim 1, wherein said polynucleotide is DNA, and is optionally first transcribed into RNA in vitro and the RNA is then translated in a host cell.

4. A method according to claim 2, wherein the host cell is an *E. coli* host cell.

5. A method according to claim 4, wherein the *E. coli* host cell is *E. coli* RV308.

6. A method according to claim 1, comprising expressing rPA from an expression vector comprising said polynucleotide.

7. A method according to claim 6, wherein the expression vector comprises the cpg leader sequence encoded by SEQ ID NO: 3.

8. A method according to claim 6, wherein the vector is plasmid pMTL1015, encoded by SEQ ID NO: 4.

9. A method according to claim 6, wherein the vector is expressed in *E. coli* RV308.

10. A method according to claim 6, further comprising initial steps of transforming the expression vector into a host cell, and culturing the transformed host cell in a growth medium.

11. A method according to claim 10, wherein said growth medium is free of animal products.

12. A method according to claim 10, comprising culturing the transformed host cells at a temperature of less than 40° C.

13. A method according to claim 10, further comprising harvesting the host cell.

14. A method according to claim 13, further comprising extracting rPA from the host cell.

15. A method according to claim 14, further comprising a separation step.

16. A method according to claim 15, wherein the separation step is selected from one or more chromatography steps, and one or more filtration steps.

17. A method according to claim 16, wherein at least one of said filtration step(s) is a diafiltration step.

18. A method according to claim 16, wherein at least one of said chromatography step(s) is selected from an ion-exchange chromatography step and a hydrophobic charge chromatography step.

19. A method according to claim 2, comprising:
(a) obtaining host cells that express the polynucleotide or an expression vector comprising said polynucleotide;
(b) extracting the expressed rPA from the host cells;
(c) subjecting the extracted rPA to a diafiltration step;
(d) subjecting the diafiltered rPA to at least one chromatography step selected from anion exchange and hydrophobic charge chromatography; and
(e) carrying out a further diafiltration step.

20. A method according to claim 1, wherein said polynucleotide further comprises a polynucleotide encoding a secretion sequence.

21. A method according to claim 1, wherein said polynucleotide further comprises a polynucleotide encoding a secretion sequence for periplasmic translocation of said recombinant *Bacillus anthracis* Protective Antigen (rPA).

22. A method according to claim 1, wherein said polynucleotide further comprises a polynucleotide encoding a secretion sequence for extracellular translocation of said recombinant *Bacillus anthracis* Protective Antigen (rPA).

23. A method according to claim 21, wherein said secretion sequence is cleavable from said recombinant *Bacillus anthracis* Protective Antigen (rPA) during periplasmic translocation.

24. A method according to claim 22, wherein said secretion sequence is cleavable from said recombinant *Bacillus anthracis* Protective Antigen (rPA) during extracellular translocation.

25. A method according to claim 20, wherein said secretion sequence is encoded by the nucleic acid sequence of SEQ ID NO:3.

26. A method according to claim 1, wherein said polynucleotide further comprises a codon encoding a methionine residue at the 5' end.

27. A method according to claim 26, wherein said polynucleotide comprises the nucleic acid sequence of SEQ ID NO:7.

28. A method according to claim 6, wherein said expression vector further comprises a promoter that is selected so as to ensure that said rPA polypeptide is highly expressed.

29. A method according to claim 28, wherein said promoter is a malate dehydrogenase (mdh) promoter.

30. A method according to claim 6, wherein said expression vector further comprises a selectable marker.

31. A method according to claim 6, wherein said expression vector expresses said polynucleotide in the absence of a chemical inducer.

32. A method according to claim 28, wherein said expression vector is plasmid pMTL1015, comprising the nucleic acid sequence of SEQ ID NO:4.

33. A method according to claim 21, wherein said expression vector is deposited with the ECACC under the accession number 04061401.

34. A method according to claim 6, wherein the expression vector further comprises the nucleic acid sequence of SEQ ID NO:4.

35. A method according to claim 6, wherein the expression vector is deposited with the ECACC under the accession number 04052501.

* * * * *

UNITED STATES PATENT AND TRADEMARK OFFICE
CERTIFICATE OF CORRECTION

PATENT NO.         : 8,440,427 B2
APPLICATION NO.    : 13/534911
DATED              : May 14, 2013
INVENTOR(S)        : John Brehm et al.

It is certified that error appears in the above-identified patent and that said Letters Patent is hereby corrected as shown below:

On The Title Page, Item (56) References Cited

Col. 1, line 46, please delete "Brehra" and insert --Brehm--

Col. 2, line 20, please delete "colt" and insert --coli--

Page 2

Col. 1, line 33, please delete "juman" and insert --human--

Signed and Sealed this
Fourth Day of August, 2015

Michelle K. Lee
*Director of the United States Patent and Trademark Office*